US006800455B2

(12) United States Patent (10) Patent No.: US 6,800,455 B2
Stanton et al. (45) Date of Patent: Oct. 5, 2004

(54) SECRETED FACTORS

(75) Inventors: Lawrence W. Stanton, Redwood City, CA (US); R. Tyler White, Fremont, CA (US)

(73) Assignee: Scios Inc., Sunnyvale, CA (US)

( * ) Notice: Subject to any disclaimer, the term of this patent is extended or adjusted under 35 U.S.C. 154(b) by 0 days.

(21) Appl. No.: 09/809,545

(22) Filed: Mar. 14, 2001

(65) Prior Publication Data

US 2002/0110804 A1 Aug. 15, 2002

Related U.S. Application Data

(60) Provisional application No. 60/193,548, filed on Mar. 31, 2000.

(51) Int. Cl.$^7$ ................................................. C12P 21/06
(52) U.S. Cl. ....................... 435/69.1; 435/6; 435/252.3; 435/325; 435/320.1; 536/23.1; 536/23.5; 536/24.31
(58) Field of Search .............................. 536/23.1, 23.5, 536/24.3, 24.31; 435/320.1, 252.3, 325, 69.1, 6

(56) References Cited

U.S. PATENT DOCUMENTS

| 4,873,191 A | 10/1989 | Wagner et al. ............... 800/25 |
| 5,716,785 A | 2/1998 | Van Gelder et al. ............ 435/6 |
| 5,744,305 A | 4/1998 | Fodor et al. .................. 435/6 |
| 5,800,992 A | 9/1998 | Fodor et al. .................. 435/6 |
| 5,807,522 A | 9/1998 | Brown et al. ................ 422/50 |

FOREIGN PATENT DOCUMENTS

| EP | 0373203 B | 8/1994 |
| WO | WO 00/11942 | 3/2000 |
| WO | WO 00/35473 | 6/2000 |

OTHER PUBLICATIONS

Branch, Trends in Biological Sciences 23: 45 (Feb. 1998).*
Bonaldo et al, Genome Res. 6: 791 (1996).*
Kennell et al, Progr. Nucl. Acid Res. Mol. Biol. 11: 259 (1971).*
Database EBI/SWALL 'online! (Mar. 1, 2002) Cros et al. Gene expression alterations revealed by supression substractive hybridization in rat soleus muscle disuse atrophy: Database accession No. Q8VD50XP002195683.
Stanton et al., "Altered Patterns of Gene Expression in Response to Myocardial Infraction" Circ. Res. 86(9):939:945 (Mar. 2000).
Stanton et al., "Cardiac Gene Expression Profiling in rat Myocardial Infarction Using DNA Microarrays", Circulation, American Heart Association 98(17)SUPP;: 1746 (Oct. 1998).
Stanton, Lawrence "Altered transcriptional responses in myocarial infarction "Cardiovascular Genomics 1–8(Jan. 30, 2000).
Willenbrock: Regulation of cardiac adrenomedullin–mRNA in different stages of experimental heart failure: Life Sciences 65 (21):2247–2249 (Discussion) (1999).
Arola et al., "Experimental Myocarditis Induced by Two Different Coxsackievirus B3 Variants: Aspects of Pathogenesis and Comparison of Diagnostic Methods" *J. Med. Virol.* 47: 251–259 (1995).
Chow et al., "Differential Effects of Myocarditic Variants of Coxsackievirus B3 in Inbred Mice" *Lab. Invest.* 64: 55–64 (1991).
Cohen et al., "A first–generation physical map of the human genome" *Nature* 266:698–701 (1993).
Copeland et al., "Development and applications of a molecular gentic linkage map of the mouse genome" *Trends in Genetics* 7:113–18 (1991).
Cowley et al., "*Autosomal–dominant polycystic kidney disease in the rat*" *Kidney Int.* 43:522–34 (1993).
DeRisi et al., "Use of a cDNA microarray to analyze gene expression patterns in human cancer" *Nat. Genet.*, 14(4):457–60 (1996).
Gordon, Jon W., "Trangenic Animals" *Intl. Rev. Cytol.* 115:171–229 (1989).
Gu et al., "Deletion of a DNA Polymerase β Gene Segment in T Cells Using Cell Type–Specific Gene Targeting" *Science* 265:103–06 (1994).
Heller et al., "Discovery and analysis of inflammatory disease–related genes using cDNA micoarrays" *Proc. Natl. Acad. Sci. USA,* 94(6)2150–55 (1997).

(List continued on next page.)

Primary Examiner—James Martinell
(74) Attorney, Agent, or Firm—Morrison & Foerster LLP

(57) ABSTRACT

The invention concerns new secreted factors encoded by clones P00184_D11 (SEQ ID NO:1), P00185_D11 (SEQ ID NO:3), P00188_D12 (SEQ ID NO:5), P00188_E01 (SEQ ID NO:7), P00194_G01 (SEQ ID NO:9), P00194_G05 (SEQ ID NO:11), P00194_H10 (SEQ ID NO:13), P00199_D08 (SEQ ID NO:15), P00203_D04 (SEQ ID NO:17), P00203_E06 (SEQ ID NO:19), P00209_F06 (SEQ ID NO:21), P00219_D02 (SEQ ID NO:23), P00219_F06 (SEQ ID NO:25), P00220_H05 (SEQ ID NO:27), P00222_G03 (SEQ ID NO:29), P00225_C01 (SEQ ID NO:32), P00227_D11 (SEQ ID NO:34), P00228_F03 (SEQ ID NO:36), P00233_H08 (SEQ ID NO:38), P00235_G08 (SEQ ID NO:40), P00239_C11 (SEQ ID NO:42), P00240_E05 (SEQ ID NO:45), P00247_A04 (SEQ ID NO:50), P00248_B04 (SEQ ID NO:52), P00249_F09 (SEQ ID NO:54), P00258_A10 (SEQ ID NO:56), P00262_C10 (SEQ ID NO:58), P00269_H08 (SEQ ID NO:62), P00628_H02 (SEQ ID NO:66), P00629_C08 (SEQ ID NO:68), P00641_G11 (SEQ ID NO:71), P00648_E12 (SEQ ID NO:73), P00697_C03 (SEQ ID NO:75), and other mammalian homologues and variants of such factor, as well as polynucleotides encoding them. The invention further concerns methods and means for producing such factors and their use in the diagnosis and treatment of various cardiac, renal or inflammatory diseases.

5 Claims, 59 Drawing Sheets

OTHER PUBLICATIONS

Hohenadl et al., "Strand–specific detection of enteroviral RNA in myocardial tissue by in situ hybridization" *Mol. Cell. Probes* 5: 11–20 (1991).

Hubank and Schatz, "Identifying differences in mRNA expression by representational difference analysis of cDNA" *Nucl. Acids Res.* 22(25):5640–5648 (1994).

Jiang and Fisher, "Use of a Sensitive an Efficient Subtraction Hybridization Protocol for the Identification of Genes Differentially Regulated During the Induction of Differentiation in Human Melanoma Cells" *Mol. Cell. Different.* 1:285–299 (1993).

Jiang et al., "*The melanoma differentiation–associated gene mda–6, which encodes the cyclin–dependent kinase inhibitor p21, is differentially expressed during growth, differentiation an progression in human melanoma cells*"*Oncogene* 10, 1855–1864 (1995).

Kaspareit–Rittinghaus et al., "*A New Rat Model for Polycystic Kidney Disease of Humans*" *Transplant Proc.* 6:2582–3 (1990).

Lavitrano et al., "Sperm Cells as Vectors for Introducing Foreign DNA into Eggs: Genetic Transformation of Mice" *Cell* 57:717–23 (1989).

Liang and Pardee, "Differential Display of Eukaryotic Messenger RNA by Means of the Polymerase Chain Reaction" *Science* 257:967–971 (1992).

Lo, Cecilia W., "Transformation by Iontophoretic Microinjection of DNA: Multiple Integrations Without Tandem Insertions" *Mol. Cell. Biol.* 3:1803–14 (1983).

McClelland and Welsh, "RNA Fingerprinting by Arbitrarily Primed PCR" *PCR Methods and Applications* 4:S66–81 (1994).

McManus et al., "Direct Myocardial Injury by Enterovirus: A Central Role in the Evolution of Murine Myocarditis" *Clin. Immunol. Immunopathol.* 68:159–169 (1993).

Melnick et al., "Pathogenesis of coxsackie Virus Infection" *J. Expert. Med.* 93: 247–266 (1951).

Ralph et al., "*RNA fingerprinting using arbitrarily primed PCR identifies differentially regulated RNAs in mink lung (My1Lu) cells growth arrested by transforming growth factor β1*" *Proc. Natl. Acad. Sci. USA* 90: 10710–10714 (1993).

Sagerstrom et al., "*Subtractive Cloning: Past, Present, and Future*" *Annu. Rev. Biochem.* 66: 751–783 (1997).

Schena et al., "*Quantitative Monitoring of Gene Expression Patterns with a Complementary DNA Microarray*" *Science* 270:467–470 (1995).

Schunkert et al., "Increased Rat Cardiac Angiotensin Converting Enzyme Activity and mRNA Expression in Pressure Overload Left Ventricular Hypertrophy" *J. Clin. Invest.* 86(6):1913–20 (1990).

Small et al., "Analysis of a Transgenic Mouse Containing Simian Virus 40 and v–myc Sequences" *Mol. Cell Biol* 5:642–48 (1985).

Thompson et al., "Germ Line Transmission an Expression of a Corrected HPRT Gene Produced by gene Targeting in Embryonic Stem Cells" *Cell* 56:313–21 (1989).

Velculescu et al. "*Serial Analysis of Gene Expression*" *Science* 270:484–487 (1995).

Wan et al., "*Cloning differentially expressed mRNAs*" *Nature Biotechnology* 14:1685–1691 (1996).

Wang and Hanson "*Parenteral Formulations of Proteins and Peptides: Stability and Stabilizers*", *Journal of Parenteral Science and Technology*, Technical Report No. 10, Supp. 42–2S (1988).

Watson et al., "*Differential cDNA Screening Strategies to Identify Novel Stage–Specific Proteins in the Developing Mammalian Brian*" *Development Neuroscience* 15:77–86 (1993).

Zhang et al., "*Gene Expression Profiles in Normal and Cancer Cells*" *Science* 276:1268–1272 (1997).

* cited by examiner

FIGURE 1

```
      gcggccgccc ctgacacaat ggctcagctt atgcctcagc gcagttcgct ccaccccaga    60
      atggcatcct gcagaataca cggcccctca tcccatccc  gcgccagaga caccggccag   120
      cccactgtcc ccgccacaca ttaaacttga tcctcctaca cagacgcact cggagcagag   180
      cgcttataca agcgcacagc cgtctccggc accgccacac agacagatga tgccgccccg   240
      accgacggcc agcccagac  acaaccttct gaaaacacag aaaacaagtc ccagcccaag   300
      cggctgcatg tgtccaacat ccccttccgg ttcgggatc  cagacctccg acaaatgttt   360
      ggccaatttg gtaaaatatt agatgttgaa attattttta atgagcgggg ctcgaaggga   420
      tttggtttcg taactttcga aaatagtgcg gatgcggaca gggcgaggga gaaattgcac   480
      ggtaccgtgg tagagggccg taaaatcgag gttaataatg cgacagcacg cgtg atg      537
                                                                     Met
                                                                       1
```

| | | | | | | | | | | | | | | | | |
|---|---|---|---|---|---|---|---|---|---|---|---|---|---|---|---|---|
| act | aat | aaa | aag | gcc | gtg | aac | ccc | tac | acc | aat | ggc | tgg | aaa | tta | aat | 585 |
| Thr | Asn | Lys | Lys | Ala | Val | Asn | Pro | Tyr | Thr | Asn | Gly | Trp | Lys | Leu | Asn | |
| | | | 5 | | | | 10 | | | | | 15 | | | | |

| | | | | | | | | | | | | |
|---|---|---|---|---|---|---|---|---|---|---|---|---|
| cca | gtt | gtg | ggc | gcg | gtc | tac | agc | ccc | gac | ttc | tat | gca | ggc | acg | gtg | 633 |
| Pro | Val | Val | Gly | Ala | Val | Tyr | Ser | Pro | Asp | Phe | Tyr | Ala | Gly | Thr | Val | |
| | | 20 | | | | 25 | | | | 30 | | | | | | |

| ctg | ttg | tgc | cag | gcc | aac | cag | gag | gga | tct | tcc | atg | tac | agt | ggc | ccc | 681 |
|---|---|---|---|---|---|---|---|---|---|---|---|---|---|---|---|---|
| Leu | Leu | Cys | Gln | Ala | Asn | Gln | Glu | Gly | Ser | Ser | Met | Tyr | Ser | Gly | Pro | |
| | 35 | | | | 40 | | | | | 45 | | | | | | |

| agt | tca | ctt | gta | tat | act | tct | gca | atg | cct | ggc | ttt | cca | tat | ccg | gcc | 729 |
|---|---|---|---|---|---|---|---|---|---|---|---|---|---|---|---|---|
| Ser | Ser | Leu | Val | Tyr | Thr | Ser | Ala | Met | Pro | Gly | Phe | Pro | Tyr | Pro | Ala | |
| 50 | | | | | 55 | | | | 60 | | | | | 65 | | |

| gcc | act | gct | gca | gct | gca | tac | cga | ggg | gct | cac | ctt | cga | ggc | cgt | ggt | 777 |
|---|---|---|---|---|---|---|---|---|---|---|---|---|---|---|---|---|
| Ala | Thr | Ala | Ala | Ala | Ala | Tyr | Arg | Gly | Ala | His | Leu | Arg | Gly | Arg | Gly | |
| | | | 70 | | | | 75 | | | | | 80 | | | | |

| cgc | acc | gtg | tac | aac | acc | ttc | aga | gct | gcg | gcg | ccc | cca | ccc | cca | atc | 825 |
|---|---|---|---|---|---|---|---|---|---|---|---|---|---|---|---|---|
| Arg | Thr | Val | Tyr | Asn | Thr | Phe | Arg | Ala | Ala | Ala | Pro | Pro | Pro | Pro | Ile | |
| | | | 85 | | | | | 90 | | | | 95 | | | | |

| ccg | gcc | tat | ggc | gga | gta | gtg | tat | caa | gag | cca | gtg | tat | ggc | aat | aaa | 873 |
|---|---|---|---|---|---|---|---|---|---|---|---|---|---|---|---|---|
| Pro | Ala | Tyr | Gly | Gly | Val | Val | Tyr | Gln | Glu | Pro | Val | Tyr | Gly | Asn | Lys | |
| | | | 100 | | | | 105 | | | | 110 | | | | | |

| ttg | cta | cag | ggt | ggt | tac | gct | gca | tac | cgc | tac | gcc | cag | ccc | acc | cct | 921 |
|---|---|---|---|---|---|---|---|---|---|---|---|---|---|---|---|---|
| Leu | Leu | Gln | Gly | Gly | Tyr | Ala | Ala | Tyr | Arg | Tyr | Ala | Gln | Pro | Thr | Pro | |
| | | 115 | | | | 120 | | | | | 125 | | | | | |

| gcc | act | gct | gct | gcc | tac | agt | gac | agt | tac | gga | cga | gtt | tat | gct | gcc | 969 |
|---|---|---|---|---|---|---|---|---|---|---|---|---|---|---|---|---|
| Ala | Thr | Ala | Ala | Ala | Tyr | Ser | Asp | Ser | Tyr | Gly | Arg | Val | Tyr | Ala | Ala | |
| 130 | | | | 135 | | | | | 140 | | | | | 145 | | |

| gac | ccc | tac | cac | cac | aca | ctt | gct | cca | gcc | ccc | acc | tac | ggc | gtt | ggt | 1017 |
|---|---|---|---|---|---|---|---|---|---|---|---|---|---|---|---|---|
| Asp | Pro | Tyr | His | His | Thr | Leu | Ala | Pro | Ala | Pro | Thr | Tyr | Gly | Val | Gly | |
| | | | 150 | | | | | 155 | | | | 160 | | | | |

| gcc | atg | aat | gct | ttt | gcg | ccc | ttg | acc | gat | gcc | aag | act | agg | agc | cat | 1065 |
|---|---|---|---|---|---|---|---|---|---|---|---|---|---|---|---|---|

FIGURE 1 (cont.)

```
      Ala Met Asn Ala Phe Ala Pro Leu Thr Asp Ala Lys Thr Arg Ser His
                      165                 170                 175 gct gat gat gtg ggt ctc gtt ctt tct tca ttg cag gct agt ata tac    1113
      Ala Asp Asp Val Gly Leu Val Leu Ser Ser Leu Gln Ala Ser Ile Tyr
              180                 185                 190 caa ggg gga tac aac cgt ttt gct cca tat taaatgataa aaccattaaa      1163
      Gln Gly Gly Tyr Asn Arg Phe Ala Pro Tyr
          195                 200 caaacaagca aaaacaaaa caaaaacaaa aaaaccaacc ttccaatgtg gggagagagg   1223
      aagctttccg aggcccgagt gttgcgacac atgcagtagg acatcacttt agcaactcaa  1283
      agaaacaacg aaaaaaaaaa aaaaaaaaaa aataagcggc cgaaggggtt cgctaga     1340
```

FIGURE 2

```
tctagcgaac cccttcgcga aggggttcgc ctgtgctggt gggcgcggtg gcccgaagcc      60
ttggactcac tgcaggactg tgcagggaac cactgtccaa gcatcgggct aatagggggc     120
gcctgcctcg gtttacccct cagcgtctgg tgaaatcccg cagcgtctag ggaaagatcc     180
gttctgctcc gcgagggaaa cagagccgtt gac atg gtt gca acg ggc agt ttg     235
                                  Met Val Ala Thr Gly Ser Leu
                                   1               5 agc agt aag aac acg gcc agc att tca gag ttg ctg gac ggt ggc tct     283
Ser Ser Lys Asn Thr Ala Ser Ile Ser Glu Leu Leu Asp Gly Gly Ser
         10              15                  20 cac cct ggg agt ctg cta agt gat ttc gac tac tgg gat tat gtc gtc     331
His Pro Gly Ser Leu Leu Ser Asp Phe Asp Tyr Trp Asp Tyr Val Val
     25                  30                  35 cct gag ccc aac ctc aac gag gtg gtg ttt gaa gag aca aca tgc cag     379
Pro Glu Pro Asn Leu Asn Glu Val Val Phe Glu Glu Thr Thr Cys Gln
 40                  45                  50                  55 aat ttg gtt aaa atg ttg gag aac tgt ctg tcc aag tca aag caa acc     427
Asn Leu Val Lys Met Leu Glu Asn Cys Leu Ser Lys Ser Lys Gln Thr
                 60                  65                  70 aaa ctc ggt tgc tct aag gtc ctg gtt cct gag aaa ctg acc cag aga     475
Lys Leu Gly Cys Ser Lys Val Leu Val Pro Glu Lys Leu Thr Gln Arg
             75                  80                  85 att gcc caa gat gtc ctg cgg ctc tca tcc aca gag ccc tgc ggc ctt     523
Ile Ala Gln Asp Val Leu Arg Leu Ser Ser Thr Glu Pro Cys Gly Leu
         90                  95                 100 cgg ggc tgt gtt atg cac gtg aac ttg gaa att gaa aat gtg tgt aaa     571
Arg Gly Cys Val Met His Val Asn Leu Glu Ile Glu Asn Val Cys Lys
 105                 110                 115 aag ctg gat agg att gtg tgt gat gct agt gtg gtg ccg acc ttt gag     619
Lys Leu Asp Arg Ile Val Cys Asp Ala Ser Val Val Pro Thr Phe Glu
 120                 125                 130                 135 ctc acg ctg gtg ttc aag cag gag agc tgc tcc tgg acc agc ctc aag     667
Leu Thr Leu Val Phe Lys Gln Glu Ser Cys Ser Trp Thr Ser Leu Lys
                 140                 145                 150 gac ttc ttc ttt agc gga ggt cgc ttc tcg tcg ggc ctt aag cga act     715
Asp Phe Phe Phe Ser Gly Gly Arg Phe Ser Ser Gly Leu Lys Arg Thr
             155                 160                 165 ctg atc ctc agc tcg gga ttt cga ctt gtt aag aaa aaa ctg tac tct     763
Leu Ile Leu Ser Ser Gly Phe Arg Leu Val Lys Lys Lys Leu Tyr Ser
         170                 175                 180 ctg att gga acg aca gtc att gag gag tgc tga ggaggaaaaa acaattaaag   816
Leu Ile Gly Thr Thr Val Ile Glu Glu Cys  *
```

```
                185              190
FIGURE 2 (cont.)
5.  gtccctaatg agtggctaac aaaaanaaaa nnnnnnnnnn nnnnngcggn c         867
```

FIGURE 3

```
    tctagcgaac ccct tcggtg gacagaacag cctgagtcag g atg aaa gct ctc agg              56
                                                    Met Lys Ala Leu Arg
                                                     1                 5 gct gtc ctc ctg atc ttg cta ctc agt gga cag cca ggg agc agc tgg               104
    Ala Val Leu Leu Ile Leu Leu Leu Ser Gly Gln Pro Gly Ser Ser Trp
                     10                  15                  20 gca caa gaa gct ggc gat gtg gac ctg gag cta gag cgc tac agc tac               152
    Ala Gln Glu Ala Gly Asp Val Asp Leu Glu Leu Glu Arg Tyr Ser Tyr
                     25                  30                  35 gat gat gac ggt gat gac gat gat gac gat gat gaa gaa gag gaa gag               200
    Asp Asp Asp Gly Asp Asp Asp Asp Asp Asp Asp Glu Glu Glu Glu Glu
                 40                  45                  50 gag gag acc aac atg atc cct ggc agc agg gac aga gca ccg cct cta               248
    Glu Glu Thr Asn Met Ile Pro Gly Ser Arg Asp Arg Ala Pro Pro Leu
             55                  60                  65 cag tgc tac ttc tgc caa gtg ctt cac agc ggg gag agc tgc aac gag               296
    Gln Cys Tyr Phe Cys Gln Val Leu His Ser Gly Glu Ser Cys Asn Glu
     70                  75                  80                  85 aca cag aga tgc tcc agc agc aag ccc ttc tgt atc aca gtc atc tcc               344
    Thr Gln Arg Cys Ser Ser Ser Lys Pro Phe Cys Ile Thr Val Ile Ser
                     90                  95                 100 cat ggc aaa act gac aca ggt gtc ctg acg acc tac tcc atg tgg tgt               392
    His Gly Lys Thr Asp Thr Gly Val Leu Thr Thr Tyr Ser Met Trp Cys
                    105                 110                 115 act gat acc tgc cag ccc atc gtg aag aca gtg gac agc acc caa atg               440
    Thr Asp Thr Cys Gln Pro Ile Val Lys Thr Val Asp Ser Thr Gln Met
                120                 125                 130 acc cag acc tgt tgc cag tcc aca ctc tgc aat att cca ccc tgg cag               488
    Thr Gln Thr Cys Cys Gln Ser Thr Leu Cys Asn Ile Pro Pro Trp Gln
            135                 140                 145 agc ccc caa atc cac aac cct ctg ggt ggc cgg gca gac agc ccc ttg               536
    Ser Pro Gln Ile His Asn Pro Leu Gly Gly Arg Ala Asp Ser Pro Leu
    150                 155                 160                 165 aag ggt ggg acc aga cat cct caa ggt gac agg ttt agc cac ccc cag               584
    Lys Gly Gly Thr Arg His Pro Gln Gly Asp Arg Phe Ser His Pro Gln
                    170                 175                 180 gtt gtc aag gtt act cat cct cag agt gat ggg gct cac ttg tct aag               632
    Val Val Lys Val Thr His Pro Gln Ser Asp Gly Ala His Leu Ser Lys
                185                 190                 195 ggt ggc aag gct aac cag ccc cag gga aat ggg gcc gga ttc cct gca               680
```

FIGURE 3 (cont.)

Gly Gly Lys Ala Asn Gln Pro Gln Gly Asn Gly Ala Gly Phe Pro Ala
        200                 205                 210 ggc tgg agc aaa ttt ggt aac gta gtt ctc ctg ctc acc ttc ctc acc    728
Gly Trp Ser Lys Phe Gly Asn Val Val Leu Leu Leu Thr Phe Leu Thr
    215                 220                 225 agt ctg tgg gca tca ggg gcc taa agactcgtcc tcccccaacc aggacccttc   782
Ser Leu Trp Ala Ser Gly Ala
230                 235 agcctttcct ccctgacaac cagcttcaga gaataaactt gaatgtcttt tgccatctaa   842
aaaaaaaaaa aaaaaaaaaa aaagcggccg cc                                874

FIGURE 4

```
tctagcgaac  cccttcgagc  gaaccccttc  ggccagtacc  ctgagccctg  gtccctcctg        60
gagctgcccc  acagctctga  ctgtggactg  agggatgtta  ggcggatcac  ctgagcctcc       120
agaggctcac  acta atg agc ggg cgc tct ctt ctt agc cac tgt tgc att            170
             Met Ser Gly Arg Ser Leu Leu Ser His Cys Cys Ile
              1           5                       10 tgg ttt tca ttg act cct ggg cct cgt ttg agt gac act gtc ctt gtc             218
Trp Phe Ser Leu Thr Pro Gly Pro Arg Leu Ser Asp Thr Val Leu Val
         15              20                  25 ttt tgt ttc aga gct ctc cca gtg tta gtg gac tca gat gag gaa att             266
Phe Cys Phe Arg Ala Leu Pro Val Leu Val Asp Ser Asp Glu Glu Ile
     30              35              40 atg acc aga tct gaa ata gct gaa aaa atg ttc tct tca gaa aag ata             314
Met Thr Arg Ser Glu Ile Ala Glu Lys Met Phe Ser Ser Glu Lys Ile
 45              50              55              60 atg tga tcagggcccc agtgggtcca gtgtgcatgg gagcgcggtc aggtgatggg              370
Met * aaaggcctgg ctctcgtcaa aactgacagc tgcgctatga tacatgtctc actttgttgt          430
cttggagatc tgtgtatgca ggtgaagaac tcaagtgtgg gagggtctgc cgcctcagaa          490
agccatcttt gaaacggact cataaagtca gttttgttgc cattaagttg cctgattttg          550
gaaacaattt aagaagtgtt aaagacatgt gttcagatgc ctcttaggcg gcagccacag          610
gcatgccagg ttgtgtccct cagttttctc cagacaaaag aatctgcagc tgggcgtggc          670
ggcacactac tgcagttgaa agtctgtaa tttcaaggcc aagcctggtc tacatagttc           730
caggacaacc agagagatct acatagtgag accctgcctc aaaacacaga accnnanna           790
naaaaaaaaa aaaaaaaaag cggccgc                                              817
```

FIGURE 5

```
tctagcgaac cccttcgcac atgggttcct gctgaccaag gggacatggc tctgaagatg      60
atgaggctgg ttactcagca ggagtagctg agctgagctg gccctggagg ccctggaggc     120
cctggagtag ggcccagg atg cag gtg cta atg tct atc ccc ggc gct ctt      171
                    Met Gln Val Leu Met Ser Ile Pro Gly Ala Leu
                     1               5                   10 ctt ccc gac tct acc atg gga tgt aac tcc agg agc ccc tgc cat ctc      219
Leu Pro Asp Ser Thr Met Gly Cys Asn Ser Arg Ser Pro Cys His Leu
             15                  20                  25 ccg tac caa aag act gtg gct tcc gtg tct act cag aaa tca gtt cta      267
Pro Tyr Gln Lys Thr Val Ala Ser Val Ser Thr Gln Lys Ser Val Leu
            30                  35                  40 ctt cgt aaa cag tgt tta aaa cca gac tca ttt aat cag agt gaa gga      315
Leu Arg Lys Gln Cys Leu Lys Pro Asp Ser Phe Asn Gln Ser Glu Gly
            45                  50                  55 ttg cag tcc att ggc ttc tta gca cag aag cag ctg ata aca caa gta      363
Leu Gln Ser Ile Gly Phe Leu Ala Gln Lys Gln Leu Ile Thr Gln Val
 60                  65                  70                  75 aac ccc agc cct tga gaggtagaag caagaggatc agaggttcaa gcgcatcctc      418
Asn Pro Ser Pro * ggctccatca caagttcaaa agccgcctgc accaaatggg agtccttgtc tcaaaaaaaa     478
aaaaaaaaaa agcaaagaaa gcaaaggact cgatgacatg atttatagac aaaagcagtg     538
ggagaaaata ctaaagcccc actgagctgc cagccaggtg tctgtgacta caggtctttt     598
atctgctcat atatattttt acaaaaaatg aaattcatat tggtcgctat tttgctggct     658
gctttgctcc cgatcaacat gatttgcacg tttttccat caataaatgt gccatgatat     718
ttttaaaaaa aaaaaaaaaa aaaaaaaaaa gggcncc                             755
```

FIGURE 6

```
tctagcgaac cccttcgcag ctctctgacc tgcgtcgccg ccgctctccg ctcttgattt      60
cgccgtg atg tcg acc gca atg aac ttc ggg acc aaa agc ttc cag ccg      109
        Met Ser Thr Ala Met Asn Phe Gly Thr Lys Ser Phe Gln Pro
          1           5                  10 cgg ccc cca gac aaa ggc agc ttc ccg cta gac cac ttc ggt gag tgt      157
Arg Pro Pro Asp Lys Gly Ser Phe Pro Leu Asp His Phe Gly Glu Cys
 15              20                  25                      30 aaa agc ttt aag gaa aaa ttc atg aag tgt ctc cgc gac aag aac tat      205
Lys Ser Phe Lys Glu Lys Phe Met Lys Cys Leu Arg Asp Lys Asn Tyr
                 35                  40                  45 gaa aat gct ctg tgc aga aat gaa tct aaa gag tat tta atg tgc agg      253
Glu Asn Ala Leu Cys Arg Asn Glu Ser Lys Glu Tyr Leu Met Cys Arg
             50                  55                  60 atg caa agg cag ctg atg gca cca gaa cca cta gag aaa ctc ggc ttt      301
Met Gln Arg Gln Leu Met Ala Pro Glu Pro Leu Glu Lys Leu Gly Phe
         65                  70                  75 aga gac ata atg gag gag aaa ccg gag gca aag gac aaa tgt tga          346
Arg Asp Ile Met Glu Glu Lys Pro Glu Ala Lys Asp Lys Cys  *
     80                  85                  90 gaatcactgg gctgtgtccc cctacctgga gcagagctga gcccttctgc ccaccgtgga     406
gagagctgag ccatcctgtg ctgcccagag gagggctct ccgtgtcgac tttggctcat     466
ccctgcagca cagaccaaac tgctttctct actgaccaca cttctgcttc agagagnggt     526
ttctcctgtc tgngtgtggc acaggatctg ctcanggctg aacactgatg tgatatgata     586
tcccacctag tgtggccgca caccaaaagg cctggacagg atttcacagt gactcaacct     646
gagtcctcac acccggaacc tgtcagcgaa aaccaancga agcaaaatgn ctggcttttg     706
gcttacaaac cccatnattt gntttccctt ctcttgggtc tttgttttga caaanctggc     766
atacaaagtn ggaaggggga aataaaaaaa aaaaaaaaaa                           806
```

FIGURE 7

```
tctagcgaac cccttcncga aggggttcgc cgagaggtgg gagccaaaag gatggagcat    60
ccgccggtgg tggctggtgg ccgcaatctt ggtggtcctg atcggggttg tcttagtctg   120
cctgatagtc tacttcgcca acgcagcgca cagcgaggcc tgtaagaacg ggttgcggtt   180
gcaggatgag tgccgaaaca ccacgcacct gttgaagcac cagctnaccc gcgcccagga   240
cagcctgctg cagacggag atg cag gca aac tcc tgc aac cag acc gtg atg    292
              Met Gln Ala Asn Ser Cys Asn Gln Thr Val Met
              1               5                      10 gac ctt cgg gat tcc ctg aag aag aag gtg tct naa acc cag gag caa     340
Asp Leu Arg Asp Ser Leu Lys Lys Lys Val Ser Xaa Thr Gln Glu Gln
            15                  20                  25 can gcc cgc atc aag gaa ctt gag aat aag atc gag agg ctg aac caa     388
Xaa Ala Arg Ile Lys Glu Leu Glu Asn Lys Ile Glu Arg Leu Asn Gln
        30                  35                  40 gag ctg gag aaa ttt gag gac cca aaa gga aat ttc tac cac agt gca     436
Glu Leu Glu Lys Phe Glu Asp Pro Lys Gly Asn Phe Tyr His Ser Ala
        45                  50                  55 ngt gaa ctc aag cgg gtt cgt ggt ggn ctt can cct act tgt gct ttg     484
Xaa Glu Leu Lys Arg Val Arg Gly Gly Leu Xaa Pro Thr Cys Ala Leu
        60                  65                  70                  75 tgg cgg gac tgt tct nca ctt ttt ang acc caa taa ttgggangta          530
Trp Arg Asp Cys Ser Xaa Leu Phe Xaa Thr Gln  *
        80                  85 caaacctgtg taggcattgn nggtngtaat ggcttttgag ggggtcctgg caccc
ttaag   590
atgtgaaanac cattangnng gacccaaaat gnnttttctt gntttgaact ggggcggacc   650
cggagtgggg ggcnggaaat aanntattnn ggnnggaaan aaaaaaaaaa aaaaaaaaaa   710
gcggccc                                                             717
```

FIGURE 8

```
tctagcgaac cccttcgccc agctgctaga agccaggctg gcctggtgag gc atg agc         58
                                                         Met Ser
                                                          1 atg aag atg aac cca ggt gac aag gac aag atg ttg ctc ttc tcc cca          106
Met Lys Met Asn Pro Gly Asp Lys Asp Lys Met Leu Leu Phe Ser Pro
         5                  10                  15 ccc ttt gac ccc tgt ctt cta agg cat cta gga agg aac cag tgt cct          154
Pro Phe Asp Pro Cys Leu Leu Arg His Leu Gly Arg Asn Gln Cys Pro
        20                  25                  30 tgg tac tga tttacttaga ttcaacctaa gggtccagcc actgactaag                  203
Trp Tyr *
 35 gccaaggcca ttttccata cctgggaggg tagagattca gggttgtggg taagtgggca         263
ctaaacatgg atttgcaagg gaaaacgaca gggcatcgag ctaaatttga atttacatga       323
aattctgaaa tgtacttgta tgaagaaact gttatctgaa acctaactta aatgggcatc       383
ctgccttttg tctggtgaga aatgaaagtg atctacaata agtgtcaaag caacaaggcc       443
cctctggata tgtctaggcc aggatgagga tactaagtgc cttcaaagcg agagggaggc       503
aggccaagaa cactgcccta ctgaaaggca ggcttggccg gctagggcct ccaaggccct       563
gatccctgag gcaccacagc cacaacttgt gtaggcctgg cccaggtcag tgaataggtt       623
ctaggcagtg gttctcaacc ttcctaatgc tgcaacccct caatacagtt tctcctgttg       683
tagtaatccc caaccataaa attattttca ttgcgacttc ataactggac ttttgctact       743
gttatgaatc ataatgtaaa tattttttgg agctagaggt ttaccaaggg ggttgtgagc       803
cataggttga aaaccattgt tctaggaata gctccagggg tggtttctga ggcccccgca       863
aggtgggatc tatggggcag ggttggatct tctccaagag cccccaacag gatatatata       923
tatatatata tatatatata tatatatata tactttgata gcatcccatg                   983
gaacgactgt ctcctgatac taaagggagc ttggaagaaa ccaaggctga gagaagttgt      1043
agagtgggaa ggtaggcgaa gggattgagg tgacacagtg atagccccttt caggggtgggg   1103
tctacccnag acagcagata aaggccttag gatgggagat tactctggct gctcagaggg      1163
gaacacaggg acacagcacc aataaaatct ctttcttttc aaaaaaaaaa aaaaaaaaaa      1223
aaaaagcggn cc                                                          1235
```

FIGURE 9

```
tctagcgaac ccttcgatt ttattagctc ttgcttctcc attcctcata atttatgaat      60
tatacagcct tcgcttgaat acgcgtctga agttatgctt tgtgttgttg tgggtttttt    120
ttttttttc ttttctttt ttttggagct ggggaccgaa cccagggcct tgttgctcta     180
ccactgagct aaatccccaa cccctgttgt gtgttttaaa taagtctctt actgtccatt    240
ttgtaattag tgttgttacc ttgtaataat agacatcata caaagtttcc tcttttttgt    300
gccagtgctg agaacatgag aaacatttaa tgagtatttg tttgttaaat aatatttata    360
acggctagaa tggcagacac ac atg gta gca cat gat ggt gat ttt cgg ggg     412
                          Met Val Ala His Asp Gly Asp Phe Arg Gly
                           1               5                    10 cct ttt gtt tgc tca gag ctg gta atc tct gcc ggt tgg ttt gct ttg   460
          Pro Phe Val Cys Ser Glu Leu Val Ile Ser Ala Gly Trp Phe Ala Leu
                           15                  20                  25 cct ggt ctg gga cta acc tca cat ttt ctc act ctt gct ttc cga gag   508
          Pro Gly Leu Gly Leu Thr Ser His Phe Leu Thr Leu Ala Phe Arg Glu
                       30                  35                  40 att agt cat cct tcc tgt cct act ggg ctc tcg ata gcg ctc atc agc   556
          Ile Ser His Pro Ser Cys Pro Thr Gly Leu Ser Ile Ala Leu Ile Ser
                   45                  50                  55 ata ctg cat ttc aat ccc agc gaa ggg gtt cgc cga agg ggt tcg cta   604
          Ile Leu His Phe Asn Pro Ser Glu Gly Val Arg Arg Arg Gly Ser Leu
               60                  65                  70 ggc cag tgt gat gga tat ctg cag aat tc                           633
          Gly Gln Cys Asp Gly Tyr Leu Gln Asn
           75                  80
```

FIGURE 10

```
tctagcgaac cccttcgcct ttctccaaag ccttcccgtt tcctcttgac agctacgggc    60
tgaggcagcc attcctgcag cagcgctcgg ccggtgaagg gccgaactga cgcctcctag   120
atctgtctcg gctgaattac tctcacccgt ttccattctg tgtgcaccag aaatctgaga   180
tccaggagta tcaacagcaa ag atg tct aat gag cca ccc cct cct tat cca    232
                         Met Ser Asn Glu Pro Pro Pro Pro Tyr Pro
                           1           5                        10 gga ggg cct aca gcc cca cta ctg gag gaa aaa agt gga gcc cca cat    280
Gly Gly Pro Thr Ala Pro Leu Leu Glu Glu Lys Ser Gly Ala Pro His
              15                  20                  25 acc cca ggc cga acc ttt cca gct gtg atg cag cca cca ggc atg        328
Thr Pro Gly Arg Thr Phe Pro Ala Val Met Gln Pro Pro Gly Met
            30                  35                  40 cca ctg ccc tct gtt gac att gcc ccc ccg ccc tat gag ccg cct ggc    376
Pro Leu Pro Ser Val Asp Ile Ala Pro Pro Pro Tyr Glu Pro Pro Gly
            45                  50                  55 cat cca ggg cct aag cct ggt ttw atg ccc ccc acn tta cca cac att    424
His Pro Gly Pro Lys Pro Gly Xaa Met Pro Pro Thr Leu Pro His Ile
        60                  65                  70 cna ana acc ttn ntn tgt aaa agt taa ataanaangg agggattcga           471
Xaa Xaa Thr Xaa Xaa Cys Lys Ser  *
75                  80 ncccctnca acnggtttca agccaattty mtaaccattt tgttttttc wtttaaaaaa    531
aaaaaaaaaa aaaaaaaaaa aaaaaaaaaa aaaaaaaag gggaaaaaaa aaaaaaaaaa   591
aaaaaagggg ggcccc                                                  607
```

FIGURE 11

```
tctagcgaac cccttcgcaa agtcctaagc cttac atg aga aaa ttt aag aca              53
                                      Met Arg Lys Phe Lys Thr
                                       1               5 ccc tta atg att gcg gaa gaa aaa tac aga caa caa agg gaa gag ctt            101
Pro Leu Met Ile Ala Glu Glu Lys Tyr Arg Gln Gln Arg Glu Glu Leu
            10                  15                  20 gag aaa cag aga cgg gag agt tct tgc cat agc atc atc aaa aca gaa            149
Glu Lys Gln Arg Arg Glu Ser Ser Cys His Ser Ile Ile Lys Thr Glu
        25                  30                  35 acc cag cac cgc agc tta tca gag aaa gag aaa gaa aca gag tta caa            197
Thr Gln His Arg Ser Leu Ser Glu Lys Glu Lys Glu Thr Glu Leu Gln
    40                  45                  50 aaa gca gct gag gca atg tcc act ccc aga aag gat tca gac ttc act            245
Lys Ala Ala Glu Ala Met Ser Thr Pro Arg Lys Asp Ser Asp Phe Thr
55                  60                  65                  70 agg gca cag ccc aac ctg gaa cct aaa agc aag gct gtg atc gcc agt            293
Arg Ala Gln Pro Asn Leu Glu Pro Lys Ser Lys Ala Val Ile Ala Ser
                75                  80                  85 gaa tgc tct gaa agc cag ctc tct aca gct tcc gca ttg aca gtc gct            341
Glu Cys Ser Glu Ser Gln Leu Ser Thr Ala Ser Ala Leu Thr Val Ala
            90                  95                 100 acc gag agg ctc cag cat gtt cta gcc gct tca gac gat aag ctt acc            389
Thr Glu Arg Leu Gln His Val Leu Ala Ala Ser Asp Asp Lys Leu Thr
        105                 110                 115 ctg cga cgg gaa ggc aca cag aac tca agt gac acc cta caa tcg aaa            437
Leu Arg Arg Glu Gly Thr Gln Asn Ser Ser Asp Thr Leu Gln Ser Lys
    120                 125                 130 aca gct tgt gag att aac cag agt cac aag gaa tgt agg aca gag caa            485
Thr Ala Cys Glu Ile Asn Gln Ser His Lys Glu Cys Arg Thr Glu Gln
135                 140                 145                 150 aca ttt gag caa cac gtg gag aag ttg ccc ttc ccc caa acc aaa ccc            533
Thr Phe Glu Gln His Val Glu Lys Leu Pro Phe Pro Gln Thr Lys Pro
                155                 160                 165 att tcc ccg agt ttc aaa gtg aaa act atc agg ctt cca gct cta gat            581
Ile Ser Pro Ser Phe Lys Val Lys Thr Ile Arg Leu Pro Ala Leu Asp
            170                 175                 180 cat acg ctg act gaa aca gat ctc agt tct gaa cgc cgc gta aag caa            629
His Thr Leu Thr Glu Thr Asp Leu Ser Ser Glu Arg Arg Val Lys Gln
        185                 190                 195 tcc gaa att gac gtt caa acc agt act aaa gaa atg aat aag gaa att            677
```

```
Ser Glu Ile Asp Val Gln Thr Ser Thr Lys Glu Met Asn Lys Glu Ile
    200             205                 210
FIGURE 11 (cont.)

aag aaa acc gaa gtg agc aca cag tgt gat aat aag caa tct gtg gct    725
Lys Lys Thr Glu Val Ser Thr Gln Cys Asp Asn Lys Gln Ser Val Ala
215             220                 225                 230 gaa aaa tat ttt caa tta cct aaa aca gag aaa cgg gtg acg gta caa    773
Glu Lys Tyr Phe Gln Leu Pro Lys Thr Glu Lys Arg Val Thr Val Gln
                235                 240                 245 atg ccc aaa gac tat gca gcg aaa agt cat caa agc aaa ctc caa aca    821
Met Pro Lys Asp Tyr Ala Ala Lys Ser His Gln Ser Lys Leu Gln Thr
            250                 255                 260 gtt ccc aag aag cat gga gga ttg ggg gag ttt gac aga ggg aat gtc    869
Val Pro Lys Lys His Gly Gly Leu Gly Glu Phe Asp Arg Gly Asn Val
            265                 270                 275 ctg ggg agg gaa gga aaa aat cag gac tcc tcc atg agc agt aca aaa    917
Leu Gly Arg Glu Gly Lys Asn Gln Asp Ser Ser Met Ser Ser Thr Lys
280                 285                 290 gaa agc agg gta ata gtt gaa aga aag caa gaa cat cta cag gac cag    965
Glu Ser Arg Val Ile Val Glu Arg Lys Gln Glu His Leu Gln Asp Gln
295                 300                 305                 310 agc gta cca agg tta gtc caa caa aag att atc ggt gaa agc ctg gac    1013
Ser Val Pro Arg Leu Val Gln Gln Lys Ile Ile Gly Glu Ser Leu Asp
                315                 320                 325 tca cgg gtt cag aat ttt cag cag aca caa aca caa act tct agg att    1061
Ser Arg Val Gln Asn Phe Gln Gln Thr Gln Thr Gln Thr Ser Arg Ile
            330                 335                 340 gag cat aaa gaa ctg tcc caa cct tac agt gag aaa aaa tgt ctt aga    1109
Glu His Lys Glu Leu Ser Gln Pro Tyr Ser Glu Lys Lys Cys Leu Arg
            345                 350                 355 gac aag gac aaa caa caa aaa cag gtc tcc tct aac act gac gat tca    1157
Asp Lys Asp Lys Gln Gln Lys Gln Val Ser Ser Asn Thr Asp Asp Ser
360                 365                 370 aag caa gag ata aca caa aaa caa tct tca ttt tcc tct gtg aga gaa    1205
Lys Gln Glu Ile Thr Gln Lys Gln Ser Ser Phe Ser Ser Val Arg Glu
375                 380                 385                 390 tcc cag cag gat gga gaa aaa tgt gcc ata aaa ata ttg gaa ttc ttg    1253
Ser Gln Gln Asp Gly Glu Lys Cys Ala Ile Lys Ile Leu Glu Phe Leu
                395                 400                 405 aga aaa cgt gaa gaa cta cag cag att ttg tct agg gta aaa cag ttt    1301
Arg Lys Arg Glu Glu Leu Gln Gln Ile Leu Ser Arg Val Lys Gln Phe
            410                 415                 420 gaa gca gat tca aat aaa agt ggc ctt aaa aca ttt cag aca ctg tta    1349
```

```
      Glu Ala Asp Ser Asn Lys Ser Gly Leu Lys Thr Phe Gln Thr Leu Leu
              425                 430                 435
      FIGURE 11 (cont.)

aat att gct ccg gtg tgg ctg ata agt gag gag aaa aga gaa tat gga       1397
      Asn Ile Ala Pro Val Trp Leu Ile Ser Glu Glu Lys Arg Glu Tyr Gly
              440                 445                 450 gtt cgt gtt gcc atg gag aat aat tag aaaaaataaa aaaaaaaaaa             1444
      Val Arg Val Ala Met Glu Asn Asn  *
      455                 460 aaaagcggcg nc                                                         1456
```

FIGURE 12

```
gaattgtaat acgactcact atagggcgaa ttgggcccct agcgaacccc ttcgacaaca   60
tcaaagagga cagatctaac cctagactga ggccggaggc ctggaccaat tacctgaggg  120
atgtccacag agcctttgca ctgctgaaca gtcaccctga tccaaaccaa gtaaatggga  180
ctccaactgc accaagcagt ggcctcccag tcacctctgc tgagctcttg gtgccggcag  240
ag atg gct tct gca gag tca ggt gaa gac cca agt cat gtg gtt ggg    287
   Met Ala Ser Ala Glu Ser Gly Glu Asp Pro Ser His Val Val Gly
   1               5                  10                 15 gaa acg cct cct ttg acc ttg cca gcc aac ctc caa acc ctg cat ccg   335
Glu Thr Pro Pro Leu Thr Leu Pro Ala Asn Leu Gln Thr Leu His Pro
            20                  25                  30 aac aga cca acg ttg agt cca gag aga aaa ctt gaa tgg aat aac gac   383
Asn Arg Pro Thr Leu Ser Pro Glu Arg Lys Leu Glu Trp Asn Asn Asp
                35                  40                  45 att cca gaa gtg aat cgt ttg aat tct gaa cac tgg aga aaa act gag   431
Ile Pro Glu Val Asn Arg Leu Asn Ser Glu His Trp Arg Lys Thr Glu
        50                  55                  60 gag cag cca gga cgg ggg gag gtg ctt ctc ccc gaa ggt gac gtc agt   479
Glu Gln Pro Gly Arg Gly Glu Val Leu Leu Pro Glu Gly Asp Val Ser
    65                  70                  75 ggc aac ggt atg aca gag ctg ttg ccc atc ggt cgg cac caa caa aag   527
Gly Asn Gly Met Thr Glu Leu Leu Pro Ile Gly Arg His Gln Gln Lys
80                  85                  90                  95 cgt ccc cac gat gcg ggg cca gag gac cat gct ttt gaa gat caa ttg   575
Arg Pro His Asp Ala Gly Pro Glu Asp His Ala Phe Glu Asp Gln Leu
                100                 105                 110 cat cct ctc gtc cac tct gac aga act ccc gtt cat cgg gtg ttc gat   623
His Pro Leu Val His Ser Asp Arg Thr Pro Val His Arg Val Phe Asp
            115                 120                 125 gtg tcc cac ttg gag cag cct gtt cac tcc agc cac gtg gaa gga atg   671
Val Ser His Leu Glu Gln Pro Val His Ser Ser His Val Glu Gly Met
        130                 135                 140 ttg gcc aag atg gag ggg atg gca caa agg agt ggg cac caa gtc tcg   719
Leu Ala Lys Met Glu Gly Met Ala Gln Arg Ser Gly His Gln Val Ser
    145                 150                 155 aag gca gcg cct cct ctc cag tca ctt ctt gct tag attacatgtt        765
Lys Ala Ala Pro Pro Leu Gln Ser Leu Leu Ala  *
160                 165                 170 gcctaacaat gtttctttcc atgttttgat tagtaaacta actcgtggtg gcaatcatga  825
ctcccaacct tctgagctcc cccgggtacg cttgcaccgt agacgctcat gtgcgcaccg  885
tgcgggtgat gctcacacac agactcattg taattcaccg ttttaccgag aagggggggg  945
gggcgaattt tctgtgttga tgctttgttt ttggtactaa acagnatta tcttttgaat  1005
attgtaggga catgagtata taaagtctat ccagtcaaaa tggctagaat tgngcctttg  1065
```

```
taagttttaa aaacttgatg cccacatgag tctgtgagca catntttccc gcctgcctaa   1125
cggagttgga atttgtttct aaccactgta attcttcaac atcatcacct ttggttcagt   1185
```
FIGURE 12 (cont.)

```
gattttgcac tttgagtttg gatactgtgt ctgcttggtt ggtagtgtta gtattttct    1245
tttaaacagg cttatcagag ttgcacactt tgtcctaggc agggcaaagg aatagacgcc   1305
cagcaaggac acacagtata ggtaacatac tgcttatcgt acgcttttcc cacaaagcat   1365
tgcatgtgtt tttacctcga cgtgctaaag ttgattagca gaaaggcatg actcacaatt   1425
ttggtggtaa aaataaacc ctgagggagc aagcaataac taaaacaaga ttgagctgct    1485
ctctctgtgc ttactaaata gatgctcgcc ctgctaatgc ttgccctctt gaaagaagaa   1545
acaggatgca cactgcttta tttcaatctt cctctttttt tcttggtttc accagtgagc   1605
gtaagcattg gaaaaatatg tgtagtctta tctttctata agacgatttt aataaactaa   1665
aatcacaaat gctgtaaagt ttgtgcgcac cagaatggag gctaacttca taaacattgt   1725
gctgtgcgaa tattcctaaa atgatcccca agctgtggtt ttctagaaga catagttcag   1785
aaccgctttt gaaaaatctg tcctcgtgag ctcactcagt ttctgtcgga cttttagaga   1845
cagtggaagg attacctcat tgagacgttt ccgtgtcctc ttcaactcca cagggtcttg   1905
acggtggctt tgttttcct tctagactat tcaaacatgt agataagtta tattttctt    1965
taagtgttta aagtaaacac ttttcaaaaa aaaaaaaaa aaaaaaaaa gcggccgc       2023
```

FIGURE 13

```
tctagcgaac cccttcgggg gttttcatc atg gag ctg tcg cgg cgg att tgt         53
                                Met Glu Leu Ser Arg Arg Ile Cys
                                    -25                 -20 ctc gtc cga ctg tgg ctg ttg cta ctg tca ttc tta ctg ggc ttc agc        101
Leu Val Arg Leu Trp Leu Leu Leu Leu Ser Phe Leu Leu Gly Phe Ser
        -15                 -10                  -5 gcg gga tct gcc ctc aac tgg cgg gaa caa gaa ggc aag gaa gta tgg        149
Ala Gly Ser Ala Leu Asn Trp Arg Glu Gln Glu Gly Lys Glu Val Trp
     1              5                  10 gat tac gtg act gtt cga gag gat gca cgc atg ttc tgg tgg ctc tac        197
Asp Tyr Val Thr Val Arg Glu Asp Ala Arg Met Phe Trp Trp Leu Tyr
 15                  20                  25                  30 tat gcc acc aac cct tgc aag aac ttc tca gag ctg cct ctg gtc atg        245
Tyr Ala Thr Asn Pro Cys Lys Asn Phe Ser Glu Leu Pro Leu Val Met
                 35                  40                  45 tgg ctt cag ggt ggt cca ggt ggt tct agc act gga ttt gga aac ttt        293
Trp Leu Gln Gly Gly Pro Gly Gly Ser Ser Thr Gly Phe Gly Asn Phe
             50                  55                  60 gag gaa atc ggc cct ctt gac acc cga ctc aag cca cgg aac act acc        341
Glu Glu Ile Gly Pro Leu Asp Thr Arg Leu Lys Pro Arg Asn Thr Thr
             65                  70                  75 tgg ctg cag tgg gcc agt ctc ctg ttc gtg gac aat cct gtg ggc acg        389
Trp Leu Gln Trp Ala Ser Leu Leu Phe Val Asp Asn Pro Val Gly Thr
         80                  85                  90 ggc ttc agt tac gtg aac acg aca gat gcc tac gca aag gac ctg gac        437
Gly Phe Ser Tyr Val Asn Thr Thr Asp Ala Tyr Ala Lys Asp Leu Asp
 95                 100                 105                 110 acg gtg gct tcc gac atg atg gtc ctc ctg aaa tcc ttc ttt gat tgt        485
Thr Val Ala Ser Asp Met Met Val Leu Leu Lys Ser Phe Phe Asp Cys
                115                 120                 125 cat aaa gaa ttc cag acg gtt ccg ttc tac att ttc tca gaa tcc tac        533
His Lys Glu Phe Gln Thr Val Pro Phe Tyr Ile Phe Ser Glu Ser Tyr
            130                 135                 140 gga gga aag atg gct gct ggc atc agt tta gaa ctt cac aag gct att        581
Gly Gly Lys Met Ala Ala Gly Ile Ser Leu Glu Leu His Lys Ala Ile
            145                 150                 155 cag caa ggg acc atc aag tgc aac ttc tct ggg gtt gct ttg ggt gac        629
Gln Gln Gly Thr Ile Lys Cys Asn Phe Ser Gly Val Ala Leu Gly Asp
        160                 165                 170 tcc tgg atc tcc cct gtg gat tca gtg ctg tcc tgg gga cct tac ctg        677
```

```
     Ser Trp Ile Ser Pro Val Asp Ser Val Leu Ser Trp Gly Pro Tyr Leu
     175                 180                 185                 190
     FIGURE 13 (cont.)

tac agc gtg tct ctc ctt gat aat aaa ggc ttg gct gag gtg tcc gac    725
     Tyr Ser Val Ser Leu Leu Asp Asn Lys Gly Leu Ala Glu Val Ser Asp
                         195                 200                 205 att gcg gag caa gtc ctc aat gaa aaa caa ggg ctt cta caa gga agc    773
     Ile Ala Glu Gln Val Leu Asn Glu Lys Gln Gly Leu Leu Gln Gly Ser
                 210                 215                 220 cac tca gct gtg ggg gaa agc aga aat gat cat tga aaagaacacc         819
     His Ser Ala Val Gly Glu Ser Arg Asn Asp His  *
                 225                 230 gacggggtaa acttctataa catcttaact aaaagcaccc ccgacacctc tatggagtcg   879
     agcctcgagt tcttccggag cccctttagtt cgtctctgtc agcgccacgt gagacaccta  939
     caaggagacg ccttaagtca gctcatgaac ggtcccatca aaaagaagct caaaattatc   999
     cctgacgacg tctcctgggg agcccagtcg tcctccgtct tcataagcat ggaagaggac  1059
     ttcatgaagc ctgtcatcga catcgtggat acgttgctgg aactcggggt caatgtgact  1119
     gtgtacaatg ggcagctgga tctcattgtg gacaccatag gtcaggagtc ctgggttcag  1179
     aagctgaagt ggccacagct gtccagattc aatcagctaa aatggaaggc cctgtacacc  1239
     gatcctaagt cttcagaaac atctgcattt gtcaagtcct atgagaacct agcgttctac  1299
     tggatcctaa aggcgggtca catggttcct gctgaccaag gggacatggc tctgaagatg  1359
     atgaggctgg ttactcagca ggagtagctg agctgagctg gccctggagg ccctggaggc  1419
     cctggagtag ggcccaggat gcaggtgcta atgtctatcc ccggcgctct tcttcccgac  1479
     tctaccatgg gatgtaactc caggagcccc tgccatctcc cgtaccaaaa gactgtggct  1539
     tccgtgtcta ctcagaaatc agttctactt cgtaaacagt gtttaaaacc agactcattt  1599
     aatcagagtg aaggattgca gtccattggc ttcttagcac agaagcagct gataacacaa  1659
     gtaaacccca gcccttgaga ggtagaagca agaggatcag aggttcaagc gcatcctcgg  1719
     ctccatcaca agttcaaaag ccgcctgcac caaatgggag tccttgtctc aaaaaaaaaa  1779
     aaaaaaaaaa aaaaagcggc cgc                                          1802
```

FIGURE 14

```
tctagcgaac cccttcgcga aggggttcgc taggttgcgt ttgtggagaa aaatctgttc     60
tacctcaggg ctgtgagaac ggcactcctg atg tct gag aaa gag aaa caa gat    114
                                 Met Ser Glu Lys Glu Lys Gln Asp
                                  1               5 tgg ctg aag gat cct ccg ttc ctt cag aga cct ggg tgg aga gca tta    162
Trp Leu Lys Asp Pro Pro Phe Leu Gln Arg Pro Gly Trp Arg Ala Leu
        10              15              20 ggg aca cga aga aca gag tag cggaagaaga gttcttaagt aataagttta       213
Gly Thr Arg Arg Thr Glu  *
        25              30 cctcctgact ggctcacatc actgccttac tctgtagaaa gcaggtcatc tcatggattt    273
cccctccca cccccccagc tggatcattt tttgactcag ggaaaataat taaattattg    333
tccaactgtt agtgttgatc ggtaacagca gaaaggcaga aagttcctga taatctcaat   393
attatctttt caaaagtatt ttcctggaat gttgtttgct ttggcattac aaagttctgt   453
actcttaaaa atattttgac ttgctgggca tggaggtcac acctttaatc cagaggcagg   513
catggatcca caggagttca aggccgcctg gctacaaagc gagttcaagg gcagccaggg   573
ctacacagag agaccttgtc tcntnaccnn tnannaaaaa acnaaaaagc cggccgc      630
```

FIGURE 15

```
tctagcgaac cccttcggta tagtctttag gtagtggctt agtccctgga agctctggtt      60
gcttggcatt tcaacgtgct tcttaaataa ctgttttatt agtcagtaca ag atg ctt     118
                                                         Met Leu
                                                           1 tgt ata tca gat ctg aaa tat ctt aaa att atc act tgc att gta aat       166
Cys Ile Ser Asp Leu Lys Tyr Leu Lys Ile Ile Thr Cys Ile Val Asn
         5                  10                  15 tac tat tcc ttt cgc aga aat aat gaa tgc ttc aag aaa aaa aaa agc       214
Tyr Tyr Ser Phe Arg Arg Asn Asn Glu Cys Phe Lys Lys Lys Lys Ser
         20                  25                  30 tgt ttg tat tgg gtt taa aacgtttcca aacaccaatt attctttact              262
Cys Leu Tyr Trp Val  *
 35 taagtcatcc gatctagtta ttaaattatt attactgcct tcacactatc aaagatggta     322
aatatctgat agaatcatat tcaaaatact tctgtttcac atttcttgag aaagtactga     382
ctgtctgagt tctttctcaa gaaatgtgaa acagaagtat tttgaatcga aggggttcgc     442
tag                                                                   445
```

FIGURE 16

```
tctagcgaac cccttcggaa gaactgtata tttgtgcctt gttctgcaag ttaaaaagct    60
ggtccagaca gtgtcataga attaactttt catttctgta ttaattttag gactgcaaaa   120
atcccaaagc tgtatactta gattggattc aataaaaagt ttaagtttac tnaanaaaaa   180
aaaaaaaaaa aaaaaaaaaa aaaaaaaaaa aaaaaaaaaa aaaanaaaaa aaaaaaaagg   240
aaaaaaaaaa ncggncnnaa aaaaggnggc cgc                                273
```

FIGURE 17

```
tctagcgaac cccttcgggg gaacccaagc ggcttcgccc aggcattcgc gcgggcgccc      60
gcggtctggg tcccacctcc tctgctttcg caccccttgaa gttttggagc accaggaaaa    120
gagggcaagg aaggagaggg gaagcgaaag catatcctaa aacatttact taaaggagga    180
aagaaaaggg gtcgcagaa atg gct ggg gca att ata gaa aac atg agc acc     232
                      Met Ala Gly Ala Ile Ile Glu Asn Met Ser Thr
                       1               5                       10 aag aag ctc tgc att gtt gga ggg att ctt ctg gtt ttc caa atc gtt      280
Lys Lys Leu Cys Ile Val Gly Gly Ile Leu Leu Val Phe Gln Ile Val
             15                  20                  25 gcc ttt ctg gtg gga ggc ttg atc gct cca gca ccc aca acg gca gtg      328
Ala Phe Leu Val Gly Gly Leu Ile Ala Pro Ala Pro Thr Thr Ala Val
             30                  35                  40 tcc tac gtg gca gca aaa tgt gtg gat gtc cgg aag aac cac cat aaa      376
Ser Tyr Val Ala Ala Lys Cys Val Asp Val Arg Lys Asn His His Lys
             45                  50                  55 aca aga tgg ctg atg ccc tgg gga cca aac aag tgt aac aag atc aat      424
Thr Arg Trp Leu Met Pro Trp Gly Pro Asn Lys Cys Asn Lys Ile Asn
 60              65                  70                      75 gac ttc gaa gaa gca att cca agg gaa att gaa gcg aat gac att gtg      472
Asp Phe Glu Glu Ala Ile Pro Arg Glu Ile Glu Ala Asn Asp Ile Val
                 80                  85                  90 ttt tct gta cac att ccc ctc cct tct atg gag atg agc cca tgg ttc      520
Phe Ser Val His Ile Pro Leu Pro Ser Met Glu Met Ser Pro Trp Phe
             95                  100                 105 cag ttt atg ctg ttt atc ctg cag ata gac att gct ttc aag cta aac      568
Gln Phe Met Leu Phe Ile Leu Gln Ile Asp Ile Ala Phe Lys Leu Asn
         110                 115                 120 aac caa atc aga gaa aat gca gaa gtt tcc atg gat gtt tcc ctg ggt      616
Asn Gln Ile Arg Glu Asn Ala Glu Val Ser Met Asp Val Ser Leu Gly
         125                 130                 135 tac cgt gat gat atg ttt tct gag tgg act gaa atg gcg cac gaa aga      664
Tyr Arg Asp Asp Met Phe Ser Glu Trp Thr Glu Met Ala His Glu Arg
140              145                 150                 155 gta cca cgt aaa ctc aga tgc act ttc aca tcc ccc aag acc cca gag      712
Val Pro Arg Lys Leu Arg Cys Thr Phe Thr Ser Pro Lys Thr Pro Glu
             160                 165                 170 cat gaa ggt cgt cat tat gaa tgt gat gtc ctt cct ttc atg gaa att      760
His Glu Gly Arg His Tyr Glu Cys Asp Val Leu Pro Phe Met Glu Ile
             175                 180                 185 ggg tca gtg gct cat aag tat tac ctt cta aat atc cgg cta cct gta      808
Gly Ser Val Ala His Lys Tyr Tyr Leu Leu Asn Ile Arg Leu Pro Val
```

FIGURE 17 (cont.)

```
aat gag aag aag aaa atc aat gtt gga att ggg gaa ata aag gac att      856
Asn Glu Lys Lys Lys Ile Asn Val Gly Ile Gly Glu Ile Lys Asp Ile
    205                 210                 215 cgg ttg gtg gga atc cac caa aat gga ggt ttc act aag gta tgg ttt      904
Arg Leu Val Gly Ile His Gln Asn Gly Gly Phe Thr Lys Val Trp Phe
220                 225                 230                 235 gct atg aag acc ttc ctc aca ccc agc atc ttc atc att atg gtg tgg      952
Ala Met Lys Thr Phe Leu Thr Pro Ser Ile Phe Ile Ile Met Val Trp
            240                 245                 250 tat tgg aga agg atc acc atg atg tcc cga cct cca gtg ctt ctg gaa     1000
Tyr Trp Arg Arg Ile Thr Met Met Ser Arg Pro Pro Val Leu Leu Glu
                255                 260                 265 aaa gtc atc ttt gcc ctt ggg att tcc atg acc ttt atc aat atc cct     1048
Lys Val Ile Phe Ala Leu Gly Ile Ser Met Thr Phe Ile Asn Ile Pro
        270                 275                 280 gtg gaa tgg ttt tcc att gga ttt gat tgg acc tgg atg ctg tta ttt     1096
Val Glu Trp Phe Ser Ile Gly Phe Asp Trp Thr Trp Met Leu Leu Phe
    285                 290                 295 ggt gac ata cga cag ggc atc ttc tat gca atg ctt ctt tcc ttc tgg     1144
Gly Asp Ile Arg Gln Gly Ile Phe Tyr Ala Met Leu Leu Ser Phe Trp
300                 305                 310                 315 atc atc ttc tgt ggc gag cac atg atg gat caa cat gag cgg aat cac     1192
Ile Ile Phe Cys Gly Glu His Met Met Asp Gln His Glu Arg Asn His
            320                 325                 330 att gca ggg tat tgg aag caa gtt gga cca att gct gtt ggc tct ttc     1240
Ile Ala Gly Tyr Trp Lys Gln Val Gly Pro Ile Ala Val Gly Ser Phe
                335                 340                 345 tgc ctc ttc ata ttt gac atg tgt gag aga gga gtg caa ctc aca aat     1288
Cys Leu Phe Ile Phe Asp Met Cys Glu Arg Gly Val Gln Leu Thr Asn
        350                 355                 360 cct ttc tac agt atc tgg act aca gat gtt gga aca gaa ctg gct atg     1336
Pro Phe Tyr Ser Ile Trp Thr Thr Asp Val Gly Thr Glu Leu Ala Met
    365                 370                 375 gct ttc atc att gtg gca ggt atc tgc ctc tgc ctc tac ttc ctg ttt     1384
Ala Phe Ile Ile Val Ala Gly Ile Cys Leu Cys Leu Tyr Phe Leu Phe
380                 385                 390                 395 ctg tgt ttc atg gta ttt caa gta ttc aga aac atc agt ggg aaa cag     1432
Leu Cys Phe Met Val Phe Gln Val Phe Arg Asn Ile Ser Gly Lys Gln
            400                 405                 410 tct agc ctc cca gcc atg agc aaa gtc cgg agg ctg cac tat gag ggt     1480
```

```
Ser Ser Leu Pro Ala Met Ser Lys Val Arg Arg Leu His Tyr Glu Gly
         415             420                 425
```
FIGURE 17 (cont.)

```
ctg att ttc agg ttc aag ttc ctc atg ctg atc acc ttg gct tgt gct    1528
Leu Ile Phe Arg Phe Lys Phe Leu Met Leu Ile Thr Leu Ala Cys Ala
         430             435                 440 gcc atg act gtt atc ttc ttc att gtt agt cag gtg aca gaa ggc cat    1576
Ala Met Thr Val Ile Phe Phe Ile Val Ser Gln Val Thr Glu Gly His
         445             450                 455 tgg aaa tgg ggt ggg gtc aca gtt caa gtg agc agt gct ttc ttc act    1624
Trp Lys Trp Gly Gly Val Thr Val Gln Val Ser Ser Ala Phe Phe Thr
460              465                 470                 475 gga atc tat ggg atg tgg aac ctg tat gtc ttt gct ttg atg ttc ttg    1672
Gly Ile Tyr Gly Met Trp Asn Leu Tyr Val Phe Ala Leu Met Phe Leu
                 480             485                 490 tat gca cca tcc cat aag aac tat ggg gaa gac cag tct aat ggt gac    1720
Tyr Ala Pro Ser His Lys Asn Tyr Gly Glu Asp Gln Ser Asn Gly Asp
         495             500                 505 ctg ggt gtc cac agc ggg gaa gaa ctg cag ctc act acc aca atc acc    1768
Leu Gly Val His Ser Gly Glu Glu Leu Gln Leu Thr Thr Thr Ile Thr
         510             515                 520 cat gta gat gga ccg act gag atc tac aag ttg acc cgt aaa gaa gca    1816
His Val Asp Gly Pro Thr Glu Ile Tyr Lys Leu Thr Arg Lys Glu Ala
         525             530                 535 cag gag tag taggctatgg cattcatcct cagggcaggt gatgaagcca            1865
Gln Glu *
540 agttgctggt gcatgctgac cctcatgaat atgctttcgt atctttatgt cccaggatca  1925
tttttatcct gtcacgttta caagaacatt tctgacatgc atacgtttac ttttaccatg  1985
tattagttac ttttatattt ctgtgataaa acaccatgag aaatacaatt tacagaagca  2045
aaaaaaaaaa aaaaaaaaaa aaaagcggcc gc                                2077
```

FIGURE 18

```
tctaacgaac cccttcggag cgatgga atg aga aag gcc cag aat gtg tta agt        54
                             Met Arg Lys Ala Gln Asn Val Leu Ser
                              1               5 ctg tgc agg gga agt gtc ctg agg gga ggg tct ttg gga ggg tcg aag         102
Leu Cys Arg Gly Ser Val Leu Arg Gly Gly Ser Leu Gly Gly Ser Lys
 10              15              20              25 gcc agg atg gca aag tga aggtagctga ggttgcagtc ttgggtgccc                150
Ala Arg Met Ala Lys  *
                 30 actgctgtgc atctgtctgg ttatctaccc ctactttggg ctgacaactg cagggttggg       210
tgtaggctgt ctcactgcat gccgggaagc tggagaagct ccacgggaac attgagggcc       270
atggctttga gacactgcag agcatccttg gtctctgtaa ccacgtcacc taaccctgac       330
aattccagac ccttcttcca ttgtccttgt gaaccatttg ggcttatctt tccctcttag       390
tcgcaagggt caaaccaagg gtcagtcaag tagatgactg tcaccttggg cctccccaga       450
ctctgctgcc ggggttggga gaccaaagta gaaactgcca ctacaaggcc ccaggatgag       510
gtctctgttc tgtggacctg ctccccagat acaggcctca gacccatagg acgtggccgg       570
tgctcaggga cacccaatcc ccggcctcac tccatcgagt actgacttct ttctctagtg       630
ccttgggggt ctccatcctt cagttatggt atgaagaatc tatgcaaact gtataagctt       690
ctgctcacca ataaacgctt tatttaaagc ttannnnnnn nnnannnnnn nnnnnaagcg       750
gncgc                                                                   755
```

FIGURE 19

```
tctagcgaac cccttcgcag aaacccaaag ttacagacca gaccctaccc aacatccagt        60
cagcaatcca gctggagaaa cgcttgag atg aca agg gac ttt cag aag caa          112
                              Met Thr Arg Asp Phe Gln Lys Gln
                                1               5 gcc ttg ata aga cag gaa aag cag aat tct aat aaa gat atg agg aaa         160
Ala Leu Ile Arg Gln Glu Lys Gln Asn Ser Asn Lys Asp Met Arg Lys
        10              15              20 aat gac atg ggc ctt caa cct ctg cct gta ggg aag gac gca cac agt         208
Asn Asp Met Gly Leu Gln Pro Leu Pro Val Gly Lys Asp Ala His Ser
    25              30              35              40 gca cca gga gtg aca gtc tct ggg aaa aac cac aaa aga act cag gca         256
Ala Pro Gly Val Thr Val Ser Gly Lys Asn His Lys Arg Thr Gln Ala
                45              50              55 cct gac aag aaa cag aga att gat gtt tgt cta gaa agc cag gac ttt         304
Pro Asp Lys Lys Gln Arg Ile Asp Val Cys Leu Glu Ser Gln Asp Phe
            60              65              70 cta atg aag aca aat act tcc aag gag tta aaa atg gca atg gag agg         352
Leu Met Lys Thr Asn Thr Ser Lys Glu Leu Lys Met Ala Met Glu Arg
        75              80              85 tcc ttt aat cca gtc aac ctt tcc ctg act gtg gtg taa aagaaaatga         401
Ser Phe Asn Pro Val Asn Leu Ser Leu Thr Val Val  *
        90              95              100 ggacgccctt ctctccatct tcccctcctt cttctccttc caattgcgtc atctgaaatt       461
gaatttcctc tcctcctcca ccacctataa tgctgtgcct gaaaaaaatg agtttcctcc       521
ctcatcaccc acagagaagt caagggctga acttgagagc ctcccaaccc tgcctcttcc       581
tccaccacca ggagatgaga aatctgatca ggaatgtcta ccaacatccc tacctcctcc       641
ccctcccaca gctccatccc aaccagcaca tcttctttcc tcctctgttc tagaacatca       701
cagtgaagca tttttacaac agtattcccg aaaagaaacc ttggactctc atcggcttca       761
ctcacaggct aaaatcctaa caggaaaatc accaccccca acactcccca aacccaaact       821
tcccgagaga atcaaagcta agatgagcca ggattcacca agcggtgaat tggaaagatc       881
tctgtcagat gtggaaatta aaactaccct ctcaaaggat cagaaaagtt cgctggtggc       941
agaaagccgt gagcacacag aggccaagca agaagtattc cgaaaaagcc ttggaagaaa      1001
acagctgtcc attagctctg caaactccct ctctcagaca gttccagaaa tcccagcacc      1061
caaggaaaaa cagacagcac cccttgttaa atctcactca ttcccatcag gttcagaaca      1121
acaaagtcct aagccttaca tgagaaaatt taagacaccc ttaatgattg cggaagaaaa      1181
atacagacaa caaagggaag agcttgagaa acagagacgg gagagttctt gccatagcat      1241
catcaaaaca gaaacccagc accgcagctt atcaaanntt aaaaaaaaaa aaaannnagc      1301
ggncgcccg                                                              1310
```

FIGURE 20

```
tctagcgaac ccctccgctt tttttttttt tttttttttt ttttcccccc tttcctattt      60
attaatgggg ggaagtatgt ttatgtggga tttatccact tcttttagat tctcctacct     120
gttgatctgt aattattcct agtagtctct tagagttctt agaagcatgc tgttaccgct     180
aatatttcct tttggtttgg atcttactta aacatattgt ttccttactc tcttttcat     240
cccagcttgt ctaactgaaa ggccagaccc aacttgatct atcccttaa aacttc atg     299
                                                                Met
                                                                  1 tct tgg cct gtt gat ttc tct gct cca ggt gtc acc gaa ggg gtt cgc      347
Ser Trp Pro Val Asp Phe Ser Ala Pro Gly Val Thr Glu Gly Val Arg
         5                   10                  15 cta gcg aac ccc ttc gta aca gcc aag gtt ttt gag aca gag gtt tca      395
Leu Ala Asn Pro Phe Val Thr Ala Lys Val Phe Glu Thr Glu Val Ser
         20                  25                  30 aca gca ttc ctg gag gag aca caa agg aca gat gag tca cat gaa gga      443
Thr Ala Phe Leu Glu Glu Thr Gln Arg Thr Asp Glu Ser His Glu Gly
         35                  40                  45 tgg gag gag gga agg tgg ctg ttg ata ggt att ttg aga cac tct att      491
Trp Glu Glu Gly Arg Trp Leu Leu Ile Gly Ile Leu Arg His Ser Ile
    50                   55                  60                  65 tga gtcctacaca acactccccc ctccccccaa accatttta tgtctattga            544
 * cctttcctct agtcatacag ggaaattcac agttacctac aaagaaccac taattgtaac    604
aagtcaagag gaaacttatt tttgataatg actcattgaa gatgttttga aaatttaaaa    664
ataagctctg ttagcagaag tctgtnngaa aagcangaag gaantgtttg tttattanat    724
aaataaaagg cggcgaggac aacaaaaaaa aaaaaaaaaa aagcggccgc                774
```

FIGURE 21

```
tctagcgaac ccettcgcga aggggttcgc cgaagggggtt cgcttcagga gttaatgtag    60
acttgactta agcatcctga tttaaccaag a atg gtg gca cac aac ttt aac       112
                                  Met Val Ala His Asn Phe Asn
                                   1               5 ccc cat gct ggg gaa gca gag gca cac tta atc tgt gtg agt ccc agg      160
Pro His Ala Gly Glu Ala Glu Ala His Leu Ile Cys Val Ser Pro Arg
         10                  15                  20 cca tcc agg gat acc gta gta gtg aga ccc tgt ctc aca aaa caa aga      208
Pro Ser Arg Asp Thr Val Val Val Arg Pro Cys Leu Thr Lys Gln Arg
         25                  30                  35 atg gga att tag ggctggtggg gctcagcatg caactgtgcc tgttacctag          260
Met Gly Ile *
 40 tctggcctga gttcaattcc caagactcaa tgtatgagga gagaaacgat ttctgaactc   320
attcattgat ctccaaatgt gtggtatagg tgcccttccc ttaaataaaa caaacaaaca   380
aaaaacaaca aaaacaacaa accccaata aatgtatatt taattttaaa agactgtact    440
tgggcatggt acttcacatc tacagttacg acattctaga ggctcaggcc tgggaattgc   500
tatgaatttg aggccagtct gggttagagt gacttctcat ctaggcagga ctacgtaata   560
agtctttgcc caaaaataaa cagcaaccca aataagagca acaagaattc tccctccaaa   620
tagtaacctg ggcctggaga gacagcttag caactgagtg cttgccgagc catcgaggac   680
tggagtctgg attccagcac ccgtgtgaca gacaagctgg gcgttcactc atgctgatga   740
accccaaggc tgaggagaca ctgactcttc tctggccctg ttcatgctgt ccacaggtgc   800
ccaagtagca gttaagtaga ctgtcagaca acatggctgg ctttttaagc aagaacagta   860
actgaagaaa tacacttttg aagtactgtt aatttgctt aaaacttggt agggagctgg    920
aggatggctc agtggttaag agcactgact gctcttccag aggtcctgag ttcaattcc    980
agcaaccaca tggtggctca caaccatctg taatgagctc tgatgccctc ttttggtgt   1040
gtctgaagac agcgacagtg tactcatata aaataaaata aatcttttt tttttttaaaa  1100
gaaatttgtc agagatatgg caggaagggt atattttac ctatttacct ggtgggctaa   1160
tcctggtatt tttttcaaaa ttaagatact atataggagc cgcgaagggg tcgctaggcc   1220
agtgtgatgg atatctgcag aattcggtta gccgaattc                         1259
```

FIGURE 22

```
tctagcgaac cccttcgtct cctcttaaac atcttaagac aagctgttat catctacact      60
gctcttagta ctgttctttt ctaagattct tctaatatga cacattaaga ctttcttaaa     120
atgtacaact gctacgctga tctaaacatt caaagtgcac acatttcgct atgaagccac     180
gtgaccagag tcctggggac taatttctgt cttagtcaga ttcctattgc tatatgaaga     240
aatacc atg ata gtg tca act ttt ata aag aaa aag tat tcc ttt ggg        288
       Met Ile Val Ser Thr Phe Ile Lys Lys Lys Tyr Ser Phe Gly
        1               5                  10 aat agt tta aag gat cag agg gtt agt gca tta tca tca cag cag gaa       336
Asn Ser Leu Lys Asp Gln Arg Val Ser Ala Leu Ser Ser Gln Gln Glu
 15              20              25              30 gcg tgg cag tgg gag ccc aga ttt cta tat cca gat ttt cat gaa gca       384
Ala Trp Gln Trp Glu Pro Arg Phe Leu Tyr Pro Asp Phe His Glu Ala
            35              40              45 tga cgagagctcc tgggcctggc gcgagcttct gaaacctgaa agtgacatat            437
 * ttcttccaat aaggccacaa ctactgctat aaggccacat ctcctaactg tgtcactatc     497
tatgagcctg tacagtctat ttcttttaca ccactgcatc atctaagagc tgatacccgt     557
taagttagtc atgaaaatat tcaacttcta gggttctgtt ttcttctcta taaaatattg     617
aaaatgataa ttaatgtata ctttacagaa ctgtatttga agtacaactt gatggacata     677
aatcaccaca gttgggtcaa aattgtatat atatatatat atatatatat atatatatat     737
atatatcaaa aaaaaaaaaa aaaaaaaaaa aagcggccgc                           777
```

FIGURE 23

```
tctagcgaac cccttcgtac atttcaccct agaaataaat agaccttcta gctctgacag      60
aaagtagtgc ttgcctagga ggagctgggc tggccagttc ctccttcttg cacacttagc     120
ctgtttgctg aaggcttgtt tcaatggaaa actgaaatgg acccactaat gtctcgattc     180
ttctctcctt cactaagtct gtgaagtcat cagcgttttg tcttttgtgt gtgaataccg     240
aggagaattt cctcacccag tgccttcagg agccatgatg gctgcctcag aataagcaca     300
gatacacttg agcaactggt gcagaaaacc cgacttctaa attattaagg aacaggataa     360
ttgcttgtta caataattag aataatgtaa ttaggataat tgcttttaaa aaatcttccc     420
acctttcccc ccccaaatat taataattcc aactaaatcc tctggggccc ttccagtttc     480
cacaacggaa agagcctaac gtattctaaa gactgggcat attttttttt tccagattag     540
tgagtgttca tgagctatta agaggccaag tgttttttca agatggtgtc atttcattct     600
aacatatcta acatgcaaag gacttaaaaa aataatttgc aaaataatct gtttcaagtc     660
tatgaggaag ctgaagagcc tactccggag gaaactccag aagagcctcc tagcatagag     720
gaagaagaga tagtggagga agaggaggag gaggaggtgc ccccgcccag aggtacagcc     780
gctttgatga gttcagcatt ccaaagcctt ggtgctgctg gaccctactc attagccata     840
tactttcctg gaagcacagc cacgaggcct ggagggtgca cactcgtaat gactggagct     900
ttgtgggcct ttcctttccc ctaacgtttc ctccttcccc gcaatctgac cataaatgag     960
gagatttttt ttttctctta ctacactttt tgcaatccta gtttgcaatc ctcagtgtgg    1020
ctggctttca gttcaaatgc tggagaacca tgtatctgtg tggtgagagc attcattttc    1080
aagactaatt cttaaaccgc ttatccccgg agacagaaac cgtggcagag ttgctatcct    1140
ctgagctggg gtggtcatga tgatcagtta ggttactaac atcttcctaa atgaatcgt    1200
gttttgtgtt gctctgtttt catttggatg acagggtgtt gttctgtttg atgcgtgtgg    1260
gttttttccaa catgtccgta aaaatatctt ttaagcacca gangtagtga agaaagctgt    1320
gcaaacagca cccgctcctg tccccaagaa awccgaggcg ccccccccaaa ggtatatc     1378
```

FIGURE 24

```
tctagcgaac cccttcgcga accccttcgc tgcatcctca taaagctacc tcaagacaga      60
gcgtaactgc ctcattctag gagtggactc ggggaagaca gcagacacac catcagggag     120
cccctgggta tctccagaac atg gca agc cgt gga tac ctg cat cac ctg ctg    173
                     Met Ala Ser Arg Gly Tyr Leu His His Leu Leu
                      1               5                  10 act gca gag gga gcc tgg gag gag ttt gta tca aag gcc aag ttg ccc      221
Thr Ala Glu Gly Ala Trp Glu Glu Phe Val Ser Lys Ala Lys Leu Pro
         15              20                  25 agg gat agg gca gtg gcc ctc cac aaa gca ctg agg gat ctg aca gca      269
Arg Asp Arg Ala Val Ala Leu His Lys Ala Leu Arg Asp Leu Thr Ala
        30               35                  40 ctc ttg gcc ata gca gaa aga ggc aga tct cgg aaa ggc tgg aaa ggc      317
Leu Leu Ala Ile Ala Glu Arg Gly Arg Ser Arg Lys Gly Trp Lys Gly
        45              50                   55 aag gag aag ttt gtg aaa gca ttt cct tgc ttg aaa gca gac ttg gag      365
Lys Glu Lys Phe Val Lys Ala Phe Pro Cys Leu Lys Ala Asp Leu Glu
 60              65                   70                       75 gag cac atc agc cag ctc tat gcc cta gcc gac cat gct gag gaa ctg      413
Glu His Ile Ser Gln Leu Tyr Ala Leu Ala Asp His Ala Glu Glu Leu
                 80                   85                  90 cac agg ggc tgc acc gtc tcc aac atg gtg gct gac tcc ttc agt gtt      461
His Arg Gly Cys Thr Val Ser Asn Met Val Ala Asp Ser Phe Ser Val
             95                  100                 105 gcc tcc gac atc ctg aac atc ttt ggt ctc ttt ctg gca cct gag tca      509
Ala Ser Asp Ile Leu Asn Ile Phe Gly Leu Phe Leu Ala Pro Glu Ser
        110                  115                 120 gca gag gga agt ctg gtg ctc tcg gca gca ggc ttg ggg ctg ggg gta      557
Ala Glu Gly Ser Leu Val Leu Ser Ala Ala Gly Leu Gly Leu Gly Val
        125                 130                 135 gca gct act gtg act aat gtt gct act tca atc atg aag gaa aca agc      605
Ala Ala Thr Val Thr Asn Val Ala Thr Ser Ile Met Lys Glu Thr Ser
140                 145                 150                 155 agg gtt ttg gat gga gtc gaa gct ggt cac cat ggt tca acc gcc atg      653
Arg Val Leu Asp Gly Val Glu Ala Gly His His Gly Ser Thr Ala Met
                160                 165                 170 gat ata ctg gag gaa gct ggc aca agt gtg gct agg att gcc agc gag      701
Asp Ile Leu Glu Glu Ala Gly Thr Ser Val Ala Arg Ile Ala Ser Glu
        175                 180                 185 atc cct cag gct acc aga gat atc acc aga gac ctg gaa gcc ctt gag      749
Ile Pro Gln Ala Thr Arg Asp Ile Thr Arg Asp Leu Glu Ala Leu Glu
        190                 195                 200
```

```
cag cac atg aat gcc ctc agt ctg gtc aga gcc aac cct cgc cta gaa    797
Gln His Met Asn Ala Leu Ser Leu Val Arg Ala Asn Pro Arg Leu Glu
        205                 210                 215 gaa gat gcc agg gcc ctc atc aat gca ggt agc atc cct gcc caa cgg    845
Glu Asp Ala Arg Ala Leu Ile Asn Ala Gly Ser Ile Pro Ala Gln Arg
220                 225                 230                 235 gct aaa cag gtg cgg gcc agt ctg aaa gga acc cct ctg gca atg agc    893
Ala Lys Gln Val Arg Ala Ser Leu Lys Gly Thr Pro Leu Ala Met Ser
                240                 245                 250 aag gaa gac cgg atc cgc agt gcc acc acc act ggg gtc acc ctc ttg    941
Lys Glu Asp Arg Ile Arg Ser Ala Thr Thr Thr Gly Val Thr Leu Leu
            255                 260                 265 cgt gat gtg ggg agc ctt gtg aac gag tcg aag cag ttg tac gaa ggg    989
Arg Asp Val Gly Ser Leu Val Asn Glu Ser Lys Gln Leu Tyr Glu Gly
        270                 275                 280 tct gct tcc gaa tcg gca gca gca cta agg aag ctg gct cag gag ctg   1037
Ser Ala Ser Glu Ser Ala Ala Ala Leu Arg Lys Leu Ala Gln Glu Leu
285                 290                 295 gag gag aag cta ggg gag ctc atg aaa ttc tac gag aca atc tga       1082
Glu Glu Lys Leu Gly Glu Leu Met Lys Phe Tyr Glu Thr Ile  *
300                 305                 310 tcaggtttca gccagtcacc ccatccccaa gacatgcaga catcagggga gaggatctgg 1142
acagaggtag ggaccatgga ggtgctgtta gaaggagagc aagactacag tcaggtccga 1202
gggacatagt gtggaggcct gtttgatgaa cacarcaggt taraggatgg agcagtggat 1262
caaagtgaga tccactggag cctgagacsa gggaccagag gatgtgctgc aagagggact 1322
gggaaaattg aaatctanac taaacatgga aaaaaggcag tttcgaaaga ctagaaaacc 1382
ctccccatct gagccattgg aaaccccaca aaacacaaac cagagagaaa agtgtgtgct 1442
ctctaaacaa gtcgtggccc ccagttcccc agcccactcc caccctcagg ggtggcatca 1502
aataaattgt ttccatttca aaaaaaaaan naaanaaaaa aaaagcggcc gc         1554
```

```
tctagcgaac cccttcggct ttttctgatt taaagtgaag aaatggccat atttgcttga    60
taatcttcag ttgtgtctct ggaactcaac aaagaacgca ttttatgaaa tatacagctg   120
tcttcggtaa agccaacttt cttacacata tttcgggaag taattaacta caatttggac   180
ttatagttac aaggttgcct tcgaaacact gctctaaatg tgtctcgtgt tggggtgcta   240
ctttgcttat gtgtaaattt cacagtaatg caatagagaa agggtgtttg tgggtgtggc   300
ttgtgggggg gattgttttg ttgttgttgt ttgagataaa gcttcattct gtagccagga   360
aagcctggaa tttactgtgt catcccaggt agcttcaaac tggtgcctat cctgcctcag   420
cctccaacgt gttgcaattg caggagtaac ctaccacatc ctgcagctac agtgatctag   480
aacctccccg tcgaagcccc accaccatag aaaccaattt gcattaagtt ttagaattcc   540
caacccaact aaagtttaat aaaaaaagaa aaacaaaaca agatttaaat cattctttcc   600
ctcattcttt ttnnagatnc agggctcncc tagttttnaa caaaacagtn ngcagngnng   660
ggnncccncg gngggnnttt tttncnttgn gccncntngc anccccaccen cccaggcngg   720
atngggnggg gtataaaagt nttancnggc anatgnnctn ggngcanacc caagtntatc   780
aggncctnan ttncencccca ganaactaga nanctntngc atagtanang ccccntgtgn   840
agatttnaaa nccncctgtn cacaganana gaancttana tagaaaantc aaaatatttn   900
gggcccaan gttnccccacc ctgtagagng ggncccccaaa ancngccnec aganagenng   960
atatntgagt tntgacctnt attctttact acnacgentt gagagaatat tntgntgggg  1020
ccctanccac atgttttgnc ccaagantgt aaanccactt naannctgng ggatatctcn  1080
ctgcanacag aagtgcccng cgggattta aaaaaaaaa taaaaaaaaa aaaggngcen  1140
cc                                                                1142
```

FIGURE 26

```
tctagcgaac cccttcgtgg agactgtgga agttatgtat gaataggaga gtgtgtgttg    60
tgtaacacag acagaaggac attggatcat gttgaacccg cacccccaac tatgagtgat   120
ggtatggaaa gaatgcgaac atttaaactg cgccaatgcg gcggccatct tggtggagaa   180
gttcctagcc gagctttgat gtgattttt tgatggtaca atgcagcgag catggccacg    240
ggagctttga atccagccga cagctccgag atttgccctt ccagtgctct tgcctaccgt   300
agagaggact gctgagatgg gattccttgt gacaagccta cttacccttta actgccagca  360
tttgtaaggt gcaatcttgt gtattggttt tttattttga cagttttgaa aacatgtttg   420
ntgntcttgg tgtttttcca gtaaaagtaa tcacaaagga aaaaaaaatt aaaaaaaaaa   480
aaaaaaaaaa aaaagcggcc gc                                            502
```

FIGURE 27

```
tctagcgaac cccttcgcct tcatatggtt ttacactgta tgcatctcac cgcggcccgg   60
aacctttctt ctcatcccaa tcctgtttga ggggacgggg ggcagggacg gacaacccaa  120
gacaagggat atttgtgctg tgggtattgc atcttatgga gggctgtagc taactgggac  180
tcctgggtga ccccaacagg cctttgatcc tctgtctctc cccgcttgat ctttcttacc  240
ttatgcttcc ccaagtgcag ctgagggact acacagtggc tcccgcccca ctccaaacac  300
aggaaatcaa tctcaggag aggagataag aagtgaggag aagccaagat tcaaccaata  360
gatggtaatt gctcctggga ccgccccccc aagcatcatt tccataggaa ggactgagtt  420
tggctcctga agcccagtgg agtacctttc tctgcctgaa ttctgttgtg atccctggcc  480
aagtcctctt tccagaaacc ccacctttaa aaccagctga gaaggacctt cttctctatg  540
tttaataggt aactttccat agcttagctt ccctgcagtc tcccgagtgc ccagttaaaa  600
ttctgccata ggtcaaaagt ggggttgaga ggtgaagtca gaggccatgc atggagctca  660
gaacgtttct aaacctcctg tgattcattg agtagcccct agactctaga aggctcagat  720
gccaaaaagg ktgactttat aatttcttag ggtcttctca tgggatcgkt ttcagagtgg  780
gcattcacta aatgatagca agtttattaa ttgtttccca gygcctgatc tctttatttn  840
cccagggctt ccaaccagag cccttggttg aaagtctccc acccacccc cacccctgaga  900
cttggtggnt ttctgagatt ccccagggat ggcaaaattg gcattcttac agggagccct  960
gacttctagc acgttaccta gatttttttac cctgctctct ctgcctattt tactatggga 1020
tcactgntct ctttggactt aaggaaccac cttgaagtag agtgaggtga ccacgtgttg 1080
gtggcgaaga atataagcat tggtccttaa aagagaactt ctatgaagtc aggctgcaag 1140
ctttaacatg gcacaagttg caccttactg gctgctaagt ctggatgtca accaaaggtc 1200
aactctntaa ttaaagaaaa gcaagggaga aganaggtgg aagnggcttn cataaacttt 1260
attcaaaatg tctaccagga atggtggtga caccaataat cccacatgtt ggatgtngag 1320
gcaggaagaa tgatggtaag gggcatcctc actacataat gagttgaggc tngactaggt 1380
taactntgct tnaaaaaaaa aaaaaaaaaa aaaaaaaagg ggngcc              1426
```

FIGURE 28

```
tctagcgaac cccttcgcaa gaactcagac tgctcctgcc tgacttccta ggtgtcatag    60
ctctcttctg ccgccagt atg aca tca tca agg aca acg agc cca ata aca    111
                    Met Thr Ser Ser Arg Thr Thr Ser Pro Ile Thr
                     1           5                      10 aca agg aaa aaa cca aga gtg cat cag aga cca gca ccc cag agc acc    159
Thr Arg Lys Lys Pro Arg Val His Gln Arg Pro Ala Pro Gln Ser Thr
             15                  20                  25 agg gtg ggg gtc tcc tcc gaa gca aga tat gaa acc ctt tca gtg ctt    207
Arg Val Gly Val Ser Ser Glu Ala Arg Tyr Glu Thr Leu Ser Val Leu
         30                  35                  40 gct ctg agc agc tca gaa gta gaa tgc gag agg acc tca ctg ttc tga    255
Ala Leu Ser Ser Ser Glu Val Glu Cys Glu Arg Thr Ser Leu Phe  *
         45                  50                  55 cgatgattgt ccaacacaca tccggccctc tccgtgtctc ctcccaccac catcttctcc    315
tatcaccggg cttactatct tctctcctgg ctttcctctt tctgatggcg gttcctgaag    375
cctccaacta accccctaact cggggagcgc ctcgacagtg tttgtggcta aggctacact    435
cagagacaga gttgcagaat gagggagacc cagcccgagg gacgccattg ctgggaggta    495
gactgggtgc gagggccctt ggcacaggac tcacatctgg gctgttcagc ttgacccgaa    555
ggctgtgtgt gaaagggga aaaagacaag attgccaggc agggctgttg ttttttgtggc    615
ttcgagggac aagaacctgg ctaaaaggca gcagccctgc tgttctttt ctcctctgtc    675
ctgtttccta ccttacaaga agtccatgca accaaccggg gctctggcac ttttcttgtt    735
tatttccctc ctggcttcca aacaagccct ctgtggacat catcaaagca tggataaccc    795
cctctgcagg ggtgggcttc attctccgct ggtccctgta gccttcctgg acacagggtg    855
aaagttgtaa aagtggtagg agtgcagcta gccacaggtt ctccttttcc catctcagtc    915
tgaccaagga ggctgaacta ccaacccaaa ttcagcgaaa aaaaaaaaaa aaaaaaaaa    975
aagcggccgc                                                         985
```

FIGURE 29

```
tctagcgaac cccttcgcgg ggacagacat ggagaaggag atggaggacc ccctggctgg      60
agcagaccaa cagaataggc aactatggct ggagaaccgg gtatcagagt aatgcttgac    120
ctcgggaaac accaaatttc ttcttccgat cgcagaagta gtactcggcg aaattcacta    180
ggtaggaggc tcctcatctg ggaagaaccg gtgcctgggg ggacctggct ggataggt      238
atg ggg gat cga ggc cgg tcc cct agt ctc cgg tcc ccc cat ggc agt      286
Met Gly Asp Arg Gly Arg Ser Pro Ser Leu Arg Ser Pro His Gly Ser
-35             -30             -25             -20 cct cca act cta agc acc ctc act ctg ctg ctc ctc tgt gga cag          334
Pro Pro Thr Leu Ser Thr Leu Thr Leu Leu Leu Leu Cys Gly Gln
        -15             -10                     -5 gct cac tcc cag tgc aag atc ctc cgc tgc aat gcc gag tac gtc tcg      382
Ala His Ser Gln Cys Lys Ile Leu Arg Cys Asn Ala Glu Tyr Val Ser
            1               5                       10 tcc act ctg agc ctt cgg gga ggg ggc tca ccg gac acg cca cat gga      430
Ser Thr Leu Ser Leu Arg Gly Gly Gly Ser Pro Asp Thr Pro His Gly
        15              20                      25 ggc ggc cgt ggt ggg ccg gcc tca ggt ggc ttg tgt cgc gcc ctg cgc      478
Gly Gly Arg Gly Gly Pro Ala Ser Gly Gly Leu Cys Arg Ala Leu Arg
    30              35                      40              45 tcc tac gct ctc tgc acg cgg cgc acc gcc cgc acc tgc cgc ggg gac      526
Ser Tyr Ala Leu Cys Thr Arg Arg Thr Ala Arg Thr Cys Arg Gly Asp
                50                      55                  60 ctc gct ttc cac tcc gcg gtg cat ggc ata gag gac ctg atg atc cag      574
Leu Ala Phe His Ser Ala Val His Gly Ile Glu Asp Leu Met Ile Gln
            65                      70                  75 cac aac tgc tca cgc cag ggt ccc acg gcc tcg ccc ccg gcc cgg ggt      622
His Asn Cys Ser Arg Gln Gly Pro Thr Ala Ser Pro Pro Ala Arg Gly
        80                      85                  90 cct gcc ctg ccc ggg gcc ggc cca gcg ccc ctg acc cca gat ccc tgt      670
Pro Ala Leu Pro Gly Ala Gly Pro Ala Pro Leu Thr Pro Asp Pro Cys
        95                      100                 105 gac tat gaa gcc cgg ttt tcc agg ctg cac ggt cga acc ccg ggt ttc      718
Asp Tyr Glu Ala Arg Phe Ser Arg Leu His Gly Arg Thr Pro Gly Phe
110                 115                 120                 125 ttg cat tgt gct tcc ttt gga gac ccc cat gtg cgc agc ttc cac aat      766
Leu His Cys Ala Ser Phe Gly Asp Pro His Val Arg Ser Phe His Asn
                130                 135                 140 cac ttt cac aca tgc cgc gtc caa gga gct tgg ccc cta cta gat aac      814
His Phe His Thr Cys Arg Val Gln Gly Ala Trp Pro Leu Leu Asp Asn
                145                 150                 155 gac ttc ctc ttt gtc caa gcc acc agc tcc ccg gta gca tcg gga gcc      862
```

```
Asp Phe Leu Phe Val Gln Ala Thr Ser Ser Pro Val Ala Ser Gly Ala
        160                 165                 170
FIGURE 29 (cont.)

aac gct acc acc atc cgg aag atc act atc ata ttt aaa aac atg cag      910
Asn Ala Thr Thr Ile Arg Lys Ile Thr Ile Ile Phe Lys Asn Met Gln
        175                 180                 185 gaa tgc att gac cag aaa gtc tac cag gct gag gta gac aat ctt cct      958
Glu Cys Ile Asp Gln Lys Val Tyr Gln Ala Glu Val Asp Asn Leu Pro
190                 195                 200                 205 gca gcc ttt gaa gat ggt tct gtc aat ggg ggc gac cga cct ggg ggc     1006
Ala Ala Phe Glu Asp Gly Ser Val Asn Gly Gly Asp Arg Pro Gly Gly
                210                 215                 220 tcg agt ttg tcc att caa act gct aac ctt ggg agc cac gtg gag att     1054
Ser Ser Leu Ser Ile Gln Thr Ala Asn Leu Gly Ser His Val Glu Ile
            225                 230                 235 cga gct gcc tac att gga aca act ata atc gtt cgt cag aca gct gga     1102
Arg Ala Ala Tyr Ile Gly Thr Thr Ile Ile Val Arg Gln Thr Ala Gly
        240                 245                 250 cag ctc tcc ttc tcc atc agg gta gcg gag gat gtg gca cgg gcc ttc     1150
Gln Leu Ser Phe Ser Ile Arg Val Ala Glu Asp Val Ala Arg Ala Phe
    255                 260                 265 tct gct gag cag gat cta cag ctg tgt gtt ggg gga tgc cct ccg agc     1198
Ser Ala Glu Gln Asp Leu Gln Leu Cys Val Gly Gly Cys Pro Pro Ser
270                 275                 280                 285 cag cga ctc tct cgc tca gag cgc aat cgc cgt ggg gcg ata gcc ata     1246
Gln Arg Leu Ser Arg Ser Glu Arg Asn Arg Arg Gly Ala Ile Ala Ile
                290                 295                 300 gat act gcc aga agg ttg tgt aag gaa ggg ctt ccg gtt gaa gat gcc     1294
Asp Thr Ala Arg Arg Leu Cys Lys Glu Gly Leu Pro Val Glu Asp Ala
            305                 310                 315 tac ttc caa tcc tgc gtc ttt gat gtt tca gtc tcc ggt gac ccc aac     1342
Tyr Phe Gln Ser Cys Val Phe Asp Val Ser Val Ser Gly Asp Pro Asn
        320                 325                 330 ttt act gtg gca gct cag tca gct ctg gac gat gcc cga gtc ttc ttg     1390
Phe Thr Val Ala Ala Gln Ser Ala Leu Asp Asp Ala Arg Val Phe Leu
    335                 340                 345 acc gat ttg gag aac ttg cac ctt ttc cca gta gat gcg ggg cct ccc     1438
Thr Asp Leu Glu Asn Leu His Leu Phe Pro Val Asp Ala Gly Pro Pro
350                 355                 360                 365 ctc tct cca gcc acc tgc cta gtc cgg ctt ctt tcg gtc ctc ttt gtt     1486
Leu Ser Pro Ala Thr Cys Leu Val Arg Leu Leu Ser Val Leu Phe Val
                370                 375                 380 ctg tgg ttt tgc att cag taa gtaggccagc aacccgtgac tagtttggaa       1537
```

```
Leu Trp Phe Cys Ile Gln  *
                385
FIGURE 29 (cont.)

acggtttgag gagagaggtt gatgtgagaa aacacaaaga tgtgccaaag gaaacagtgg   1597
ggacaggaga caacgacctt actcaatcac acgaggttgc agtccagggc tgaaatgacc   1657
ctagaataaa gattctgaga cagggttttg cactccagac cttggtatgg gctccccatg   1717
aatttcccca ttagtgattt cccacttgta gtgaaattct actctctgta cacctgatat   1777
cactcctgca aggctagaga ttgtgagagc gctaagggcc agcaaaacat taaagggctg   1837
agatatctta aaggcagaaa ctagaaaagg ggaaaccatg attatctata agaaaatcaa   1897
aagagggggtt tgggaattta gctcagtggt agagcacttg cctagcaagc gcaaggccct   1957
gggttcggtc cccagctcct aaaaaaaaaa aaaaaaaaaa aaaaagcggc cgc          2010
```

FIGURE 30

```
tctagcgaac ccttcgtgg ggattaaggt tctctatagc taagcctgtc nga atg          56
                                                          Met
                                                          1 aca aca ccc aga gat ctc acc tgg ggt ggt ggg agc act ctc tgt ctt       104
Thr Thr Pro Arg Asp Leu Thr Trp Gly Gly Gly Ser Thr Leu Cys Leu
            5               10                  15 gag gga aca tgt acc tac tct ctc ctt cca caa gag cca cat aca ctt       152
Glu Gly Thr Cys Thr Tyr Ser Leu Leu Pro Gln Glu Pro His Thr Leu
         20              25              30 aga agt tcc agt gaa gat cta tgt gct tca gaa gag agg gga ctt gga       200
Arg Ser Ser Ser Glu Asp Leu Cys Ala Ser Glu Glu Arg Gly Leu Gly
     35              40              45 ggt gaa agg ggg agt ggg agg ggg gct tga ggacctanct gaaagatttt        250
Gly Glu Arg Gly Ser Gly Arg Gly Ala *
 50              55 angctgaaag aacttccttg attcaaagac atatgtcagt ngacccaaca atgagaatga     310
atatgagggc caggaaaact tgtgggaatc agtctcaaga cngaaacnga gaaagaaaga     370
aaagtggnta ggactcanat tggggaacct gggtagacag gagtggcnag ggaagaaagg    430
gatcttgggt tntccacagt ttgagacaca tccggngntc gaccctattc ccngaagccn    490
cannanatgt tgcttccccn tcnntnnaat gggcctggng gtcctnctcc ctttncccng    550
gacatgaaaa ngtnttctgc nnanataacc cccntctttc ctccccttn antntgtccc     610
taccnttttg tcccttttn ttttnaaaaa annaaaataa aggggnncnn tnttcccttn     670
gaaaaaaaaa aaaaaaaaaa aaaaaaccgc ccncc                               705
```

FIGURE 31

```
tctagcgaac cccttcgcga aggggttcgc ttacattcac gcttaagcat attaactgta      60
catattaact gatttagagg atact atg gat tcc aca tct tcc ctg agc ata       112
                          Met Asp Ser Thr Ser Ser Leu Ser Ile
                            1               5 ggg att gat ttg aaa aat gac agg gtt ggc tgt cga ccc cca tcg gag       160
Gly Ile Asp Leu Lys Asn Asp Arg Val Gly Cys Arg Pro Pro Ser Glu
     10              15              20              25 gaa gca ggt aag gaa tca ctt agg aga act gat ctc aac att ctt cag       208
Glu Ala Gly Lys Glu Ser Leu Arg Arg Thr Asp Leu Asn Ile Leu Gln
             30              35              40 ttc ttt cta tta ttt act tgt tta gcc tgg agt taa attcccactc            254
Phe Phe Leu Leu Phe Thr Cys Leu Ala Trp Ser  *
             45              50 cttgtgagca cttctaattt gaaatccac ttcttcaat attttcgaaa tttaaaactg       314
atggatgacg tgacaaaact tccacgagtt aagaattctc cacctctgat ctcatcgcag     374
cagggcacaa tccaaggcat gtgaattgac ttccaggttt atgtgacata taatgaatt      434
ctgtctctag atttggatcc cattctccta aatatctcac catgcatgtg cagatattct     494
aaagtctaaa aatatctgat attgcaaact tttctggtca aaacattttg gatgagccat     554
ttaacagcca aggtatttga gacagaggtt tcaacagcat tcctggagga gacacaaagg     614
acagatgagt cacatgaagg atgggaggag ggaaggtggc tgttgatagg tattttgaga     674
cactctattt gagtcctaca caacactccc cctcccccc ctcccccaa accattttta       734
tgtctattga cctttcctct agtcatacag ggacattcac agttacctac aaagaaccag     794
aattgtaaca agtcaagagg aaacttattt ttgataatga ctcattgaag atgttttgaa     854
aatttaaaaa taagctcttg taagcagaag tctgtgagaa aagcaagaag gaattgtttg     914
tttattaaat aaataaaagg cnnannnnaa aaaaaaaaa aaaaangcgg ccgc            968
```

FIGURE 32

```
tctagcgaac ccctcggca gacagcatcc ctcccaaggc tactcagggt ttaaaccctg    60
cttctgaagt gacatgtcct gcaaagaaag tccccacgtg ggtgtttcca ccaccactgt   120
cagctctgta gctgtgcaag ctggggactc caagatcgtg atagccgttg tcaagtgtgg   180
caaatgggtg cggctccaac tggctgaggc acagcccaat ctcctagaaa ttgggagcag   240
tcaag                                                              290
```

```
      atg aaa cca gaa aac tgc ttc acg atc acg agc tcc ttc tgg cca   290
      Met Lys Pro Glu Asn Cys Phe Thr Ile Thr Ser Ser Phe Trp Pro
        1               5                  10                  15 agc tta agg cct tgg aag atc gtg tgt ggg gac tct tac agg aag cag    338
Ser Leu Arg Pro Trp Lys Ile Val Cys Gly Asp Ser Tyr Arg Lys Gln
                20                  25                  30 aca gga cgg ctg aag caa aca agg agc aaa gtg agg tgt cga tgc cat    386
Thr Gly Arg Leu Lys Gln Thr Arg Ser Lys Val Arg Cys Arg Cys His
            35                  40                  45 ggc cag act ctg ggc gaa gca tgg gcc acc ctg gtc ttc atg ctt gaa    434
Gly Gln Thr Leu Gly Glu Ala Trp Ala Thr Leu Val Phe Met Leu Glu
        50                  55                  60 aga aga agg gag ctc ctc gga ctg aca tct gag ttt ttt caa agc gcc    482
Arg Arg Arg Glu Leu Leu Gly Leu Thr Ser Glu Phe Phe Gln Ser Ala
    65                  70                  75 ttg gag ttt gct ata aaa ata gac caa gct gaa gat ttt ctg cag aat    530
Leu Glu Phe Ala Ile Lys Ile Asp Gln Ala Glu Asp Phe Leu Gln Asn
80                  85                  90                  95 cct cac gag ttt gag agt gcc gaa gcc tta cag tca ctt ctt ctg ctt    578
Pro His Glu Phe Glu Ser Ala Glu Ala Leu Gln Ser Leu Leu Leu Leu
                100                 105                 110 cat gac cga cac gcc aaa gaa ctc tta gaa cga tct cta gtc ctt tta    626
His Asp Arg His Ala Lys Glu Leu Leu Glu Arg Ser Leu Val Leu Leu
            115                 120                 125 aac aaa agc caa caa ctc act gac ttc ata gaa aaa ttc aag tgt gat    674
Asn Lys Ser Gln Gln Leu Thr Asp Phe Ile Glu Lys Phe Lys Cys Asp
        130                 135                 140 gga tct cct gtg aat tct gag ctc atc cag gga gct cag agc agt tgt    722
Gly Ser Pro Val Asn Ser Glu Leu Ile Gln Gly Ala Gln Ser Ser Cys
    145                 150                 155 ctg aag atc gac agc ctc ctt gaa ctt ctg caa gac agg aga agg cag    770
Leu Lys Ile Asp Ser Leu Leu Glu Leu Leu Gln Asp Arg Arg Arg Gln
160                 165                 170                 175 ctg gac aag cac ttg cag caa cag agg cag gag ttg tct cag gtt ctg    818
Leu Asp Lys His Leu Gln Gln Gln Arg Gln Glu Leu Ser Gln Val Leu
                180                 185                 190 cag tta tgt ctg tgg gac caa caa gaa agc cag gtt tct tgt tgg ttt    866
```

```
      Gln Leu Cys Leu Trp Asp Gln Gln Glu Ser Gln Val Ser Cys Trp Phe
                  195                 200                 205
     FIGURE 32 (cont.)

cag aaa aca ata aga gat ctg cag gaa cag agt ctg ggt tca tcc ctt      914
     Gln Lys Thr Ile Arg Asp Leu Gln Glu Gln Ser Leu Gly Ser Ser Leu
             210                 215                 220 tca gac aac aaa gag tta atc cgt aag cac gag gac ctg cca tca aag      962
     Ser Asp Asn Lys Glu Leu Ile Arg Lys His Glu Asp Leu Pro Ser Lys
             225                 230                 235 caa aga gtc cct gca gtt tag gaattgaaca gaacagtttc ctgattgaat        1013
     Gln Arg Val Pro Ala Val  *
     240                 245 gatcttggcg cctyyttanc ggntgcagat ggtggggctt cctctggntt ctcatcctct   1073
     tccactaatc tggatttttg ttcccctggt gtgccacatc actttaattt gaaagaaaaa   1133
     aaataaattg ggccggaaaa aaaaaaaaaa aaaaaaaaar rrscggccnc              1183
```

FIGURE 33

```
tctagcgaac ccctccgcgc aagatggccg cttcccagac cgctccgcgg catcttcaag      60
atgcgcgaga agaacgtgca atctcgcgag atcaggctcg ctcgcgggca gtctgctcgc     120
agcctaccct tcctaggagt tggaggaggg aaagctagat tcgattaaga gcaaaaaatt     180
gttccagcag cagagcagct gtccaaggaa gtatccaaag gaactgcacc tcagtaaact     240
cctggcaagt cttaggatat gacaaagggc acaggatgca ttatgagaaa ggaaggctaa     300
ggttttcaag aacacagatt tacatcaaac ttgcgttctg aattaatctt tgagaatact     360
ggactgtgag ctagacattg agtaagaggt ttgttatatc aagaatgtga tctaaaaaaa     420
aaacattcat atcttcctcc cacaagagga tattttgaaa ctgtgggtca aagtcagact     480
acaggagagc cctcaaatat gccaaatgtg acagacagca ggattttgaa aatatagtgg     540
gagtatgtga agatgttcca gtcaaagaga cattgtttcc aaaggaaaga aagtccagtc     600
gcctcacagg aattgtgtat tccctggtag taatgcaaat ggaccacata tggctttctt     660
ctttaaagag aatacctaat tttagctaca gagtaaaatg ctgatgatac aaaccgtgac     720
aagtggaggg acaagaaagt aaatggactg atggtgccat tgtggactgg gagggtaaaa     780
gctgtacatt tgtgaacaaa aagatttcct tgttatggtc agccatgatt ctaactgcta     840
aatggaggca gtaacaacat gacctaaaga gtaaacatcc agagatggaa tgttctcaat     900
gtctgaaaag gagcagatat ctggtgtatg tgaatgtatg ctagagattt tttacaagcc     960
tgtggtgaat tagtaattgt attttatttt gaaagttaaa caggtaatta gaaaccccaa    1020
aaaaaaaaaa aataaaaaaa aagcggccgc c                                   1051
```

FIGURE 34

```
tctagcgaac cccttcgctg aaaccaccgt tcacacggga aacctgggtt aggcttttgt    60
cctcagtgac acagaggatg tagtccacag ctaggtagaa atgtcaggtt cccaacacta   120
ctccagctgt gactttgatg cttgggggat ggggtcgcag gctatttct  ctgctttaac   180
agttcataga atttaacaga taagagttag tgtctttcat gtggcctcac tctggagtta   240
tgagaacata cacacggttt acagcttttc aatatnccttt tccctggcca tcaagtattt   300
tgaaagtgtg ccaccttta  acctttgcgc tttatttttt tttctttttt taaagntgaa   360
ggtgataatt cttctatata tgatgaaact caatgtctac tgaaataagt gtaaccttag   420
ctatncacgt ttatntttta aaaccacgct atggagatat taccccgagt tctgtcnttt   480
ngcaagattt acagnacctt cccncccccc cttttagcat tnaataaaaa natattgggg   540
agcncnntna aaaaaaaaaa aatnaanaaa agcggc                             576
```

FIGURE 35

```
tctagcgaac cccttcgcgt gatctgatcc gagctgagac ttggggagct ctggctccgt      60
gttggctgca gcatccccca tggtcttgtc tgaggtgtcc tgtgactcga ctcttcagaa     120
ctcaatgaag tagatgactt gactacaatg tggaaacatc atg aca gaa agt gtg      175
                                              Met Thr Glu Ser Val
                                                1               5 gtt tgt acc ggg gcc gtc agc act gta aag gaa gtc tgg gaa gaa aga       223
Val Cys Thr Gly Ala Val Ser Thr Val Lys Glu Val Trp Glu Glu Arg
                10                  15                  20 ata aag aaa cat cat gaa gat gtg aaa cga gag aag gaa ttt cag caa       271
Ile Lys Lys His His Glu Asp Val Lys Arg Glu Lys Glu Phe Gln Gln
            25                  30                  35 aag cta gtg cgg atc tgg gaa gac cga gtg agt tta act aag ctg aaa       319
Lys Leu Val Arg Ile Trp Glu Asp Arg Val Ser Leu Thr Lys Leu Lys
        40                  45                  50 gag aag gtg acc agg gaa gat gga aga atc att cta agg ata gag aaa       367
Glu Lys Val Thr Arg Glu Asp Gly Arg Ile Ile Leu Arg Ile Glu Lys
    55                  60                  65 gag gaa tgg aag act ctc cct tct tcc tta ctg aaa ctg aat cag cta       415
Glu Glu Trp Lys Thr Leu Pro Ser Ser Leu Leu Lys Leu Asn Gln Leu
70                  75                  80                  85 cag gag tgg caa ctt cat agg acc gga ttg ttg aaa att cct gaa ttc       463
Gln Glu Trp Gln Leu His Arg Thr Gly Leu Leu Lys Ile Pro Glu Phe
                90                  95                  100 att gga aga ttc cag cat ctc att ggt cta gac tta tct cgg aac aca       511
Ile Gly Arg Phe Gln His Leu Ile Gly Leu Asp Leu Ser Arg Asn Thr
            105                 110                 115 att tca gag atc ccc ccg agg cat tgg act gnt cac tta gac ttc aag       559
Ile Ser Glu Ile Pro Pro Arg His Trp Thr Xaa His Leu Asp Phe Lys
        120                 125                 130 gaa ctg att ctt agc tac aca aaa tca a                                 587
Glu Leu Ile Leu Ser Tyr Thr Lys Ser
    135                 140
```

FIGURE 36

```
tctagcgaac cccttcggtt ctgttggcta cacagctgca gagccatggc tgaccgttca    60
ctgtcagggg cacatgttac actaagcttc atgacagtga tgtaataatg ttacacattt   120
gtcttgtagt tatgtattga agtttctgtc ctgttttgtg taaaaatgta tccactcttg   180
tatatattta gacttgaaac taccacacaa atattggaac ggtttgcttt atgaagttaa   240
aagtatcctt ccgaatggaa ctaacttgct ttgtgctcag acatatacta tgctgatgta   300
ttttgcaata tactatctta aattaaatct ggtcactttg ttgccttttt aaaaagtgtg   360
gtatttcaag tagagttatt ttcctgaaat atatttgcaa actcaagctg ctttataatc   420
aaggaatatt tttattgatt gaagaaaatg actgctgcaa ttcaaaagtg aacttatttt   480
attatataga tgatttctta aaagctattt ataccatgat acaaaatcat gtagtgatcc   540
tgggagtctg tagttcttcc tgttaataac attcaacact gtatgctaga ggcagcaatg   600
ccaacactga agttattttg ggtgaaaacc gtcgttctgn cctgtttagc tggggattat   660
taaatccata taatgtatgt gcttatgtat gctacatgtg caagttaggt gtttcctttg   720
tgttctgctt attaaatgtc attcagattc acttcctgaa ttctaataaa gagggaagct   780
attggaaaaa ataaaaaaaa aaaaaaaaaa gcggccgcc                          819
```

FIGURE 37

```
tctagcgaac cccttcggtg gcgcacgccg gtaggatttg ccacgcaaat gctggaatta      60
aagacatgca gcagcagcgc cctgtggttt tggttttta tttgattgct tatttttatc     120
taattttaa ttttttgtgt atgaacgttt tatctgcatt tatgtctctg taccacattc     180
gtgcctggtg ctatggaggc caaaaaagga tttttaggccc gagattgtag ttatagatgg     240
ttgtgggctg ccaatctgag tgctgaaaat taaacctggg tactctgaaa gaccagccag     300
tgctcttaac tatcaggcca cctctccagc actatttat tttattttat ttgtggagat     360
agggtctctc tctctgtatc ctagtctaac ttaaaacata aagaatattc tgtatcagta     420
tccttgagta ctaggattct aggcacctgt cattatgcct agattttaa cagtgtgtgt     480
taattctaca taaaaatgaa tttcattatt acattttcac acttgtgaag aatatacttt     540
gatcatattc ccttctcctg atactttttc ctatccttcc tcccactcc attagttccc      600
ttcttctttt cagagtctac cttctacttt ttactttgat tttttccc ccacattctg      660
tggttgagag aatgcatatt acagttgtat ttctgaatct ggctaggtac attcacttaa     720
cataattaat gatcctgggc gagcgaaggg gttcncctan caacccctt cggttcaata     780
ccatttcaga gatgggcatt tccctcaatg aaatacacaa gtaaacattc cgacattgtc     840
tttaggagtg tttgttaaaa aaaaaaaaa aaaaaaccan ancccaaaan caaaaaaaaa     900
aaagctttgc accttgcaaa agtggtcctg gcgtgggtag attgctgtta atcctttatc     960
aataacgttc tatagagaat atataaatat atatataatt atatctccta gtccctgcct    1020
cttaagagcc gaaaatgcat gggtgttgta gacattcggt tgcactaaat tcctctctga    1080
attttggctg ctgaagccgt tcatttagca actgtttata ggtggttgat gaatggttcc    1140
ttatctccat ttcttcctat gtagcttaag ccgcttcctt cacagaatct aataatctcg    1200
tctaggccat tagccctgcc ctttcttaac attcttgtat ttgttgaatt tggcctcctc    1260
gaaagcaata gcaactgggt ggcccaccca agttttaacg cccctgattc catctatggc    1320
atttgtacca aatataagtt ggatgcattt attttagaca caaagctta ttttttcgac    1380
atcgtgtttc aagaaaaaaa acaaatagaa taacaataac tatgactttg aggccaatca    1440
ttttaggtg tgtgttgaa gcatagaacg tctnttaaac tctcaatggt tccttcaaat    1500
gatgagttag tatgtaacgt aaatagcagt ttctctctct ctctctctct ttttatttt    1560
tccanataga gcactatgta aatttagcat atcaataata caggaactat ccnccaaaaa    1620
aaaaaaaaaa aaaaaaaaaa gcggccgc                                      1648
```

FIGURE 38

```
tctagcgaac cccttcgtag aactaggagc cagtgttgac cacggtcggt ggctggatac    60
cccactgcat gctgcagcaa ggcagtccag tgtggaggtc atcaatctgc tcactgagta   120
tggggctaac ctgaaactca gaaactcgca gggcaaaagt gctcttgagc tcgctgctcc   180
caaaagtagt gtggagcagg cactcctgct ccatgaaggt ccacctgctc tttctcagct   240
ctgccgcttg tgtgtccgga agtgcttggg ccgcac atg tca tca agc cat cta    294
                                       Met Ser Ser Ser His Leu
                                         1               5 cgc act agg tct gcc aga acc cct gga aaa att cct ctt ata cca ata    342
Arg Thr Arg Ser Ala Arg Thr Pro Gly Lys Ile Pro Leu Ile Pro Ile
         10              15                  20 gtt gga aac atg ttg cct gct gta gga cac tta ata tac aca ttc agt    390
Val Gly Asn Met Leu Pro Ala Val Gly His Leu Ile Tyr Thr Phe Ser
         25              30                  35 ggc tta acc cac tat cct aaa aat ctg ctt acc taa ttagaataaa         436
Gly Leu Thr His Tyr Pro Lys Asn Leu Leu Thr  *
         40              45 gccttcataa atccaaatac ttgcgttgaa caaactcctg gttaggttaa tggntgccaa   496
gagataacca gaaacctttc aagttttta ctcttggtaa tttaaaatca aactgaaata    556
gatggaaaat aataatctat ttttggataa ttcaaggacc cttcagtatc tggggctggg   616
gtccgcattt tgnatactgg atagacacac acacaggtag gatanggtaa atnaactact   676
taaagaatgg cctgggattt aagtcctcca gatattttt aggtngnggt ttcctaaaat    736
aaaattctgg agtgccaaaa aaaaaaaaaa aaaaaaaag cgggcc                  782
```

FIGURE 39

```
gtctagcgaa ccccttcggg aaacttcaac aaaggtacca gcaactacag cgccttgtcc    60
acccagattt cttcagccaa aagtctcaga ctgagaaacg gttctcggag aagcattcga   120
ccctggtgaa tgatgcctac aagactcttc aggcccccgt gagcagagga ctatatcttc   180
taaagctcca aggaatagaa attcctgaag ggacagatta tagaacagac agtcagttcc   240
ttgtggaaat c atg gaa atc aat gaa aaa ctc gca gac gcc aaa agt gag   290
            Met Glu Ile Asn Glu Lys Leu Ala Asp Ala Lys Ser Glu
             1               5                  10 gca gcc atg gaa gag gta gaa gcc act gtc aga gct aaa cag aaa gaa   338
Ala Ala Met Glu Glu Val Glu Ala Thr Val Arg Ala Lys Gln Lys Glu
         15                  20                  25 ttt acg gac aat ata aac aga gct ttt gaa caa ggt gat ttt gaa aaa   386
Phe Thr Asp Asn Ile Asn Arg Ala Phe Glu Gln Gly Asp Phe Glu Lys
 30                  35                  40                  45 gcc aag gaa ctt ctt aca aaa atg aga tac ttt tca aac ata gaa gaa   434
Ala Lys Glu Leu Leu Thr Lys Met Arg Tyr Phe Ser Asn Ile Glu Glu
             50                  55                  60 aag atc aag tta agc aag aac cct ctc tag ttgctaactt aaaggtttaa     484
Lys Ile Lys Leu Ser Lys Asn Pro Leu  *
                 65                  70 aaataaactt tgtatttctt cannnnnnan nnnnannntn nnnnagcggc cgcc         538
```

FIGURE 40

```
tctagcgaac cccttcgcga aggggttcgc ttcttaccct gtggagaaag gggcaggagg      60
aacctcctgt gttaggagga agctggagct taccactgtg agaggacaga tgtggactga     120
gaattttctt agtgctcagt ggcacttccc aaggactccc ctcccttgt gctctgtgcg      180
gttttagga cagctaagat gactgccacc tgttgtggca ggcccgattt gtcttgttct      240
ccccttactg tacccgata taatctctgt tgatcaacag gactacccca agaatccaca     300
tgttctcccc cgtaaccagg cagctgtctg gttcatgcct tcttcccttc aaacccaacc     360
cagcgcccct tgttagtgaag aggtggtcca tggactgatg acaagttatt agcactggat   420
gctgtttcca tagtgacaag cctataccct ttcccaccct ttagtgcgca gtgggctgct    480
gcttcagtat cctcccagct cagtttatt agatcaaagc tgcccttggg caccatgttg     540
gccacctcaa tcaccagcca aaatggtcgc tttgtccacc agaggtcaag ccatctttct    600
ggcgctgtag ttcccagctc cttctaggga acaggaagtt gatattgcca tgggggaggt    660
ggcggggtgt ggccgtcacc tcaatagttt tactgtaaaa gggaaatttg aacaagaaca    720
acaacaaaaa aaaaaaaaaa acaaagaaaa aaataaaaaa ctttaaaagt tgaaaaaaaa    780
aaaaaaaaaa aaaaaagcg gccgc                                           805
```

FIGURE 41

```
tctagcgaac ccctccgctg ggacccgcaa ctaccaactg ccgcctggat cctaggtgag      60
ctgtgggctc tgacagcgct gtggctaac atg gca ccc aaa aag aag act ctc      113
                                Met Ala Pro Lys Lys Lys Thr Leu
                                 1               5 aag aag aac aaa ccc gag atc aat gag atg acc atc atc gtg gaa gac      161
Lys Lys Asn Lys Pro Glu Ile Asn Glu Met Thr Ile Ile Val Glu Asp
         10              15                  20 agc ccc cta aac aag ctg aat gct cta aat ggg ctc ctg ggg gga gaa      209
Ser Pro Leu Asn Lys Leu Asn Ala Leu Asn Gly Leu Leu Gly Gly Glu
     25              30                  35                  40 aac agc ctt agc tgt gtt tct ttc gaa cta aca gac act tct tat ggt      257
Asn Ser Leu Ser Cys Val Ser Phe Glu Leu Thr Asp Thr Ser Tyr Gly
                 45                  50                  55 ccc aac ctc ctg gaa ggt tta agt aaa atg cgt caa gag agc ttt cta      305
Pro Asn Leu Leu Glu Gly Leu Ser Lys Met Arg Gln Glu Ser Phe Leu
             60                  65                  70 tgt gac ttg gtc atc ggt cca aaa cca agt cct ttg atg tcc ata agt      353
Cys Asp Leu Val Ile Gly Pro Lys Pro Ser Pro Leu Met Ser Ile Ser
         75                  80                  85 caa gtg atg gct tcc tgc agc gag tct tct ata ata tcc tta aaa cga      401
Gln Val Met Ala Ser Cys Ser Glu Ser Ser Ile Ile Ser Leu Lys Arg
     90                  95                 100 tcc atc gac aaa aag ggt aga cct caa tga tatcgnccct ttagggctac         451
Ser Ile Asp Lys Lys Gly Arg Pro Gln  *
105                 110 caccgtgata gcatatgcat acacnggaaa gctgcccttt ctttatacac aataaggaag     511
catcattcct gctgctgtgt acctccagat ccacactctt gtgaagatgt gcagcgactt     571
tctgatccga gagatcagtg ttgagaactg catgtatgtt gttaacatgg ctgaaacata     631
ctgcttgaaa aatgcgaaag caacggccca gaaattatc cgggataact tcattgaatt      691
tgccgactcc gaacaattta tgaagctgac gtttgaacag attaatgagc ttctcataga     751
tgatgacttg cagttgcctt ctgagctggt agcattccag attgcaatga aatggataga     811
attcaaccaa aagagagtga agcacgctgc ggatctttta agcaatattc gctttggtac     871
catctctgca caagacctgg tcaattacgt tcaaaccgta ccgagaatga tgcaagacgc     931
tgattgtcat aaactgcttg tggatgctat gaactaccac ttactacctt atcatcaaaa     991
cacgttgcaa tctaggcgga caagaattag aggcggctgc cgggttctga tcactgtcgg    1051
gggacgccct ggcctgactg agaagtccct tagtagagac gtttatatag agaccctgaa    1111
aatggatgga gcaagcttac agaaatgcca gccaagagtt tcaatcagtg tgtggctgtg    1171
atggatggat tcctttatgt agcaggtggt gaggaccaga atgatgcgag aaaccaagcc    1231
aagcatgcag tcagcaattt ctgcaggtac cgatcccgc ttcaacacgt ggatccacct    1291
gggcagcatg aaccagaagc gcacgcactt cagcctgagc gtgttcaacg ggctcctgta    1351
cgccggtggn gggcnccagt gnganggata tctgcagaat tcggctagcc gaattc        1407
```

FIGURE 42

```
tctagcgaac cccttcggac actgccagca tagacagcag cccctgctac tgtcccacca      60
ctgtacccca gagccccgac tagcagt atg ccg gga gcg cca ggg cct ggg cct    114
                              Met Pro Gly Ala Pro Gly Pro Gly Pro
                                1                 5 gag gtg gct gca gcc ttt gag gaa cgg ttg agt cag gca cta cag gaa      162
Glu Val Ala Ala Ala Phe Glu Glu Arg Leu Ser Gln Ala Leu Gln Glu
 10              15                  20                  25 ctg cag gca gtg gct gaa gca ggc cgg tca gcg gtg acc cag gca gct      210
Leu Gln Ala Val Ala Glu Ala Gly Arg Ser Ala Val Thr Gln Ala Ala
                 30                  35                  40 gat gca gcc cta gcc act gta gag cca gtg gct cag gca tct gaa gag      258
Asp Ala Ala Leu Ala Thr Val Glu Pro Val Ala Gln Ala Ser Glu Glu
             45                  50                  55 ctt cgg gcc gag aca gca gcc ctg agc cgg cgg ctg gat gcc ctg acc      306
Leu Arg Ala Glu Thr Ala Ala Leu Ser Arg Arg Leu Asp Ala Leu Thr
         60                  65                  70 agg cag gtg gag gtg ctg agc cta cgg ctg ggt gtt cca ctc gtg ccg      354
Arg Gln Val Glu Val Leu Ser Leu Arg Leu Gly Val Pro Leu Val Pro
     75                  80                  85 gac ctg gag tcc gag cta gag ccc agc gag ctg ttg ctg gct gct gcc      402
Asp Leu Glu Ser Glu Leu Glu Pro Ser Glu Leu Leu Leu Ala Ala Ala
 90                  95                 100                 105 gac cct gag gcc ctc ttc cag gca agc tga ggatgctggg accccgtgg         452
Asp Pro Glu Ala Leu Phe Gln Ala Ser  *
                 110 ccacccgcct gcctttagca cccgccgcag ctcttctgcg ggcccctctc gaagcagcag    512
tctcatggag cccgatccag cagagccccc ctctgccaca gtggaagcag ctaatggaac    572
agagcagact ctggacaaag tgaacaaagg ccagagaggg cggagccccc tgagtgcaga    632
ggagctgatg gccattgagg acgaaggaat cctggacaag atgctggacc aggctacgaa    692
ctttgaagag cggaagctca tccgggctgc gctccgtgag ctccgacaaa gaaagagaga    752
ccagagggac aaggaacgag aacggcggct acgagggca cgggcccggc caggcgagag    812
ccgaagcaat atggctacta cagagaccac caccaggcac aagccagagg gcggctgatg    872
gctcggcggt cagcacagtt accaaaactg agcgggtcgt ccactccaat gacggcacgc    932
agactgcgcg caccaccaca gtggagtcga gtttcgtgag gcgctcggag aatggcagca    992
gcaagcaagc agcagcacca cggtccaaac caagaccttt tcctcttcct cttcctcatc   1052
caaaaaaatg ggcagtatct tcgaccgaga ggaccaaacc agctcacgtt ctggcagcct   1112
ggcggccctc gaaaacgcc aggcagagaa gaagaaagag ctcatgaagg cacagagtct    1172
gcccaagacc taagcgtccc aagcacgcaa ggccatgatt gagaaactag agaaggaagg   1232
ctcttcgggc agtcctggca caccccgtac agcggtacag cgttctacca gcttcggagt   1292
ccccaacgcc aacagcatca agcagatgtt gctggactgg tgccgagcca agacccgtgg   1352
ctacgagcac gtggacatcc agaacttctc tccagctgga gtgatgggat ggctttctgt   1412
gccctggtgc acaatttctt ccctgaggct tttgactatg gacagcttag cccacaaaac   1472
cggcgccaga actttgaaat ggccttctca tctgctgaga cccatgcgga ctgcccgcag   1532
ctcctggata cagaggacat ggtgcggctt cgagagcctg actggaagtg cgtgtacacg   1592
tacatccagg agttctaccg ctgtctggtc cagaaggggc tggtaaaaac caaaaagtcc   1652
```

FIGURE 43

```
tctagcgaac cccttcgctc cagggcgttt gcctcctgct gacttgctct tcaccattag      60
acaagcctga cgtcaagacc cca atg gct aac gaa gct aac cct tgc cca tgt     113
                         Met Ala Asn Glu Ala Asn Pro Cys Pro Cys
                          1               5                  10 gac att ggt cac agg cta gac tat ggt ggc atg ggc cag gaa gtt cag       161
Asp Ile Gly His Arg Leu Asp Tyr Gly Gly Met Gly Gln Glu Val Gln
             15                  20                  25 gtt gag cac atc aag gca tat gtc acc cgg tcc cct gtg gat gca ggc       209
Val Glu His Ile Lys Ala Tyr Val Thr Arg Ser Pro Val Asp Ala Gly
             30                  35                  40 aaa gct gtg att gtt gtc cag gat ata ttt ggc tgg cag ctg tcc aac       257
Lys Ala Val Ile Val Val Gln Asp Ile Phe Gly Trp Gln Leu Ser Asn
             45                  50                  55 acc agg tat atg gct gac atg att gct gga aat gga tac aca act att       305
Thr Arg Tyr Met Ala Asp Met Ile Ala Gly Asn Gly Tyr Thr Thr Ile
    60                  65                  70 gcc cag act tct ttg tgg gtc aag agc cat ggg acc cgg ctg gtg att       353
Ala Gln Thr Ser Leu Trp Val Lys Ser His Gly Thr Arg Leu Val Ile
    75                  80                  85                  90 ggt cca cct tcc ctg agt ggt tga aatcaagaaa tgccagaaaa atcaaccgag      407
Gly Pro Pro Ser Leu Ser Gly  *
                         95 aggttgatgc tgtcttgagg tatctgaaac aacagtgtca tgcccagaag attggcattg     467
tgggcttctg ctggggggt attgtggtgc accacgtgat gacgacatat ccagaagtca      527
gagcgggggt gtctgtctat ggtatcatca gagattctga agatgtttat aatttgaaga     587
acccaacgtt gtttatcttt gcagaaaatg atgctgtgat tccacttgag caggtttcta    647
tactgatcca gaagcttaaa gaacactgca tagttaatta ccaagttaag acattttctg    707
ggcaaactca tggctttgtg catcggaaga gagaagactg ctcccctgca gacaaaccct    767
acattgagga agcgaggagg aatctcatcg aatggctgaa caagtatatt taacagcact    827
caagcacaaa ttttgaataa ttaaattgac ccgaataatt aaattgaccc gaat           881
```

```
taacccctgc ttggggcccc acggatgctg gtggactgtg tacccttggt ggaggtggag   1712
gacatgatga tcatgggcaa aaagccagac cctaagtgcg tcttcaccta cgtgcaatcg   1772
FIGURE 42 (cont.)

ctgtacaacc acctgcggcg ccatgagctg cgcctgcgcg gcaagaatgt ctagccactg   1832
ctcacaccgc ctgcgctgca ggctgctgtc ccacgccccc aacaccggnc cctncagtgn   1892
gcctgccact gntgcccgtn tgtcgaaaca cctntcccct tgtcacacgc agngntttga   1952
taaattattt gntttnaaca aaaaaaaaaa aaaaaaaaaa aaaagcggcc gc           2004
```

FIGURE 44

Regulated expression of Full-length novel clones:

| Seq ID | CloneID | Kidney PKD | Kidney Na+ Ang2 | Hyp 10w | Heart LV 2w | 4w | 8w | 12w | 16w | Heart Spt 2w | 4w | 8w | 12w | 16w |
|---|---|---|---|---|---|---|---|---|---|---|---|---|---|---|
| 1 | P00184_D11 | — | — | — | — | ▽ | ▽ | ▽ | — | — | — | — | ▼ | ▼ |
| 2 | P00185_D11 | — | — | ▽ | ▽ | — | — | ▽ | — | — | — | — | — | — |
| 3 | P00188_D12 | — | — | ▽ | ▽ | — | — | — | — | — | — | — | — | — |
| 4 | P00188_E01 | — | — | — | ▲ | ▲ | ▲ | ▲ | ▲ | — | — | — | — | ▲ |
| 5 | P00194_G01 | — | — | — | ▲ | ▲ | — | ▲ | ▲ | — | — | — | — | — |
| 6 | P00194_G05 | — | — | — | — | — | ▲ | ▲ | ▲ | — | — | — | — | ▲ |
| 7 | P00194_H10 | | | — | ▲ | — | — | — | — | — | — | — | — | — |
| 8 | P00199_D08 | — | — | — | ▽ | ▽ | — | — | ▽ | — | — | — | — | — |
| 9 | P00203_D04 | ▲ | ▲ | ▽ | — | ▲ | — | — | — | — | — | — | — | — |
| 10 | P00203_E06 | — | — | ▽ | ▽ | ▽ | ▽ | ▽ | ▽ | — | — | — | — | — |
| 11 | P00209_F06 | | | — | ▲ | ▲ | — | ▲ | ▲ | — | — | — | — | — |
| 12 | P00219_D02 | — | — | — | — | — | — | ▲ | — | — | — | — | — | — |
| 13 | P00219_F06 | — | — | — | ▲ | ▲ | ▲ | ▲ | — | — | — | — | — | — |
| 14 | P00220_H05 | — | — | — | — | — | — | — | ▲ | ▲ | — | — | — | — |
| 15 | P00222_G03 | | | — | — | ▽ | ▽ | ▽ | — | — | ▽ | — | ▽ | — |
| 16 | P00223_F07 | | | ▽ | — | — | — | — | — | — | — | — | — | — |
| 17 | P00225_C01 | | | — | — | — | ▲ | ▲ | ▲ | — | — | ▲ | ▲ | ▲ |
| 18 | P00227_D11 | | | — | ▲ | — | — | — | ▲ | — | — | — | — | — |
| 19 | P00228_F03 | | | — | ▲ | ▲ | — | ▲ | ▲ | ▲ | — | — | — | — |
| 20 | P00233_H08 | — | — | — | ▲ | ▲ | ▲ | ▲ | ▲ | — | — | — | — | — |
| 21 | P00235_G08 | ▲ | — | — | — | — | — | — | — | — | ▽ | — | ▽ | — |
| 22 | P00239_C11 | — | — | ▲ | ▲ | — | — | — | ▲ | ▲ | — | — | — | — |
| 23 | P00240_B04 | — | — | ▽ | — | — | — | ▽ | — | — | ▽ | — | ▽ | — |
| 24 | P00240_E05 | | | ▽ | — | — | — | — | — | — | — | — | — | — |
| 25 | P00241_E12 | | | — | — | — | — | ▽ | — | ▽ | ▽ | — | ▽ | — |
| 26 | P00245_D06 | ▲ | — | — | ▽ | — | — | — | — | — | — | — | — | — |
| 27 | P00246_D12 | | | — | — | — | — | — | — | — | ▽ | — | ▽ | — |
| 28 | P00247_A04 | | | — | ▽ | ▽ | ▽ | — | ▽ | — | — | — | — | — |
| 29 | P00248_B04 | | | ▽ | — | — | — | — | — | — | — | — | — | — |

FIGURE 44 (CONT.)

| Seq ID | CloneID | Kidney PKD | Kidney Na+ Ang2 | Kidney Hyp 10w | Heart LV 2w | 4w | 8w | 12w | 16w | Heart Spt 2w | 4w | 8w | 12w | 16w |
|---|---|---|---|---|---|---|---|---|---|---|---|---|---|---|
| 30 | P00249_F09 |  |  | — | ▲ | ▲ | ▲ | ▲ | ▲ | — | ▲ | — | ▲ | ▲ |
| 31 | P00258_A10 |  |  | — | ▲ | ▲ | ▲ | ▲ | ▲ | — | — | — | — | — |
| 32 | P00262_C10 |  |  | ▲ | — | ▽ | — | — | — | — | — | — | — | — |
| 33 | P00263_G06 |  |  | ▲ | — | — | — | — | — | — | — | — | — | — |
| 34 | P00267_F08 | — | — | ▽ | — | ▲ | — | ▲ | — | — | — | — | — | — |
| 35 | P00269_H08 |  |  | ▲ | — | ▽ | — | ▽ | ▽ | — | — | — | — | — |
| 36 | P00312_C04 |  |  |  | — | — | ▽ | — | — | — | — | ▽ | — | — |
| 37 | P00324_H02 |  |  |  | — | ▽ | ▽ | ▽ | — | — | ▽ | ▽ | ▽ | ▼ |
| 38 | P00628_H02 | ▲ | — |  | — | — | ▲ | ▽ | ▽ | — | — | — | — | — |
| 39 | P00629_C08 |  |  |  | — | ▽ | — | — | ▽ | — | — | — | — | — |
| 40 | P00634_G11 |  |  |  |  |  |  |  |  |  |  |  |  |  |
| 41 | P00641_G11 | — | — | ▲ | — | — | — | — | — | — | — | — | — | — |
| 42 | P00648_E12 |  |  |  |  |  |  |  |  |  |  |  |  |  |
| 43 | P00697_C03 | ▽ | — | — | — | — | — | ▽ | ▽ | — | — | — | — | — |

SECRETED FACTORS

SECRETED FACTORS

This application claims benefit under Title 35, United States Code §119(e) of U.S. provisional application No. 60/193,548 filed on Mar. 31, 2000.

FIELD OF THE INVENTION

The present invention concerns secreted factors encoded by genes differentially regulated in certain diseased tissues. More particularly, the invention concerns nucleic acid encoding novel secreted polypeptide factors, the encoded polypeptides, and compositions containing and methods and means for producing them. The invention further concerns methods based on the use of such nucleic acids and/or polypeptides in the diagnosis and treatment of various diseases, in particular cardiac, renal, or inflammatory diseases.

BACKGROUND OF THE INVENTION

Gene expression patterns, including changes in gene expression between normal and diseased tissues or tissues in various stages of disease progression provide valuable insight into the molecular determinants of normal and abnormal cellular physiology. Accordingly, genes that are differentially expressed in subjects suffering from a disease, such as cardiac, renal or inflammatory disease, relative to normal subjects, are useful targets for intervention to diagnose, prevent or treat such diseases.

Techniques have been developed to efficiently analyze the level of expression of specific genes in cells and tissues. Procedures that can be used to identify and clone differentially expressed genes include, for example, subtractive hybridization (Jiang and Fisher, *Mol. Cell. Different.* 1:285–299 [1993]; Jiang etal., *Oncogene* 10, 1855–1864 [1995]; Sagerstrom et al., *Annu. Rev. Biochem.* 66: 751–783 [1997]); differential RNA display (DDRT-PCR) (Watson et al., *Developmental Neuroscience* 15:77–86 [1993]; Liang and Pardee, *Science* 257:967–971 [1992]); RNA fingerprinting by arbitrarily primed PCR (RAP-PCR) (Ralph et al., *Proc. Natl. Acad. Sci. USA* 90:10710–10714 [1993]; McClelland and Welsh, *PCR Methods and Applications* 4:S66–81 [1994]); representational difference analysis (RDA) (Hubank and Schatz, *Nucl. Acids Res.* 22:5640–5648 [1994]); serial analysis of gene expression (SAGE) (Velculescu et al., *Science* 270:484–487 [1995]; Zhang et al., *Science* 276:1268–1272 [1997]); electronic subtraction (Wan et al., *Nature Biotechnology* 4:1685–1691 [1996]); combinatorial gene matrix analyses (Schena et al., *Science* 270:467–470 [1995]), and various modifications and improvements of these and similar techniques.

A particularly attractive method for assessing gene expression is the DNA microarray technique. In this method, nucleotide sequences of interest are plated, or arrayed, on a porous or non-porous substrate that can be paper, nylon or other type of membrane, filter, chip, glass slide or any other suitable solid support. The arrayed sequences are then hybridized with specific DNA probes from cells or tissues of interest. Microarrays of biological materials have been described in a number of patents and patent applications, including, for example, U.S. Pat. Nos. 5,744,305; 5,800,992; 5,807,522; 5,716,785; and European Patent No. 0 373 203.

The DNA microarray technique can be used to monitor the expression level of large numbers of genes simultaneously (to produce a transcript image), and to identify genetic variants, mutations and polymorphisms. This information may be used to determine gene function, understanding the genetic basis of disease, diagnosing disease, and developing and monitoring the activities of therapeutic agents.

An important application of the microarray method allows for the assessment of differential gene expression in pairs of mRNA samples from two different tissues, or in the same tissue comparing normal versus disease states or time progression of the disease. Microarray analysis allows one to analyze the expression of known genes of interest, or to discover novel genes expressed differentially in tissues of interest. Thus, an attractive application of this technology is as a fundamental discovery tool to identify new genes, and their corresponding expression products, which contribute to the pathogenesis of disease and related conditions.

Microarray technology has been successfully applied to large-scale analysis of human gene expression to identify cancer-specific genes and inflammatory-specific genes (DeRisi et al., *Nat. Genet.,* 14(4):457–60 [1996]; Heller et al., *Proc. Natl. Acad. Sci. USA,* 94(6):2150–55 [1997]). DeRisi et al. examined a pre-selected set of 870 different genes for their expression in a melanoma cell line and a non-tumorigenic version of the same cell line. The microarray analysis revealed a decrease in expression for 15/870 (1.7%) and an increase in expression for 63/870 (7.3%) of the genes in non-tumorigenic relative to tumorigenic cells (differential expression values <0.52 or >2.4 were deemed significant). Heller et al. employed microarrays to evaluate the expression of 1000 genes in cells taken from normal and inflamed human tissues. The results indicated that altered expression was evident in genes encoding inflammatory mediators such as IL-3, and a tissue metalloprotease. These results illustrate the utility of applying microarray technology to complex human diseases.

It would be beneficial to discover differentially expressed genes that are related to diseases or various disease states. It would further be beneficial to develop methods and compositions for the diagnostic evaluation and prognosis of conditions involving such diseases, for the identification of subjects exhibiting a predisposition to such conditions, for modulating the effect of these differentially expressed genes and their expression products, for monitoring patients undergoing clinical evaluation for the prevention and treatment of a disease, specifically cardiac, kidney or inflammatory disease, and for monitoring the efficacy of compounds used in clinical trials.

Secreted proteins mediate key biological processes including cell to cell interactions as well as important cellular functions such as cell growth and differentiation, and most protein-based drugs are secreted proteins including insulin, growth hormone, interferons, tissue plasminogen activator ( tPA), and erythropoietin (EPO). It would, therefore, be particularly desirable to identify novel differentially expressed genes encoding secreted proteins.

SUMMARY OF TIE INVENTION

In one aspect, the present invention concerns an isolated nucleic acid molecule comprising a poly- or oligonucleotide selected from the group consisting of:

(a) a polynucleotide encoding a polypeptide having at least about 80% sequence identity with amino acids selected from the group consisting of: 1 to 1203 of SEQ ID NO: 2, amino acids 1 to 193 of SEQ ID NO: 4, amino acids 1 to 236 of SEQ ID NO:6, amino acids 1 to 61 of SEQ ID NO: 8, amino acids 1 to 79 of SEQ ID NO:10, amino acids 1 to 92 of SEQ ID NO:12, amino acids 1 to 86 of SEQ ID NO:14, amino acids 1 to 36 of SEQ ID NO:16, amino acids 1 to 83 of SEQ ID NO:18, amino acids 1 to 82 of SEQ ID NO:20, amino acids 1 to 462 of SEQ ID NO:22, amino acids 1 to 170 of SEQ ID NO:24, amino acids −26 to 233 of FIG. 13 (amino acids 1 to 259 of SEQ ID NO:26), amino acids 1 to 30 of SEQ ID NO:28, amino acids 1 to 39 of SEQ ID NO:30, amino acids 1 to 541 of SEQ ID NO: 33, amino acids 1 to 30 of SEQ ID NO:35, amino acids 1 to 100 of SEQ ID NO:37, amino acids 1 to 65 of SEQ ID NO:39, amino acids 1 to 42 of SEQ ID NO:41, amino acids 1 to 46 of SEQ ID NO:43, amino acids 1 to 313 of SEQ ID NO:46, amino acids 1 to 58 of SEQ ID NO:51, amino acids −35 to 387 of FIG. 29 (amino acids 1 to 422 of SEQ ID NO:53), amino acids 1 to 58 of SEQ ID NO:55, amino acids 1 to 52 of SEQ ID NO:57, amino acids 1 to 245 of SEQ ID NO:59, amino acids 1 to 142 of SEQ ID NO:63, amino acids 1 to 49 of SEQ ID NO:67, amino acids 1 to 70 of SEQ ID NO:69, amino acids 1 to 113 of SEQ ID NO: 72, and amino acids 1 to 114 of SEQ ID NO:74, and amino acids 1 to 97 of SEQ ID NO:76; or a transmembrane domain (membrane spanning segment/region) deleted or inactivated variant thereof;

(b) a polynucleotide encoding a polypeptide having at least about 80% sequence identity with amino acids 1 to 233 of SEQ ID NO: 26, or amino acids 1 to 387 of SEQ ID NO: 53;

(c) a polynucleotide encoding amino acids selected from the group consisting of: 1 to 203 of SEQ ID NO: 2, amino acids 1 to 193 of SEQ ID NO: 4, amino acids 1 to 236 of SEQ ID NO:6, amino acids 1 to 61 of SEQ ID NO: 8, amino acids 1 to 79 of SEQ ID NO:10, amino acids 1 to 92 of SEQ ID NO:12, amino acids 1 to 86 of SEQ ID NO:14, amino acids 1 to 36 of SEQ ID NO:16, amino acids 1 to 83 of SEQ ID NO:18, amino acids 1 to 82 of SEQ ID NO:20, amino acids 1 to 462 of SEQ ID NO:22, amino acids 1 to 170 of SEQ ID NO:24, amino acids −26 to 233 of FIG. 13 (amino acids 1 to 259 of SEQ ID NO:26), amino acids 1 to 30 of SEQ ID NO:28, amino acids 1 to 39 of SEQ ID NO:30, amino acids 1 to 541 of SEQ ID NO: 33, amino acids 1 to 30 of SEQ ID NO:35, amino acids 1 to 100 of SEQ ID NO:37, amino acids 1 to 65 of SEQ ID NO:39, amino acids 1 to 42 of SEQ ID NO:41, amino acids 1 to 46 of SEQ ID NO:43, amino acids 1 to 313 of SEQ ID NO:46, amino acids 1 to 58 of SEQ ID NO:51, amino acids −35 to 387 of FIG. 29 (amino acids 1 to 422 of SEQ ID NO:53), amino acids 1 to 58 of SEQ ID NO:55, amino acids 1 to 52 of SEQ ID NO:57, amino acids 1 to 245 of SEQ ID NO:59, amino acids 1 to 142 of SEQ ID NO:63, amino acids 1 to 49 of SEQ ID NO:67, amino acids 1 to 70 of SEQ ID NO:69, amino acids 1 to 113 of SEQ ID NO: 72, and amino acids 1 to 114 of SEQ ID NO:74, and amino acids 1 to 97 of SEQ ID NO:76; or a transmembrane domain (membrane spanning segment/region) deleted or inactivated variant thereof;

(d) a polynucleotide selected from the group consisting of: a polynucleotide hybridizing under stringent conditions with the complement of the coding region of SEQ ID NO: 1, wherein said polynucleotide encodes a polypeptide having at least one biological activity o [the polypeptide encoded by clone P00184_D11 (SEQ ID NO: 1), a polynucleotide hybridizing under stringent conditions with the complement of the coding region of SEQ ID NO: 3, wherein said polynucleotide encodes a polypeptide having at least one biological activity of the polypeptide encoded by clone P00185_D11 (SEQ ID NO: 3); a polynucleotide hybridizing under stringent conditions with the complement of the coding region of SEQ ID NO: 5, wherein said polynucleotide encodes a polypeptide having at least one biological activity of the polypeptide encoded by clone P00188_D12 (SEQ ID NO: 5), a polynucleotide hybridizing under stringent conditions with the complement of the coding region of SEQ ID NO: 7, wherein said polynucleotide encodes a polypeptide having at least one biological activity of the polypeptide encoded by clone P00188_E01 (SEQ ID NO: 7), a polynucleotide hybridizing under stringent conditions with the complement of the coding region of SEQ ID NO: 9, wherein said polynucleotide encodes a polypeptide having at least one biological activity of the polypeptide encoded by clone P00194_G01 (SEQ ID NO: 9), a polynucleotide hybridizing under stringent conditions with the complement of the coding region of SEQ ID NO: 11, wherein said polynucleotide encodes a polypeptide having at least one biological activity of the polypeptide encoded by clone P00194_G05 (SEQ ID NO: 11), a polynucleotide hybridizing under stringent conditions with the complement of the coding region of SEQ ID NO: 13, wherein said polynucleotide encodes a polypeptide having at least one biological activity of the polypeptide encoded by clone P00194_H10 (SEQ ID NO:13), a polynucleotide hybridizing under stringent conditions with the complement of the coding region of SEQ ID NO: 15, wherein said polynucleotide encodes a polypeptide having at least one biological activity of the polypeptide encoded by clone P00199_D08 (SEQ ID NO: 15), a polynucleotide hybridizing under stringent conditions with the complement of the coding region of SEQ ID NO: 17, wherein said polynucleotide encodes a polypeptide having at least one biological activity of the polypeptide encoded by clone P00203_D04 (SEQ ID NO: 17), a polynucleotide hybridizing under stringent conditions with the complement of the coding region of SEQ ID NO: 19, wherein said polynucleotide encodes a polypeptide having at least one biological activity of the polypeptide encoded by clone P00203_E06 (SEQ ID NO: 19), a polynucleotide hybridizing under stringent conditions with the complement of the coding region of SEQ ID NO: 21, wherein said polynucleotide encodes a polypeptide having at least one biological activity of the polypeptide encoded by clone P00209_F06 (SEQ ID NO: 21), a polynucleotide hybridizing under stringent conditions with the complement of the coding region of SEQ ID NO: 23, wherein said polynucleotide encodes a polypeptide having at least one biological activity of the polypeptide encoded by clone P00219_D02 (SEQ ID NO: 23), a polynucleotide hybridizing under stringent conditions with the complement of the coding region of SEQ ID NO: 25, wherein said polynucleotide encodes a polypeptide having at least one biological activity of the polypeptide encoded by clone P00219_F06 (SEQ ID NO: 25), a polynucleotide hybridizing under stringent conditions with the complement of the coding region of SEQ ID NO: 27, wherein said polynucleotide encodes a polypeptide having at least one biological activity of the polypeptide encoded by clone P00220_H05 (SEQ ID NO: 27), a polynucleotide hybridizing under stringent conditions with the complement of the coding region of SEQ ID NO: 29, wherein said polynucleotide encodes a polypeptide having at least one biological activity of the polypeptide encoded by clone P00222_G03 (SEQ ID NO: 29), a polynucleotide hybridizing under stringent conditions with the complement of the polynucleotide of SEQ ID NO: 31 (clone P00223_F07), a polynucleotide hybridizing under stringent conditions with the complement of the coding region of SEQ ID NO: 32, wherein said polynucleotide encodes a polypeptide having at least one biological activity of the polypeptide encoded by clone P00225_C01 (SEQ ID NO: 32), a polynucleotide hybridizing under stringent conditions with the complement of the coding region of SEQ ID NO: 34, wherein said polynucleotide encodes a polypeptide having at least one biological activity of the polypeptide encoded by clone P00227_D11 (SEQ ID NO: 34), a polynucleotide hybridizing under stringent conditions with the complement of the coding region of SEQ ID NO: 36, wherein said polynucleotide encodes a polypeptide having at least one biological activity of the polypeptide encoded by clone P00228_F03 (SEQ ID NO: 36), a polynucleotide hybridizing under stringent conditions with the complement of the coding region of SEQ ID NO: 38, wherein said polynucleotide encodes a polypeptide having at least one biological activity of the polypeptide encoded by clone P00233_H08 (SEQ ID NO: 38), a polynucleotide hybridizing under stringent conditions with the complement of the coding region of SEQ ID NO: 40, wherein said polynucleotide encodes a polypeptide having at least one biological activity of the polypeptide encoded by clone P00235_G08 (SEQ ID NO: 40), a polynucleotide hybridizing under stringent conditions with the complement of the coding region of SEQ ID NO: 42, wherein said polynucleotide encodes a polypeptide having at least one biological activity of the polypeptide encoded by clone P00239_C11 (SEQ ID NO: 42), a polynucleotide hybridizing under stringent conditions with the complement of the polynucleotide of SEQ ID NO: 44 (clone P00240_B04), a polynucleotide hybridizing under stringent conditions with the complement of the coding region of SEQ ID NO: 45, wherein said polynucleotide encodes a polypeptide having at least one biological activity of the polypeptide encoded by clone P00240_E05 (SEQ ID NO: 45), a polynucleotide hybridizing under stringent conditions with the complement of the polynucleotide of SEQ ID NO: 47 (clone P00241_E12), a polynucleotide hybridizing under stringent conditions with the complement of the polynucleotide of SEQ ID NO: 48 (clone P00245_D06), a polynucleotide hybridizing under stringent conditions with the complement of the polynucleotide of SEQ ID NO: 49 (clone P00246_D12), a polynucleotide hybridizing under stringent conditions with the complement of the coding region of SEQ ID NO: 50, wherein said polynucleotide encodes a polypeptide having at least one biological activity of the polypeptide encoded by clone P00247_A04 (SEQ ID NO: 50), a polynucleotide hybridizing under stringent conditions with the complement of the coding region of SEQ ID NO: 52, wherein said polynucleotide encodes a polypeptide having at least one biological activity of the polypeptide encoded by clone P00248_B04 (SEQ ID NO: 52), a polynucleotide hybridizing under stringent conditions with the complement of the coding region of SEQ ID NO: 54, wherein said polynucleotide encodes a polypeptide having at least one biological activity of the polypeptide encoded by clone P00249_F09 (SEQ ID NO: 54), a polynucleotide hybridizing under stringent conditions with the complement of the coding region of SEQ ID NO: 56, wherein said polynucleotide encodes a polypeptide having at least one biological activity of the polypeptide encoded by clone P00258_A10 (SEQ ID NO: 56), a polynucleotide hybridizing under stringent conditions with the complement of the coding region of SEQ ID NO: 58, wherein said polynucleotide encodes a polypeptide having at least one biological activity of the polypeptide encoded by clone P00262_C10 (SEQ ID NO: 58), a polynucleotide hybridizing under stringent conditions with the complement of the polynucleotide of SEQ ID NO: 60 (clone P00263_G06), a polynucleotide hybridizing under stringent conditions with the complement of the polynucleotide of SEQ ID NO: 61 (clone P00267_F08), a polynucleotide hybridizing under stringent conditions with the complement of the coding region of SEQ ID NO: 62, wherein said polynucleotide encodes a polypeptide having at least one biological activity of the polypeptide encoded by clone P00269_H08 (SEQ ID NO: 62), a polynucleotide hybridizing under stringent conditions with the complement of the polynucleotide of SEQ ID NO: 64 (clone P00312_C04), a polynucleotide hybridizing under stringent conditions with the complement of the polynucleotide of SEQ ID NO: 65 (clone P00324_H02), a polynucleotide hybridizing under stringent conditions with the complement of the coding region of SEQ ID NO: 66, wherein said polynucleotide encodes a polypeptide having at least one biological activity of the polypeptide encoded by clone P00628_H02 (SEQ ID NO: 66), a polynucleotide hybridizing under stringent conditions with the complement of the coding region of SEQ ID NO: 68, wherein said polynucleotide encodes a polypeptide having at least one biological activity of the polypeptide encoded by clone P00629_C08 (SEQ ID NO: 68), a polynucleotide hybridizing under stringent conditions with the complement of the polynucleotide of SEQ ID NO: 70 (clone P00634_G11), a polynucleotide hybridizing under stringent conditions with the complement of the coding region of SEQ ID NO: 71, wherein said polynucleotide encodes a polypeptide having at least one biological activity of the polypeptide encoded by clone P00641_G11 (SEQ ID NO: 71), a polynucleotide hybridizing under stringent conditions with the complement of the coding region of SEQ ID NO: 73, wherein said polynucleotide encodes a polypeptide having at least one biological activity of the polypeptide encoded by clone P00648_E12 (SEQ ID NO: 73), and a polynucleotide hybridizing under stringent conditions with the complement of the coding region of SEQ ID NO: 75 wherein said polynucleotide encodes a polypeptide having at least one biological activity of the polypeptide encoded by clone P00697_C03 (SEQ ID NO: 75);

(e) a polynucleotide encoding at least about 50 contiguous amino acids from amino acids selected from the group consisting of: amino acids 1 to 203 of SEQ ID NO: 2, wherein said polynucleotide encodes a polypeptide having at least one biological activity of the polypeptide encoded by clone P00184_D11 (SEQ ID NO: 1), a polynucleotide encoding at least about 50 contiguous amino acids from amino acids 1 to 193 of SEQ ID NO: 4, wherein said polynucleotide encodes a polypeptide having at least one biological activity of the polypeptide encoded by clone P00185_D11 (SEQ ID NO: 3); a polynucleotide encoding at least about 50 contiguous amino acids from amino acids 1 to 236 of SEQ ID NO: 6, wherein said polynucleotide encodes a polypeptide having at least one biological activity of the polypeptide encoded by clone P00188_D12 (SEQ ID NO: 5), a polynucleotide encoding at least about 50 contiguous amino acids from amino acids 1 to 61 of SEQ ID NO: 8, wherein said polynucleotide encodes a polypeptide having at least one biological activity of the polypeptide encoded by clone P00188_E01 (SEQ ID NO: 7), a polynucleotide encoding at least about 50 contiguous amino acids from amino acids 1 to 79 of SEQ ID NO: 10, wherein said polynucleotide encodes a polypeptide having at least one biological activity of the polypeptide encoded by clone P00194_G01 (SEQ ID NO: 9), a polynucleotide encoding at least about 50 contiguous amino acids from amino acids 1 to 92 of SEQ ID NO: 12, wherein said polynucleotide encodes a polypeptide having at least one biological activity of the polypeptide encoded by clone P00194_G05 (SEQ ID NO: 11), a polynucleotide encoding at least about 50 contiguous amino acids from amino acids 1 to 86 of SEQ ID NO: 14, wherein said polynucleotide encodes a polypeptide having at least one biological activity of the polypeptide encoded by clone P00194_H10 (SEQ ID NO:13), a polynucleotide encoding at least about 50 contiguous amino acids from amino acids 1 to 36 of SEQ ID NO: 16, wherein said polynucleotide encodes a polypeptide having at least one biological activity of the polypeptide encoded by clone P00199_D08 (SEQ ID NO: 15), a polynucleotide encoding at least about 50 contiguous amino acids from amino acids 1 to 83 of SEQ ID NO: 18, wherein said polynucleotide encodes a polypeptide having at least one biological activity of the polypeptide encoded by clone P00203_D04 (SEQ ID NO: 17), a polynucleotide encoding at least about 50 contiguous amino acids from amino acids 1 to 82 of SEQ ID NO: 20, wherein said polynucleotide encodes a polypeptide having at least one biological activity of the polypeptide encoded by clone P00203_E06 (SEQ ID NO: 19), a polynucleotide encoding at least about 50 contiguous amino acids from amino acids 1 to 462 of SEQ ID NO: 22, wherein said polynucleotide encodes a polypeptide having at least one biological activity of the polypeptide encoded by clone P00209_F06 (SEQ ID NO: 21), a polynucleotide encoding at least about 50 contiguous amino acids from amino acids 1 to 170 of SEQ ID NO: 24, wherein said polynucleotide encodes a polypeptide having at least one biological activity of the polypeptide encoded by clone P00219_D02 (SEQ ID NO: 23), a polynucleotide encoding at least about 50 contiguous amino acids from amino acids −26 to 233 of FIG. 13 (amino acids 1 to 259 of SEQ ID NO:26), wherein said polynucleotide encodes a polypeptide having at least one biological activity of the polypeptide encoded by clone P00219_F06 (SEQ ID NO: 25), a polynucleotide encoding at least about 50 contiguous amino acids from amino acids 1 to 30 of SEQ ID NO: 28, wherein said polynucleotide encodes a polypeptide having at least one biological activity of the polypeptide encoded by clone P00220_H05 (SEQ ID NO: 27), a polynucleotide encoding at least about 50 contiguous amino acids from amino acids 1 to 39 of SEQ ID NO: 30, wherein said polynucleotide encodes a polypeptide having at least one biological activity of the polypeptide encoded by clone P00222_G03 (SEQ ID NO: 29), a polynucleotide encoding at least about 50 contiguous amino acids from amino acids 1 to 541 of SEQ ID NO: 33, wherein said polynucleotide encodes a polypeptide having at least one biological activity of the polypeptide encoded by clone P00225_C01 (SEQ ID NO: 32), a polynucleotide encoding at least about 50 contiguous amino acids from amino acids 1 to 30 of SEQ ID NO: 35, wherein said polynucleotide encodes a polypeptide having at least one biological activity of the polypeptide encoded by clone P00227_D11 (SEQ ID NO: 34), a polynucleotide encoding at least about 50 contiguous amino acids from amino acids 1 to 100 of SEQ ID NO: 37, wherein said polynucleotide encodes a polypeptide having at least one biological activity of the polypeptide encoded by clone P00228_F03 (SEQ ID NO: 36), a polynucleotide encoding at least about 50 contiguous amino acids from amino acids 1 to 65 of SEQ ID NO: 39, wherein said polynucleotide encodes a polypeptide having at least one biological activity of the polypeptide encoded by clone P00233_H08 (SEQ ID NO: 38), a polynucleotide encoding at least about 50 contiguous amino acids from amino acids 1 to 65 of SEQ ID NO: 39, wherein said polynucleotide encodes a polypeptide having at least one biological activity of the polypeptide encoded by clone P00235_G08 (SEQ ID NO: 40), a polynucleotide encoding at least about 50 contiguous amino acids from amino acids 1 to 46 of SEQ ID NO: 43, wherein said polynucleotide encodes a polypeptide having at least one biological activity of the polypeptide encoded by clone P00239_C11 (SEQ ID NO: 42), a polynucleotide encoding at least about 50 contiguous amino acids from amino acids 1 to 313 of SEQ ID NO: 46, wherein said polynucleotide encodes a polypeptide having at least one biological activity of the polypeptide encoded by clone P00240_E05 (SEQ ID NO: 45), a polynucleotide encoding at least about 50 contiguous amino acids from amino acids 1 to 58 of SEQ ID NO: 51, wherein said polynucleotide encodes a polypeptide having at least one biological activity of the polypeptide encoded by clone P00247_A04 (SEQ ID NO: 50), a polynucleotide encoding at least about 50 contiguous amino acids from amino acids −35 to 387 of FIG. 29 (amino acids 1 to 422 of SEQ ID NO:53), wherein said polynucleotide encodes a polypeptide having at least one biological activity of the polypeptide encoded by clone P00248_B04 (SEQ ID NO: 52), a polynucleotide encoding at least about 50 contiguous amino acids from amino acids 1 to 58 of SEQ ID NO: 55, wherein said polynucleotide encodes a polypeptide having at least one biological activity of the polypeptide encoded by clone P00249_F09 (SEQ ID NO: 54), a polynucleotide encoding at least about 50 contiguous amino acids from amino acids 1 to 52 of SEQ ID NO: 57, wherein said polynucleotide encodes a polypeptide having at least one biological activity of the polypeptide encoded by clone P00258_A10 (SEQ ID NO: 56), a polynucleotide encoding at least about 50 contiguous amino acids from amino acids 1 to 245 of SEQ ID NO: 59, wherein said polynucleotide encodes a polypeptide having at least one biological activity of the polypeptide encoded by clone P00262_C10 (SEQ ID NO: 58), a polynucleotide encoding at least about 50 contiguous amino acids from amino acids 1 to 142 of SEQ ID NO: 63, wherein said polynucleotide encodes a polypeptide having at least one biological activity of the polypeptide encoded by clone P00269_H08 (SEQ ID NO: 62), a polynucleotide encoding at least about 50 contiguous amino acids from amino acids 1 to 49 of SEQ ID NO: 67, wherein said polynucleotide encodes a polypeptide having at least one biological activity of the polypeptide encoded by clone P00628_H02 (SEQ ID NO: 66), a polynucleotide encoding at least about 50 contiguous amino acids from amino acids 1 to 70 of SEQ ID NO: 69, wherein said polynucleotide encodes a polypeptide having at least one biological activity of the polypeptide encoded by clone P00629_C08 (SEQ ID NO: 68), a polynucleotide encoding at least about 50 contiguous amino acids from amino acids 1 to 113 of SEQ ID NO: 72, wherein said polynucleotide encodes a polypeptide having at least one biological activity of the polypeptide encoded by clone P00641_G11 (SEQ ID NO: 71), a polynucleotide encoding at least about 50 contiguous amino acids from amino acids 1 to 114 of SEQ ID NO: 74, wherein said polynucleotide encodes a polypeptide having at least one biological activity of the polypeptide encoded by clone P00648_E12 (SEQ ID NO: 73), a polynucleotide encoding at least about 50 contiguous amino acids from amino acids 1 to 97 of SEQ ID NO: 76, wherein said polynucleotide encodes a polypeptide having at least one biological activity of the polypeptide encoded by clone P00697_C03 (SEQ ID NO: 75);

(f) a polynucleotide encoding at least about 50 contiguous amino acids from amino acids 1 to 233 of SEQ ID NO: 26, wherein said polynucleotide encodes a polypeptide having at least one biological activity of the polypeptide encoded by clone P00219_F06 (SEQ ID NO: 25), and a polynucleotide encoding at least about 50 contiguous amino acids from amino acids 1 to 387 of SEQ ID NO: 53, wherein said polynucleotide encodes a polypeptide having at least one biological activity of the polypeptide encoded by clone P00248_B04 (SEQ ID NO: 52);

(g) a polynucleotide selected from the group consisting of SEQ ID NOS:1, 3, 5, 7, 9, 11, 13, 15, 17, 19, 21, 23, 25, 27, 29, 31, 32, 34, 36, 38, 40, 42, 44, 45, 47, 48, 49, 50, 52, 54, 56, 58, 60, 61, 62, 64, 65, 66, 68, 70, 71, 73, and 75;

(h) the complement of a polynucleotide of (a)–(g); and (i) an antisense oligonucleotide capable of hybridizing with, and inhibiting the translation of, the mRNA encoded by a gene encoding a polypeptide selected from the group consisting of: SEQ ID NOS: 2, 4, 6, 8, 10, 12, 14, 16, 18, 20, 22, 24, 26, 28, 30, 33, 35, 37, 39, 41, 43, 46, 51, 53, 55, 57, 59, 63, 67, 69, 72, 74, 76, and another mammalian (e.g. human) homologue thereof.

In another aspect, the invention concerns a vector comprising any of the poly- or oligonucleotides of (a)–(i) above.

In a further aspect, the invention concerns a recombinant host cell transformed with nucleic acid comprising any of the poly- or oligonucleotides of (a)–(i) above, or with a vector comprising any of the poly- or oligonucleotides of (a)–(i) above.

In a still further aspect, the invention concerns a recombinant method for producing a polypeptide by culturing a recombinant host cell transformed with nucleic acid comprising any of the polynucleotides of (a)–(g) above under conditions such that the polypeptide is expressed, and isolating the polypeptide.

In a different aspect, the invention concerns a polypeptide comprising:
(a) a polypeptide having at least about 80% identity with amino acids 1 to 203 of SEQ ID NO: 2, amino acids 1 to 193 of SEQ ID NO: 4, amino acids 1 to 236 of SEQ ID NO:6, amino acids 1 to 61 of SEQ ID NO: 8, amino acids 1 to 79 of SEQ ID NO:10, amino acids 1 to 92 of SEQ ID NO:12, amino acids 1 to 86 of SEQ ID NO:14, amino acids 1 to 36 of SEQ ID NO:16, amino acids 1 to 83 of SEQ ID NO:18, amino acids 1 to 82 of SEQ ID NO:20, amino acids 1 to 462 of SEQ ID NO:22, amino acids 1 to 170 of SEQ ID NO:24, amino acids −26 to 233 of FIG. 13 (amino acids 1 to 259 of SEQ ID NO:26), amino acids 1 to 30 of SEQ ID NO:28, amino acids 1 to 39 of SEQ ID NO:30, amino acids 1 to 541 of SEQ ID NO:33, amino acids 1 to 30 of SEQ ID NO: 35, amino acids 1 to 100 of SEQ ID NO:37, amino acids 1 to 65 of SEQ ID NO:39, amino acids 1 to 42 of SEQ ID NO:41, amino acids 1 to 46 of SEQ ID NO:43, amino acids 1 to 313 of SEQ ID NO:46, amino acids 1 to 58 of SEQ ID NO:51, amino acids −35 to 387 of FIG. 29 (amino acids 1 to 422 of SEQ ID NO:53), amino acids 1 to 58 of SEQ ID NO:55, amino acids 1 to 52 of SEQ ID NO:57, amino acids 1 to 245 of SEQ ID NO:59, amino acids 1 to 142 of SEQ ID NO:63, amino acids 1 to 49 of SEQ ID NO:67, amino acids 1 to 70 of SEQ ID NO:69, amino acids 1 to 113 of SEQ ID NO:72, amino acids 1 to 114 of SEQ ID NO:74, amino acids 1 to 97 of SEQ ID NO:76; or a polypeptide encoded by nucleic acid hybridizing under stringent conditions with the complement of the coding region of SEQ ID NOS:1, 3, 5, 7, 9, 11, 13, 15, 17, 19, 21, 23, 25, 27, 29, 31, 32, 34, 36, 38, 40, 42, 44, 45, 47, 48, 49, 50, 52 54, 56, 58, 60, 61, 62, 64, 65, 66, 68, 70, 71, 73, 75;

the polypeptides of (a) and (b) having at least one biological activity of the polypeptide encoded by clones P00184_D11 (SEQ ID NO:1), P00185_D11 (SEQ ID NO:3), P00188_D12 (SEQ ID NO:5), P00188_E01 (SEQ ID NO:7), P00194_G01 (SEQ ID NO:9), P00194_G05 (SEQ ID NO:11), P00194_H10 (SEQ ID NO:13), P00199_D08 (SEQ ID NO:15), P00203_D04 (SEQ ID NO:17), P00203_E06 (SEQ ID NO:19), P00209_F06 (SEQ ID NO:21), P00219_D02 (SEQ ID NO:23), P00219_F06 (SEQ ID NO:25), P00220_H05 (SEQ ID NO:27), P00222_G03 (SEQ ID NO:29), P00223_F07 (SEQ ID NO:31), P00225_C01 (SEQ ID NO:32), P00227_D11 (SEQ ID NO:34), P00228_F03 (SEQ ID NO:36), P00233_H08 (SEQ ID NO:38), P00235_G08 (SEQ ID NO:40), P00239_C11 (SEQ ID NO:42), P00240_B04 (SEQ ID NO:44), P00240_E05 (SEQ ID NO:45), P00241_E12 (SEQ ID NO:47), P00245_D06 (SEQ ID NO:48), P00246_D12 (SEQ ID NO:49), P00247_A04 (SEQ ID NO:50), P00248_B04 (SEQ ID NO:52), P00249_F09 (SEQ ID NO:54), P00258_A10 (SEQ ID NO:56), P00262_C10 (SEQ ID NO:58), P00263_G06 (SEQ ID NO:60), P00267_F08 (SEQ ID NO:61), P00269_H08 (SEQ ID NO:62), P00312_C04 (SEQ ID NO:64), P00324_H02 (SEQ ID NO:65), P00628_H02 (SEQ ID NO:66), P00629_C08 (SEQ ID NO:68), P00634_G11 (SEQ ID NO:70), P00641_G11 (SEQ ID NO:71), P00648_E12 (SEQ ID NO:73), P00697_C03 (SEQ ID NO:75);

In another aspect, the invention concerns a composition comprising a polypeptide as hereinabove defined in admixture with a pharmaceutically acceptable carrier. In a specific embodiment, the composition is a pharmaceutical composition, preferably for the treatment of a cardiac, renal or inflanmmatory disease, comprising an effective amount of a polypeptide of the present invention.

In yet another aspect, the invention concerns an antibody specifically binding a polypeptide of the present invention (as hereinabove defined).

In a further aspect, the invention concerns an antagonist or agonist of a polypetide of the present invention.

In a still further aspect, the invention concerns a composition, preferably a pharmaceutical composition, comprising an effective amount of an antibody herein, in admixture with a pharmaceutically acceptable carrier.

The invention further concerns a composition, preferably a pharmaceutical composition, comprising an effective amount of an antagonist or agonist of the present invention, in admixture with a pharmaceutically acceptable carrier.

In a further aspect, the invention concerns a method for the treatment of a cardiac, renal or inflammatory disease, comprising administering to a patient in need an effective amount of a polypeptide of the present invention or an antagonist or agonist thereof.

In a different aspect, the invention concerns a method for the treatment of a cardiac, renal or inflammatory disease, comprising administering to a patient in need an effective amount of a poly- or oligonucleotide of the present invention (as hereinabove defined).

The invention also concerns a method for the treatment of a cardiac, renal or inflammatory disease, comprising administering to a patient in need an effective amount of an antibody specifically binding to a polypeptide of the present invention.

In a further aspect, the invention concerns a method for screening a subject for a cardiac, renal or inflammatory disease characterized by the differential expression of the endogenous homologue of the proteins of SEQ ID NOS: 2, 4, 6, 8, 10, 12, 14, 16, 18, 20, 22, 24, 26, 28, 30, 33, 35, 37, 39, 41, 43, 46, 51, 53, 55, 57, 59, 63, 67, 69, 72, 74, or 76 comprising the steps of:

measuring the expression in the subject of the endogenous homologue of the protein of SEQ ID NOS: 2, 4, 6, 8, 10, 12, 14, 16, 18, 20, 22, 24, 26, 28, 30, 33, 35, 37, 39, 41, 43, 46, 51, 53, 55, 57, 59, 63, 67, 69, 72, 74, or 76; and determining the relative expression of such endogenous homologue in the subject compared to its expression in normal subjects, or compared to its expression in the same subject at an earlier stage of development of the cardiac, renal or inflammatory disease. The subject is preferably human and, accordingly, the endogenous protein is a human homologue of the rat proteins of SEQ ID NOS: 2, 4, 6, 8, 10, 12, 14, 16, 18, 20, 22, 24, 26, 28, 30, 33, 35, 37, 39, 41, 43, 46, 51, 53, 55, 57, 59, 63, 67, 69, 72, 74, or 76.

In a still further aspect, the invention concerns an array comprising one or more oligonucleotides complementary to reference RNA or DNA encoding a protein of SEQ ID NOS: 2, 4, 6, 8, 10, 12, 14, 16, 18, 20, 22, 24, 26, 28, 30, 33, 35, 37, 39, 41, 43, 46, 51, 53, 55, 57, 59, 63, 67, 69, 72, 74, or 76 or another mammalian (e.g. human) homologue thereof, where the reference DNA or RNA sequences are obtained from both a biological sample from a normal subject and a biological sample from a subject exhibiting a cardiac, renal, or inflanmmatory disease, or from biological samples taken at different stages of a cardiac, renal, or inflammatory disease.

In yet another aspect, the invention concerns a method for detecting cardiac, kidney, or inflammatory disease in a human patient comprising the steps of:

providing an array of oligonucleotides at known locations on a substrate, which array comprises oligonucleotides complementary to reference DNA or RNA sequences encoding a human homologue of the proteins of SEQ ID NOS: 2, 4, 6, 8, 10, 12, 14, 16, 18, 20, 22, 24, 26, 28, 30, 33, 35, 37, 39, 41, 43, 46, 51, 53, 55, 57, 59, 63, 67, 69, 72, 74, or 76, where the reference DNA or RNA sequences are obtained from both a biological sample from a normal patient and a biological sample from a patient potentially exhibiting cardiac, renal, or inflammatory disease, or from a patient exhibiting cardiac, renal, or inflammatory disease, taken at different stages of such disease (jointly referred to as "the test patient");

exposing the array, under hybridization conditions, to a first sample of cDNA probes constructed from mRNA obtained from a biological sample from a corresponding biological sample of a normal patient or from a test patient at a certain stage of the disease;

exposing the array, under hybridization conditions, to a second sample of cDNA probes constructed from MRNA obtained from a biological sample obtained from the test patient (if the first sample was taken at a certain stage of the disease, the second sample is taken at a different stage of the disease);

quantifying any hybridization between the first sample of cDNA probes and the second sample of cDNA probes with the oligonucleotide probes on the array; and determining the relative expression of genes encoding the human homologue of the protein of SEQ ID NO: 2 in the biological samples from the normal patient and the test patient, or in the biological samples taken from the test patient at different stages of the disease.

The invention further concerns a diagnostic kit comprising an array herein (as defined above) for detecting and diagnosing a disease, specifically cardiac, kidney or inflammatory disease. This kit may comprise control oligonucleotide probes, PCR reagents and detectable labels. In addition, this kit may comprise biological samples taken from human subjects, said samples comprising blood or tissue, preferably cardiac tissue, more preferably left ventricle cells. Such diagnostic kits may also comprise antibodies (including poly- and monoclonal antibodies) to a polypeptide of the present invention, including the polypeptide of SEQ ID NOS: 2, 4, 6, 8, 10, 12, 14, 16, 18, 20, 22, 24, 26, 28, 30, 33, 35, 37, 39, 41, 43, 46, 51, 53, 55, 57, 59, 63, 67, 69, 72, 74, or 76 and further mammalian (e.g. human) homologues thereof.

BRIEF DESCRIPTION OF THE FIGURES

FIG. 1 shows the nucleotide sequence (SEQ ID NO: 1) of the clone P0184_D11 and deduced amino acid sequence of the polypeptide (SEQ ID NO: 2) enoded by the clone.

FIG. 2 shows the nucleotide sequence (SEQ ID NO: 3) of the clone P0185_D11 and deduced amino acid sequence of the polypeptide (SEQ ID NO: 4) enoded by the clone.

FIG. 3 shows the nucleotide sequence (SEQ ID NO: 5) of the clone P0188_D12 and deduced amino acid sequence of the polypeptide (SEQ ID NO: 6) enoded by the clone.

FIG. 4 shows the nucleotide sequence (SEQ ID NO: 7) of the clone P0188_E01 and deduced amino acid sequence of the polypeptide (SEQ ID NO: 8) enoded by the clone.

FIG. 5 shows the nucleotide sequence (SEQ ID NO: 9) of the clone P0194_G01 and deduced amino acid sequence of the polypeptide (SEQ ID NO: 10) enoded by the clone.

FIG. 6 shows the nucleotide sequence (SEQ ID NO: 11) of the clone P0194_G05 and deduced amino acid sequence of the polypeptide (SEQ ID NO: 12) enoded by the clone.

FIG. 7 shows the nucleotide sequence (SEQ ID NO: 13) of the clone P0194_H10 and deduced amino acid sequence of the polypeptide (SEQ ID NO: 14) enoded by the clone.

FIG. 8 shows the nucleotide sequence (SEQ ID NO: 15) of the clone P0199_D08 and deduced amino acid sequence of the polypeptide (SEQ ID NO: 16) enoded by the clone.

FIG. 9 shows the nucleotide sequence (SEQ ID NO: 17) of the clone P0203_D04 and deduced amino acid sequence of the polypeptide (SEQ ID NO: 18) enoded by the clone.

FIG. 10 shows the nucleotide sequence (SEQ ID NO: 19) of the clone P0203_E06 and deduced amino acid sequence of the polypeptide (SEQ ID NO: 20) enoded by the clone.

FIG. 11 shows the nucleotide sequence (SEQ ID NO: 21) of the clone P0209_F06 and deduced amino acid sequence of the polypeptide (SEQ ID NO: 22) enoded by the clone.

FIG. 12 shows the nucleotide sequence (SEQ ID NO: 23) of the clone P0219_D02 and deduced amino acid sequence of the polypeptide (SEQ ID NO: 24) enoded by the clone.

FIG. 13 shows the nucleotide sequence (SEQ ID NO: 25) of the clone P0219_F06 and deduced amino acid sequence of the polypeptide (SEQ ID NO: 26) enoded by the clone. The underlined amino acid residues at the N-terminal end represent a putative signal peptide.

FIG. 14 shows the nucleotide sequence (SEQ ID NO: 27) of the clone P0220_H05 and deduced amino acid sequence of the polypeptide (SEQ ID NO: 28) enoded by the clone.

FIG. 15 shows the nucleotide sequence (SEQ ID NO: 29) of the clone P0222_G03 and deduced amino acid sequence of the polypeptide (SEQ ID NO: 30) enoded by the clone.

FIG. 16 shows the nucleotide sequence (SEQ ID NO: 31) of the clone P0184_D11.

FIG. 17 shows the nucleotide sequence (SEQ ID NO: 32) of the clone P0225_C01 and deduced amino acid sequence of the polypeptide (SEQ ID NO: 33) enoded by the clone.

FIG. 18 shows the nucleotide sequence (SEQ ID NO: 34) of the clone P0227_D11 and deduced amino acid sequence of the polypeptide (SEQ ID NO: 35) enoded by the clone.

FIG. 19 shows the nucleotide sequence (SEQ ID NO: 36) of the clone P0228_F03 and deduced amino acid sequence of the polypeptide (SEQ ID NO: 37) enoded by the clone.

FIG. 20 shows the nucleotide sequence (SEQ ID NO: 38) of the clone P0233_H08 and deduced amino acid sequence of the polypeptide (SEQ ID NO: 39) enoded by the clone.

FIG. 21 shows the nucleotide sequence (SEQ ID NO: 40) of the clone P0235_G08 and deduced amino acid sequence of the polypeptide (SEQ ID NO: 41) enoded by the clone.

FIG. 22 shows the nucleotide sequence (SEQ ID NO: 42) of the clone P0239_C11 and deduced amino acid sequence of the polypeptide (SEQ ID NO: 43) enoded by the clone.

FIG. 23 shows the nucleotide sequence (SEQ ID NO: 44) of the clone P0184_D11.

FIG. 24 shows the nucleotide sequence (SEQ ID NO: 45) of the clone P0240_E05 and deduced amino acid sequence of the polypeptide (SEQ ID NO: 46) enoded by the clone.

FIG. 25 shows the nucleotide sequence (SEQ ID NO: 47) of the clone P0241_E12.

FIG. 26 shows the nucleotide sequence (SEQ ID NO: 48) of the clone P0245_D06.

FIG. 27 shows the nucleotide sequence (SEQ ID NO: 49) of the clone P0246_D12.

FIG. 28 shows the nucleotide sequence (SEQ ID NO: 50) of the clone P0247_A04 and deduced amino acid sequence of the polypeptide (SEQ ID NO: 51) enoded by the clone.

FIG. 29 shows the nucleotide sequence (SEQ ID NO: 52) of the clone P0248_B04 and deduced amino acid sequence of the polypeptide (SEQ ID NO: 53) enoded by the clone. The underlined amino acid residues at the N-terminal end represent a putative signal peptide.

FIG. 30 shows the nucleotide sequence (SEQ ID NO: 54) of the clone P0249_F09 and deduced amino acid sequence of the polypeptide (SEQ ID NO: 55) enoded by the clone.

FIG. 31 shows the nucleotide sequence (SEQ ID NO: 56) of the clone P0258_A10 and deduced amino acid sequence of the polypeptide (SEQ ID NO: 57) enoded by the clone.

FIG. 32 shows the nucleotide sequence (SEQ ID NO: 58) of the clone P0262_C10 and deduced amino acid sequence of the polypeptide (SEQ ID NO: 59) enoded by the clone.

FIG. 33 shows the nucleotide sequence (SEQ ID NO: 60) of the clone P0263 G06.

FIG. 34 shows the nucleotide sequence (SEQ ID NO: 61) of the clone P0267_F08.

FIG. 35 shows the nucleotide sequence (SEQ ID NO: 62) of the clone P0269_H08 and deduced amino acid sequence of the polypeptide (SEQ ID NO: 63) enoded by the clone.

FIG. 36 shows the nucleotide sequence (SEQ ID NO: 64) of the clone P0312_C04.

FIG. 37 shows the nucleotide sequence (SEQ ID NO: 65) of the clone P0324_H02.

FIG. 38 shows the nucleotide sequence (SEQ ID NO: 66) of the clone P0628_H02 and deduced amino acid sequence of the polypeptide (SEQ ID NO: 67) enoded by the clone.

FIG. 39 shows the nucleotide sequence (SEQ ID NO: 68) of the clone P0629_C08 and deduced amino acid sequence of the polypeptide (SEQ ID NO: 69) enoded by the clone.

FIG. 40 shows the nucleotide sequence (SEQ ID NO: 70) of the clone P0634_G11.

FIG. 41 shows the nucleotide sequence (SEQ ID NO: 71) of the clone P0641_G11 and deduced amino acid sequence of the polypeptide (SEQ ID NO: 72) enoded by the clone.

FIG. 42 shows the nucleotide sequence (SEQ ID NO: 73) of the clone P0648_E12 and deduced amino acid sequence of the polypeptide (SEQ ID NO: 74) enoded by the clone.

FIG. 43 shows the nucleotide sequence (SEQ ID NO: 75) of the clone P0697_C03 and deduced amino acid sequence of the polypeptide (SEQ ID NO: 76) enoded by the clone.

FIG. 44 shows the results of differential expression of clones P00184_D11, P00185_D11, P00188_D12, P00188_E01, P00194_G01, P00194_G05, P00194_H10, P00199_D08, P00203_D04, P00203_E06, P00209_F06, P00219_D02, P00219_F06, P00220_H05, P00222_G03, P00223_F07, P00225_C01, P00227_D11, P00228_F03, P00233_H08, P00235_G08, P00239_C11, P00240_B04, P00240_E05, P00241_E12, P00245_D06, P00246_D12, P00247_A04, P00248_B04, P00249_F09, P00258_A10, P00262_C10, P00263_G06, P00267_F08, P00269_H08, P00312_C04, P00324_H02, P00628_H02, P00629_C08, P00634_G11, P00641_G11, P00648_E12, and P00697_C03 in various heart and kidney disease models in the rat.

DETAILED DESCRIPTION OF THE INVENTION

A. Definitions

Unless defined otherwise, technical and scientific terms used herein have the same meaning as commonly understood by one of ordinary skill in the art to which this invention belongs. Singleton et al., Dictionary of Microbiology and Molecular Biology $2^{nd}$ ed., J. Wiley & Sons (New York, N.Y. 1994), and March, Advanced Organic Chemistry Reactions, Mechanisms and Structure $4^{th}$ ed., John Wiley & Sons (New York, N.Y. 1992), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The term "polynucleotide", when used in singular or plural, generally refers to any polyribonucleotide or polydeoxribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes DNAs and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The term "polypeptide", in singular or plural, is used herein to refer to any peptide or protein comprising two or more amino acids joined to each other in a linear chain by peptide bonds. As used herein, the term refers to both short chains, which also commonly are referred to in the art as peptides, oligopeptides and oligomers, and to longer chains, commonly referred to in the art as proteins. Polypeptides, as defined herein, may contain amino acids other than the 20 naturally occurring amino acids, and may include modified amino acids. The modification can be anywhere within the polypeptide molecule, such as, for example, at the terminal amino acids, and may be due to natural processes, such as processing and other post-translational modifications, or may result from chemical and/or enzymatic modification techniques which are well known to the art. The known modifications include, without limitation, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formulation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature, such as, for instance, Creighton, T. E., Proteins—Structure And Molecular Properties, $2^{nd}$ Ed., W. H. Freeman and Company, New York (1993); Wold, F., "Posttranslational Protein Modifications: Perspectives and Prospects," in Posttranslational Covalent Modification of Proteins, Johnson, B. C., ed., Academic Press, New York (1983), pp. 1–12; Seifter et al., "Analysis for protein modifications and nonprotein cofactors," Meth. Enzymol. 182:626–646 (1990), and Rattan et al., Ann. N.Y Acad. Sci. 663:48–62 (1992).

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in E. coli, prior to proteolytic processing, almost invariably will be N-formyhnethionine.

Modifications that occur in a polypeptide often will be a function of how the polypeptide is made. For polypeptides made by expressing a cloned gene in a host, for instance, the nature and extent of the modifications in large part will be determined by the host cell posttranslational modification capacity and the modification signals present in the polypeptide amino acid sequence. For instance, it is well known that glycosylation usually does not occur in certain bacterial hosts such as E. coli. Accordingly, when glycosylation is desired, a polypeptide is expressed in a glycosylating host, generally eukaryotic host cells. Insect cells often carry out the same posttranslational glycosylations as mammalian cells and, for this reason, insect cell expression systems have been developed to express efficiently mammalian proteins having native patterns of glycosylation.

It will be appreciated that the same type of modification may be present in the same or varying degree at several sites in a given polypeptide. Also, a given polypeptide may contain many types of modifications.

It will be appreciated that polypeptides are not always entirely linear. For instance, polypeptides may be branched as a result of ubiquitination, and they may be circular, with or without branching, generally as a result of posttranslational events, including natural processing and events brought about by human manipulation which do not occur naturally. Circular, branched and branched circular polypeptides may be synthesized by non-translation natural process and by entirely synthetic methods, as well. Such structures are within the scope of the polypeptides as defined herein.

The term "amino acid sequence variant" refers to molecules with some differences in their amino acid sequences as compared to a reference (e.g. native sequence) polypeptide. The amino acid alterations may be substitutions, insertions, deletions or any desired combinations of such changes in a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Insertional variants are those with one or more amino acids inserted immediately adjacent to an amino acid at a particular position in a native amino acid sequence. Immediately adjacent to an amino acid means connected to either the α-carboxy or α-amino functional group of the amino acid.

Deletional variants are those with one or more amino acids in the native amino acid sequence removed. Ordinarily, deletional variants will have one or two amino acids deleted in a particular region of the molecule.

The amino acid sequence variants within the scope of the present invention may contain amino acid alterations, including substitutions and/or insertions and/or deletions in any region of the polypeptide of SEQ ID NO: 1, including the N- and C-terminal regions. The amino acid sequence variants of the present invention show at least about 75%, more preferably at least about 85%, even more preferably at least about 90%, most preferably at least about 95% amino acid sequence identity with a polypeptide of SEQ ID NO: 1 or with a native homologue thereof in another mammalian species, including humans.

"Sequence identity" is defined as the percentage of amino acid residues in a candidate sequence that are identical with the amino acid residues in a native polypeptide sequence, after aligning the sequences and introducing gaps, if necessary, to achieve the maximum percent sequence identity, and not considering any conservative substitutions as part of the sequence identity. The % sequence identity values are generated by the NCBI BLAST2.0 software as defined by Altschul et al., (1997), "Gapped BLAST and PSI-BLAST: a new generation of protein database search programs", Nucleic Acids Res., 25:3389–3402. The parameters are set to default values, with the exception of the Penalty for mismatch, which is set to −1.

"Stringent" hybridization conditions are sequence dependent and will be different with different environmental parameters (e.g., salt concentrations, and presence of organics). Generally, stringent conditions are selected to be about 5° C. to 20° C. lower than the thermal melting point ($T_m$) for the specific nucleic acid sequence at a defined ionic strength and pH. Preferably, stringent conditions are about 5° C. to 10° C. lower than the thermal melting point for a specific nucleic acid bound to a complementary nucleic acid. The $T_m$ is the temperature (under defined ionic strength and pH) at which 50% of a nucleic acid (e.g., tag nucleic acid) hybridizes to a perfectly matched probe "Stringent" wash conditions are ordinarily determined empirically for hybridization of each set of tags to a corresponding probe array. The arrays are first hybridized (typically under stringent hybridization conditions) and then washed with buffers containing successively lower concentrations of salts, or higher concentrations of detergents, or at increasing temperatures until the signal to noise ratio for specific to non-specific hybridization is high enough to facilitate detection of specific hybridization. Stringent temperature conditions will usually include temperatures in excess of about 30° C., more usually in excess of about 37° C., and occasionally in excess of about 45° C. Stringent salt conditions will ordinarily be less than about 1000 mM, usually less than about 500 mM, more usually less than about 400 mM, typically less than about 300 mM, preferably less than about 200 mM, and more preferably less than about 150 mM. However, the combination of parameters is more important than the measure of any single parameter. See, e.g., Wetmur et al., *J. Mol. Biol.* 31:349–70 (1966), and Wetnur, *Critical Reviews in Biochemistry and Molecular Biology* 26(34):227–59 (1991). In a preferred embodiment, "stringent conditions" or "high stringency conditions," as defined herein, may be hybridization in 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

As used herein, the term "polynucleotide encoding a polypeptide" and grammatical equivalents thereof, encompass polynucleotides which include a sequence encoding a polypeptide of the present invention, including polynucleotides that comprise a single continuous region or discontinuous regions encoding the polypeptide (for example, interrupted by introns) together with additional regions, that also may contain coding and/or non-coding sequences.

"Antisense oligodeoxynucleotides" or "antisense oligonucleotides" (which terms are used interchangeably) are defined as nucleic acid molecules that can inhibit the transcription and/or translation of target genes in a sequence-specific manner. The term "antisense" refers to the fact that the nucleic acid is complementary to the coding ("sense") genetic sequence of the target gene. Antisense oligonucleotides hybridize in an antiparallel orientation to nascent mRNA through Watson-Crick base-pairing. By binding the target mRNA template, antisense oligonucleotides block the successful translation of the encoded protein. The term specifically includes antisense agents called "ribozymes" that have been designed to induce catalytic cleavage of a target RNA by addition of a sequence that has natural self-splicing activity (Warzocha and Wotowiec, "Antisense strategy: biological utility and prospects in the treatment of hematological malignancies." *Leuk. Lymnhoma* 24:267–281 [1997]).

The terms "vector", "polynucleotide vector", "construct" and "polynucleotide construct" are used interchangeably herein. A polynucleotide vector of this invention may be in any of several forms, including, but not limited to, RNA, DNA, RNA encapsulated in a retroviral coat, DNA encapsulated in an adenovirus coat, DNA packaged in another viral or viral-like form (such as herpes simplex, and adeno-associated virus (AAV)), DNA encapsulated in liposomes, DNA complexed with polylysine, complexed with synthetic polycationic molecules, conjugated with transferrin, complexed with compounds such as polyethylene glycol (PEG) to immunologically "mask" the molecule and/or increase half-life, or conjugated to a non-viral protein. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyaanides.

The term "antagonist" is used in the broadest sense and includes any molecule that partially or fully blocks, inhibits or neutralizes a biological activity exhibited by a polypeptide of the present invention. In a similar manner, the term "agonist" is used in the broadest sense and includes any molecule that mimics a biological activity exhibited by a polypeptide of the present invention, for example, by specifically changing the function or expression of such polypeptide, or the efficiency of signaling through such polypeptide, thereby altering (increasing or inhibiting) an already existing biological activity or triggering a new biological activity.

The term "recombinant" when used with reference to a cell, animal, or virus indicates that the cell, animal, or virus encodes a foreign DNA or RNA. For example, recombinant cells optionally express nucleic acids (e.g., RNA) not found within the native (non-recombinant) form of the cell.

The term "antibody" is used in the broadest sense and specifically covers monoclonal antibodies (including agonist, antagonist, and neutralizing antibodies), polyclonal antibodies, multi-specific antibodies (e.g., bispecific antibodies), as well as antibody fragments. The monoclonal antibodies specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA* 81:6851–6855 [1984]). The monoclonal antibodies further include "humanized" antibodies or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a CDR of the recipient are replaced by residues from a CDR of a non-human species (donor antibody) such as mouse, rat or rabbit having the desired specificity, affinity, and capacity. In some instances, Fv FR residues of the human immunoglobulin are replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., *Nature,* 321:522–525 (1986); and Reichmann et al., *Nature,* 332:323–329 (1988). The humanized antibody includes a PRIMATIZED® antibody wherein the antigen-binding region of the antibody is derived from an antibody produced by immunizing macaque monkeys with the antigen of interest.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., *Protein Eng.* 8(10) :1057–1062 (1995)); single-chain antibody molecules; and multispecific antibodies formed from antibody fragments.

The terms "differentially expressed gene," "differential gene expression" and their synonyms, which are used interchangeably, refer to a gene whose expression is activated to a higher or lower level in a subject suffering from a disease, specifically a cardiac, kidney or inflammatory disease state, relative to its expression in a normal or control subject. The terms also include genes whose expression is activated to a higher or lower level at different stages of the same disease. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example. Differential gene expression may include a comparison of expression between two or more genes, or a comparison of the ratios of the expression between two or more genes, or even a comparison of two differently processed products of the same gene, which differ between normal subjects and subjects suffering from a disease, specifically a cardiac, kidney or inflammatory disease state, or between various stages of the same disease. Differential expression includes both quantitative, as well as qualitative, differences in the temporal or cellular expression pattern in a gene or its expression products among, for example, normal and diseased cells, or among cells which have undergone different disease events or disease stages. For the purpose of this invention, "differential gene expression" is considered to be present when there is at least an about 1.4-fold, preferably at least about 1.8-fold, more preferably at least about 2.0-fold, most preferably at least about 2.5-fold difference between the expression of a given gene in normal and diseased subjects, or in various stages of disease development in a diseased subject.

"Cardiac disease" includes congestive heart failure, myocarditis, dilated congestive cardiomyopathy, hypertrophic cardiomyopathy, restrictive cardiomyopathy, mitral valve disease, aortic valve disease, tricuspid valve disease, angina pectoris, myocardial infarction, cardiac arrhythmia, pulmonary hypertension, arterial hypertension, renovascular hypertension, arteriosclerosis, atherosclerosis, and cardiac tumors, along with any disease or disorder that relates to the cardiovascular system and related disorders, as well as symptoms indicative of, or related to, cardiac disease and related disorders.

As used herein, "heart failure" refers to an abnormality of cardiac finction where the heart does not pump blood at the rate needed for the requirements of metabolizing tissues. The heart failure can be caused by any number of factors, including ischemic, congenital, rheumatic, or idiopathic forms.

As used herein "congestive heart failure" refers to a syndrome characterized by left ventricular dysfunction, reduced exercise tolerance, impaired quality of life, and markedly shortened life expectancy. Decreased contractility of the left ventricle leads to reduced cardiac output with consequent systemic arterial and venous vasoconstriction. This vasoconstriction, which appears to be mediated, in part, by the renin-angiotensis system, promotes the vicious cycle of further reductions of stroke volume followed by an increased elevation of vascular resistance.

As used herein "infarct" refers to an area of necrosis resulting from an insufficiency of blood supply. "Myocardial infarction" refers to myocardial necrosis resulting from the insufficiency of coronary blood supply.

"Kidney disease" includes acute renal failure, glomerulonephritis, chronic renal failure, azotemia, uremia, immune renal disease, acute nephritic syndrome, rapidly progressive nephritic syndrome, nephrotic syndrome, Berger's Disease, chronic nephritic/proteinuric syndrome, tubulointerstital disease, nephrotoxic disorders, renal infarction, atheroembolic renal disease, renal cortical necrosis, malignant nephroangiosclerosis, renal vein thrombosis, renal tubular acidosis, renal glucosuria, nepbrogenic diabetes insipidus, Bartter's Syndrome, Liddle's Syndrome, polycystic kidney disease, medullary cystic disease, medullary sponge kidney, hereditary nephritis, and nail-patella syndrome, along with any disease or disorder that relates to the renal system and related disorders, as well as symptoms indicative of, or related to, renal or kidney disease and related disorders.

The phrases "polycystic kidney disease" "PKD" and "polycystic renal disease" are used interchangeably, and refer to a group of disorders characterized by a large number of cysts distributed throughout dramatically enlarged kidneys. The resultant cyst development leads to impairment of kidney function and can eventually cause kidney failure. "PKD" specifically includes autosomal dominant polycystic kidney disease (ADPKD) and recessive autosomal recessive polycystic kidney disease (ARPKD), in all stages of development, regardless of the underlying cause.

"Inflammatory disease" includes myocarditis, asthma, chronic inflammnation, autoimmune diabetes, tumor angiogenesis, rheumatoid arthritis (RA), rheumatoid spondylitis, osteoarthritis, gouty arthritis and other arthritic conditions, sepsis, septic shock, endotoxic shock, Gram-negative sepsis, toxic shock syndrome, asthma, adult respiratory distress syndrome, stroke, reperfusion injury, CNS injuries such as neural trauma and ischemia, psoriasis restenosis, cerebral malaria, chronic pulmonary inflammatory disease, silicosis, pulmonary sarcosis, bone resorption diseases such as osteoporosis, graft versus host reaction, Crohn's Disease, ulcerative colitis including inflammatory bowel disease (IBD), Alzheimer's disease, and pyresis, along with any disease or disorder that relates to inflammation and related disorders, as well as symptoms indicative of, or related to, inflammation and related disorders.

The terms "treat" or "treatment" refer to both therapeutic treatment and prophylactic or preventative measures, wherein the object is to prevent or slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

"Chronic" administration refers to administration of the agent(s) in a continuous mode as opposed to an acute mode, so as to maintain the desired effect for an extended period of time.

"Intermittent" administration is treatment that is not consecutively done without interruption, but rather is cyclic in nature.

Administration "in combination with" one or more further therapeutic agents includes simultaneous (concurrent) and consecutive administration in any order.

An "individual" is a vertebrate, preferably a mammal, more preferably a human.

"Mammal" for purposes of treatment refers to any animal classified as a mammal, including humans, domestic and farm animals, and zoo, sports, or pet animals, such as dogs, horses, cats, cows, etc. Preferably, the mammal herein is human.

An "effective amount" is an amount sufficient to effect beneficial or desired therapeutic (including preventative) results. An effective amount can be administered in one or more administrations.

"Active" or "activity" means a qualitative biological and/or immunological property.

The phrase "immunological property" means immunological cross-reactivity with at least one epitope of the reference (native sequence) polypeptide molecule, wherein, "immunological cross-reactivity" means that the candidate polypeptide is capable of competitively inhibiting the qualitative biological activity of the reference (native sequence) polypeptide. The immunological cross-reactivity is preferably "specific", which means that the binding affinity of the immunologically cross-reactive molecule identified to the corresponding polypeptide is significantly higher (preferably at least about 2 times, more preferably at least about 4-times, most preferably at least about 6-times higher) than the binding affinity of that molecule to any other known native polypeptide.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

B. Modes of Carrying Out the Invention

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manuar", $2^{nd}$ edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", $4^{th}$ edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

1. Identification of Differential Gene Expression and Further Characterization of Differentially Expressed Genes The present invention is based on the identification of genes that are differentially expressed in the left ventricle in the Myocardial Infarction Model, as described in the Examples. Such models of differential gene expression can be utilized, among other things, for the identification of genes which are differentially expressed in normal cells versus cells in a disease state, specifically cardiac, kidney or inflammatory disease state, in cells within different diseases, among cells within a single given disease state, in cells within different stages of a disease, or in cells within different time stages of a disease.

Once a particular differentially expressed gene has been identified through the use of one model, its expression pattern can be further characterized, for example, by studying its expression in a different model. A gene may be regulated one way, i.e., the gene can exhibit one differential gene expression pattern, in a given model, but can be regulated differently in another model. The use, therefore, of multiple models can be helpful in distinguishing the roles and relative importance of particular genes in a disease, specifically cardiac, kidney or inflammatory disease.

a. In Vitro Models of Differential Gene Expression

A suitable model that can be utilized within the context of the present invention to discover differentially expressed genes is the in vitro specimen model. In a preferred embodiment, the specimen model uses biological samples from subjects, e.g., peripheral blood, cells and tissues, including surgical and biopsy specimens. Such specimens can represent normal peripheral blood and tissue or peripheral blood and tissue from patients suffering from a disease, specifically cardiac, kidney or inflammatory disease, or having undergone surgical treatment for disorders involving a disease, such as, for example, coronary bypass surgery. Surgical specimens can be procured under standard conditions involving freezing and storing in liquid nitrogen (see Karmali et al., Br. J. Cancer 48:689–96 [1983]). RNA from specimen cells is isolated by, for example, differential centrifugation of homogenized tissue, and analyzed for differential expression relative to other specimen cells, preferably using microarray analysis.

Cell lines can also be used to identify genes that are differentially expressed in a disease, specifically cardiac, kidney or inflammatory disease. Differentially expressed genes are detected, as described herein, by comparing the pattern of gene expression between the experimental and control conditions. In such models, genetically matched disease cell lines (e.g., variants of the same cell line) may be utilized. For example, the gene expression pattern of two variant cell lines can be compared, wherein one variant exhibits characteristics of one disease state while the other variant exhibits characteristics of another disease state.

Alternatively, two variant cell lines, both of which exhibit characteristics of the same disease, specifically cardiac, kidney or inflammatory disease, but which exhibit differing degrees of disease disorder severity may be used. Further, genetically matched cell lines can be utilized, one of which exhibits characteristics of a disease, specifically cardiac, kidney or inflammatory disease, state, while the other exhibits a normal cellular phenotype. In accordance with this aspect of the invention, the cell line variants are cultured under appropriate conditions, harvested, and RNA is isolated and analyzed for differentially expressed genes, as with the other models. In a preferred embodiment, microarray analysis is used.

b. In Vivo Models of Differential Gene Expression

In the in vivo model, animal models of a disease, specifically cardiac, kidney or inflammatory disease, and related disorders, can be utilized to discover differentially expressed gene sequences. The in vivo nature of such disease models can prove to be especially predictive of the analogous responses in living patients, particularly human patients. Animal models for a disease, specifically cardiac, kidney or inflammatory disease, which can be utilized for in vivo models include any of the animal models described below. In a preferred embodiment, RNA from both the normal and disease state model is isolated and analyzed for differentially expressed genes using microarray analysis.

As presented in the examples, three representative in vivo cardiac disease models, a representative kidney disease model, and a representative inflammatory disease model have been successfully utilized to identify differentially expressed genes, and are believed to be useful to further characterize the genes and polypeptides of the present invention. These genes are expressed at higher or lower levels in the disease state, relative to the normal state, and preferably are expressed at least about a two-fold higher or lower level relative to the normal state at at least one time point.

Representative in vivo animal models for use in the present invention include the following: general inflammation—carrageenan-induced paw edema, arachidonic acid-induced ear inflammation; arthritis—adjuvant-induced polyarthritis, collagen-induced arthritis, streptococcal cell wall-induced arthritis; multiple sclerosis—experimental autoimmune encephalomyelitis (EAE); Systemic Lupus Erythematosis (SLE); NZB—spontaneous SLE mouse, DNA/anti-DNA immune complex-induced SLE; insulin-dependent diabetes mellitus—NOD spontaneous diabetes mouse; inflammatory bowel disease—acetic acid or trinitrobenzene sulfonic (TNBS)-induced ulcerative colitis; respiratory disease—antigen-induced bronchoconstriction (asthma), lipopolysaccharide (LPS)-induced acute respiratory distress syndrome (ARDS); analgesia—acetic acid-induced or phenylquinone-induced writhing, latency of tail-withdrawal (hot plate); transplant organ rejection—allograft rejection (kidney, lung, heart)-acute and chronic arteriolsclerosis; kidney disease—unilateral nephrectomy (acute renal failure), cyclosporin-induced nephropathy, accelerated crescentic anti-glomerular basement membrane (GBM) glomerulonephritis, soluble immune complex-induced nephritis (see generally Aziz, *Bioassays* 17:8 703–12 [1995]); and cardiac disease—spontaneous cardiomyopathic hamsters (heart failure), myocardial infarction (MI) model. pacing-induced model of failure (Riegger model), arrhythmias following myocardial infarction (Harris model), aconitine/chloroform-induced arrhythmisa, carotid artery injury (restenosis), balloon angioplasty (restenosis). One skilled in the art understands that the present invention is not limited to the in vivo models recited above and that any known models can be used within the context of the present invention.

C. Microarray Technique

In a preferred embodiment of the present invention, microarrays are utilized to assess differential expression of genes. In one aspect of the present invention, DNA microarrays are utilized to assess the expression profile of genes expressed in normal subjects and subjects suffering from a disease, specifically cardiac, kidney or inflammatory disease. Identification of the differentially expressed disease genes can be performed by: constructing normalized and subtracted cDNA libraries from mRNA extracted from the cells or tissue of healthy animals and an animal model of disease or of healthy patients and diseased patients, for example, using any of the in vitro or in vivo models described above; purifying the DNA of cDNA libraries of clones representing healthy and diseased cells or tissue, microarraying the purified DNA for expression analysis; and probing microarrays to identify the genes from the clones that are differentially expressed using labeled cDNA from healthy and diseased cells or tissues.

In a specific embodiment of the microarray technique, PCR amplified inserts of cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scarmed by confocal laser microscopy. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., *Proc. Natl. Acad. Sci. USA* 93(20):106–49 [1996]).

In a specific embodiment, in vivo models of disease states are used to detect differentially expressed genes. By way of example, three representative cardiac disease models, a representative kidney disease model, and a representative inflammatory disease model were successfully utilized to identify specific differentially expressed genes. Summarizing the representative general protocol used for such in vivo models, separate DNA libraries were constructed from niRNA extracted from disease state tissue and normal tissue. From these libraries, at least 20,000 unidentified cDNA clones were preferably chosen for analysis and microarrayed on chips. Probes generated from normal and disease tissue, from multiple time points, were hybridized to the microarray. By this approach, genes, which are differentially expressed in normal and diseased tissue, were revealed and further identified by DNA sequencing. The analysis of the clones for differential expression reveal genes whose expression is elevated or decreased in association with a disease, specifically cardiac, kidney or inflammatory disease, in the specific in vivo model chosen.

d. Further Characterization of Differentially Expressed Genes

The differentially expressed genes of the present invention are screened to obtain more information about the biological function of such genes. This information can, in turn, lead to the designation of such genes or their gene products as potential therapeutic or diagnostic molecules, or targets for identifying such molecules.

The goal of the follow-up work after a differentially expressed gene has been identified is to identify its target cell type(s), function and potential role in disease pathology. To this end, the differentially expressed genes are screened to identify cell types responding to the gene product, to better understand the mechanism by which the identified cell types respond to the gene product, and to fined known signaling pathways that are affected by the expression of the gene.

When further characterization of a differentially expressed gene indicates that a modulation of the gene's expression or a modulation of the gene product's activity can inhibit or treat a disease, specifically cardiac, kidney or inflammatory disease, the differentially expressed gene or its gene product becomes a potential drug candidate, or a target for developing a drug candidate for the treatment of a cardiac, kidney or inflammatory disease, or may be used as a diagnostic.

Where further characterization of a differentially expressed gene reveals that modulation of the gene expression or gene product cannot retard or treat a target disease, the differentially expressed gene may still contribute to developing a gene expression diagnostic pattern correlative of a disease or its disorders. Accordingly, such genes may be useful as diagnostics.

A variety of techniques can be utilized to further characterize the differentially expressed genes after they are identified.

First, the nucleotide sequence of the identified genes, which can be obtained by utilizing standard techniques well known to those of skill in the art, can be used to further characterize such genes. For example, the sequence of the identified genes can reveal homologies to one or more known sequence motifs, which can yield information regarding the biological function of the identified gene product.

Second, an analysis of the tissue or cell type distribution of the mRNA produced by the identified genes can be conducted, utilizing standard techniques well known to those of skill in the art. Such techniques can include, for example, Northern analyses, microarrays, real time (RT-coupled PCR), and RNase protection techniques. In a preferred embodiment, transcriptional screening is used, which may be based on the transfection of cells with an inducible promoter-luciferase plasmid construct, real time PCR, or microarrays, the real time PCR and microarray approached being particularly preferred. Such analyses provide information as to whether the identified genes are expressed in further tissues expected to contribute to a disease, specifically cardiac, kidney or inflammatory disease. These techniques can also provide quantitative information regarding steady state MRNA regulation, yielding data concerning which of the identified genes exhibits a high level of regulation preferably in tissues which can be expected to contribute to a disease state. Additionally, standard in situ hybridization techniques can be utilized to provide information regarding which cells within a given tissue express the identified gene. Specifically, these techniques can provide information regarding the biological function of an identified gene relative to a disease, specifically cardiac, kidney or inflammatory disease, where only a subset of the cells within the tissue is thought to be relevant to the disorder.

Third, the sequences of the identified differentially expressed genes can be used, utilizing standard techniques, to place the genes onto genetic maps, e.g., mouse (Copeland et al., *Trends in Genetics* 7:113–18 (1991)) and human genetic maps (Cohen et al., *Nature* 266:698–701 [1993]). This mapping information can yield information regarding the genes' importance to human disease by identifying genes that map within genetic regions to which known genetic disease disorders map.

After the follow-up screening is completed, relevant, targeted in vivo and in vitro systems can be used to more directly assess the biological function of the identified genes. In vivo systems can include animal systems that naturally exhibit symptoms of a disease, specifically cardiac, kidney or inflammatory disease, or ones engineered to exhibit such symptoms. Animals of any species, including, but not limited to, mice, rats, rabbits, guinea pigs, pigs, micro-pigs, goats, and non-human primates, e.g. baboons, monkeys, and chimpanzees, can be used to generate animal models of a disease, specifically cardiac, kidney or inflammatory disease. Any technique known in the art can be used to introduce a target gene transgene into animals to produce the founder lines of transgenic animals. Such techniques include, pronuclear microinjection (Hoppe et al., U.S. Pat. No. 4,873,191 (1989)); retrovirus mediated gene transfer into germ lines (Van der Fatten et al., *Proc. Natl. Acad. Sci. USA* 82:6148–52 (1985)); gene targeting in embryonic stem cells (Thompson et al., *Cell* 56:313–21 (1989)); electroporation of embryos (Lo, *Mol. Cell. Biol.* 3:1803–14 (1983)); and sperm-mediated gene transfer (Lavitrano et al., *Cell* 57:717–23 (1989)). For a review of such techniques, see Gordon, *Intl. Rev. Cytol.* 115:171–229 (1989). Further techniques will be detailed below, in connection with the gene therapy applications of the polynucleotides of the present invention.

The present invention provides for transgenic animals that carry the transgene in all their cells, as well as animals which carry the transgene in some, but not all their cells, i.e., mosaic animals. The transgene can be integrated, either as a single transgene or in concatamers, e.g., head-to-head tandems or head-to-tail tandems. The transgene can also be selectively introduced into and activated in a particular cell type by following, for example, the teaching of Lasko et al., Proc. Natl. Acad. Sci. USA 89:6232–36 (1992). The regulatory sequences required for such a cell-type specific activation depends upon the particular cell type of interest, and will be apparent to those of skill in the art.

When it is desired that the transgene be integrated into the chromosomal site of the endogenous target gene, gene targeting is preferred. Briefly, when such a technique is to be utilized, vectors containing some nucleotide sequences homologous to the endogenous target gene of interest are designed for the purpose of integrating, via homologous recombination with chromosomal sequences, into and disrupting the function of the nucleotide sequence of the endogenous target gene. The transgene can also be selectively introduced into a particular cell type, thus inactivating the endogenous gene of interest in only that cell type, by following the teaching of Gu et al. (*Science* 265:103–06 [1994]). The regulatory sequences required for such a cell-type specific inactivation depends upon the particular cell type of interest, and will be apparent to those of skill in the art.

Once transgenic animals have been generated, the expression of the recombinant target gene and protein can be assayed using standard techniques. Initial screening can be accomplished by Southern blot analysis or PCR techniques to analyze animal tissues to assay whether integration of the transgene has taken place. The level of MnRNA expression of the transgene in the tissues of the transgenic animals can also be assessed using techniques which include Northern blot analysis of tissue samples obtained from the animal, in situ hybridization analysis, and RT-coupled PCR. Samples of target gene-expressing tissue can also be evaluated immunocytochemically using antibodies specific for the transgenic product of interest.

The transgenic animals that express target gene niRNA or target gene transgene peptide (detected immunocytochemically, using antibodies directed against target gene product epitopes) at easily detectable levels should then be further evaluated to identify those animals which display disease characteristics or symptoms. Additionally, specific cell types within the transgenic animals can be analyzed for cellular phenotypes characteristic of a disease, specifically cardiac, kidney or inflarumatory disease. Such cellular phenotypes can include, for example, differential gene expression characteristic of cells within a given disease state of interest. Further, such cellular phenotypes can include an assessment of a particular cell type diagnostic pattern of expression and its comparison to known diagnostic expression profiles of the particular cell type in animals exhibiting a disease, specifically cardiac, kidney or inflammatory disease. Such transgenic animals serve as suitable models. Once transgenic founder animals are produced, they can be bred, inbred, outbred, or crossbred to produce colonies of the particular animal.

The animal models described above and in the Examples, can be used to generate cell lines for use in cell-based in vitro assays to further characterize the differentially expressed genes of the invention and their gene products. Techniques that can be used to derive a continuous cell line from transgenic animals are disclosed, for example, by Small et al., *Mol. Cell Biol.* 5:642–48 (1985).

Alternatively, cells of a cell type known to be involved in a cardiac, kidney or inflammratory disease can be transfected with sequences capable of increasing or decreasing the amount of target gene expression within the cell. For example, sequences of the differentially expressed genes herein can be introduced into, and overexpressed in, the genome of the cell of interest, or if endogenous target gene sequences are present, they can either be overexpressed or, be disrupted in order to underexpress or inactivate target gene expression.

The information obtained through such characterizations can suggest relevant methods for the treatment of a disease, specifically cardiac, kidney or inflammatory disease, involving the gene of interest. For example, treatment can include a modulation of gene expression or gene product activity. Characterization procedures such as those described herein can indicate where such modulation should involve an increase or a decrease in the expression or activity of the gene or gene product of interest.

2. Production of Polvnucleotides and Polypeptides

The polypeptides of the present invention are preferably produced by techniques of recombinant DNA technology. DNA encoding a native polypeptide herein can be obtained from cDNA libraries prepared from tissue believed to possess the corresponding mRNA and to express it at a detectable level. For example, cDNA library can be constructed by obtaining polyadenylated mRNA from a cell line known to express the desired polypeptide, and using the mRNA as a template to synthesize double-stranded cDNA. In the present case, a suitable source for the desired mRNA may be heart tissue obtained from normal heart or from the Myocardial Infarction Model (MI model) mentioned above, and described in detail in the Examples. The polypeptide genes of the present invention can also be obtained from a genomic library, such as a human genomic cosmid library.

Libraries, either cDNA or genomic, are screened with probes designed to identify the gene of interest or the protein encoded by it. For cDNA expression libraries, suitable probes include monoclonal and polyclonal antibodies that recognize and specifically bind to a polypeptide of SEQ ID NOs:2, 4, 6, 8, 10, 12, 14, 16, 18, 20, 22, 24, 26, 28, 30, 33, 35, 37, 39, 41, 43, 46, 51, 53, 55, 57, 59, 63, 67, 69, 72, 74, and 76. For cDNA libraries, suitable probes include oligonucleotide probes (generally about 20–80 bases) that encode known or suspected portions of a polypeptide herein, from the same or different species, and/or complementary or homologous cDNAs or fragments thereof that encode the same or a similar gene. Appropriate probes for screening genomic libraries include, without limitation, oligonucleotides, cDNAs, or fragments thereof that encode the same or a similar gene, and/or homologous genomic DNAs or fragments thereof. Screening the cDNA and genomic libraries with the selected probe may be conducted using standard protocols as described, for example, in Chapters 10–12 of Sambrook et al., *Molecular Cloning: A Laboratory Manual.* New York, Cold Spring Harbor Laboratory Press (1989).

According to a preferred method, carefully selected oligonucleotide probes are used to screen cDNA libraries from various tissues, preferably from heart and/or kidney tissues. The oligonucleotide sequences selected as probes should be sufficient in length and sufficiently unique and unambiguous that false positives are minimized. The actual sequences can be designed based on regions of SEQ ID NO: 2 which have the least codon redundancy. The oligonucleotides may be degenerate at one or more positions. The use of degenerate oligonucleotides is of particular importance where a library is screened from a species in which preferential codon usage is not known.

The oligonucleotides must be labeled such that they can be detected upon hybridization to DNA in the library screened. Preferably, the 5' end of the oligonucleotide is radiolabeled, using APT (e.g. $\gamma^{32}P$) and polynucleotide kinase. However, other labeling, e.g. biotinylation or enzymatic labeling are also suitable.

Alternatively, to obtain DNA encoding a homologue of rat polypeptides specifically disclosed herein in another mammalian species, e.g. in humans, one only needs to conduct hybridization screening with labeled rat DNA or fragments thereof, selected following the principles outlined above, in order to detect clones which contain homologous sequences in the cDNA libraries obtained from appropriate tissues (e.g. heart or kidney) of the particular animal, such as human (cross-species hybridization). Full-length clones can then be identified, for example, by restriction endonuclease analysis and nucleic acid sequencing. If full-length clones are not identified, appropriate fragments are recovered from the various clones and ligated at restriction sites common to the fragments to assemble a full-length clone. cDNAs encoding the polypeptides of the present invention can also be identified and isolated by other known techniques, such as by direct expression cloning or by using the PCR technique, both of which are well known are described in textbooks, such as those referenced hereinbefore.

Once the sequence is known, the nucleic acid encoding a particular polypeptide of the present invention can also be obtained by chemical synthesis, following known methods, such as the phosphoramidite method (Beaucage and Caruthers, *Tetrahedron Letters* 22:1859 [1981]; Matteucci and Caruthers, *Tetrahedron Letters* 21:719 [1980]; and Matteucci and Caruthers, *J. Amer. Chem. Soc.* 103: 3185 [1981]), and the phosphotriester approach (Ito et al., *Nucleic Acids Res.* 10:1755–1769 [1982]).

The cDNA encoding the desired polypeptide of the present invention is inserted into a replicable vector for cloning and expression. Suitable vectors are prepared using standard techniques of recombinant DNA technology, and are, for example, described in the textbooks cited above. Isolated plasmids and DNA fragments are cleaved, tailored, and ligated together in a specific order to generate the desired vectors. After ligation, the vector containing the gene to be expressed is transformed into a suitable host cell.

Host cells can be any eukaryotic or prokaryotic hosts known for expression of heterologous proteins.

The polypeptides of the present invention can be expressed in eukaryotic hosts, such as eukaryotic microbes (yeast), cells isolated from multicellular organisms (martmalian cell cultures), plants and insect cells.

While prokaryotic host provide a convenient means to synthesize eukaryotic proteins, when made this fashion, proteins usually lack many of the immunogenic properties, three-dimensional conformation, glycosylation, and other features exhibited by authentic eukaryotic proteins. Eukaryotic expression systems overcome these limitations.

Yeasts are particularly attractive as expression hosts for a number of reasons. They can be rapidly growth on inexpensive (minimal) media, the recombinant can be easily selected by complementation, expressed proteins can be specifically engineered for cytoplasmic localization or for extracellular export, and are well suited for large-scale fermentation.

*Saccharomyces cerevisiae* is the most commonly used among lower eukaryotic hosts. However, a number of other genera, species, and strains are also available and useful herein, such as *Pichia pastoris* (EP 183,070; Sreekrishna et al, *J. Basic Microbiol.* 28:165–278 [1988]). Yeast expression systems are commercially available, and can be purchased, for example, from Invitrogen (San Diego, Calif.). Other yeasts suitable for VEGF expression include, without limitation, Kluyveromyces hosts (U.S. Pat. No. 4,943,529), e.g. *Kluyveromyces lactis*; *Schizosaccharomyces pombe* (Beach and Nurse, *Nature* 290:140 (1981); Aspergillus hosts, e.g. *A. niger* (Kelly and Hynes, *EMBO J.* 4:475–479 [1985]) and *A. nidulans* (Ballance et al., *Biochem. Biophys. Res. Commun.* 112:284–289 [1983]), and Hansenula hosts, e.g. *Hansenula polymorpha*.

Preferably a methylotrophic yeast is used as a host in performing the methods of the present invention. Suitable methylotrophic yeasts include, but are not limited to, yeast capable of growth on methanol selected from the group consisting of the genera Pichia and Hansenula. A list of specific species which are exemplary of this class of yeasts may be found, for example, in C. Anthony, *The Biochemistry of Methylotrophs*, 269 (1982). Presently preferred are methylotrophic yeasts of the genus Pichia such as the auxotrophic *Pichia pastoris* GS115 (NRRL Y-15851); *Pichia pastoris* GS190 (NRRL Y-18014) disclosed in U.S. Pat. No. 4,818,700; and *Pichia pastoris* PPF1 (NRRL Y-18017) disclosed in U.S. Pat. No. 4,812,405. Auxotrophic *Pichia pastoris* strains are also advantageous to the practice of this invention for their ease of selection. It is recognized that wild type *Pichia pastoris* strains (such as NRRL Y-11430 and NRRL Y-1 1431) may be employed with equal success if a suitable transforming marker gene is selected, such as the use of SUC2 to transform *Pichia pastoris* to a strain capable of growth on sucrose, or if an antibiotic resistance marker is employed, such as resistance to G418. *Pichia pastoris* linear plasmids are disclosed, for example, in U.S. Pat. No. 5,665,600.

Suitable promoters used in yeast vectors include the promoters for 3-phosphoglycerate kinase (Hitzeman et al., *J. Biol. Chem.* 255:2073 [1980]); and other glycolytic enzymes (Hess et al., *J. Adv. Enzyme Res.* 7:149 [1968]; Holland et al., *Biochemistry* 17:4900 [1978]), e.g., enolase, glyceraldehyde-3-phosphate dehydrogenase, hexokinase, pyvurate decarboxylase, phosphoffiuctokinase, glucose-6-phosphate isomerase, 3-phosphoglycerate mutase, pyruvate kinase, triosephosphate somerase, phosphoglucose isomerase, and glucokinase. In the constructions of suitable expression plasmids, the termination sequences associated with these genes are also ligated into the expression vector 3' of the sequence desired to be expressed to provide polyadenylation of the mRNA and termination. Other promoters that have the additional advantage of transcription controlled by growth conditions are the promoter regions for alcohol oxidase 1 (AOX1, particularly preferred for expression in Pichia), alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter and termination sequences, with or without an origin of replication, is suitable. Yeast expression systems are commercially available, for example, from Clontech Laboratories, Inc. (Palo Alto, Calif., e.g. pYEX 4T family of vectors for *S. cerevisiae*), Invitrogen (Carlsbad, Calif., e.g. pPICZ series Easy Select Pichia Expression Kit) and Stratagene (La Jolla, Calif., e.g. ESP™ Yeast Protein Expression and Purification System for *S. pombe* and pESC vectors for *S. cerevisiae*).

Cell cultures derived from multicellular organisms may also be used as hosts to practice the present invention. While both invertebrate and vertebrate cell cultures are acceptable, vertebrate cell cultures, particularly mammalian cells, are preferable. Examples of suitable cell lines include monkey kidney CV1 cell line transformed by SV40 (COS-7, ATCC CRL 1651); human embryonic kidney cell line 293S (Graham et al, *J. Gen. Virol.* 36:59 [1977]); baby hamster kidney cells (BHK, ATCC CCL 10); Chinese hamster ovary (CHO) cells (Urlaub and Chasin, *Proc. Natl. Acad. Sci. USA* 77:4216 [1980]; monkey kidney cells (CVI-76, ATCC CCL 70); African green monkey cells (VERO-76, ATCC CRL-1587); human cervical carcinoma cells (HELA, ATCC CCL 2); canine kidney cells (MDCK, ATCC CCL 34); human lung cells (W138, ATCC CCL 75); and human liver cells (Hep G2, HB 8065).

Suitable promoters used in mammalian expression vectors are often of viral origin. These viral promoters are commonly derived from cytomeagolavirus (CMV), polyoma virus, Adenovirus2, and Simian Virus 40 (SV40). The SV40 virus contains two promoters that are termed the early and late promoters. They are both easily obtained from the virus as one DNA fragment that also contains the viral origin of replication (Fiers et al., Nature 273:113 [1978]). Smaller or larger SV40 DNA fragments may also be used, provided they contain the approximately 250-bp sequence extending from the HindIII site toward the BglI site located in the viral origin of replication. An origin of replication may be obtained from an exogenous source, such as SV40 or other virus, and inserted into the cloning vector. Alternatively, the host cell chromosomal mechanism may provide the origin of replication. If the vector containing the foreign gene is integrated into the host cell chromosome, the latter is often sufficient.

Eukaryotic expression systems employing insect cell hosts may rely on either plasmid or baculoviral expression systems. The typical insect host cells are derived from the fall army worm (*Spodoptera frugiperda*). For expression of a foreign protein these cells are infected with a recombinant form of the baculovirus *Autographa californica* nuclear polyhedrosis virus which has the gene of interest expressed under the control of the viral polyhedrin promoter. Other insects infected by this virus include a cell line known commercially as "High 5" (Invitrogen) which is derived from the cabbage looper (*Trichoplusia ni*). Another baculovirus sometimes used is the *Bombyx mori* nuclear polyhedorsis virus which infect the silk worm (*Bombyx mori*). Numerous baculovirus expression systems are commercially available, for example, from Invitrogen (Bac-N-Blue™), Clontech (BacPAK™ Baculovirus Expression System), Life Technologies (BAC-TO-BAC™), Novagen (Bac Vector System™), Pharmingen and Quantum Biotechnologies). Another insect cell host is common fruit fly, *Drosophila melanogaster*, for which a transient or stable plasmid based transfection kit is offered commercially by Invitrogen (The DES™ System).

Prokaryotes are the preferred hosts for the initial cloning steps, and are particularly useful for rapid production of large amounts of DNA, for production of single-stranded DNA templates used for site-directed mutagenesis, for screening many mutants simultaneously, and for DNA sequencing of the mutants generated. *E. coli* strains suitable for the production of the polypeptides of the present invention include, for example, BL21 carrying an inducible T7 RNA polymerase gene (Studier et al., Methods Enzymol. 185:60–98 [1990]); AD494 (DE3); EB105; and CB (*E. coli* B) and their derivatives; K12 strain 214 (ATCC 31,446); W3110 (ATCC 27,325); X1776 (ATCC 31,537); HB101 (ATCC 33,694); JM101 (ATCC 33,876); NM522 (ATCC 47,000); NM538 (ATCC 35,638); NM539 (ATCC 35,639), etc. Many other species and genera of prokaryotes may be used as well. Prokaryotes, e.g. *E. coli*, produce the polypeptides of the present invention in an unglycosylated form.

Vectors used for transformation of prokaryotic host cells usually have a replication site, marker gene providing for phenotypic selection in transformed cells, one or more promoters compatible with the host cells, and a polylinker region containing several restriction sites for insertion of foreign DNA. Plasmids typically used for transformation of *E. coli* include pBR322, pUC18, pUC19, pUC118, pUC119, and Bluescript M13, all of which are commercially available and described in Sections 1.12–1.20 of Sambrook et al., supra. The promoters commonly used in vectors for the transformation of prokaryotes are the T7 promoter (Studier et al., supra); the tryptophan (trp) promoter (Goeddel et al., Nature 281:544 [1979]); the alkaline phosphatase promoter (phoA); and the P-lactamase and lactose (lac) promoter systems. In *E. coli*, some polypeptides accumulate in the form of inclusion bodies, and need to be solubilized, purified, and refolded. These steps can be carried out by methods well known in the art.

Many eukaryotic proteins, including the polypeptide of SEQ ID NOS: 26 and 53 disclosed herein, contain an endogenous signal sequence as part of the primary translation product. This sequence targets the protein for export from the cell via the endoplasmic reticulum and Golgi apparatus. The signal sequence is typically located at the amino terminus of the protein, and ranges in length from about 13 to about 36 amino acids. Although the actual sequence varies among proteins, all known eukaryotic signal sequences contain at least one positively charged residue and a highly hydrophobic stretch of 10–15 amino acids (usually rich in the amino acids leucine, isoleucine, valine and phenylalanine) near the center of the signal sequence. The signal sequence is normally absent from the secreted form of the protein, as it is cleaved by a signal peptidase located on the endoplasmic reticulum during translocation of the protein into the endoplasmic reticulum. The protein with its signal sequence still attached is often referred to as the pre-protein, or the immature form of the protein, in contrast to the protein from which the signal sequence has been cleaved off, which is usually referred to as the mature protein. Proteins may also be targeted for secretion by linking a heterologous signal sequence to the protein. This is readily accomplished by ligating DNA encoding a signal sequence to the 5' end of the DNA encoding the protein, and expressing the fusion protein in an appropriate host cell. Prokaryotic and eukaryotic (yeast and mammalian) signal sequences may be used, depending on the type of the host cell. The DNA encoding the signal sequence is usually excised from a gene encoding a protein with a signal sequence, and then ligated to the DNA encoding the protein to be secreted. Alternatively, the signal sequence can be chemically synthesized. The signal must be functional, i.e. recognized by the host cell signal peptidase such that the signal sequence is cleaved and the protein is secreted. A large variety of eukaryotic and prokaryotic signal sequences is known in the art, and can be used in performing the process of the present invention. Yeast signal sequences include, for example, acid phosphatase, alpha factor, alkaline phosphatase and invertase signal sequences. Prokaryotic signal sequences include, for example LamB, OmpA, OmpB and OmpF, MalE, PhoA, and P lactamase.

Mammalian cells are usually transformed with the appropriate expression vector using a version of the calcium phosphate method (Graham et al., Virology 52:546 [1978]; Sambrook et al., supra, sections 16.32–16.37), or, more recently, lipofection . However, other methods, e.g. protoplast fusion, electroporation, direct microinjection, etc. are also suitable.

Yeast hosts are generally transformed by the polyethylene glycol method (Hinnen, Proc. Natl. Acad, Sci. USA 75:1929 [1978]). Yeast, e.g. *Pichia pastoris*, can also be transformed by other methodologies, e.g. electroporation.

Prokaryotic host cells can, for example, be transformed using the calcium chloride method (Sambrook et al., supra, section 1.82), or electroporation.

More recently, techniques have been developed for the expression of heterologous proteins in the milk of non-human transgenic animals. For example, Krimpenfort et al., *Biotechnology* 9:844–847 (1991) describes microinjection of fertilized bovine oocytes with genes encoding human proteins and development of the resulting embryos in surrogate mothers. The human genes were fused to the bovine.alpha.S.sub.1 casein regulatory elements. This general technology is also described in PCT Application WO91/08216 published Jun. 13, 1991. PCT application WO88/00239, published Jan. 14, 1988, describes procedures for obtaining suitable regulatory DNA sequences for the products of the mammary glands of sheep, including beta lactoglobulin, and the construction of transgenic sheep modified so as to secrete foreign proteins in milk. PCT publication WO88/01648, published Mar. 10, 1988, generally describes construction of transgenic animals which secrete foreign proteins into milk under control of the regulatory sequences of bovine alpha lactalbumin gene. PCT application WO88/10118, published Dec. 29, 1988, describes construction of transgenic mice and larger mammals for the production of various recombinant human proteins in milk. Thus, techniques for construction of appropriate host vectors containing regulatory sequences effective to produce foreign proteins in mammary glands and cause the secretion of said protein into milk are known in the art.

Among the milk-specific protein promoters are the casein promoters and the beta lactoglobulin promoter. The casein promoters may, for example, be selected from an alpha casein promoter, a beta casein promoter or a kappa casein promoter. Preferably, the casein promoter is of bovine origin and is an alpha S-1 casein promoter. Among the promoters that are specifically activated in mammary is the long terminal repeat (LTR) promoter of the mouse mammary tumor virus (MMTV). The milk-specific protein promoter or the promoters that are specifically activated in mammary tissue may be derived from either cDNA or genomic sequences. Preferably, they are genomic in origin.

Signal peptides that are useful in expressing heterologous proteins in the milk of transgenic amammals include milk-specific signal peptides or other signal peptides useful in the secretion and maturation of eukaryotic and prokaryotic proteins. Preferably, the signal peptide is selected from milk-specific signal peptides or the signal peptide of the desired recombinant protein product, if any. Most preferably, the milk-specific signal peptide is related to the milk-specific promoter used in the expression system of this invention.

The present invention includes amino acid sequence variants of the native rat polypeptides specifically disclosed herein or their analogues in any other animal, e.g. mammalian species, including humans. Such amino acid sequence variants can be produced by expressing the underlying DNA sequence in a suitable recombinant host cell, as described above, or by in vitro synthesis of the desired polypeptide. The nucleic acid sequence encoding a polypeptide variant of the present invention is preferably prepared by site-directed mutagenesis of the nucleic acid sequence encoding the corresponding native (e.g. human) polypeptide. Particularly preferred is site-directed mutagenesis using polymerase chain reaction (PCR) amplification (see, for example, U.S. Pat. No. 4,683,195 issued Jul. 28, 1987; and *Current Protocols In Molecular Biology*, Chapter 15 (Ausubel et al., ed., 1991). Other site-directed mutagenesis techniques are also well known in the art and are described, for example, in the following publications: *Current Protocols In Molecular Biology*, supra, Chapter 8; *Molecular Cloning: A Laboratory Manual.*, $2^{nd}$ edition (Sambrook et al., 1989); Zoller et al., *Methods Enzymol.* 100:468–500 (1983); Zoller & Smith, *DNA* 3:479–488 (1984); Zoller et al., *Nucl. Acids Res.*, 10:6487 (1987); Brake et al., *Proc. Natl. Acad. Sci. USA* 81:4642–4646 (1984); Botstein et al., *Science* 229:1193 (1985); Kunkel et al., *Methods Enzymol.* 154:367–82 (1987), Adelman et al., *DNA* 2:183 (1983); and Carter et al., *Nucl. Acids Res.*, 13:4331 (1986). Cassette mutagenesis (Wells et al., *Gene*, 34:315 [1985]), and restriction selection mutagenesis (Wells et al., *Philos. Trans. R. Soc. London SerA*, 317:415 [1986]) may also be used.

Amino acid sequence variants with more than one amino acid substitution may be generated in one of several ways. If the amino acids are located close together in the polypeptide chain, they may be mutated simultaneously, using one oligonucleotide that codes for all of the desired amino acid substitutions. If, however, the amino acids are located some distance from one another (e.g. separated by more than ten amino acids), it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant.

The amino acid sequence variants of the present invention include polypeptides in which the membrane spanning (transmembrane) region or regions are deleted or inactivated. Deletion or inactivation of these portions of the molecule yields soluble proteins, which are no longer capable of membrane anchorage. Inactivation may, for example, be achieved by deleting sufficient residues (but less than the entire transmembrane region) to produce a substantially hydrophilic hydropathy profile at this site, or by substituting with heterologous residues which accomplish the same result. For example, the transmembrane region(s) may be substituted by a random or predetermined sequence of about 5 to 50 serine, threonine, lysine, arginine, glutamine, aspartic acid and like hydrophilic residues, which altogether exhibit a hydrophilic hydropathy profile. Like the transmembrane region deletional variants, these variants are "soluble", i.e. secreted into the culture medium of recombinant hosts. Soluble variants of the native polypeptides of the present invention may be used to make fusions at their N- or C-terninus to immunogenic polypeptides, e.g. bacterial polypeptides such as beta-lactamase or an enzyme encoded by the *E. coli* trp locus, or yeast protein, and C-termninal fusions with proteins having a long half-life such as immunoglobulin regions (preferably immunoglobulin constant regions to yield imnnmunoadhesins), albumin, or ferritin, as described in WO 89/02922 published on Apr. 6, 1989. For the production of immunoglobulin fusions see also U.S. Pat. No. 5,428,130 issued Jun. 27, 1995.

3. Production of Antibodies

The present invention includes antibodies that specifically bind a polypeptide of SEQ ID NO: 2 or another mammalian (e.g. human) homologue of such polypeptide. Such antibodies find utility as reagents used, for example, in analytical chemistry or process sciences, as diagnostic and/or therapeutics.

Methods of preparing polyclonal antibodies are known in the art. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. It may be useful to conjugate the immunizing agent to a protein known to be immunogenic in the mammal being immunized, such as serum albumin, or soybean trypsin inhibitor. Examples of adjuvants which may be employed include Freund's complete adjuvant and MPL-TDM.

According to one approach, monoclonal antibodies may be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice,* Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. Preferred immortalized cell lines are those that fuse efficiently, support stable high level expression of antibody by the selected antibody-producing cells, and are sensitive to a medium such as HAT medium.

The culture medium in which the hybridoma cells are cultured can then be assayed for the presence of monoclonal antibodies directed against the particular polypeptide used, such as a rat polypeptide of SEQ ID NO: 2 or its human homologue. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.,* 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Alternatively, monoclonal antibodies may be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies).

The hybridoma cells discussed above serve as a preferred source of such DNA. Once isolated, the DNA may be placed into expression vectors, which are then transfected into host cells such as COS cells, Chinese hamster ovary (CHO) cells, or myeloma cells that do not otherwise produce immunoglobulin protein, to obtain the synthesis of monoclonal antibodies in the recombinant host cells.

The antibodies, including antibody fragments, such as Fv, Fab, Fab', F(ab')$_2$ or other antigen-binding subsequences of antibodies, may be humanized. Humanized antibodies contain minimal sequence derived from a non-human immunoglobulin. More specifically, in humanized antibodies residues from a complementary determining region (CDR) of a human imununoglobulin (the recipient) are replaced by residues from a CDR of a non-human species (donor antibody) such as mouse, rat or rabbit having the desired specificity, affinity and capacity. In some instances, Fv framework residues of the human immunoglobulin are also replaced by corresponding non-human residues. Humanized antibodies may additionally comprise residues that are found neither in the recipient antibody nor in the imported CDR or framework sequences [Jones et al., *Nature,* 321:522–525 (1986); Riechmann et al., *Nature,* 332:323–329 (1988)].

Methods for humanizing non-human antibodies are well known in the art. Generally, a humanized antibody has one or more amino acid residues introduced into it from a non-human source. These non-human amino acid residues are often referred to as "import" residues, which are typically taken from an "import" variable domain. Humanization can be essentially performed following the method of Winter and co-workers [Jones et al., *Nature* 321:522–525 (1986); Riechmann et al., *Nature,* 332:323–327 (1988); Verhoeyen et al., *Science,* 239:1534–1536 (1988)], by substituting rodent CDRs or CDR sequences for the corresponding sequences of a human antibody. In addition, human antibodies can be produced using various techniques known in the art, including phage display libraries [Hoogenboom and Winter, *J. Mol. Biol,* 227:381 (1991); Marks et al., *J. Mol. Biol.,* 222:581 (1991)]. The techniques of Cole et al. and Boerner et al. are also available for the preparation of human monoclonal antibodies (Cole et al., *Monoclonal Antibodies and Cancer Therapy,* Alan R. Liss, p. 77 (1985) and Boemer et al., *J. Immunol.,* 147(1):86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779–783 (1992); Lonberg et al., *Nature* 368 856–859 (1994); Morrison, *Nature* 368, 812–13 (1994); Fishwild et al., *Nature Biotechnology* 14, 845–51 (1996); Neuberger, *Nature Biotechnology* 14, 826 (1996); Lonberg and Huszar, *Intern. Rev. Immunol.* 13 65–93 (1995).

The antibodies may be bispecific, in which one specificity is for polypeptide of the present invention, and the other specificity for another protein, such as, a second polypeptide of the present invention or another polypeptide.

4. Uses a. Polynucleotides

The differentially expressed genes identified in accordance with the present invention may be used to design specific oligonucleotide probes and primers. In certain preferred embodiments, the term "primer" as used here includes any nucleic acid capable of priming template-dependent synthesis of a nascent nucleic acid. In certain other embodiments, the nucleic acid may be able to hybridize a template, but not be extended for synthesis of nascent nucleic acid that is complementary to the template.

In certain embodiments of the present invention the term "template" may refer to a nucleic acid that is used in the creation of a complementary nucleic acid strand to the "template" strand. The template may be either RNA or DNA, and the complementary strand may also be RNA or DNA. In certain embodiments the complementary strand may comprise all or part of the complementary sequence to the template, or may include mutations so that it is not an exact, complementary strand to the template. Strands that are not exactly complementary to the template strand may hybridize specifically to the template strand in detection assays described here, as well as other assays known in the art, and such complementary strands that can be used in detection assays are part of the invention.

When used in combination with nucleic acid amplification procedures, these probes and primers enable the rapid analysis of cell, tissue, or peripheral blood samples. In certain aspects of the invention, the term "amplification" may refer to any method or technique known in the art or described herein for duplicating or increasing the number of copies or amount of a target nucleic acid or its complement. The term "amplicon" refers to the target sequence for amplification, or that part of a target sequence that is amplified, or the amplification products of the target sequence being amplified. In certain other embodiments, an "amplicon" may include the sequence of probes or primers used in amplification. This analysis assists in detecting and diagnosing a disease, specifically cardiac, kidney or inflammatory disease, and in determining optimal treatment courses for individuals at varying stages of disease progression.

In light of the present disclosure, one skilled in the art may select segments from the identified genes for use in detection, diagnostic, or prognostic methods, vector constructs, antibody production, kits, or any of the embodiments described herein as part of the present invention. For example, in certain embodiments the sequences selected to design probes and primers may include repetitive stretches of adenine nucleotides (poly-A tails) normally attached at the ends of the RNA for the identified differentially expressed gene. In certain other embodiments, probes and primers may be specifically designed to not include these or other segments from the identified genes, as one of ordinary skill in the art may deem certain segments more suitable for use in the detection methods disclosed.

For example, where a genomic sequence is disclosed, one may use sequences that correspond to exon regions of the gene in most cases. One skilled in the art may select segments from the published exon sequences, or may assemble them into a reconstructed mRNA sequence that does not contain intronic sequences. Indeed, one skilled in the art may select or assemble segments from any of the identified gene sequences into other useful forms, such as coding segment reconstructions of MnRNA sequences from published genomic sequences of the identified differentially expressed genes, as part of the present invention. Such assembled sequences would be useful in designing probes and primers, as well as providing coding segments for protein translation and for detection, diagnosis, and prognosis embodiments of the invention described herein.

Primers can be designed to amplify transcribed portions of the differentially expressed genes of the present invention that would include any length of nucleotide segment of the transcribed sequences, up to and including the full length of each gene. It is preferred that the amplified segments of identified genes be an amplicon of at least about 50 to about 500 base pairs in length. It is more preferred that the amplified segments of identified genes be an amplicon of at least about 100 to about 400 base pairs in length, or no longer in length than the amplified segment used to normalize the quantity of message being amplified in the detection assays described herein. Such assays include RNA diagnosticing methods, however, differential expression may be detected by other means, and all such methods would fall within the scope of the present invention. The predicted size of the gene segment, calculated by the location of the primers relative to the transcribed sequence, would be used to determine if the detected amplification product is indeed the gene being amplified. Sequencing the amplified or detected band that matches the expected size of the amplification product and comparison of the band's sequence to the known or disclosed sequence of the gene would confirm that the correct gene is being amplified and detected.

The identified differentially expressed genes may also be used to identify and isolate full-length gene sequences, including regulatory elements for gene expression, from genomic human DNA libraries. The cDNA sequences or portions thereof, identified in the present disclosure may be used as hybridization probes to screen genomic human (or other mammalian) DNA libraries by conventional techniques. Once partial genomic clones have been identified, "chromosomal walking" may isolate full-length genes (also called "overlap hybridization"). See Chinault et al, *Gene* 5:111–26 (1979). Once a partial genomic clone has been isolated using a cDNA hybridization probe, nonrepetitive segments at or near the ends of the partial genomic clone may be used as hybridization probes in further genomic library screening, ultimately allowing isolation of entire gene sequences for the disease, specifically cardiac, kidney or inflammatory disease, state genes of interest. It will be recognized that full-length genes may be obtained using small ESTs via technology currently available and described in this disclosure (Sambrook et al., supra; Chinault et al., supra). Sequences identified and isolated by such means may be useful in the detection of disease genes using the detection and diagnostic methods described herein, and are part of the invention.

As described before, the identified rat gene may be used as a hybridization probe to screen human or other mammalian cDNA libraries by conventional techniques. Comparison of cloned cDNA sequences with known human or animal cDNA or genomic sequences may be performed using computer programs and databases known in the art.

The polynucleotides of the present invention are also useful in antisense-mediated gene inhibition, first introduced by Stephenson and Zamecnik (*Proc. Natl. Acad. Sci. USA* 75:285–288 [1978]; see also, Zamecnik et al., *Proc. Natl. Acad. Sci. USA* 83, 4143–4146 [1986]). This technique is based on the discovery that synthetic DNA fragments can inhibit the transcription and/or translation of selected genes in a sequence-specific manner. Since its inception, the technique has found important diagnostic and clinical therapeutic applications in many fields of oncology, vascular and genetic diseases, and in the treatment of HIV and other virus infections. To date, two main antisense strategies have been employed: transfection of cells with antisense cDNA and treatment of cells with antisense oligodeoxynucleotides (ODNs), the use of ODNs derived from the translation initiation site, e.g., between the −10 and +10 regions of the target gene nucleotide sequence of interest being preferred. According to the present invention, molecules can be designed to reduce or inhibit either normal or, if appropriate, mutant target gene activity, using antisense technology. For further details see, for example, Wagner, "Gene inhibition using antisense oligodeoxynucleotides." *Nature* 372:333–335 (1992); Tonkinson and Stein, "Antisense oligodeoxynucleotides as clinical therapeutic agents." *Cancer Invest.* 14:54–65 (1996); Askari and McDonnell, "Antisense-oligonucleotide therapy." *N. Engl. J. Med.* 334:316–318 (1996); Redekop and Naus, "Transfection with bFGF sense and antisense cDNA resulting in modification of malignant glioma growth." *J. Neurosurg.* 82:83–90 (1997); Saleh et al., "Inhibition of growth of C6 glioma cells in vivo by expression of antisense vascular endothelial growth factor sequence." *Cancer Res.* 56:393–401 (1996).

Oligodeoxynucleotides can be used for the inhibition of gene transcription in the form of triple helix structures. The base composition of these oligodeoxynucleotides must be designed to promote triple helix formation via Hoogsteen base pairing rules, which generally require sizeable stretches of either purines or pyrimidines to be present on one strand of a duplex. Nucleotide sequences can be pyrimidine-based, which will result in TAT and CGC+ triplets across the three associated strands of the resulting triple helix. The pyrimidine-rich molecules provide base complementarily to a purine-rich region of a single strand of the duplex, in a parallel orientation to that strand. In addition, nucleic acid molecules can be chosen that are purine-rich and, for example, contain a stretch of G residues. These molecules form a triple helix with a DNA duplex that is rich in GC pairs, in which the majority of the purine residues are located on a single strand of the targeted duplex, resulting in GGC triplets across the three strands in the triplex. Alternatively, creating a "switchback" nucleic acid molecule can increase the potential sequences that can be targeted for triple helix formation. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also covers the use of ribozymes. Ribozymes are enzymatic RNA molecules capable of catalyzing the specific cleavage of RNA (Rossi, *Current Biology* 4:469–71 [1994]). The mechanism of ribozyme action involves sequence specific hybridization of the ribozyme molecule to complementary target RNA, followed by an endonucleolytic cleavage. The composition of ribozyme molecules must include one or more sequences complementary to the target gene mRNA and must include the well-known catalytic sequence responsible for mRNA cleavage. For this sequence, see U.S. Pat. No. 5,093,246, which is incorporated by reference herein in its entirety. Within the scope of the present invention are engineered hammerhead motif ribozyme molecules that specifically and efficiently catalyze endonucleolytic cleavage of RNA sequences encoding target gene proteins.

Specific ribozyme cleavage sites within any potential RNA target are initially identified by scanning the molecule of interest for ribozyme cleavage sites which include the following sequences, GUA, GUU and GUC. Once identified, short RNA sequences of between 15 and 20 ribonucleotides corresponding to the region of the target gene containing the cleavage site can be evaluated for predicted structural features, such as secondary structure, that can render the oligonucleotide sequence unsuitable. The suitability of candidate sequences can also be evaluated by testing their accessibility to hybridization with complementary oligonucleotides, using ribonuclease protection assays.

In instances where the antisense, ribozyme, or triple helix molecules are utilized to reduce or inhibit mutant gene expression, it is possible that the transcription or translation of mRNA produced by normal alleles is also reduced or inhibited. As a result, the concentration of normal gene product may be lower than is necessary for a normal phenotype. In such cases, to ensure that substantially normal levels of gene activity are maintained, nucleic acid molecules that encode and express the polypeptide encoded by the gene targeted, can be introduced into cells via gene therapy methods, such as those described below. The nucleic acid sequence used in gene therapy is selected such that it does not contain sequences susceptible to the antisense, ribozyme, or triple helix treatments utilized. Alternatively, where the target gene encodes an extracellular protein, it can be preferable to co-admmister normal target gene protein into the cell or tissue in order to maintain the requisite level of cellular or tissue target gene activity.

The present invention also contemplates the use of "peptide nucleic acids" (PNAs). PNAs have a peptide-like backbone instead of the normal sugar and phosphate groups of DNA. PNAs may be used to turn on specific genes, by binding to a promoter region of a gene to initiate RNA transcription. This approach is particularly useful where a particular disease or disorder is characterized by the under-expression of a particular gene, or where the increased expression of an identified gene has a beneficial effect on the treatment of a disease, in particular cardiac, kidney or inflammatory disease. Chimeric molecules of PNA and DNA may also be considered. The DNA portion will allow enzymes attacking DNA-RNA hybrids to cut the RNA part of the complex into pieces (leading to dissociation of the drug molecule, which can then be reused), whereas the PNA portion will contribute stability and selectivity.

As noted before, the polynucleotides of the present invention can also be used in gene therapy. In gene therapy applications, genes are introduced into cells in order to achieve in vivo synthesis of a therapeutically effective genetic product, for example for replacement of a defective gene. Gene therapy includes both conventional gene therapy where a lasting effect is achieved by a single treatment, and the administration of gene therapeutic agents, which involves the one time or repeated administration of a therapeutically effective DNA or RNA.

There are a variety of techniques available for introducing nucleic acid into viable cells. The techniques differ depending upon whether the nucleic acid in transferred into cultured cells in vitro, or in vivo in the cells of the intended host. Techniques suitable for the transfer of the nucleic acid into mammalian cells in vitro include the use of liposomes, electroporation, microinjection, cell fusion, DEAE-dextran, the calcium phosphate method, etc. The currently preferred in vivo gene transfer methods include transfection with viral (typically retroviral) vectors and viral coat protein-liposome mediated transfection (Dzau et al., *Trends in Biotechnolozy* 11, 205–210 [1993]). In some situations it is desirable to provide the nucleic acid source with an agent that targets the target cells, such as an antibody specific for a cell surface membrane protein or the target cells, a ligand for a receptor on the target cells, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. For review of gene marking and gene therapy protocols see Anderson et al, Science 256, 808–813 (1992).

The information provided by the present invention can also be used to detect genetic lesions in a differentially expressed gene of the present invention, thereby determining if a subject with the lesioned gene is at risk for a disorder characterized by differentially expressed gene expression or polypeptide activity. In preferred embodiments, the methods include detecting, in a biological sample from a subject, the presence or absence of a genetic lesion characterized by, for example, an alteration affecting the integrity of a gene encoding an polypeptide or the misexpression of the gene. For example, such genetic lesions can be detected by ascertaining the existence of at least one of: a deletion of one or more nucleotides from a gene; an addition of one or more nucleotides to a gene; a substitution of one or more nucleotides of a gene; a chromosomal rearrangement of a gene; an alteration in the level of a messenger RNA transcript of a gene; aberrant modification of a gene, such as of the methylation pattern of the genomic DNA; the presence of a non-wild type splicing pattern of a messenger RNA transcript of a gene; a non-wild type level of a gene protein; allelic loss of a gene; and inappropriate post-translational modification of a gene protein. As described herein, there are a large number of assay techniques known in the art that can be used for detecting lesions in a gene.

In certain embodiments, detection of a lesion may involve the use of a probe/primer in, such as anchor PCR or RACE PCR, or, alternatively, in LCR (see, e.g., Landegran et al., Science 241: 1077–80 [1988]; and Nakazawa et al., Proc. Natl. Acad. Sci. USA 91: 360–64 [1994]), the latter of which can be particularly useful for detecting point mutations in the cardiac gene (see Abravaya et al., Nucleic Acids Res. 23: 675–82 [1995]). This method can include the steps of collecting a biological sample from a subject, isolating nucleic acid (e.g., genomic, mRNA or both) from the cells of the sample, contacting the nucleic acid sample with one or more primers which specifically hybridize to an differentially expressed gene under conditions such that hybridization and amplification of the cardiac gene (if present) occurs, and detecting the presence or absence of an amplification product, or detecting the size of the amplification product and comparing the length to a control sample.

In an alternative embodiment, mutations in a differentially expressed gene from a sample can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see U.S. Pat. No. 5,498,531) can be used to score for the presence of specific mutations by development or loss of a ribozyme cleavage site.

The arrays of immobilized DNA fragments may also be used for genetic diagnostics. To illustrate, a microarray containing multiple forms of a mutated gene or genes can be probed with a labeled mixture of a subject DNA, which will preferentially interact with only one of the immobilized versions of the gene.

The detection of this interaction can lead to a medical diagnosis. Arrays of immobilized DNA fragments can also be used in DNA probe diagnostics. For example, the identity of a differentially expressed gene of the present invention can be established unambiguously by hybridizing a sample of a subject's DNA to an array comprising known differentially expressed DNA. Other molecules of genetic interest, such as cDNAs and RNAs can be immobilized on the array or alternately used as the labeled probe mixture that is applied to the array.

b. Polypeptides

The native polypeptides of the present invention, and their equivalents in other mammalian (e.g. human) species, can be used to identify interacting proteins and genes encoding such proteins. Interacting proteins and their genes may be part of the signaling pathway in which the differentially expressed genes identified herein participate, and thus are valuable diagnostic and therapeutic candidates or targets. Among the traditional methods employed are co-immunoprecipitation, cross-linking and co-purification through gradients or chromatographic columns. Using procedures such as these allows for the identification of interactive gene products. Once identified, an interactive gene product can be used, using standard techniques, to identify its corresponding interactive gene. For example, at least a portion of the amino acid sequence of the interactive gene product can be ascertained using techniques well known to those of skill in the art, such as the Edman degradation technique (see, e.g., Creighton, Proteins: Structures and Molecular Principles, W.H. Freeman & Co. (New York, N.Y. [1983], pp. 34–49). The amino acid sequence obtained can be used as a guide for the generation of oligonucleotide mixtures that can be used to screen for interactive gene sequences. Screening can be accomplished, for example, by standard hybridization or PCR techniques. Techniques for the generation of oligonucleotide mixtures and the screening are well known.

Additionally, methods can be employed which result in the simultaneous identification of interactive genes that encode the protein interacting with a protein involved in a disease, specifically cardiac, kidney or inflammatory disease. These methods include, for example, probing expression libraries with a labeled protein known or suggested to be involved in a disease, using this protein in a manner similar to the well known technique of antibody probing of λgtII libraries.

A particularly suitable technique for studying protein-protein interactions is the yeast two-hybrid assay. Many transcriptional activators, such as yeast GAL4, consist of two physically discrete modular domains, one acting as the DNA-binding domain, while the other one functioning as the transcription activation domain. The yeast two-hybrid system takes advantage of this property, and employs two hybrid proteins, one in which the target protein is fused to the DNA-binding domain of GAL4, and another, in which candidate activating proteins are fused to the activation domain. The expression of a GAL1-calZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions using the yeast two-hybrid technique is available from Clontech. For further details see e.g. Fields and Song, Nature (London) 340:245–246 (1989); Chien et al., Proc. Natl. Acad. Sci. USA 88:9578–9582 (1991); and Chevray and Nathans, Proc. Natl. Acad. Sci. USA 89:5789–5793 (1992).

Polypeptides of the present invention may also be used to generate antibodies, using well-known techniques, some of which have been detailed above.

The polypeptides of the present invention are also useful in assays for identifying lead compounds for therapeutically active agents for the treatment of cardiac, kidney or inflammatory diseases. Candidate compounds include, for example, peptides such as soluble peptides, including Ig-tailed fusion peptides (e.g. immunoadhesins) and members of random peptide libraries (see, e.g., Lam et al., *Nature* 354:82–84 (1991); Houghten et al., *Nature* 354:84–86 (1991)) and combinatorial chemistry-derived molecular libraries made of D- or L-configuration amino acids; phosphopeptides (e.g., members of random and partially degenerate, directed phosphopeptide libraries, see, e.g., Songyang et al, *Cell* 72:767–78 (1993); antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and small organic and inorganic molecules (e.g., molecules obtained from combinatorial and natural product libraries).

Such screening assays are preferably amenable to high-throughput screening of chemical libraries, and are particularly suitable for identifying small molecule drug candidates. Small molecules, which are usually less than 10 K molecular weight, are desirable as therapeutics since they are more likely to be permeable to cells, are less susceptible to degradation by various cellular mechanisms, and are not as apt to elicit immune response as proteins. Small molecules include but are not limited to synthetic organic or inorganic compounds, and peptides. Many pharmaceutical companies have extensive libraries of such molecules, which can be conveniently screened by using the assays of the present invention. the assays can be performed in a variety of formats, including protein-protein binding assays, biochemical screening assays, immunoassays, cell based assays, etc. Such assay formats are well known in the art.

In a preferred embodiment, the screening assays of the present invention involve contacting a biological sample obtained from a subject having a disease, specifically cardiac, kidney or inflammatory disease, characterized by the differential expression of a gene identified herein, with a candidate compound or agent. The expression of the gene or the activity of the gene product is then determined in the presence and absence of the test compound or agent. When expression of differentially expressed gene mRNA or polypeptide is greater (preferably statistically significantly greater) in the presence of the candidate compound than in its absence, the candidate compound may be identified as a stimulator of differentially expressed gene expression. Alternatively, when differentially expressed gene expression is less (preferably statistically significantly less) in the presence of the candidate compound than in its absence, the candidate compound may be identified as an inhibitor of differentially expressed gene expression. The level of differentially expressed gene expression in the cells can be determined by methods described herein for detecting differentially expressed gene mRNA or protein.

Compounds identified via assays such as those described herein can be useful, for example, in elaborating the biological function of the target gene product, and for treating a cardiac, kidney or inflammatory disease, or ameliorating symptoms of such disease. In instances when a disease state or disorder results from a lower overall level of target gene expression, target gene product, or target gene product activity in a cell involved in the disease, compounds that interact with the target gene product can include ones accentuating or amplifying the activity of the bound target gene protein. Such compounds would bring about an effective increase in the level of target gene activity, thus treating the disease, disorder or state, or ameliorating its symptoms. Where mutations within the target gene cause aberrant target gene proteins to be made, which have a deleterious effect that leads to a disease, compounds that bind target gene protein can be identified that inhibit the activity of the bound target gene protein.

5. Pharmaceutical Compositions

Pharmaceutical compositions of the present invention can comprise a polynucleotide of the present invention, a product of the genes identified herein, or other therapeutically active compounds, including organic small molecules, peptides, polypeptides, antibodies etc. identified with the aid of the differentially expressed genes identified herein.

Suitable forms, in part, depend upon the use or the route of entry, for example oral, transdermal, inhalation, or by injection. Such forms should allow the agent or composition to reach a target cell whether the target cell is present in a multicellular host or in culture. For example, pharmacological agents or compositions injected into the blood stream should be soluble. Other factors are known in the art, and include considerations such as toxicity and forms that prevent the agent or composition from exerting its effect.

The active ingredient, when appropriate, can also be formulated as pharmaceutically acceptable salts (e.g., acid addition salts) and/or complexes. Pharmaceutically acceptable salts are non-toxic at the concentration at which they are administered. Pharmaceutically acceptable salts include acid addition salts such as those containing sulfate, hydrochloride, phosphate, sulfonate, sulfamate, sulfate, acetate, citrate, lactate, tartrate, methanesulfonate, ethanesulfonate, benzenesulfonate, p-toluenesulfonate, cyclolexylsulfonate, cyclohexylsulfamate and quinate. Pharmaceutically acceptable salts can be obtained from acids such as hydrochloric acid, sulfuric acid, phosphoric acid, sulfonic acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfonic acid, cyclohexylsulfamic acid, and quinic acid. Such salts may be prepared by, for example, reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Carriers or excipients can also be used to facilitate administration of the compound. Examples of carriers and excipients include calcium carbonate, calcium phosphate, various sugars such as lactose, glucose, or sucrose, or types of starch, cellulose derivatives, gelatin, vegetable oils, polyethylene glycols and physiologically compatible solvents. The compositions or pharmaceutical composition can be administered by different routes including, but not limited to, intravenous, intra-arterial, intraperitoneal, intrapericardial, intracoronary, subcutaneous, and intramuscular, oral, topical, or transmucosal.

The desired isotonicity of the compositions can be accomplished using sodium chloride or other pharmaceutically acceptable agents such as dextrose, boric acid, sodium tartrate, propylene glycol, polyols (such as mannitol and sorbitol), or other inorganic or organic solutes.

Pharmaceutical compositions can be formulated for a variety of modes of administration, including systemic and topical or localized administration. Techniques and formulations generally may be found in *Remington's Pharmaceu-* tical Sciences, 18th Edition, Mack Publishing Co., Easton, Pa. 1990. See also, Wang and Hanson "Parenteral Formulations of Proteins and Peptides: Stability and Stabilizers", Journal of Parenteral Science and Technology, Technical Report No. 10, Supp. 42–2S (1988). A suitable administration format can best be determined by a medical practitioner for each patient individually.

For systemic administration, injection is preferred, e.g., intramuscular, intravenous, intra-arterial, intracoronary, intrapericardial, intraperitoneal, subcutaneous, intrathecal, or intracerebrovascular. For injection, the compounds of the invention are formulated in liquid solutions, preferably in physiologically compatible buffers such as Hank's solution or Ringer's solution. Alternatively, the compounds of the invention are formulated in one or more excipients (e.g., propylene glycol) that are generally accepted as safe as defined by USP standards. They can, for example, be suspended in an inert oil, suitably a vegetable oil such as sesame, peanut, olive oil, or other acceptable carrier. Preferably, they are suspended in an aqueous carrier, for example, in an isotonic buffer solution at pH of about 5.6 to 7.4. These compositions can be sterilized by conventional sterilization techniques, or can be sterile filtered. The compositions can contain pharmaceutically acceptable auxiliary substances as required to approximate physiological conditions, such as pH buffering agents. Usefiul buffers include for example, sodium acetate/acetic acid buffers. A form of repository or "depot" slow release preparation can be used so that therapeutically effective amounts of the preparation are delivered into the bloodstream over many hours or days following transdermal injection or delivery. In addition, the compounds can be formulated in solid form and redissolved or suspended immediately prior to use. Lyophilized forms are also included.

Alternatively, certain compounds identified in accordance with the present invention can be administered orally. For oral administration, the compounds are formulated into conventional oral dosage forms such as capsules, tablets and tonics.

Systemic administration can also be by transmucosal or transdernal. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents can be used to facilitate permeation. Transmucosal administration can be, for example, through nasal sprays or using suppositories.

For administration by inhalation, usually inhalable dry power compositions or aerosol compositions are used, where the size of the particles or droplets is selected to ensure deposition of the active ingredient in the desired part of the respiratory tract, e.g. throat, upper respiratory tract or lungs. Inhalable compositions and devices for their administration are well known in the art. For example, devices for the delivery of aerosol medications for inspiration are known. One such device is a metered dose inhaler that delivers the same dosage of medication to the patient upon each actuation of the device. Metered dose inhalers typically include a canister containing a reservoir of medication and propellant under pressure and a fixed volume metered dose chamber. The canister is inserted into a receptacle in a body or base having a mouthpiece or nosepiece for delivering medication to the patient. The patient uses the device by manually pressing the canister into the body to close a filling valve and capture a metered dose of medication inside the chamber and to open a release valve which releases the captured, fixed volume of medication in the dose chamber to the atmosphere as an aerosol mist. Simultaneously, the patient inhales through the mouthpiece to entrain the mist into the airway. The patient then releases the canister so that the release valve closes and the filling valve opens to refill the dose chamber for the next administration of medication. See, for example, U.S. Pat. No. 4,896,832 and a product available from 3M Healthcare known as Aerosol Sheathed Actuator and Cap.

Another device is the breath actuated metered dose inhaler that operates to provide automatically a metered dose in response to the patient's inspiratory effort. One style of breath actuated device releases a dose when the inspiratory effort moves a mechanical lever to trigger the release valve. Another style releases the dose when the detected flow rises above a preset threshold, as detected by a hot wire anemometer. See, for example, U.S. Pat. Nos. 3,187,748; 3,565,070; 3,814,297; 3,826,413; 4,592,348; 4,648,393; 4,803,978.

Devices also exist to deliver dry powdered drugs to the patient's airways (see, e.g. U.S. Pat. No. 4,527,769) and to deliver an aerosol by heating a solid aerosol precursor material (see, e.g. U.S. Pat. No. 4,922,901). These devices typically operate to deliver the drug during the early stages of the patient's inspiration by relying on the patient's inspiratory flow to draw the drug out of the reservoir into the airway or to actuate a heating element to vaporize the solid aerosol precursor.

Devices for controlling particle size of an aerosol are also known, see, for example, U.S. Pat. Nos. 4,790,305; 4,926,852; 4,677,975; and 3,658,059.

For topical administration, the compounds of the invention are formulated into ointments, salves, gels, or creams, as is generally known in the art.

If desired, solutions of the above compositions can be thickened with a thickening agent such as methyl cellulose. They can be prepared in emulsified form, either water in oil or oil in water. Any of a wide variety of pharmaceutically acceptable emulsifying agents can be employed including, for example, acacia powder, a non-ionic surfactant (such as a Tween), or an ionic surfactant (such as alkali polyether alcohol sulfates or sulfonates, e.g., a Triton).

Compositions useful in the invention are prepared by mixing the ingredients following generally accepted procedures. For example, the selected components can be mixed simply in a blender or other standard device to produce a concentrated mixture which can then be adjusted to the final concentration and viscosity by the addition of water or thickening agent and possibly a buffer to control pH or an additional solute to control tonicity.

The amounts of various compounds for use in the methods of the invention to be administered can be determined by standard procedures. Generally, a therapeutically effective amount is between about 100 mg/kg and $10^{-12}$ mg/kg depending on the age and size of the patient, and the disease or disorder associated with the patient. Generally, it is an amount between about 0.05 and 50 mg/kg of the individual to be treated. The determination of the actual dose is well within the skill of an ordinary physician.

The invention is further illustrated in the following non-limiting examples.

EXAMPLES

Example 1

Identification of Differentially Expressed Rat Genes Referred to by Clone ID Number 1. In Vivo Model of Myocardial Infarction Genes P00184_D11 (SEQ ID NO:1), P00185_D11 (SEQ ID NO:3), P00188_D12 (SEQ ID NO:5), P00188_E01 (SEQ ID NO:7), P00194_G01 (SEQ ID NO:9), P00194_G05 (SEQ ID NO:11), P00194_H10 (SEQ ID NO:13), P00199_D08 (SEQ ID NO:15), P00203_D04 (SEQ ID NO:17), P00203_E06 (SEQ ID NO:19), P00209_F06 (SEQ ID NO:21), P00219_D02 (SEQ ID NO:23), P00219_F06 (SEQ ID NO:25), P00220_H05 (SEQ ID NO:27), P00222_G03 (SEQ ID NO:29), P00223_F07 (SEQ ID NO:31), P00225_C01 (SEQ ID NO:32), P00227_D11 (SEQ ID NO:34), P00228_F03 (SEQ ID NO:36), P00233_H08 (SEQ ID NO:38), P00235_G08 (SEQ ID NO:40), P00239_C11 (SEQ ID NO:42), P00240_B04 (SEQ ID NO:44), P00240_E05 (SEQ ID NO:45), P00241_E12 (SEQ ID NO:47), P00245_D06 (SEQ ID NO:48), P00246_D12 (SEQ ID NO:49), P00247_A04 (SEQ ID NO:50), P00248_B04 (SEQ ID NO:52), P00249_F09 (SEQ ID NO:54), P00258_A10 (SEQ ID NO:56), P00262_C10 (SEQ ID NO:58), P00263_G06 (SEQ ID NO:60), P00267_F08 (SEQ ID NO:61), P00269_H08 (SEQ ID NO:62), P00312_C04 (SEQ ID NO:64), P00324_H02 (SEQ ID NO:65), P00628_H02 (SEQ ID NO:66), P00629_C08 (SEQ ID NO:68), P00634_G11 (SEQ ID NO:70), P00641_G11 (SEQ ID NO:71), P00648_E12 (SEQ ID NO:73), and P00697_C03 (SEQ ID NO:75), were identified by analysis of left ventricular heart tissue obtained from an in vivo model of left ventricle myocardial infarction (MI) (Pfeffer et al, Circ. Res. 57:84–95 [1985]). Specifically, male Sprague-Dawley rats at age 7–10 weeks were anesthetized with ketamine (80 mg/kg IP) and xylazine (10 mg/kg IP). The thorax and abdomen was shaved, after which the areas were scrubbed with providone-iodine and 70% isopropyl alcohol a minimum of three times, beginning at the incision line and continuing in a circular motion proceeding toward the periphery. The rats were intubated and placed on a respirator with room air at a rate of 55 breaths/min. A left thoracotomy was performed between the fourth and fifth ribs, after which the heart was exteriorized and the left anterior descending coronary artery (LAD) ligated with silk suture. The same surgical procedure was employed for sham-operated rats, however, the suture was passed through the left ventricular wall and the LAD was not occluded.

Following the surgical procedure, negative pressure in the thoracic was quickly reestablished and the wound closed with a purse-string suture using 3–0 non-absorbable suture material. Butorphanoll (0.1 mg/kg. SQ) was provided post surgery as a prophylactic analgesic. The rats were extubated when they recovered their gag reflex and allowed recovering in a warming chamber. Seventy-five percent of the rats had large infarcts on their left ventricle free walls and perioperative mortality rate is about 50%, which is comparable to the published data.

Tissue was collected 2 week, 4 week, 8 week, 12 week and 16 week post-surgery. Blood was collected the day before surgery and the day before sacrifice for measurement of plasma atrial natriuretic peptide (ANP) level. On the day of necropsy, each heart was divided transversely into two halves so that the infarcted area is bisected. One half of the heart was used for histological evaluation, and the other for mRNA microarray analysis.

2. In Vivo Model of Septum Myocardial Infarction

Septum tissue was obtained from diseased rat hearts obtained through the left ventricle rat MI model of Pfeffer et al., as described above. Poly A+ mRNA was prepared from each of these septums for assessment of differentially expressed genes in the disease state, using microarray analysis in a preferred embodiment.

3. Preparation of Normalized cDNA Libraries

Poly A+ mRNA was prepared from each of the animals, for assessment of differentially expressed genes in the disease state, using microarray analysis. Total RNA was isolated from homogenized tissue by acid phenol extraction (Chomczynski and Sacchi, Anal. Biochem. 162(1):156–9 [1987]). Poly A+ mRNA was selected from total RNA by oligo dT hybridization utilizing a polyA Spin mRNA Isolation Kit (New England BioLabs, Beverly, Mass.) according to manufacturers' protocols. A directionally cloned cDNA library was first generated by conventional methods. Briefly, double stranded cDNA was generated by priming first strand synthesis for reverse transcription using oligo dT primers which contain a Not I restriction site. After second strand synthesis, Xba I adapters were added to the 5' end of the cDNA, and the cDNA size was selected for >500 bp and ligated into the corresponding restriction sites of phagemid vector pCR2.1 (Invitrogen, San Diego Calif.).

From the total cDNA library, a normalized library was generated as detailed elsewhere (see, e.g. Bonaldo et al, Genome Res. 6(9):791–806 [1996]) and described here briefly. Phagemid vector pCR2.1 contains an F1 origin of replication. Thus, the cDNA library can be propagated as single stranded phage with an appropriate helper virus. Single stranded, circular DNA was extracted from the phage library and served as "tester" DNA in the hybridization step of normalization. The other component of the hybridization, "driver" DNA, was generated from the library by PCR amplification using a set of the following primers specific for the region of the vector, which flanks the cloned inserts:

| | |
|---|---|
| 5'CGTATGTTGTGTGGAATTGTGAGCG | (SEQ ID NO:77) |
| 5'GATGTGCTGCAAGGCGATTAAGTTG | (SEQ ID NO:78) |

Purified tester DNA (50 ng) and driver DNA (0.5 μg) were combined in 120 mM NaCl, 50% formamide, 10 mM Tris (pH 8.0), 5 mM EDTA, and 1% SDS. A set of oligonucleotides (10 μg each), corresponding to polylinker sequence (same strand as tester DNA) which is present in the PCR product, was included in the hybridization reaction to block annealing of vector-specific sequences which are in common between tester and driver DNA. The oligonucleotide sequences were as follows:

| | |
|---|---|
| 5'GCCGCCAGTGTGCTGGAATTCGGCTAGC | (SEQ ID NO: 79) |
| 5'CGAATTCTGCAGATATCCATCACACTGG | (SEQ ID NO: 80) |
| 5'CTAGAGGGCCCAATTCGCCCTATAG | (SEQ ID NO: 81) |
| 5'TGAGTCGTATTACAATTCACTGGCC | (SEQ ID NO: 82) |
| 5'GCTCGGATCCACTAGTAACG | (SEQ ID NO: 83) |
| 5'TTTTTTTTTTTTTTTTTT | (SEQ ID NO: 84) |

The reaction mixture, under oil, was heated 3 min. at 80° C., and hybridization performed at 30° C. for 24 hr (calculated $C_o t \sim 5$). Single stranded circles were purified from the reaction mixture by hydroxylapatite (HAP) chromatography, converted to double strand DNA, and electroporated into bacteria to yield a normalized cDNA library representative of genes expressed in the left ventricle of rat. To evaluate the effectiveness of the normalization protocol, the frequency of a few clones (ANP, BNP, actin, and myosin) was assessed in both in the starting library and the normalized library. The frequency of abundant cDNAs (actin and myosin) was reduced and roughly equivalent to rarer cDNA clones (ANP and BNP). Clone frequency in the two libraries was determined with standard screening techniques by immobilizing colonies onto nylon membranes and hybridizing with radiolabeled DNA probes.

Certain genes, unexpressed in a normal tissue and turned on in diseased tissue, may be absent from the normalized cDNA library generated from normal tissue. To obtain disease-specific clones to include on the microarray, one can repeat the normalization strategy using diseased tissue obtained from the appropriate disease model. However, since most genes are expressed commonly between normal and diseased tissue, microarraying normalized libraries from diseased and normal tissue may introduce significant redundancy, a subtracted library can be made using protocols similar to those used to generate normalized libraries. Again, the method of Bonaldo et al., supra, as described here briefly, is used.

To make a subtracted library, a total cDNA library is generated from the tissue obtained from the disease model (e.g., left ventricle taken from the MI Model). The cDNA library is directionally cloned in pCR2.1 vector and single stranded tester DNA derived as described above for library normalization. The driver DNA is generated by PCR amplification of cloned inserts from the total cDNA library prepared from the left ventricle of normal rat. Hybridization occurs between sequences, which are in common to normal and diseased hearts. For this subtracted library, the reaction is driven more thoroughly (calculated $C_o t \sim 27$) than normalization by using more driver (1.5 µg vs. 0.5 µg) and longer hybridization time (48 hr vs. 24 hr). Purification of nonhybridized, single stranded circles by HAP chromatography, conversion to double strand DNA, and electroporation into bacteria yields a subtracted cDNA library enriched for genes which are expressed in diseased rat hearts. To test that the library is truly subtracted, colony hybridization is performed with probes for ANP, BNP, actin, and myosin. The subtracted library has a high frequency of ANP and BNP clones since they are elevated significantly in the hypertrophic rat heart. Actin and myosin clones are absent since they are expressed equally in normal and diseased left ventricle.

4. Microarray Analysis

High quality DNA is important for the microarray printing process. A microtiter plate protocol for PCR amplification of DNA and its subsequent purification was established that provides acceptable quality and quantity of DNA for printing on microarrays. Specifically, the following PCR probes were synthesized that amplify insert DNA from the vector pCR2.1 that was used for library construction.:

5'CGTATGTTGTGTGGAATTGTGAGCG    (SEQ ID NO: 85)

5'GATGTGCTGCAAGGCGATTAAGTTG    (SEQ ID NO: 86)

After 30 cycles of amplification each PCR product was passed over a gel filtration column to remove unincorporated primers and salts. To maintain robustness, the columns were packed in 96-well filter plates and liquid handling was performed using a robotic liquid handler (Biomek 2000, Beckman).

To test the quality of DNA prepared by this PCR method, 96 purified samples from a single microtiter plate were produced as a microarray. Using the robotic liquid handler, 85 µl of PCR reaction mixture was aliquoted into each well of a thin walled, 0.2 ml 96-well plate. The reaction mixture contained 0.2 mM each dNTP, 1.25 units of Taq polymerase, and 1×Taq buffer (Boehringer Mannheim). Primers, 1 µm each, are from vector regions, which flank the cloning site of pCR2.1 and include a 5' primary amine with a 6-carbon linker to facilitate attachment of DNA product to the glass surface of the microarray chip. 1.0 µl of bacterial culture of individual cDNA clones was added to each well. PCR conditions were: 2 min., 95° C. to denature, then 30 cycles of 95° C., 30 sec./65° C., 40 sec./72° C., 1 min. 30 sec., and a final extension of 72° C., 5 min. using a MJRsearch PTC 100 thermocycler.

PCR products were purified by gel filtration over Sephacryl 400 (Sigma). Briefly, 400 µl of pre-swollen Sephacryl 400 was loaded into each well of a 96-well filter plate (PallBiosupport) and spun into a collection plate at 800 g for 1 min. Wells were washed 5 times with 0.2×SSC. PCR reaction mixtures were loaded onto the column and purified DNA (flow-through) was collected at 800 g for 1 min. Samples were dried down at 50° C. overnight and arrayed.

Fluorescent probe pairs were synthesized by reverse transcription of poly A+ RNA using, separately, Cy3 dCTP and Cy5 dCTP (Amersham). In 16.5 µl, 1 µg poly A+ RNA and 2 µg of oligo dT 21 mer, were denatured at 65° C., 5 min. and annealed at 25° C., 10 min. Reverse transcription was performed for 2 hours at 37° C. with Superscript RT (Life Technologies, Gaithersburg, Md.) in 1×buffer, 10 units RNase block, 500 µM each dATP/dGTP/dTTP, 280 µM dCTP, 40 µM Cy5 or Cy3 dCTP, and 200 units RT. RNA is degraded in 0.1 M NaOH, 65° C. for 10 min. Labeled cDNA was purified by successive filtration with Chroma Spin 30 spin columns (Clontech) following manufacturer's instructions. Samples were dried at room temperature in the dark using a covered Speed-Vac. Probes were applied to the test chip for hybridization and the data collected essentially as described in Schena et al., cited above The intensity of hybridization signal at each element reflected the level of expression of the mRNA for each gene in the rat ventricle. Digitized signal data was stored and prepared for analysis.

A series of control DNA elements were included on each chip to ensure consistency in labeling and hybridization between experiments and to aid in balancing the signal when two fluorescence channels are used. For each element hybridized with dual labeled probes, absolute and relative intensity of signal was determined. The results from these and other experiments indicate that these methods for production of template DNA and labeled cDNA probes are suitable for generating high quality microarrays within a preferred embodiment of the methods of the present invention. The evaluation of tens of thousands of genes for expression generates a large amount of data that can be manipulated by commercially available software packages that facilitate handling this type and quantity of data. The expression data can be stored, analyzed, and sorted from each experiment using this software. In addition, expression of each clone can be tracked from experiment to experiment using known methodologies.

The novel secreted factor of the present invention was identified from expression data from the following experiments: A 10,000 clone microarray (10K) from a normalized normal rat left ventricle (LV) cDNA library was probed in duplicate. A 3,000 clone array, which included differentially expressed clones from the 10K library, was also probed in duplicate. Included on the microarray with the unidentified genes were a set of known clones. These known clones were included because they represent genes of particular interest and help evaluate the sensitivity of the microarray methodology. Indeed, any genes of particular interest may be included on such microarrays. By way of example, ANP, BNP, endothelin, β-myosin heavy chain, and α-actin are genes that change expression levels in the LVH model, and thus they serve as useful positive controls in the in vivo model exemplified herein.

The intensity of hybridization signal at each element of the microarray reflected the level of expression of the mRNA for each gene. For each element hybridized with dual labeled probes, absolute and relative intensity of signal was determined, which translates into the relative expression levels of the subject genes. The numeric data obtained reflect the relative expression level of the gene in the disease state as compared to the expression level of the gene in the normal, or non-disease state. Positive numbers are indicative of genes expressed at higher levels in the diseased tissue relative to normal tissue, and negative values are indicative of lower expression in disease. Data are the average values from multiple experiments performed with separate DNA arrays (n=4 for MI left ventricle and septum). Array probes were generated from RNA pooled from multiple animals (n=4 for MI).

The data also reflect expression levels of genes in certain disease models over various time points. For example, gene expression in the myocardial infarction model was compared at 2, 4, 8, 12, and 16 weeks for the representative genes in the disease state versus the normal state. Indeed, such experimentation provides valuable data regarding the temporal relationship of gene expression levels in disease states and provides important insights regarding the treatment, diagnosis, and modulation of differentially expressed disease state genes, as discussed in detail infra.

One to two percent of the clones assayed on microarrays were found to be differentially expressed. Secondary chips may be used for more extensive hybridizations, including examination of individual animals, and more thorough evaluation of time points. In a preferred embodiment, clones that reproducibly scored in microarray analysis to be at least about 1.8-fold elevated or decreased were microarrayed on separate secondary chips and their expression levels determined. It is understood, however, that differentially expressed genes exhibiting less than about a two-fold change in expression, e.g., less than one, one-half, or one-quarter, or greater than about a two-fold change in expression, e.g., greater than three, five, ten, twenty, one hundred-fold, or one thousand-fold, are within the scope of the present invention.

5. Microarray Results

Using the foregoing protocols, it was found that in the MI model, the expression level of the gene corresponding to the clones were differentially expressed in heart and kidney. This differential expression suggests the possible involvement of these genes in the development and/or progress of MI. The results are summarized in FIG. 44.

6. Sequence Analysis

The differentially expressed partial and full-length clones P00184_D11 (SEQ ID NO:1), P00185_D11(SEQ ID NO:3), P00188_D12 (SEQ ID NO:5), P00188_E01 (SEQ ID NO:7), P00194_G01 (SEQ ID NO:9), P00194_G05 (SEQ ID NO:11), P00194_H10 (SEQ ID NO:13), P00199_D08 (SEQ ID NO:15), P00203_D04 (SEQ ID NO:17), P00203_E06 (SEQ ID NO:19), P00209_F06 (SEQ ID NO:21), P00219_D02 (SEQ ID NO:23), P00219_F06 (SEQ ID NO:25), P00220_H05 (SEQ ID NO:27), P00222_G03 (SEQ ID NO:29), P00223_F07 (SEQ ID NO:31), P00225_C01 (SEQ ID NO:32), P00227_D11 (SEQ ID NO:34), P00228_F03 (SEQ ID NO:36), P00233_H08 (SEQ ID NO:38), P00235_G08 (SEQ ID NO:40), P00239_C11 (SEQ ID NO:42), P00240_B04 (SEQ ID NO:44), P00240_E05 (SEQ ID NO:45), P00241_E12 (SEQ ID NO:47), P00245_D06 (SEQ ID NO:48), P00246_D12 (SEQ ID NO:49), P00247_A04 (SEQ ID NO:50), P00248_B04 (SEQ ID NO:52), P00249_F09 (SEQ ID NO:54), P00258_A10 (SEQ ID NO:56), P00262_C10 (SEQ ID NO:58), P00263_G06 (SEQ ID NO:60), P00267_F08 (SEQ ID NO:61), P00269_H08 (SEQ ID NO:62), P00312_C04 (SEQ ID NO:64), P00324_H02 (SEQ ID NO:65), P00628_H02 (SEQ ID NO:66), P00629_C08 (SEQ ID NO:68), P00634_G11 (SEQ ID NO:70), P00641_G11 (SEQ ID NO:71), P00648_E12 (SEQ ID NO:73), and P00697_C03 (SEQ ID NO:75) were sequenced (SEQ ID NOs: 1, 3, 5, 7, 9, 11, 13, 15, 17, 19, 21, 23, 25, 27, 29, 31, 32, 34, 36, 38, 40, 42, 44, 45,47, 48, 49, 50, 52, 54, 56, 58, 59, 60, 61, 62, 64, 65, 66, 68, 70, 71, 73, and 75), and the deduced amnino acid sequence was determined (SEQ ID NOs: 2, 4, 6, 8, 10, 12, 14, 16, 18, 20, 22, 24, 26, 28, 30, 33, 35, 37, 39, 41, 43, 46, 51, 53, 55, 57, 59, 63, 67, 69, 72, 74, and 76). FIGS. 1–43 show the deduced amnino acid sequence of the polypeptide encoded by the clones as well as the nucleotide sequences.

The nucleotide sequences of the clones were compared with sequences in the public GenBank, EMBL, DDBJ, PDB and GENSEQ databases. The search was performed using the BLASTN 2.0.8 program with default parameters. Gap penalties: existence: 5; extension: 2. The search revealed no significant homology with sequences present in the searched databases.

7. Northern Blot Analysis

Northern blot analysis suggested that the clones are differentially expressed (see FIG. 44).

Example 2

Identification of the Human Homologue of Rat Clone

The isolated differentially expressed rat gene sequence can be labeled and used to screen a cDNA library constructed from mRNA obtained from an organism of interest. Hybridization conditions will be of a lower stringency when the cDNA library was derived from an organism different from the type of organism from which the labeled sequence was derived. Alternatively, the labeled fragment can be used to screen a genomic library derived from the organism of interest, again, using appropriately stringent conditions. Such low stringency conditions will be well known to those of skill in the art, and will vary predictably depending on the specific organisms from which the library and the labeled sequences are derived. For guidance regarding such conditions see, Sambrook et al., supra, and Ausubel et al., supra.

PCR technology can also be utilized to isolate full-length human cDNA sequences. For example, RNA can be isolated, following standard procedures, from an appropriate human cellular or tissue source. A reverse transcription reaction can be performed on the RNA using an oligonucleotide primer specific for the most 5' end of the amplified fragment for the priming of first strand synthesis. The resulting RNA/DNA hybrid can then be "tailed" with guanines using a standard terminal transferase reaction, the hybrid can be digested with RNase H, and second strand synthesis can then be primed with a poly-C primer. Thus, cDNA sequences upstream of the amplified fragment can easily be isolated. For a review of cloning strategies that can be used, see, e.g., Sambrook et al., supra, and Ausubel et al., supra.

Alternatively, the human homologue can be isolated using the CloneCapture cDNA selection Kit (Clontech, Palo Alto, Calif.): a RecA-based system for the rapid enrichment and isolation of cDNA clones of interest without library screening.

Example 3

Expression of the Clones in E. coli

The P00184_D11 (SEQ ID NO:1), P00185_D11 (SEQ ID NO:3), P00188_D12 (SEQ ID NO:5), P00188_E01 (SEQ ID NO:7), P00194_G01 (SEQ ID NO:9), P00194_G05 (SEQ ID NO:11), P00194_H10 (SEQ ID NO:13), P00199_D08 (SEQ ID NO:15), P00203_D04 (SEQ ID NO:17), P00203_E06 (SEQ ID NO:19), P00209_F06 (SEQ ID NO:21), P00219_D02 (SEQ ID NO:23), P00219_F06 (SEQ ID NO:25), P00220_H05 (SEQ ID NO:27), P00222_G03 (SEQ ID NO:29), P00225_C01 (SEQ ID NO:32), P00227_D11 (SEQ ID NO:34), P00228_F03 (SEQ ID NO:36), P00233_H08 (SEQ ID NO:38), P00235_G08 (SEQ ID NO:40), P00239_C11 (SEQ ID NO:42), P00240_E05 (SEQ ID NO:45), P00247_A04 (SEQ ID NO:50), P00248_B04 (SEQ ID NO:52), P00249_F09 (SEQ ID NO:54), P00258_A10 (SEQ ID NO:56), P00262_C10 (SEQ ID NO:58), P00269_H08 (SEQ ID NO:62), P00628_H02 (SEQ ID NO:66), P00629_C08 (SEQ ID NO:68), P00641_G11 (SEQ ID NO:71), P00648_E12 (SEQ ID NO:73), and P00697_C03 (SEQ ID NO:75) DNA is initially amplified using selected PCR primers. The primers should contain restriction enzyme sites that correspond to the restriction enzyme sites on the selected expression vector. A variety of expression vectors may be employed. An example of a suitable vector is pBR322 (derived from E. coli; see Bolivar et al., Gene, 2:95 [1977]) which contains genes for ampicillin and tetracycline resistance, or a pBR322-based vector. Other, commercially available vectors include various pUC vectors and Bluescript M13. The vector is digested with restriction enzyme and dephosphorylated. The PCR amplified sequences are then ligated into the vector. The vector will preferably include sequences that encode an antibiotic resistance gene, a promoter, such as a T7 or tryptophan (trp) promoter, a polyhis leader (including the first six STII codons, polyhis sequence, and enterokinase cleavage site), the P00184_D11 (SEQ ID NO:1), P00185_D11 (SEQ ID NO:3), P00188_D12 (SEQ ID NO:5), P00188_E01 (SEQ ID NO:7), P00194_G01 (SEQ ID NO:9), P00194_G05 (SEQ ID NO:11), P00194_H10 (SEQ ID NO:13), P00199_D08 (SEQ ID NO:15), P00203_D04 (SEQ ID NO:17), P00203_E06 (SEQ ID NO:19), P00209_F06 (SEQ ID NO:21), P00219_D02 (SEQ ID NO:23), P00219_F06 (SEQ ID NO:25), P00220_H05 (SEQ ID NO:27), P00222_G03 (SEQ ID NO:29), P00225_C01 (SEQ ID NO:32), P00227_D11 (SEQ ID NO:34), P00228_F03 (SEQ ID NO:36), P00233_H08 (SEQ ID NO:38), P00235_G08 (SEQ ID NO:40), P00239_C11 (SEQ ID NO:42), P00240_E05 (SEQ ID NO:45), P00247_A04 (SEQ ID NO:50), P00248_B04 (SEQ ID NO:52), P00249_F09 (SEQ ID NO:54), P00258_A10 (SEQ ID NO:56), P00262_C10 (SEQ ID NO:58), P00269_H08 (SEQ ID NO:62), P00628_H02 (SEQ ID NO:66), P00629_C08 (SEQ ID NO:68), P00641_G11 (SEQ ID NO:71), P00648_E12 (SEQ ID NO:73), and P00697_C03 (SEQ ID NO:75) coding region, lambda transcriptional terminator, and an argU gene.

The ligation mixture is then used to transform a selected E. coli strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized protein can then be purified using a metal chelating column under conditions that allow tight binding of the poly-his tagged protein.

Example 4

Expression of the Clones in Yeast

A yeast expression vector is constructed either for intracellular production or secretion of the protein encoded by P00184_D11 (SEQ ID NO:1), P00185_D11 (SEQ ID NO:3), P00188_D12 (SEQ ID NO:5), P00188_E01 (SEQ ID NO:7), P00194_G01 (SEQ ID NO:9), P00194_G05 (SEQ ID NO:11), P00194_H10 (SEQ ID NO:13), P00199_D08 (SEQ ID NO:15), P00203_D04 (SEQ ID NO:17), P00203_E06 (SEQ ID NO:19), P00209_F06 (SEQ ID NO:21), P00219_D02 (SEQ ID NO:23), P00219_F06 (SEQ ID NO:25), P00220_H05 (SEQ ID NO:27), P00222_G03 (SEQ ID NO:29), P00225_C01 (SEQ ID NO:32), P00227_D11 (SEQ ID NO:34), P00228_F03 (SEQ ID NO:36), P00233_H08 (SEQ ID NO:38), P00235_G08 (SEQ ID NO:40), P00239_C11 (SEQ ID NO:42), P00240_E05 (SEQ ID NO:45), P00247_A04 (SEQ ID NO:50), P00248_B04 (SEQ ID NO:52), P00249_F09 (SEQ ID NO:54), P00258_A10 (SEQ ID NO:56), P00262_C10 (SEQ ID NO:58), P00269_H08 (SEQ ID NO:62), P00628_H02 (SEQ ID NO:66), P00629_C08 (SEQ ID NO:68), P00641_G11 (SEQ ID NO:71), P00648_E12 (SEQ ID NO:73), and P00697_C03 (SEQ ID NO:75), using an appropriate yeast promoter, such the promoter of 3-phosphoglycerate kinase, or the promoter regions for alcohol oxidase 1 (AOX1, particularly preferred for expression in Pichia), alcohol dehydrogenase 2, or isocytochrome C. For secretion, the P00184_D11 (SEQ ID NO:1), P00185_D11 (SEQ ID NO:3), P00188_D12 (SEQ ID NO:5), P00188_E01 (SEQ ID NO:7), P00194_G01 (SEQ ID NO:9), P00194_G05 (SEQ ID NO:11), P00194_H10 (SEQ ID NO:13), P00199_D08 (SEQ ID NO:15), P00203_D04 (SEQ ID NO:17), P00203_E06 (SEQ ID NO:19), P00209_F06 (SEQ ID NO:21), P00219_D02 (SEQ ID NO:23), P00219_F06 (SEQ ID NO:25), P00220_H05 (SEQ ID NO:27), P00222_G03 (SEQ ID NO:29), P00225_C01 (SEQ ID NO:32), P00227_D11 (SEQ ID NO:34), P00228_F03 (SEQ ID NO:36), P00233_H08 (SEQ ID NO:38), P00235_G08 (SEQ ID NO:40), P00239_C11 (SEQ ID NO:42), P00240_E05 (SEQ ID NO:45), P00247_A04 (SEQ ID NO:50), P00248_B04 (SEQ ID NO:52), P00249_F09 (SEQ ID NO:54), P00258_A10 (SEQ ID NO:56), P00262_C10 (SEQ ID NO:58), P00269_H08 (SEQ ID NO:62), P00628_H02 (SEQ ID NO:66), P00629_C08 (SEQ ID NO:68), P00641_G11 (SEQ ID NO:71), P00648_E12 (SEQ ID NO:73), and P00697_C03 (SEQ ID NO:75) coding sequence is linked, at its 5'-end, to a mammalian or yeast signal (secretory leader) sequence, such as a yeast alpha-factor or invertase secretory signal. Alternatively, a commercially available yeast expression system is used that can be purchased, for example, from Clontech Laboratories, Inc. (Palo Alto, Calif., e.g. pYEX 4T family of vectors for *Saccharomyces cerevisiae*), Invitrogen (Carlsbad, Calif., e.g. pPICZ series Easy Select Pichia Expression Kit) or Stratagene (La Jolla, Calif., e.g. ESP™ Yeast Protein Expression and Purification System for *S. pombe* and pESC vectors for *S. cerevisiae*).

Yeast cells, such as *S. cerevisiae* AB110 strain, or *P. pastoris* GS115 (NRRL Y-15851); GS190 (NRRL Y-18014) or PPF1 (NRRL Y-18017) are then transformed by known techniques, e.g. by the polyethylene glycol method (Hinnen, *Proc. Natl. Acad, Sci. USA* 75:1929 [1978]).

The recombinant protein is subsequently isolated and purified by removing the yeast cells from the fermentation medium by centrifugation and then concentrating the medium using selected cartridge filters. The concentrate containing the expressed protein may be further purified using selected column chromatography resins.

Example 5

Expression of the Clones in Mammalian Host Cells

The P00184_D11 (SEQ ID NO:1), P00185_D11 (SEQ ID NO:3), P00188_D12 (SEQ ID NO:5), P00188_E01 (SEQ ID NO:7), P00194_G01 (SEQ ID NO:9), P00194_G05 (SEQ ID NO:11), P00194_H10 (SEQ ID NO:13), P00199_D08 (SEQ ID NO:15), P00203_D04 (SEQ ID NO:17), P00203_E06 (SEQ ID NO:19), P00209_F06 (SEQ ID NO:21), P06219_D02 (SEQ ID NO:23), P00219_F06 (SEQ ID NO:25), P00220_H05 (SEQ ID NO:27), P00222_G03 (SEQ ID NO:29), P00225_C01 (SEQ ID NO:32), P00227_D11 (SEQ ID NO:34), P00228_F03 (SEQ ID NO:36), P00233_H08 (SEQ ID NO:38), P00235_G08 (SEQ ID NO:40), P00239_C11 (SEQ ID NO:42), P00240_E05 (SEQ ID NO:45), P00247_A04 (SEQ ID NO:50), P00248_B04 (SEQ ID NO:52), P00249_F09 (SEQ ID NO:54), P00258_A10 (SEQ ID NO:56), P00262_C10 (SEQ ID NO:58), P00269_H08 (SEQ ID NO:62), P00628_H02 (SEQ ID NO:66), P00629_C08 (SEQ ID NO:68), P00641_G11 (SEQ ID NO:71), P00648_E12 (SEQ ID NO:73), and P00697_C03 (SEQ ID NO:75) genes are subjected to PCR using primers containing suitable restriction enzyme cleavage sites to allow ligation into a mammalian expression vector such as pCEP4 (Invitrogen). To facilitate the eventual recovery of the expressed protein, it is advisable to use the 3' PCR primer to extend the open reading frame of the cloned gene to include an affinity purification tag such as poly-His (E. Hochuli et al 1987, *J. Chrom.* 411, 177–184) or calmodulin binding peptide (Hathaway et al, *J. Biol. Chem.* 1981, 256(15):8183–9). Recovery of the PCR fragment may be followed by its cleavage at the new flanking restriction sites and ligation into a similarly cleaved pCEP4 preparation. Transformation of bacteria and preparation of plasmids from transformants is followed by verification of the plasmid structure by restriction analysis.

Expression of the P00184_D11 (SEQ ID NO:1), P00185_D11 (SEQ ID NO:3), P00188_D12 (SEQ ID NO:5), P00188_E01 (SEQ ID NO:7), P00194_G01 (SEQ ID NO:9), P00194_G05 (SEQ ID NO:11), P00194_H10 (SEQ ID NO:13), P00199_D08 (SEQ ID NO:15), P00203_D04 (SEQ ID NO:17), P00203_E06 (SEQ ID NO:19), P00209_F06 (SEQ ID NO:21), P00219_D02 (SEQ ID NO:23), P00219_F06 (SEQ ID NO:25), P00220_H05 (SEQ ID NO:27), P00222_G03 (SEQ ID NO:29), P00225_C01 (SEQ ID NO:32), P00227_D11 (SEQ ID NO:34), P00228_F03 (SEQ ID NO:36), P00233_H08 (SEQ ID NO:38), P00235_G08 (SEQ ID NO:40), P00239_C11 (SEQ ID NO:42), P00240_E05 (SEQ ID NO:45), P00247_A04 (SEQ ID NO:50), P00248_B04 (SEQ ID NO:52), P00249_F09 (SEQ ID NO:54), P00258_A10 (SEQ ID NO:56), P00262_C10 (SEQ ID NO:58), P00269_H08 (SEQ ID NO:62), P00628_H02 (SEQ ID NO:66), P00629_C08 (SEQ ID NO:68), P00641_G11 (SEQ ID NO:71), P00648_E12 (SEQ ID NO:73), and P00697_C03 (SEQ ID NO:75) genes can be accomplished by transient expression in 293 human embryonic kidney cells. For use of vectors such as pCEP4 having the EBV viral origin of replication, 293EBNA cells that are permissive for replication can be used. Transfection is accomplished using a lipid transfection reagent such as Lipofectamine Plus (Life Technologies, Rockville, Md.). Endotoxin-free plasmid DNA (100 μg) is added to 200 μl PLUS reagent and 10 ml DMEM-21 serum free media to give Mix A. This is incubated at room temperature for 15 minutes. Mix B is prepared from 400 μl Lipofectamine and 10 ml serum-free DMEM-21. The two mixes are then combined and incubated at room temperature for another 15 minutes. An 850 cm$^2$ roller bottle containing the cells to be transfected at 70% confluence is rinsed with serum-free media and 100 ml of serum-free DMEM-2 with 15 mM HEPES pH 7.3 and the DNA-lipid transfection mixture is then added. The cells are then placed in a roller unit at 37□ for 4 hours after which the volume of media is doubled by addition of DMEM-2 with 15 mM HEPES pH 7.3, 5% FBS and the bottle returned to roller unit overnight. Collect conditioned media every 2–3 days for 2–3 collections.

Example 6

Expression of the Clones in Baculovirus-infected Insect Cells

Baculovirus-based expression is performed using one of the commercially available baculovirus expression systems such as, for example, from Bac-N-Blue™ (Invitrogen), BacPAK™ Baculovirus Expression System (Clontech), BAC-TO-BAC™ (Life Technologies), or Bac Vector System™ (Novagen). Viral infection of insect cells (e.g. *Spodoptera frugiperda* ("Sf9") cells (ATCC CRL 1711)) and protein expression and purification are performed following manufacturers' instructions, or as described by O'Reilley et al., *Baculovirus expression vectors: A Laboratory Manual,* Oxford: Oxford University Press (1994). Optionally, the coding region of the P00184_D11 (SEQ ID NO:1), P00185_D11 (SEQ ID NO:3), P00188_D12 (SEQ ID NO:5), P00188_E01 (SEQ ID NO:7), P00194_G01 (SEQ ID NO:9), P00194_G05 (SEQ ID NO:11), P00194_H10 (SEQ ID NO:13), P00199_D08 (SEQ ID NO:15), P00203_D04 (SEQ ID NO:17), P00203_E06 (SEQ ID NO:19), P00209_F06 (SEQ ID NO:21), P00219_D02 (SEQ ID NO:23), P00219_F06 (SEQ ID NO:25), P00220_H05

(SEQ ID NO:27), P00222_G03 (SEQ ID NO:29), P00225_C01 (SEQ ID NO:32), P00227_D11 (SEQ ID NO:34), P00228_F03 (SEQ ID NO:36), P00233_H08 (SEQ ID NO:38), P00235_G08 (SEQ ID NO:40), P00239_C11 (SEQ ID NO:42), P00240_E05 (SEQ ID NO:45), P00247_A04 (SEQ ID NO:50), P00248_B04 (SEQ ID NO:52), P00249_F09 (SEQ ID NO:54), P00258_A10 (SEQ ID NO:56), P00262_C10 (SEQ ID NO:58), P00269_H08 (SEQ ID NO:62), P00628_H02 (SEQ ID NO:66), P00629_C08 (SEQ ID NO:68), P00641_G11 (SEQ ID NO:71), P00648_E12 (SEQ ID NO:73), and P00697_C03 (SEQ ID NO:75) sequence is fused upstream of an epitope tag contained within a baculovirus expression vector, such as a poly-His tag or an immunoglobulin (Ig) tag (like Fc regions of an IgG). The poly-His or Ig tag aids protein purification.

Example 7

Preparation of antibodies that bind the polypeptide encoded by P00184_D11 (SEQ ID NO:1), P00185_D11 (SEQ ID NO:3), P00188_D12 (SEQ ID NO:5), P00188_E01 (SEQ ID NO:7), P00194_G01 (SEQ ID NO:9), P00194_G05 (SEQ ID NO:11), P00194_H10 (SEQ ID NO:13), P00199_D08 (SEQ ID NO:15), P00203_D04 (SEQ ID NO:17), P00203_E06 (SEQ ID NO:19), P00209_F06 (SEQ ID NO:21), P00219_D02 (SEQ ID NO:23), P00219_F06 (SEQ ID NO:25), P00220_H05 (SEQ ID NO:27), P00222_G03 (SEQ ID NO:29), P00225_C01 (SEQ ID NO:32), P00227_D11 (SEQ ID NO:34), P00228_F03 (SEQ ID NO:36), P00233_H08 (SEQ ID NO:38), P00235_G08 (SEQ ID NO:40), P00239_C11 (SEQ ID NO:42), P00240_E05 (SEQ ID NO:45), P00247_A04 (SEQ ID NO:50), P00248_B04 (SEQ ID NO:52), P00249_F09 (SEQ ID NO:54), P00258_A10 (SEQ ID NO:56), P00262_C10 (SEQ ID NO:58), P00269_H08 (SEQ ID NO:62), P00628_H02 (SEQ ID NO:66), P00629_C08 (SEQ ID NO:68), P00641_G11 (SEQ ID NO:71), P00648_E12 (SEQ ID NO:73), and P00697_C03 (SEQ ID NO:75)

This example illustrates preparation of monoclonal antibodies that specifically bind the polypeptide encoded by P00184_D11 (SEQ ID NO:1), P00185_D11 (SEQ ID NO:3), P00188_D12 (SEQ ID NO:5), P00188_E01 (SEQ ID NO:7), P00194_G01 (SEQ ID NO:9), P00194_G05 (SEQ ID NO:11), P00194_H10 (SEQ ID NO:13), P00199_D08 (SEQ ID NO:15), P00203_D04 (SEQ ID NO:17), P00203_E06 (SEQ ID NO:19), P00209_F06 (SEQ ID NO:21), P00219_D02 (SEQ ID NO:23), P00219_F06 (SEQ ID NO:25), P00220_H05 (SEQ ID NO:27), P00222_G03 (SEQ ID NO:29), P00225_C01 (SEQ ID NO:32), P00227_D11 (SEQ ID NO:34), P00228_F03 (SEQ ID NO:36), P00233_H08 (SEQ ID NO:38), P00235_G08 (SEQ ID NO:40), P00239_C11 (SEQ ID NO:42), P00240_E05 (SEQ ID NO:45), P00247_A04 (SEQ ID NO:50), P00248_B04 (SEQ ID NO:52), P00249_F09 (SEQ ID NO:54), P00258_A10 (SEQ ID NO:56), P00262_C10 (SEQ ID NO:58), P00269_H08 (SEQ ID NO:62), P00628_H02 (SEQ ID NO:66), P00629_C08 (SEQ ID NO:68), P00641_G11 (SEQ ID NO:71), P00648_E12 (SEQ ID NO:73), and P00697_C03 (SEQ ID NO:75).

Techniques for producing the monoclonal antibodies are known in the art and are described, for instance, in Goding, supra. The immunogen may, for example, be purified protein encoded by the clone or recombinant host cells expressing P00184_D11 (SEQ ID NO:1), P00185_D11 (SEQ ID NO:3), P00188_D12 (SEQ ID NO:5), P00188_E01 (SEQ ID NO:7), P00194_G01 (SEQ ID NO:9), P00194_G05 (SEQ ID NO:11), P00194_H10 (SEQ ID NO:13), P00199_D08 (SEQ ID NO:15), P00203_D04 (SEQ ID NO:17), P00203_E06 (SEQ ID NO:19), P00209_F06 (SEQ ID NO:21), P00219_D02 (SEQ ID NO:23), P00219_F06 (SEQ ID NO:25), P00220_H05 (SEQ ID NO:27), P00222_G03 (SEQ ID NO:29), P00225_C01 (SEQ ID NO:32), P00227_D11 (SEQ ID NO:34), P00228_F03 (SEQ ID NO:36), P00233_H08 (SEQ ID NO:38), P00235_G08 (SEQ ID NO:40), P00239_C11 (SEQ ID NO:42), P00240_E05 (SEQ ID NO:45), P00247_A04 (SEQ ID NO:50), P00248_B04 (SEQ ID NO:52), P00249_F09 (SEQ ID NO:54), P00258_A10 (SEQ ID NO:56), P00262_C10 (SEQ ID NO:58), P00269_H08 (SEQ ID NO:62), P00628_H02 (SEQ ID NO:66), P00629_C08 (SEQ ID NO:68), P00641_G11 (SEQ ID NO:71), P00648_E12 (SEQ ID NO:73), and P00697_C03 (SEQ ID NO:75). Mice, such as Balb/c, are immunized with the immunogen emulsified in a selected adjuvant, for example Freund's adjuvant, and injected subcutaneously or intraperitoneally in an amount from 1–100 micrograms. Approximately 10 to 12 days later, the immunized mice are boosted with additional immunogen emulsified in the selected adjuvant. Thereafter, for several weeks, the mice may get additional boosts. Serum samples may be periodically obtained from the mice by retro-orbital bleeding for testing in ELISA assays to detect antibodies to the polypeptide encoded by P00184_D11 (SEQ ID NO:1), P00185_D11 (SEQ ID NO:3), P00188_D12 (SEQ ID NO:5), P00188_E01 (SEQ ID NO:7), P00194_G01 (SEQ ID NO:9), P00194_G05 (SEQ ID NO:11), P00194_H10 (SEQ ID NO:13), P00199_D08 (SEQ ID NO:15), P00203_D04 (SEQ ID NO:17), P00203_E06 (SEQ ID NO:19), P00209_F06 (SEQ ID NO:21), P00219_D02 (SEQ ID NO:23), P00219_F06 (SEQ ID NO:25), P00220_H05 (SEQ ID NO:27), P00222_G03 (SEQ ID NO:29), P00225_C01 (SEQ ID NO:32), P00227_D11 (SEQ ID NO:34), P00228_F03 (SEQ ID NO:36), P00233_H08 (SEQ ID NO:38), P00235_G08 (SEQ ID NO:40), P00239_C11 (SEQ ID NO:42), P00240_E05 (SEQ ID NO:45), P00247_A04 (SEQ ID NO:50), P00248_B04 (SEQ ID NO:52), P00249_F09 (SEQ ID NO:54), P00258_A10 (SEQ ID NO:56), P00262_C10 (SEQ ID NO:58), P00269_H08 (SEQ ID NO:62), P00628_H02 (SEQ ID NO:66), P00629_C08 (SEQ ID NO:68), P00641_G11 (SEQ ID NO:71), P00648_E12 (SEQ ID NO:73), and P00697_C03 (SEQ ID NO:75).

After a suitable antibody titer has been detected, the animals "positive" for antibodies can be injected with a final intravenous injection of the immunogen. Three to four days later, the mice are sacrificed and the spleen cells are harvested. The spleen cells are then fused to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against the protein encoded by P00184_D11 (SEQ ID NO:1), P00185_D11 (SEQ ID NO:3), P00188_D12 (SEQ ID NO:5), P00188_E01 (SEQ ID NO:7), P00194_G01 (SEQ ID NO:9), P00194_G05 (SEQ ID NO:11), P00194_H10 (SEQ ID NO:13), P00199_D08 (SEQ ID NO:15), P00203_D04 (SEQ ID NO:17), P00203_E06 (SEQ ID NO:19), P00209_F06 (SEQ ID NO:21), P00219_D02 (SEQ ID NO:23), P00219_F06 (SEQ ID NO:25), P00220_H05 (SEQ ID NO:27), P00222_G03 (SEQ ID NO:29), P00225_C01 (SEQ ID NO:32), P00227_D11 (SEQ ID NO:34), P00228_F03 (SEQ ID NO:36), P00233_H08 (SEQ ID NO:38), P00235_G08 (SEQ ID NO:40), P00239_C11 (SEQ ID NO:42), P00240_E05 (SEQ ID NO:45), P00247_A04 (SEQ ID NO:50), P00248_B04 (SEQ ID NO:52), P00249_F09 (SEQ ID NO:54), P00258_A10 (SEQ ID NO:56), P00262_C10 (SEQ ID NO:58), P00269_H08 (SEQ ID NO:62) P00628_H02 (SEQ ID NO:66), P00629_C08 (SEQ ID NO:68), P00641_G11 (SEQ ID NO:71), P00648_E12 (SEQ ID NO:73), and P00697_C03 (SEQ ID NO:75).

The positive hybridoma cells can be injected intraperitoneally into syngeneic Balb/c mice to produce ascites containing the antibodies. Antibodies are purified by ammonium sulfate precipitation, protein A or protein G chromatography or other techniques well known in the art.

Example 8

Further Animal Models

The biological function of the P00184_D11 (SEQ ID NO:1), P00185_D11 (SEQ ID NO:3), P00188_D12 (SEQ ID NO:5), P00188_E01 (SEQ ID NO:7), P00194_G01 (SEQ ID NO:9), P00194_G05 (SEQ ID NO:11), P00194_H10 (SEQ ID NO:13), P00199_D08 (SEQ ID NO:15), P00203_D04 (SEQ ID NO:17), P00203_E06 (SEQ ID NO:19), P00209_F06 (SEQ ID NO:21), P00219_D02 (SEQ ID NO:23), P00219_F06 (SEQ ID NO:25), P00220_H05 (SEQ ID NO:27), P00222_G03 (SEQ ID NO:29), P00223_F07 (SEQ ID NO:31), P00225_C01 (SEQ ID NO:32), P00227_D11 (SEQ ID NO:34), P00228_F03 (SEQ ID NO:36), P00233_H08 (SEQ ID NO:38), P00235_G08 (SEQ ID NO:40), P00239_C11 (SEQ ID NO:42), P00240_B04 (SEQ ID NO:44), P00240_E05 (SEQ ID NO:45), P00241_E12 (SEQ ID NO:47), P00245_D06 (SEQ ID NO:48), P00246_D12 (SEQ ID NO:49), P00247_A04 (SEQ ID NO:50), P00248_B04 (SEQ ID NO:52), P00249_F09 (SEQ ID NO:54), P00258_A10 (SEQ ID NO:56), P00262_C10 (SEQ ID NO:58), P00263_G06 (SEQ ID NO:60), P00267_F08 (SEQ ID NO:61), P00269_H08 (SEQ ID NO:62), P00312_C04 (SEQ ID NO:64), P00324_H02 (SEQ ID NO:65), P00628_H02 (SEQ ID NO:66), P00629_C08 (SEQ ID NO:68), P00634_G11 (SEQ ID NO:70), P00641_G11 (SEQ ID NO:71), P00648_E12 (SEQ ID NO:73), and P00697_C03 (SEQ ID NO:75) genes and the encoded protein are further characterized in various animal models of heart, kidney and inflammatory disorders.

1. In Vivo Model of Cardiac Hypertrophy

Rats with left ventricular hypertrophy (LVH) are produced essentially as described in Schunkert et al., *J. Clin. Invest.* 86(6):1913–20 (1990). LVH is induced by pressure overload as a result of constriction of the ascending aorta. A stainless steel clip of 0.6-mm internal diameter is placed on the aorta of anesthetized weanling rats. Control animals undergo thoracotomy as sham operation. Animals usually recover from surgery and appear healthy until about 20 weeks when a few animals may be in demise likely due to heart failure, which typically occurs at this point (Schunkert et al., 1990, supra). The animals are sacrificed and hearts examined 10 weeks and 20 weeks post-operation. Hypertrophy is evident at both time points as determined by changes in left ventricle weight and thickness. Aortic banded rats and sham operated control animals are sacrificed and measured for heart weight, left ventricle (LV) weight, left ventricle thickness, and LV weight/body weight. Usually there are 6 animals per group. Data are expressed as average with standard deviation.

LVH rats pre also examined for expression of ANP, BNP, cardiac α-actin, and/or β-myosin heavy chain mRNA, using Northern blot. Levels of these messages are expected to be elevated in the diseased animals, confirming that the banded rats were pressure overloaded and responded with cardiac hypertrophy Poly A+ mRNA is prepared from each of the animals for assessment of differentially expressed genes in the disease state, using microarray analysis in a preferred embodiment.

2. In Vivo Model of Viral Myocarditis

CVB3 infection in vice results in myocardial disease progression, which can be used as a model for examination of the pathogenesis of virus-induced human myocarditis. The virus is directly injurious to myocardial cells early following infection during the preinflammatory period as determined by light and electron microscopic cytological assessment (Arola et al., *J. Med. Virol*, 47: 251–259 [1995]; Chow et al., *Lab. Invest* 64 55–64 [1991]; McManus et al., *Clin. Immunol. Immunopathol.* 68:159–169 [1993]; Melnick et al., *J. Expert. Med.* 93 247–266 [1951]). Beginning by day two post-infection cytopathic lesions are evident in ventricular myocytes, characterized by cell vacuolar changes, contraction bands and coagulation necrosis (McManus et al., supra). By day 5 post-infection this myocardial injury becomes obscured by inflammatory infiltrates, cellular calcification, and tissue edema.

In a typical protocol, A/J (H-2$^\alpha$) mice (Jackson Laboratories, Bar Harbor, Me., 4 weeks of age) are acclimatised for one week prior to the onset of the experiment. Any mice that dies naturally during the course of the disease are not included in groups of mice to be used for RNA extraction. Mice are euthanized by $CO_2$ narcosis.

Myocarditic CVB3 (Dr. Charles J. Gauntt; University of Texas, San Antonio, Tex.) is stored at −80° C. Virus is propagated in HeLa cells (American Type Tissue Culture Collection, Rockville, Md.) and is routinely titred before the onset of all experiments using th plaque assay method, with modifications as previously described (Anderson et al., *J. Virol.* 70:4632–[1996]).

Adolescent A/J mice are infected with $1 \times 10^5$ pfu of myocarditic CVB3 or PBS sham and euthanized on days 3, 9, and 30 post-infection. Ten to fifteen mice per group (CVB3 infected or sham injected) per time-point (days 3, 9, and 30) are euthanized and heart muscle is removed. Following a wash in sterile phosphate buffered saline, a small portion of the apex of the heart is removed and fixed in 4% paraformaldehyde. The remainder of the heart is flash frozen in liquid nitrogen and stored at −80° C. for future RNA isolation.

Sections from the heart are fixed in fresh DPBS-buffered 4% paraformaldehyde overnight at 4° C. Fixed tissue is dehydrated in graded alcohols, cleared in xylene, embedded in paraffin, and sectioned for hematoxylin and eosin, and Masson's trichrome stains. Serial sections are also prepared for in situ hybridization and nick-end labelling stained. The extent and severity of virus-induced injury (including coagulation necrosis, contraction band vecrosis, and cytopathic effects), inflammation, and tissue fibrosis and calcification are evaluated and scored as previously described (Chow et al., supra).

In situ hybridization for CVB3 viral RNA localization is carried out as previously described (Anderson et al., supra; Hohenadl et al., *Mol. Cell. Probes* 5: 11–20 [1991]. Briefly, tissue sections are incubated overnight in hybridization mixture containing digoxigenin-labelled, CVB3 strand-specific riboprobes. Post-hybridization washing is followed by blocking with 2% normal lamb serum. A sheep anti-digoxgenin polclonal antibody conjugated to alkaline phosphatase (Boehringer Mannheim PQ, Laval, Canada) is developed in Sigma-Fast nitroblue tetrazolium-BCIP [5-bromo-4-chloro-3-indolylphosphate tultidinium] (Sigma Chemical Co.). The slides are counterstained in fresh carmalum and examined for reaction product by light microscopy. Poly A+ mRNA is prepared from each of the animals, as described herein, for assessment of differentially expressed genes in the disease states, using microarray.

3. In Vivo Model of Kidney Disease

In yet another representative example, an in vivo model of kidney disease is used to further characterize the differentially expressed genes of the present invention. For example, a rat model of an inherited form of autosomal dominant polycystic kidney (ADPKD) can be used, which develops in Hans:SPRD rats (Kaspareit-Rittinghaus et al., *Transplant Proc.* 6: 2582–3 [1990]; Cowley et al., *Kidney Int.* 43:522–34 [1993]). Renal cysts and renal failure is evident in six months old male heterozygous rats (Cy/+), whereas control rats (+/+) show no sign of cysts or renal failure. Diseased (Cy/+) and normal (+/+) animals are sacrificed and the kidneys removed. For cDNA microarray analysis, poly A+ mRNA is prepared, as described previously, for assessment of differentially expressed genes in the disease state, using microarray analysis in a preferred embodiment.

All references cited throughout the specification, including the examples, are hereby expressly incorporated by reference.

What is claimed is:

1. An isolated nucleic acid molecule comprising a poly- or oligonucleotide selected from the group consisting of:
   (a) a polynucleotide encoding at least 50 contiguous amino acids from amino acids 1 to 148 of SEQ ID NO: 2;
   (b) a polynucleotide encoding a polypeptide having at least 75% sequence identity with amino acids 1 to 203 of SEQ ID NO: 2 and
   (c) a polynucleotide of SEQ ID NO: 1.

2. A vector comprising and capable of expressing the poly- or oligonucleotide of claim 1.

3. A recombinant host cell transformed with nucleic acid comprising the poly- or oligonucleotide of claim 1.

4. A recombinant host cell transformed with the vector of claim 2.

5. A method for producing a polypeptide comprising culturing a recombinant host cell transformed with nucleic acid comprising any of the polynucleotides of claim 1(a)–(c) under conditions such that the polypeptide is expressed, and isolating the polypeptide.

* * * * *

SEQUENCE LISTING

<160> NUMBER OF SEQ ID NOS: 84

<210> SEQ ID NO 1
<211> LENGTH: 1340
<212> TYPE: DNA
<213> ORGANISM: Rattus norvegicus

<400> SEQUENCE: 1

```
gcggccgccc ctgacacaat ggctcagctt atgcctcagc gcagttcgct ccacccaga      60
atggcatcct gcagaataca cggcccctca tccccatccc gcgccagaga caccggccag    120
cccactgtcc ccgccacaca ttaaacttga tcctcctaca cagacgcact cggagcagag    180
cgcttataca agcgcacagc cgtctccggc accgccacac agacagatga tgccgccccg    240
accgacggcc agccccagac acaaccttct gaaaacacag aaaacaagtc ccagcccaag    300
cggctgcatg tgtccaacat cccctttccgg ttccgggatc cagacctccg acaaatgttt    360
ggccaatttg gtaaaatatt agatgttgaa attatttttta atgagcgggg ctcgaaggga    420
tttggtttcg taactttcga aaatagtgcg gatgcggaca gggcgaggga gaaattgcac    480
ggtaccgtgg tagagggccg taaaatcgag gttaataatg cgacagcacg cgtgatgact    540
aataaaaagg ccgtgaaccc ctacaccaat ggctggaaat taaatccagt tgtgggcgcg    600
gtctacagcc ccgacttcta tgcaggcacg gtgctgttgt gccaggccaa ccaggaggga    660
tcttccatgt acagtggccc cagttcactt gtatatactt ctgcaatgcc tggctttcca    720
tatccggccg ccactgctgc agctgcatac cgagggctc accttcgagg ccgtggtcgc    780
accgtgtaca acaccttcag agctgcggcg ccccaccc caatcccggc ctatggcgga    840
gtagtgtatc aagagccagt gtatggcaat aaattgctac agggtggtta cgctgcatac    900
cgctacgccc agcccacccc tgccactgct gctgcctaca gtgacagtta cggacgagtt    960
tatgctgccg accctacca ccacacactt gctccagccc ccacctacgg cgttggtgcc   1020
atgaatgctt ttgcgccctt gaccgatgcc aagactagga gccatgctga tgatgtgggt   1080
ctcgttcttt cttcattgca ggctagtata taccaagggg gatacaaccg tttttgctcca   1140
tattaaatga taaaaccatt aaacaaacaa gcaaaaaaca aacaaaaac aaaaaaacca   1200
accttccaat gtggggagag aggaagcttt ccgaggcccg agtgttgcga cacatgcagt   1260
aggacatcac tttagcaact caaagaaaca acgaaaaaaa aaaaaaaaaa aaaaataagc   1320
ggccgaaggg gttcgctaga                                              1340
```

<210> SEQ ID NO 2

<211> LENGTH: 203
<212> TYPE: PRT
<213> ORGANISM: Rattus norvegicus

<400> SEQUENCE: 2

```
Met Thr Asn Lys Lys Ala Val Asn Pro Tyr Thr Asn Gly Trp Lys Leu
  1               5                  10                  15

Asn Pro Val Val Gly Ala Val Tyr Ser Pro Asp Phe Tyr Ala Gly Thr
             20                  25                  30

Val Leu Leu Cys Gln Ala Asn Gln Glu Gly Ser Ser Met Tyr Ser Gly
         35                  40                  45

Pro Ser Ser Leu Val Tyr Thr Ser Ala Met Pro Gly Phe Pro Tyr Pro
     50                  55                  60

Ala Ala Thr Ala Ala Ala Ala Tyr Arg Gly Ala His Leu Arg Gly Arg
 65                  70                  75                  80

Gly Arg Thr Val Tyr Asn Thr Phe Arg Ala Ala Pro Pro Pro
                 85                  90                  95

Ile Pro Ala Tyr Gly Val Val Tyr Gln Glu Pro Val Tyr Gly Asn
            100                 105                 110

Lys Leu Leu Gln Gly Gly Tyr Ala Ala Tyr Arg Tyr Ala Gln Pro Thr
            115                 120                 125

Pro Ala Thr Ala Ala Ala Tyr Ser Asp Ser Tyr Gly Arg Val Tyr Ala
        130                 135                 140

Ala Asp Pro Tyr His His Thr Leu Ala Pro Ala Pro Thr Tyr Gly Val
145                 150                 155                 160

Gly Ala Met Asn Ala Phe Ala Pro Leu Thr Asp Ala Lys Thr Arg Ser
                165                 170                 175

His Ala Asp Asp Val Gly Leu Val Leu Ser Ser Leu Gln Ala Ser Ile
            180                 185                 190

Tyr Gln Gly Gly Tyr Asn Arg Phe Ala Pro Tyr
        195                 200
```

<210> SEQ ID NO 3
<211> LENGTH: 867
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 3

```
tctagcgaac cccttcgcga aggggttcgc ctgtgctggt gggcgcggtg gcccgaagcc      60
ttggactcac tgcaggactg tgcagggaac cactgtccaa gcatcgggct aatagggggc     120
gcctgcctcg gtttacccct cagcgtctgg tgaaatcccg cagcgtctag ggaaagatcc     180
gttctgctcc gcgagggaaa cagagccgtt gaccatggtt gcaacgggca gtttgagcag     240
taagaacacg gccagcattt cagagttgct ggacggtggc tctcaccctg ggagtctgct     300
aagtgatttc gactactggg attatgtcgt ccctgagccc aacctcaacg aggtggtgtt     360
tgaagagaca acatgccaga atttggttaa aatgttggag aactgtctgt ccaagtcaaa     420
gcaaaccaaa ctcggttgct ctaaggtcct ggttcctgag aaactgaccc agagaattgc     480
ccaagatgtc ctgcggctct catccacaga gccctgcggc cttcgggct gtgttatgca      540 cgtgaacttg gaaattgaaa atgtgtaa aaagctggat aggattgtgt gtgatgctag      600
tgtggtgccg acctttgagc tcacgctggt gttcaagcag gagagctgct cctggaccag     660
```

-continued

```
cctcaaggac ttcttcttta gcggaggtcg cttctcgtcg ggccttaagc gaactctgat      720
cctcagctcg ggatttcgac ttgttaagaa aaaactgtac tctctgattg aacgacagt      780 cattgaggag tgctgaggag gaaaaaacaa ttaaaggtcc ctaatgagtg ctaacaaaa      840 anaaaannnn nnnnnnnnnn ngcggnc                                         867
```

<210> SEQ ID NO 4
<211> LENGTH: 193
<212> TYPE: PRT
<213> ORGANISM: Rattus norvegicus

<400> SEQUENCE: 4

```
Met Val Ala Thr Gly Ser Leu Ser Ser Lys Asn Thr Ala Ser Ile Ser
 1               5                  10                  15

Glu Leu Leu Asp Gly Gly Ser His Pro Gly Ser Leu Leu Ser Asp Phe
            20                  25                  30

Asp Tyr Trp Asp Tyr Val Val Pro Glu Pro Asn Leu Asn Glu Val Val
        35                  40                  45

Phe Glu Glu Thr Thr Cys Gln Asn Leu Val Lys Met Leu Glu Asn Cys
    50                  55                  60

Leu Ser Lys Ser Lys Gln Thr Lys Leu Gly Cys Ser Lys Val Leu Val
65                  70                  75                  80

Pro Glu Lys Leu Thr Gln Arg Ile Ala Gln Asp Val Leu Arg Leu Ser
                85                  90                  95

Ser Thr Glu Pro Cys Gly Leu Arg Gly Cys Val Met His Val Asn Leu
           100                 105                 110

Glu Ile Glu Asn Val Cys Lys Lys Leu Asp Arg Ile Val Cys Asp Ala
       115                 120                 125

Ser Val Val Pro Thr Phe Glu Leu Thr Leu Val Phe Lys Gln Glu Ser
   130                 135                 140

Cys Ser Trp Thr Ser Leu Lys Asp Phe Phe Ser Gly Gly Arg Phe
145                 150                 155                 160

Ser Ser Gly Leu Lys Arg Thr Leu Ile Leu Ser Ser Gly Phe Arg Leu
                165                 170                 175

Val Lys Lys Lys Leu Tyr Ser Leu Ile Gly Thr Thr Val Ile Glu Glu
            180                 185                 190

Cys
```

<210> SEQ ID NO 5
<211> LENGTH: 874
<212> TYPE: DNA
<213> ORGANISM: Rattus norvegicus

<400> SEQUENCE: 5

```
tctagcgaac cccttcggtg acagaacag cctgagtcag gatgaaagct ctcagggctg      60
tcctcctgat cttgctactc agtggacagc cagggagcag ctgggcacaa gaagctggcg    120
atgtggacct ggagctagag cgctacagct acgatgatga cggtgatgac gatgatgacg    180
atgatgaaga agaggaagag gaggagacca acatgatccc tggcagcagg acagagcac    240 cgcctctaca gtgctacttc tgccaagtgc ttcacagcgg ggagagctgc aacgagacac    300
agagatgctc cagcagcaag cccttctgta tcacagtcat ctcccatggc aaaactgaca    360
caggtgtcct gacgacctac tccatgtggt gtactgatac ctgccagccc atcgtgaaga    420
cagtggacag caccccaaatg acccagacct gttgccagtc cacactctgc aatattccac    480
cctggcagag ccccaaaatc cacaaccctc tgggtggccg ggcagacagc cccttgaagg    540
```

-continued

```
gtgggaccag acatcctcaa ggtgacaggt ttagccaccc ccaggttgtc aaggttactc      600
atcctcagag tgatggggct cacttgtcta agggtggcaa ggctaaccag ccccagggaa      660
atggggccgg attccctgca ggctggagca aatttggtaa cgtagttctc ctgctcacct      720
tcctcaccag tctgtgggca tcaggggcct aaagactcgt cctcccccaa ccaggaccct      780
tcagcctttc ctccctgaca accagcttca gagaataaac ttgaatgtct tttgccatct      840
aaaaaaaaaa aaaaaaaaa aaaaagcggc cgcc                                   874
```

<210> SEQ ID NO 6
<211> LENGTH: 236
<212> TYPE: PRT
<213> ORGANISM: Rattus norvegicus

<400> SEQUENCE: 6

```
Met Lys Ala Leu Arg Ala Val Leu Leu Ile Leu Leu Ser Gly Gln
 1               5                  10                  15

Pro Gly Ser Ser Trp Ala Gln Glu Ala Gly Asp Val Asp Leu Glu Leu
                20                  25                  30

Glu Arg Tyr Ser Tyr Asp Asp Gly Asp Asp Asp Asp Asp
         35                  40                  45

Glu Glu Glu Glu Glu Glu Thr Asn Met Ile Pro Gly Ser Arg Asp
     50                  55                  60

Arg Ala Pro Pro Leu Gln Cys Tyr Phe Cys Gln Val Leu His Ser Gly
 65                  70                  75                  80

Glu Ser Cys Asn Glu Thr Gln Arg Cys Ser Ser Lys Pro Phe Cys
                 85                  90                  95

Ile Thr Val Ile Ser His Gly Lys Thr Asp Thr Gly Val Leu Thr Thr
                100                 105                 110

Tyr Ser Met Trp Cys Thr Asp Thr Cys Gln Pro Ile Val Lys Thr Val
                115                 120                 125

Asp Ser Thr Gln Met Thr Gln Thr Cys Cys Gln Ser Thr Leu Cys Asn
    130                 135                 140

Ile Pro Pro Trp Gln Ser Pro Gln Ile His Asn Pro Leu Gly Gly Arg
145                 150                 155                 160

Ala Asp Ser Pro Leu Lys Gly Gly Thr Arg His Pro Gln Gly Asp Arg
                165                 170                 175

Phe Ser His Pro Gln Val Val Lys Val Thr His Pro Gln Ser Asp Gly
                180                 185                 190

Ala His Leu Ser Lys Gly Gly Lys Ala Asn Gln Pro Gln Gly Asn Gly
            195                 200                 205

Ala Gly Phe Pro Ala Gly Trp Ser Lys Phe Gly Asn Val Val Leu Leu
        210                 215                 220

Leu Thr Phe Leu Thr Ser Leu Trp Ala Ser Gly Ala
225                 230                 235
```

<210> SEQ ID NO 7
<211> LENGTH: 817
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 7

```
tctagcgaac cccttcgagc gaaccccttc ggccagtacc ctgagccctg gtccctcctg       60
```

```
gagctgcccc acagctctga ctgtggactg agggatgtta ggcggatcac ctgagcctcc      120
agaggctcac actaatgagc gggcgctctc ttcttagcca ctgttgcatt tggtttcat       180
tgactcctgg gcctcgtttg agtgacactg tccttgtctt ttgtttcaga gctctcccag      240
tgttagtgga ctcagatgag gaaattatga ccagatctga aatagctgaa aaaatgttct     300
cttcagaaaa gataatgtga tcagggcccc agtgggtcca gtgtgcatgg gagcgcggtc     360
aggtgatggg aaaggcctgg ctctcgtcaa aactgacagc tgcgctatga tacatgtctc     420
actttgttgt cttggagatc tgtgtatgca ggtgaagaac tcaagtgtgg gagggtctgc     480
cgcctcagaa agccatcttt gaaacggact cataaagtca gttttgttgc cattaagttg     540
cctgattttg gaaacaattt aagaagtgtt aaagacatgt gttcagatgc ctcttaggcg     600
gcagccacag gcatgccagg ttgtgtccct cagttttctc cagacaaaag aatctgcagc    660
tgggcgtggc ggcacactac tggcagttga agtctgtaa  tttcaaggcc aagcctggtc     720
tacatagttc caggacaacc agagagatct acatagtgag accctgcctc aaaacacaga    780
aaccnnanna naaaaaaaaa aaaaaaaaag cggccgc                               817
```

```
<210> SEQ ID NO 8
<211> LENGTH: 61
<212> TYPE: PRT
<213> ORGANISM: Rattus norvegicus

<400> SEQUENCE: 8

Met Ser Gly Arg Ser Leu Leu Ser His Cys Cys Ile Trp Phe Ser Leu
 1               5                  10                  15

Thr Pro Gly Pro Arg Leu Ser Asp Thr Val Leu Val Phe Cys Phe Arg
            20                  25                  30

Ala Leu Pro Val Leu Val Asp Ser Asp Glu Glu Ile Met Thr Arg Ser
        35                  40                  45

Glu Ile Ala Glu Lys Met Phe Ser Ser Glu Lys Ile Met
    50                  55                  60

<210> SEQ ID NO 9
<211> LENGTH: 755
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 9
```

```
tctagcgaac cccttcgcac atgggttcct gctgaccaag gggacatggc tctgaagatg       60
atgaggctgt tactcagca ggagtagctg agctgagctg gccctggagg ccctggaggc      120
cctggagtag ggcccaggat gcaggtgcta atgtctatcc ccggcgctct tcttcccgac      180
tctaccatgg gatgtaactc caggagcccc tgccatctcc cgtaccaaaa gactgtggct      240
tccgtgtcta ctcagaaatc agttctactt cgtaaacagt gtttaaaacc agactcattt      300
aatcagagtg aaggattgca gtccattggc ttcttagcac agaagcagct gataacacaa     360
gtaaaccccca gccctgaga ggtagaagca agaggatcag aggttcaagc gcatcctcgg      420
ctccatcaca agttcaaaag ccgcctgcac caaatgggag tccttgtctc aaaaaaaaa      480
aaaaaaaaag caagaaagc aaaggactcg atgacatgat ttatagacaa agcagtggg      540
agaaatact aaagcccccac tgagctgcca gccaggtgtc tgtgactaca ggtcttttat     600
ctgctcatat atatttttac aaaaaatgaa attcatattg gtcgctattt tgctggctgc    660
```

```
tttgctcccg atcaacatga tttgcacgtt ttttccatca ataaatgtgc catgatattt      720
ttaaaaaaaa aaaaaaaaaa aaaaaaaagg gcncc                                 755
```

<210> SEQ ID NO 10
<211> LENGTH: 79
<212> TYPE: PRT
<213> ORGANISM: Rattus norvegicus

<400> SEQUENCE: 10

```
Met Gln Val Leu Met Ser Ile Pro Gly Ala Leu Leu Pro Asp Ser Thr
 1               5                  10                  15

Met Gly Cys Asn Ser Arg Ser Pro Cys His Leu Pro Tyr Gln Lys Thr
            20                  25                  30

Val Ala Ser Val Ser Thr Gln Lys Ser Val Leu Leu Arg Lys Gln Cys
        35                  40                  45

Leu Lys Pro Asp Ser Phe Asn Gln Ser Glu Gly Leu Gln Ser Ile Gly
    50                  55                  60

Phe Leu Ala Gln Lys Gln Leu Ile Thr Gln Val Asn Pro Ser Pro
65                  70                  75
```

<210> SEQ ID NO 11
<211> LENGTH: 806
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 11

```
tctagcgaac cccttcgcag ctctctgacc tgcgtcgccg ccgctctccg ctcttgattt       60
cgccgtgatg tcgaccgcaa tgaacttcgg gaccaaaagc ttccagccgc ggccccccaga    120 caaaggcagc ttcccgctag accacttcgg tgagtgtaaa agctttaagg aaaaattcat     180
gaagtgtctc cgcgacaaga actatgaaaa tgctctgtgc agaaatgaat ctaaagagta     240
tttaatgtgc aggatgcaaa ggcagctgat ggcaccagaa ccactagaga aactcggctt     300
tagagacata atggaggaga aaccggaggc aaaggacaaa tgttgagaat cactgggctg     360
tgtcccccta cctggagcag agctgagccc ttctgcccac cgtggagaga gctgagccat     420
cctgtgctgc ccagaggagg ggctctccgt gtcgactttg gctcatccct gcagcacaga     480
ccaaactgct ttctctactg accacacttc tgcttcagag agnggtttct cctgtctgng     540
tgtggcacag gatctgctca nggctgaaca ctgatgtgat atgatatccc acctagtgtg     600
gccgcacacc aaaaggcctg gacaggattt cacagtgact caacctgagt cctcacaccc     660
ggaacctgtc agcgaaaacc aancgaagca aaatgnctgg cttttggctt acaaacccca    720
tnatttgntt tcccttctct tgggtctttg ttttgacaaa nctggcatac aaagtnggaa    780 ggggggaaata aaaaaaaaaa aaaaaa                                          806
```

<210> SEQ ID NO 12
<211> LENGTH: 92
<212> TYPE: PRT
<213> ORGANISM: Rattus norvegicus

<400> SEQUENCE: 12

```
Met Ser Thr Ala Met Asn Phe Gly Thr Lys Ser Phe Gln Pro Arg Pro
 1               5                  10                  15
```

-continued

```
Pro Asp Lys Gly Ser Phe Pro Leu Asp His Phe Gly Glu Cys Lys Ser
            20                  25                  30

Phe Lys Glu Lys Phe Met Lys Cys Leu Arg Asp Lys Asn Tyr Glu Asn
        35                  40                  45

Ala Leu Cys Arg Asn Glu Ser Lys Glu Tyr Leu Met Cys Arg Met Gln
    50                  55                  60

Arg Gln Leu Met Ala Pro Glu Pro Leu Glu Lys Leu Gly Phe Arg Asp
65                  70                  75                  80

Ile Met Glu Glu Lys Pro Glu Ala Lys Asp Lys Cys
                85                  90
```

<210> SEQ ID NO 13
<211> LENGTH: 717
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 13

```
tctagcgaac cccttcncga aggggttcgc cgagaggtgg gagccaaaag gatggagcat    60
ccgccggtgg tggctggtgg ccgcaatctt ggtggtcctg atcggggttg tcttagtctg   120
cctgatagtc tacttcgcca acgcagcgca cagcgaggcc tgtaagaacg ggttgcggtt   180
gcaggatgag tgccgaaaca ccacgcacct gttgaagcac cagctnaccc gcgcccagga   240
cagcctgctg cagacggaga tgcaggcaaa ctcctgcaac cagaccgtga tggaccttcg   300
ggattccctg aagaagaagg tgtctnaaac ccaggagcaa cangcccgca tcaaggaact   360
tgagaataag atcgagaggc tgaaccaaga gctggagaaa tttgaggacc caaaaggaaa   420
tttctaccac agtgcangtg aactcaagcg ggttcgtggt ggncttcanc ctacttgtgc   480
tttgtggcgg gactgttctn cacttttttan gacccaataa ttgggangta caaacctgtg   540
taggcattgn nggtngtaat ggcttttgag ggggtcctgg caccctttaag atgtgaaanac  600
cattangnng gacccaaaat gnnttttctt gntttgaact ggggcggacc cggagtgggg   660
ggcnggaaat aanntattnn ggnnggaaan aaaaaaaaaa aaaaaaaaaa gcggccc      717
```

<210> SEQ ID NO 14
<211> LENGTH: 86
<212> TYPE: PRT
<213> ORGANISM: Rattus norvegicus
<220> FEATURE:
<221> NAME/KEY: UNSURE
<222> LOCATION: (0)...(0)
<223> OTHER INFORMATION: Xaa = any amino acid

<400> SEQUENCE: 14

```
Met Gln Ala Asn Ser Cys Asn Gln Thr Val Met Asp Leu Arg Asp Ser
1               5                   10                  15

Leu Lys Lys Lys Val Ser Xaa Thr Gln Glu Gln Xaa Ala Arg Ile Lys
            20                  25                  30

Glu Leu Glu Asn Lys Ile Glu Arg Leu Asn Gln Glu Leu Glu Lys Phe
        35                  40                  45

Glu Asp Pro Lys Gly Asn Phe Tyr His Ser Ala Xaa Glu Leu Lys Arg
    50                  55                  60

Val Arg Gly Gly Leu Xaa Pro Thr Cys Ala Leu Trp Arg Asp Cys Ser
65                  70                  75                  80

Xaa Leu Phe Xaa Thr Gln
                85
```

-continued

<210> SEQ ID NO 15
<211> LENGTH: 1235
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C or G

<400> SEQUENCE: 15

```
tctagcgaac cccttcgccc agctgctaga agccaggctg gcctggtgag gcatgagcat      60
gaagatgaac ccaggtgaca aggacaagat gttgctcttc tccccaccct ttgacccctg     120
tcttctaagg catctaggaa ggaaccagtg tccttggtac tgatttactt agattcaacc     180
taagggtcca gccactgact aaggccaagg ccattttttcc atacctggga gggtagagat     240
tcagggttgt gggtaagtgg gcactaaaca tggatttgca agggaaaacg acagggcatc     300
gagctaaatt tgaatttaca tgaaattctg aaatgtactt gtatgaagaa actgttatct     360
gaaacctaac ttaaatgggc atcctgcctt ttgtctggtg agaaatgaaa gtgatctaca     420
ataagtgtca aagcaacaag gcccctctgg atatgtctag gccaggatga ggatactaag     480
tgccttcaaa gcgagaggga ggcaggccaa gaacactgcc ctactgaaag gcaggcttgg     540
ccggctaggg cctccaaggc cctgatccct gaggcaccac agccacaact tgtgtaggcc     600
tggcccaggt cagtgaatag gttctaggca gtggttctca accttcctaa tgctgcaacc     660
cttcaataca gtttctcctg ttgtagtaat ccccaaccat aaaattattt tcattgcgac     720
ttcataactg gactttttgct actgttatga atcataatgt aaatattttt tggagctaga     780
ggtttaccaa gggggttgtg agccataggt tgaaaaccat tgttctagga atagctccag     840
gggtggtttc tgaggccccc gcaaggtggg atctatgggg cagggttgga tcttctccaa     900
gagcccccaa caggatatat atatatatat atatatatat atatatatat atatatatat     960
atatactttg atagcatccc atggaacgac tgtctcctga tactaaaggg agcttggaag    1020
aaaccaaggc tgagagaagt tgtagagtgg gaaggtaggc gaagggattg aggtgacaca    1080
gtgatagccc cttcagggtg gggtctaccc nagacagcag ataaaggcct taggatggga    1140
gattactctg gctgctcaga ggggaacaca gggacacagc accaataaaa tctctttctt    1200
ttcaaaaaaa aaaaaaaaaa aaaaaaagc ggncc                                1235
```

<210> SEQ ID NO 16
<211> LENGTH: 36
<212> TYPE: PRT
<213> ORGANISM: Rattus norvegicus

<400> SEQUENCE: 16

Met Ser Met Lys Met Asn Pro Gly Asp Lys Asp Lys Met Leu Leu Phe
1               5                   10                  15

Ser Pro Pro Phe Asp Pro Cys Leu Leu Arg His Leu Gly Arg Asn Gln
            20                  25                  30

Cys Pro Trp Tyr
        35

<210> SEQ ID NO 17
<211> LENGTH: 633
<212> TYPE: DNA
<213> ORGANISM: Rattus norvegicus

<400> SEQUENCE: 17

```
tctagcgaac cccttcgatt ttattagctc ttgcttctcc attcctcata atttatgaat    60
tatacagcct tcgcttgaat acgcgtctga agtatgctt tgtgttgttg tgggttttt    120 ttttttttc ttttcttttt ttttggagct ggggaccgaa cccagggcct tgttgctcta   180
ccactgagct aaatccccaa cccctgttgt gtgttttaaa taagtctctt actgtccatt   240
ttgtaattag tgttgttacc ttgtaataat agacatcata caaagtttcc tcttttttgt   300
gccagtgctg agaacatgag aaacatttaa tgagtatttg tttgttaaat aatatttata   360
acggctagaa tggcagacac acatggtagc acatgatggt gattttcggg ggccttttgt   420
ttgctcagag ctggtaatct ctgccggttg gtttgctttg cctggtctgg gactaacctc   480 acatttctc actcttgctt tccgagagat tagtcatcct tcctgtccta ctgggctctc   540
gatagcgctc atcagcatac tgcatttcaa tcccagcgaa ggggttcgcc gaagggttc    600 gctaggccag tgtgatggat atctgcagaa ttc                                633
```

<210> SEQ ID NO 18
<211> LENGTH: 83
<212> TYPE: PRT
<213> ORGANISM: Rattus norvegicus

<400> SEQUENCE: 18

```
Met Val Ala His Asp Gly Asp Phe Arg Gly Pro Phe Val Cys Ser Glu
 1               5                  10                  15

Leu Val Ile Ser Ala Gly Trp Phe Ala Leu Pro Gly Leu Gly Leu Thr
             20                  25                  30

Ser His Phe Leu Thr Leu Ala Phe Arg Glu Ile Ser His Pro Ser Cys
         35                  40                  45

Pro Thr Gly Leu Ser Ile Ala Leu Ile Ser Ile Leu His Phe Asn Pro
     50                  55                  60

Ser Glu Gly Val Arg Arg Arg Gly Ser Leu Gly Gln Cys Asp Gly Tyr
 65                  70                  75                  80

Leu Gln Asn
```

<210> SEQ ID NO 19
<211> LENGTH: 607
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 19

```
tctagcgaac cccttcgcct ttctccaaag ccttcccgtt tcctcttgac agctacgggc    60
tgaggcagcc attcctgcag cagcgctcgg ccggtgaagg gccgaactga cgcctcctag   120
atctgtctcg gctgaattac tctcacccgt ttccattctg tgtgcaccag aaatctgaga   180
tccaggagta tcaacagcaa agatgtctaa tgagccaccc cctccttatc caggagggcc   240
tacagcccca ctactggagg aaaaaagtgg agccccacat accccaggcc gaaccttcc    300 agctgtgatg cagccaccac caggcatgcc actgccctct gttgacattg ccccccgcc    360 ctatgagccg cctggccatc cagggcctaa gcctggtttw atgcccccca cnttaccaca   420
cattcnaana accttnntnt gtaaaagtta ataanaanag gagggattcg anccccctnc   480
aacnggtttc aagccaattt ymtaaccatt ttgttttttt cwtttaaaaa aaaaaaaaaa   540
aaaaaaaaaa aaaaaaaaaa aaaaaaaaaa ggggaaaaaa aaaaaaaaaa aaaaaagggg   600
```

<210> SEQ ID NO 20
<211> LENGTH: 82
<212> TYPE: PRT
<213> ORGANISM: Rattus norvegicus
<220> FEATURE:
<221> NAME/KEY: UNSURE
<222> LOCATION: (0)...(0)
<223> OTHER INFORMATION: Xaa = any amino acid

<400> SEQUENCE: 20

Met Ser Asn Glu Pro Pro Pro Tyr Pro Gly Gly Pro Thr Ala Pro
1               5                   10                  15
Leu Leu Glu Glu Lys Ser Gly Ala Pro His Thr Pro Gly Arg Thr Phe
            20                  25                  30
Pro Ala Val Met Gln Pro Pro Gly Met Pro Leu Pro Ser Val Asp
        35                  40                  45
Ile Ala Pro Pro Tyr Glu Pro Pro Gly His Pro Gly Pro Lys Pro
    50                  55                  60
Gly Xaa Met Pro Pro Thr Leu Pro His Ile Xaa Xaa Thr Xaa Xaa Cys
65                  70                  75                  80
Lys Ser

<210> SEQ ID NO 21
<211> LENGTH: 1456
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 21

```
tctagcgaac ccttcgcaa agtcctaagc cttacatgag aaaatttaag acacccttaa      60
tgattgcgga agaaaaatac agacaacaaa gggaagagct tgagaaacag agacgggaga    120
gttcttgcca tagcatcatc aaaacagaaa cccagcaccg cagcttatca gagaaagaga    180
agaaaacaga gttacaaaaa gcagctgagg caatgtccac tcccagaaag gattcagact    240
tcactagggc acagcccaac ctggaaccta aaagcaaggc tgtgatcgcc agtgaatgct    300
ctgaaagcca gctctctaca gcttccgcat tgacagtcgc taccgagagg ctccagcatg    360
ttctagccgc ttcagacgat aagcttaccc tgcgacggga aggcacacag aactcaagtg    420
acaccctaca atcgaaaaca gcttgtgaga ttaaccagag tcacaaggaa tgtaggacag    480
agcaaacatt tgagcaacac gtggagaagt tgcccttccc ccaaaccaaa cccatttccc    540
cgagtttcaa agtgaaaact atcaggcttc agctctaga tcatacgctg actgaaacag      600
atctcagttc tgaacgccgc gtaaagcaat ccgaaattga cgttcaaacc agtactaaag    660
aaatgaataa ggaaattaag aaaaccgaag tgagcacaca gtgtgataat aagcaatctg    720
tggctgaaaa atattttcaa ttacctaaaa cagagaaacg ggtgacggta caaatgccca    780
aagactatgc agcgaaaagt catcaaagca aactccaaac agttcccaag aagcatggag    840
gattggggga gtttgacaga gggaatgtcc tggggaggga aggaaaaaat caggactcct    900
ccatgagcag tacaaaagaa agcagggtaa tagttgaaag aaagcaagaa catctacagg    960
accagagcgt accaaggtta gtccaacaaa agattatcgg tgaaagcctg gactcacggg   1020
ttcagaattt tcagcagaca caaacacaaa cttctaggat tgagcataaa gaactgtccc   1080
aaccttacag tgagaaaaaa tgtcttagag acaaggacaa acaacaaaaa caggtctcct   1140
```

-continued

```
ctaacactga cgattcaaag caagagataa cacaaaaaca atcttcattt tcctctgtga    1200
gagaatccca gcaggatgga gaaaaatgtg ccataaaaat attggaattc ttgagaaaac    1260
gtgaagaact acagcagatt ttgtctaggg taaaacagtt tgaagcagat tcaaataaaa    1320
gtggccttaa acatttcag acactgttaa atattgctcc ggtgtggctg ataagtgagg     1380
agaaaagaga atatggagtt cgtgttgcca tggagaataa ttagaaaaaa taaaaaaaaa    1440
aaaaaaaagc ggcgnc                                                    1456
```

<210> SEQ ID NO 22
<211> LENGTH: 462
<212> TYPE: PRT
<213> ORGANISM: Rattus norvegicus

<400> SEQUENCE: 22

```
Met Arg Lys Phe Lys Thr Pro Leu Met Ile Ala Glu Glu Lys Tyr Arg
  1               5                  10                  15
Gln Gln Arg Glu Glu Leu Glu Lys Gln Arg Arg Glu Ser Ser Cys His
             20                  25                  30
Ser Ile Ile Lys Thr Glu Thr Gln His Arg Ser Leu Ser Glu Lys Glu
         35                  40                  45
Lys Glu Thr Glu Leu Gln Lys Ala Ala Glu Ala Met Ser Thr Pro Arg
     50                  55                  60
Lys Asp Ser Asp Phe Thr Arg Ala Gln Pro Asn Leu Glu Pro Lys Ser
 65                  70                  75                  80
Lys Ala Val Ile Ala Ser Glu Cys Ser Glu Ser Gln Leu Ser Thr Ala
                 85                  90                  95
Ser Ala Leu Thr Val Ala Thr Glu Arg Leu Gln His Val Leu Ala Ala
            100                 105                 110
Ser Asp Asp Lys Leu Thr Leu Arg Arg Glu Gly Thr Gln Asn Ser Ser
        115                 120                 125
Asp Thr Leu Gln Ser Lys Thr Ala Cys Glu Ile Asn Gln Ser His Lys
    130                 135                 140
Glu Cys Arg Thr Glu Gln Thr Phe Glu Gln His Val Glu Lys Leu Pro
145                 150                 155                 160
Phe Pro Gln Thr Lys Pro Ile Ser Pro Ser Phe Lys Val Lys Thr Ile
                165                 170                 175
Arg Leu Pro Ala Leu Asp His Thr Leu Thr Glu Thr Asp Leu Ser Ser
            180                 185                 190
Glu Arg Arg Val Lys Gln Ser Glu Ile Asp Val Gln Thr Ser Thr Lys
        195                 200                 205
Glu Met Asn Lys Glu Ile Lys Lys Thr Glu Val Ser Thr Gln Cys Asp
    210                 215                 220
Asn Lys Gln Ser Val Ala Glu Lys Tyr Phe Gln Leu Pro Lys Thr Glu
225                 230                 235                 240
Lys Arg Val Thr Val Gln Met Pro Lys Asp Tyr Ala Ala Lys Ser His
                245                 250                 255
Gln Ser Lys Leu Gln Thr Val Pro Lys Lys His Gly Gly Leu Gly Glu
            260                 265                 270
Phe Asp Arg Gly Asn Val Leu Gly Arg Glu Gly Lys Asn Gln Asp Ser
        275                 280                 285
Ser Met Ser Ser Thr Lys Glu Ser Arg Val Ile Val Glu Arg Lys Gln
    290                 295                 300
Glu His Leu Gln Asp Gln Ser Val Pro Arg Leu Val Gln Gln Lys Ile
305                 310                 315                 320
Ile Gly Glu Ser Leu Asp Ser Arg Val Gln Asn Phe Gln Gln Thr Gln
```

```
                           325                 330                 335
        Thr Gln Thr Ser Arg Ile Glu His Lys Glu Leu Ser Gln Pro Tyr Ser
                    340                 345                 350

Glu Lys Lys Cys Leu Arg Asp Lys Asp Lys Gln Gln Lys Gln Val Ser
                    355                 360                 365

Ser Asn Thr Asp Asp Ser Lys Gln Glu Ile Thr Gln Lys Gln Ser Ser
                370                 375                 380

Phe Ser Ser Val Arg Glu Ser Gln Gln Asp Gly Glu Lys Cys Ala Ile
        385                 390                 395                 400

Lys Ile Leu Glu Phe Leu Arg Lys Arg Glu Glu Leu Gln Gln Ile Leu
                        405                 410                 415

Ser Arg Val Lys Gln Phe Glu Ala Asp Ser Asn Lys Ser Gly Leu Lys
                    420                 425                 430

Thr Phe Gln Thr Leu Leu Asn Ile Ala Pro Val Trp Leu Ile Ser Glu
                    435                 440                 445

Glu Lys Arg Glu Tyr Gly Val Arg Val Ala Met Glu Asn Asn
            450                 455                 460

<210> SEQ ID NO 23
<211> LENGTH: 2023
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 23
gaattgtaat acgactcact atagggcgaa ttgggcccct agcgaacccc ttcgacaaca      60
tcaaagagga cagatctaac cctagactga ggccggaggc ctggaccaat tacctgaggg     120
atgtccacag agcctttgca ctgctgaaca gtcaccctga tccaaaccaa gtaaatggga     180
ctccaactgc accaagcagt ggcctcccag tcacctctgc tgagctcttg gtgccggcag     240
agatggcttc tgcagagtca ggtgaagacc caagtcatgt ggttggggaa acgcctcctt     300
tgaccttgcc agccaacctc caaaccctgc atccgaacag accaacgttg agtccagaga     360
gaaaacttga atggaataac gacattccag aagtgaatcg tttgaattct gaacactgga     420
gaaaaactga ggagcagcca ggacgggggg aggtgcttct ccccgaaggt gacgtcagtg     480
gcaacggtat gacagagctg ttgcccatcg gtcggcacca acaaaagcgt ccccacgatg     540
cggggccaga ggaccatgct tttgaagatc aattgcatcc tctcgtccac tctgacagaa     600
ctcccgttca tcgggtgttc gatgtgtccc acttggagca gcctgttcac tccagccacg     660
tggaaggaat gttggccaag atggagggga tggcacaaag gagtgggcac caagtctcga     720
aggcagcgcc tcctctccag tcacttcttg cttagattac atgttgccta acaatgtttc     780
tttccatgtt ttgattagta aactaactcg tggtggcaat catgactccc aaccttctga     840
gctcccccgg gtacgcttgc accgtagacg ctcatgtgcg caccgtgcgg gtgatgctca     900
cacacagact cattgtaatt caccgtttta ccgagaaggg ggggggggcg aattttctgt     960
gttgatgctt tgttttggt actaaaacag nattatcttt tgaatattgt agggacatga    1020
gtatataaag tctatccagt caaaatggct agaattgngc ctttgtaagt tttaaaaact    1080
tgatgcccac atgagtctgt gagcacatnt ttcccgcctg cctaacggag ttggaatttg    1140
tttctaacca ctgtaattct tcaacatcat caccttggt tcagtgattt tgcactttga    1200
gtttggatac tgtgtctgct tggttggtag tgttagtatt tttctttaa acaggcttat    1260
```

```
cagagttgca cactttgtcc taggcagggc aaaggaatag acgcccagca aggacacaca    1320
gtataggtaa catactgctt atcgtacgct tttcccacaa agcattgcat gtgtttttac    1380
ctcgacgtgc taaagttgat tagcagaaag gcatgactca caattttggt ggtaaaaaat    1440
aaaccctgag ggagcaagca ataactaaaa caagattgag ctgctctctc tgtgcttact    1500
aaatagatgc tcgccctgct aatgcttgcc ctcttgaaag aagaaacagg atgcacactg    1560
ctttatttca atcttcctct ttttttcttg gtttcaccag tgagcgtaag cattggaaaa    1620
atatgtgtag tcttatcttt ctataagacg attttaataa actaaaatca caaatgctgt    1680
aaagtttgtg cgcaccagaa tggaggctaa cttcataaac attgtgctgt gcgaatattc    1740
ctaaaatgat ccccaagctg tggttttcta aagacatag ttcagaaccg cttttgaaaa     1800
atctgtcctc gtgagctcac tcagtttctg tcggactttt agagacagtg gaaggattac    1860
ctcattgaga cgtttccgtg tcctcttcaa ctccacaggg tcttgacggt ggctttgttt    1920
ttccttctag actattcaaa catgtagata agttatattt ttctttaagt gtttaaagta    1980
aacacttttc aaaaaaaaaa aaaaaaaaaa aaaaagcggc cgc                      2023
```

<210> SEQ ID NO 24
<211> LENGTH: 170
<212> TYPE: PRT
<213> ORGANISM: Rattus norvegicus

<400> SEQUENCE: 24

```
Met Ala Ser Ala Glu Ser Gly Glu Asp Pro Ser His Val Val Gly Glu
 1               5                   10                  15

Thr Pro Pro Leu Thr Leu Pro Ala Asn Leu Gln Thr Leu His Pro Asn
             20                  25                  30

Arg Pro Thr Leu Ser Pro Glu Arg Lys Leu Glu Trp Asn Asn Asp Ile
         35                  40                  45

Pro Glu Val Asn Arg Leu Asn Ser Glu His Trp Arg Lys Thr Glu
     50                  55                  60

Gln Pro Gly Arg Gly Glu Val Leu Leu Pro Gly Asp Val Ser Gly
 65                  70                  75                  80

Asn Gly Met Thr Glu Leu Leu Pro Ile Gly Arg His Gln Gln Lys Arg
                 85                  90                  95

Pro His Asp Ala Gly Pro Glu Asp His Ala Phe Glu Asp Gln Leu His
            100                 105                 110

Pro Leu Val His Ser Asp Arg Thr Pro Val His Arg Val Phe Asp Val
        115                 120                 125

Ser His Leu Glu Gln Pro Val His Ser Ser His Val Glu Gly Met Leu
    130                 135                 140

Ala Lys Met Glu Gly Met Ala Gln Arg Ser Gly His Gln Val Ser Lys
145                 150                 155                 160

Ala Ala Pro Pro Leu Gln Ser Leu Leu Ala
                165                 170
```

<210> SEQ ID NO 25
<211> LENGTH: 1802
<212> TYPE: DNA
<213> ORGANISM: Rattus norvegicus

<400> SEQUENCE: 25

```
tctagcgaac cccttcgggg gttttcatca tggagctgtc gcggcggatt tgtctcgtcc      60
gactgtggct gttgctactg tcattcttac tgggcttcag cgcgggatct gccctcaact     120
```

-continued

```
ggcgggaaca agaaggcaag gaagtatggg attacgtgac tgttcgagag gatgcacgca      180
tgttctggtg gctctactat gccaccaacc cttgcaagaa cttctcagag ctgcctctgg      240
tcatgtggct tcagggtggt ccaggtggtt ctagcactgg atttggaaac tttgaggaaa      300
tcggccctct tgacacccga ctcaagccac ggaacactac ctggctgcag tgggccagtc      360
tcctgttcgt ggacaatcct gtgggcacgg gcttcagtta cgtgaacacg acagatgcct      420
acgcaaagga cctggacacg gtggcttccg acatgatggt cctcctgaaa tccttctttg      480
attgtcataa agaattccag acggttccgt tctacatttt ctcagaatcc tacggaggaa      540
agatggctgc tggcatcagt ttagaacttc acaaggctat tcagcaaggg accatcaagt      600
gcaacttctc tggggttgct ttgggtgact cctggatctc ccctgtggat tcagtgctgt      660
cctggggacc ttacctgtac agcgtgtctc tccttgataa taaaggcttg gctgaggtgt      720
ccgacattgc ggagcaagtc ctcaatgaaa acaagggct tctacaagga agccactcag      780
ctgtggggga agcagaaat gatcattgaa aagaacaccg acggggtaaa cttctataac      840
atcttaacta aaagcacccc cgacacctct atggagtcga gcctcgagtt cttccggagc      900
cccttagttc gtctctgtca gcgccacgtg agacacctac aaggagacgc cttaagtcag      960
ctcatgaacg gtcccatcaa aaagaagctc aaaattatcc ctgacgacgt ctcctgggga     1020
gcccagtcgt cctccgtctt cataagcatg gaagaggact tcatgaagcc tgtcatcgac     1080
atcgtggata cgttgctgga actcggggtc aatgtgactg tgtacaatgg cagctggat     1140
ctcattgtgg acaccatagg tcaggagtcc tgggttcaga agctgaagtg gccacagctg     1200
tccagattca atcagctaaa atggaaggcc ctgtacaccg atcctaagtc ttcagaaaca     1260
tctgcatttg tcaagtccta tgagaaccta gcgttctact ggatcctaaa ggcgggtcac     1320
atggttcctg ctgaccaagg ggacatggct ctgaagatga tgaggctggt tactcagcag     1380
gagtagctga gctgagctgg ccctggaggc cctggaggcc ctggagtagg gcccaggatg     1440
caggtgctaa tgtctatccc cggcgctctt cttcccgact ctaccatggg atgtaactcc     1500
aggagcccct gccatctccc gtaccaaaag actgtggctt ccgtgtctac tcagaaatca     1560
gttctacttc gtaaacagtg tttaaaacca gactcattta atcagagtga aggattgcag     1620
tccattggct tcttagcaca gaagcagctg ataacacaag taaaccccag cccttgagag     1680
gtagaagcaa gaggatcaga ggttcaagcg catcctcggc tccatcacaa gttcaaaagc     1740
cgcctgcacc aaatgggagt ccttgtctca aaaaaaaaa aaaaaaaaaa aaaagcggcc     1800
gc                                                                   1802
```

<210> SEQ ID NO 26
<211> LENGTH: 259
<212> TYPE: PRT
<213> ORGANISM: Rattus norvegicus

<400> SEQUENCE: 26

```
Met Glu Leu Ser Arg Arg Ile Cys Leu Val Arg Leu Trp Leu Leu Leu
 1               5                  10                  15

Leu Ser Phe Leu Leu Gly Phe Ser Ala Gly Ser Ala Leu Asn Trp Arg
            20                  25                  30

Glu Gln Glu Gly Lys Glu Val Trp Asp Tyr Val Thr Val Arg Glu Asp
        35                  40                  45

Ala Arg Met Phe Trp Trp Leu Tyr Tyr Ala Thr Asn Pro Cys Lys Asn
    50                  55                  60

Phe Ser Glu Leu Pro Leu Val Met Trp Leu Gln Gly Gly Pro Gly Gly
```

```
                65                  70                  75                  80
     Ser Ser Thr Gly Phe Gly Asn Phe Glu Glu Ile Gly Pro Leu Asp Thr
                         85                  90                  95

Arg Leu Lys Pro Arg Asn Thr Thr Trp Leu Gln Trp Ala Ser Leu Leu
                     100                 105                 110

Phe Val Asp Asn Pro Val Gly Thr Gly Phe Ser Tyr Val Asn Thr Thr
                 115                 120                 125

Asp Ala Tyr Ala Lys Asp Leu Asp Thr Val Ala Ser Asp Met Met Val
             130                 135                 140

Leu Leu Lys Ser Phe Phe Asp Cys His Lys Glu Phe Gln Thr Val Pro
     145                 150                 155                 160

Phe Tyr Ile Phe Ser Glu Ser Tyr Gly Gly Lys Met Ala Ala Gly Ile
                     165                 170                 175

Ser Leu Glu Leu His Lys Ala Ile Gln Gln Gly Thr Ile Lys Cys Asn
                 180                 185                 190

Phe Ser Gly Val Ala Leu Gly Asp Ser Trp Ile Ser Pro Val Asp Ser
             195                 200                 205

Val Leu Ser Trp Gly Pro Tyr Leu Tyr Ser Val Ser Leu Leu Asp Asn
     210                 215                 220

Lys Gly Leu Ala Glu Val Ser Asp Ile Ala Glu Gln Val Leu Asn Glu
     225                 230                 235                 240

Lys Gln Gly Leu Leu Gln Gly Ser His Ser Ala Val Gly Glu Ser Arg
                     245                 250                 255

Asn Asp His

<210> SEQ ID NO 27
<211> LENGTH: 630
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 27
tctagcgaac cccttcgcga aggggttcgc taggttgcgt ttgtggagaa aaatctgttc      60
tacctcaggg ctgtgagaac ggcactcctg atgtctgaga agagaaaaca agattggctg     120
aaggatcctc cgttccttca gagacctggg tggagagcat tagggacacg aagaacagag     180
tagcggaaga agagttctta agtaataagt ttacctcctg actggctcac atcactgcct     240
tactctgtag aaagcaggtc atctcatgga tttccccctc ccacccccCc agctggatca     300 tttttttgact cagggaaaat aattaaatta ttgtccaact gttagtgttg atcggtaaca     360
gcagaaaggc agaaagttcc tgataatctc aatattatct tttcaaaagt attttcctgg     420
aatgttgttt gctttggcat tacaaagttc tgtactctta aaatatttt gacttgctgg      480 gcatggaggt cacaccttta atccagaggc aggcatggat ccacaggagt tcaaggccgc     540
ctggctacaa agcgagttca agggcagcca gggctacaca gagagacctt gtctcntnac     600
cnntnannaa aaaacnaaaa agccggccgc                                      630

<210> SEQ ID NO 28
<211> LENGTH: 30
<212> TYPE: PRT
<213> ORGANISM: Rattus norvegicus

<400> SEQUENCE: 28
```

Met Ser Glu Lys Glu Lys Gln Asp Trp Leu Lys Asp Pro Pro Phe Leu
1               5                   10                  15

Gln Arg Pro Gly Trp Arg Ala Leu Gly Thr Arg Arg Thr Glu
            20                  25                  30

<210> SEQ ID NO 29
<211> LENGTH: 445
<212> TYPE: DNA
<213> ORGANISM: Rattus norvegicus

<400> SEQUENCE: 29

```
tctagcgaac cccttcggta tagtctttag gtagtggctt agtccctgga agctctggtt      60
gcttggcatt tcaacgtgct tcttaaataa ctgttttatt agtcagtaca agatgctttg     120
tatatcagat ctgaaatatc ttaaaattat cacttgcatt gtaaattact attcctttcg     180
cagaaataat gaatgcttca agaaaaaaaa aagctgtttg tattgggttt aaaacgtttc     240
caaacaccaa ttattcttta cttaagtcat ccgatctagt tattaaatta ttattactgc     300
cttcacacta tcaaagatgg taaatatctg atagaatcat attcaaaata cttctgtttc     360
acatttcttg agaaagtact gactgtctga gttctttctc aagaaatgtg aaacagaagt     420
attttgaatc gaagggttc  gctag                                           445
```

<210> SEQ ID NO 30
<211> LENGTH: 39
<212> TYPE: PRT
<213> ORGANISM: Rattus norvegicus

<400> SEQUENCE: 30

Met Leu Cys Ile Ser Asp Leu Lys Tyr Leu Lys Ile Ile Thr Cys Ile
1               5                   10                  15

Val Asn Tyr Tyr Ser Phe Arg Arg Asn Asn Glu Cys Phe Lys Lys Lys
            20                  25                  30

Lys Ser Cys Leu Tyr Trp Val
        35

<210> SEQ ID NO 31
<211> LENGTH: 273
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 31

```
tctagcgaac cccttcggaa gaactgtata tttgtgcctt gttctgcaag ttaaaaagct      60
ggtccagaca gtgtcataga attaactttt catttctgta ttaattttag gactgcaaaa     120
atcccaaagc tgtatactta gattggattc aataaaaagt ttaagtttac tnaanaaaaa     180
aaaaaaaaaa aaaaaaaaaa aaaaaaaaaa aaaaaaaaaa aaaanaaaaa aaaaaaaagg     240
aaaaaaaaaa ncggncnnaa aaaaggnggc cgc                                  273
```

<210> SEQ ID NO 32
<211> LENGTH: 2077
<212> TYPE: DNA
<213> ORGANISM: Rattus norvegicus

<400> SEQUENCE: 32

```
tctagcgaac cccttcgggg gaacccaagc ggcttcgccc aggcattcgc gcgggcgccc      60
gcggtctggg tcccacctcc tctgctttcg caccccttgaa gttttggagc accaggaaaa     120
```

-continued

```
gagggcaagg aaggagaggg gaagcgaaag catatcctaa aacatttact taaaggagga    180
aagaaaaggg gtcgcagaaa tggctggggc aattatagaa acatgagca ccaagaagct    240
ctgcattgtt ggagggattc ttctggtttt ccaaatcgtt gcctttctgg tgggaggctt    300
gatcgctcca gcacccacaa cggcagtgtc ctacgtggca gcaaaatgtg tggatgtccg    360
gaagaaccac cataaaacaa gatggctgat gccctgggga ccaaacaagt gtaacaagat    420
caatgacttc gaagaagcaa ttccaaggga aattgaagcg aatgacattg tgttttctgt    480
acacattccc ctcccttcta tggagatgag cccatggttc cagtttatgc tgtttatcct    540
gcagatagac attgctttca agctaaacaa ccaaatcaga gaaaatgcag aagtttccat    600
ggatgtttcc ctgggttacc gtgatgatat gttttctgag tggactgaaa tggcgcacga    660
aagagtacca cgtaaactca gatgcacttt cacatccccc aagacccag agcatgaagg    720
tcgtcattat gaatgtgatg tccttccttt catgggaaatt gggtcagtgg ctcataagta    780
ttaccttcta aatatccggc tacctgtaaa tgagaagaag aaaatcaatg ttggaattgg    840
ggaaataaag gacattcggt tggtgggaat ccaccaaaat ggaggtttca ctaaggtatg    900
gtttgctatg aagaccttcc tcacacccag catcttcatc attatggtgt ggtattggag    960
aaggatcacc atgatgtccc gacctccagt gcttctggaa aaagtcatct ttgcccttgg   1020
gatttccatg acctttatca atatccctgt ggaatggttt tccattggat ttgattggac   1080
ctggatgctg ttatttggtg acatacgaca gggcatcttc tatgcaatgc ttctttcctt   1140
ctggatcatc ttctgtggcg agcacatgat ggatcaacat gagcggaatc acattgcagg   1200
gtattggaag caagttggac caattgctgt tggctctttc tgcctcttca tatttgacat   1260
gtgtgagaga ggagtgcaac tcacaaatcc tttctacagt atctggacta cagatgttgg   1320
aacagaactg gctatggctt tcatcattgt ggcaggtatc tgcctctgcc tctacttcct   1380
gtttctgtgt ttcatggtat ttcaagtatt cagaaacatc agtgggaaac agtctagcct   1440
cccagccatg agcaaagtcc ggaggctgca ctatgagggt ctgattttca ggttcaagtt   1500
cctcatgctg atcaccttgg cttgtgctgc catgactgtt atcttcttca ttgttagtca   1560
ggtgacagaa ggccattgga atggggtgg ggtcacagtt caagtgagca gtgctttctt   1620
cactggaatc tatgggatgt ggaacctgta tgtctttgct ttgatgttct tgtatgcacc   1680
atcccataag aactatgggg aagaccagtc taatggtgac ctgggtgtcc acagcgggga   1740
agaactgcag ctcactacca caatcaccca tgtagatgga ccgactgaga tctacaagtt   1800
gaccccgtaaa gaagcacagg agtagtaggc tatggcattc atcctcaggg caggtgatga   1860
agccaagttg ctggtgcatg ctgaccctca tgaatatgct ttcgtatctt tatgtcccag   1920
gatcattttt atcctgtcac gtttacaaga acatttctga catgcatacg tttacttta   1980
ccatgtatta gttacttta tatttctgtg ataaaacacc atgagaaata caattacag   2040
aagcaaaaaa aaaaaaaaaa aaaaaaaaag cggccgc                            2077
```

<210> SEQ ID NO 33
<211> LENGTH: 541
<212> TYPE: PRT
<213> ORGANISM: Rattus norvegicus

<400> SEQUENCE: 33

```
Met Ala Gly Ala Ile Ile Glu Asn Met Ser Thr Lys Lys Leu Cys Ile
1               5                   10                  15
Val Gly Gly Ile Leu Leu Val Phe Gln Ile Val Ala Phe Leu Val Gly
            20                  25                  30
```

```
Gly Leu Ile Ala Pro Ala Pro Thr Thr Ala Val Ser Tyr Val Ala Ala
         35                  40                  45
Lys Cys Val Asp Val Arg Lys Asn His His Lys Thr Arg Trp Leu Met
 50                  55                  60
Pro Trp Gly Pro Asn Lys Cys Asn Lys Ile Asn Asp Phe Glu Glu Ala
 65                  70                  75                  80
Ile Pro Arg Glu Ile Glu Ala Asn Asp Ile Val Phe Ser Val His Ile
                 85                  90                  95
Pro Leu Pro Ser Met Glu Met Ser Pro Trp Phe Gln Phe Met Leu Phe
            100                 105                 110
Ile Leu Gln Ile Asp Ile Ala Phe Lys Leu Asn Asn Gln Ile Arg Glu
            115                 120                 125
Asn Ala Glu Val Ser Met Asp Val Ser Leu Gly Tyr Arg Asp Asp Met
130                 135                 140
Phe Ser Glu Trp Thr Glu Met Ala His Glu Arg Val Pro Arg Lys Leu
145                 150                 155                 160
Arg Cys Thr Phe Thr Ser Pro Lys Thr Pro Glu His Glu Gly Arg His
                165                 170                 175
Tyr Glu Cys Asp Val Leu Pro Phe Met Glu Ile Gly Ser Val Ala His
                180                 185                 190
Lys Tyr Tyr Leu Leu Asn Ile Arg Leu Pro Val Asn Glu Lys Lys Lys
            195                 200                 205
Ile Asn Val Gly Ile Gly Glu Ile Lys Asp Ile Arg Leu Val Gly Ile
            210                 215                 220
His Gln Asn Gly Gly Phe Thr Lys Val Trp Phe Ala Met Lys Thr Phe
225                 230                 235                 240
Leu Thr Pro Ser Ile Phe Ile Met Val Trp Tyr Trp Arg Arg Ile
                245                 250                 255
Thr Met Met Ser Arg Pro Pro Val Leu Leu Glu Lys Val Ile Phe Ala
                260                 265                 270
Leu Gly Ile Ser Met Thr Phe Ile Asn Ile Pro Val Glu Trp Phe Ser
            275                 280                 285
Ile Gly Phe Asp Trp Thr Trp Met Leu Leu Phe Gly Asp Ile Arg Gln
            290                 295                 300
Gly Ile Phe Tyr Ala Met Leu Leu Ser Phe Trp Ile Ile Phe Cys Gly
305                 310                 315                 320
Glu His Met Met Asp Gln His Glu Arg Asn His Ile Ala Gly Tyr Trp
                325                 330                 335
Lys Gln Val Gly Pro Ile Ala Val Gly Ser Phe Cys Leu Phe Ile Phe
            340                 345                 350
Asp Met Cys Glu Arg Gly Val Gln Leu Thr Asn Pro Phe Tyr Ser Ile
            355                 360                 365
Trp Thr Thr Asp Val Gly Thr Glu Leu Ala Met Ala Phe Ile Ile Val
            370                 375                 380
Ala Gly Ile Cys Leu Cys Leu Tyr Phe Leu Phe Leu Cys Phe Met Val
385                 390                 395                 400
Phe Gln Val Phe Arg Asn Ile Ser Gly Lys Gln Ser Ser Leu Pro Ala
                405                 410                 415
Met Ser Lys Val Arg Arg Leu His Tyr Glu Gly Leu Ile Phe Arg Phe
            420                 425                 430
Lys Phe Leu Met Leu Ile Thr Leu Ala Cys Ala Ala Met Thr Val Ile
            435                 440                 445
```

```
Phe Phe Ile Val Ser Gln Val Thr Glu Gly His Trp Lys Trp Gly Gly
    450                 455                 460
Val Thr Val Gln Val Ser Ser Ala Phe Phe Thr Gly Ile Tyr Gly Met
465                 470                 475                 480
Trp Asn Leu Tyr Val Phe Ala Leu Met Phe Leu Tyr Ala Pro Ser His
                485                 490                 495
Lys Asn Tyr Gly Glu Asp Gln Ser Asn Gly Asp Leu Gly Val His Ser
            500                 505                 510
Gly Glu Glu Leu Gln Leu Thr Thr Thr Ile Thr His Val Asp Gly Pro
        515                 520                 525
Thr Glu Ile Tyr Lys Leu Thr Arg Lys Glu Ala Gln Glu
    530                 535                 540
```

<210> SEQ ID NO 34
<211> LENGTH: 755
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 34

```
tctaacgaac cccttcggag cgatggaatg agaaaggccc agaatgtgtt aagtctgtgc    60
aggggaagtg tcctgagggg agggtctttg ggagggtcga aggccaggat ggcaaagtga   120
aggtagctga ggttgcagtc ttgggtgccc actgctgtgc atctgtctgg ttatctaccc   180
ctactttggg ctgacaactg cagggttggg tgtaggctgt ctcactgcat gccgggaagc   240
tggagaagct ccacgggaac attgagggcc atggctttga cactgcag agcatccttg    300
gtctctgtaa ccacgtcacc taaccctgac aattccagac ccttcttcca ttgtccttgt   360
gaaccatttg gcttatctt tccctcttag tcgcaagggt caaaccaagg gtcagtcaag   420
tagatgactg tcaccttggg cctccccaga ctctgctgcc ggggttggga gaccaaagta   480
gaaactgcca ctacaaggcc ccaggatgag gtctctgttc tgtggacctg ctccccagat   540
acaggcctca gacccatagg acgtggccgg tgctcaggga cacccaatcc ccggcctcac   600
tccatcgagt actgacttct ttctctagtg ccttgggggt ctccatcctt cagttatggt   660
atgaagaatc tatgcaaact gtataagctt ctgctcacca ataaacgctt tatttaaagc   720
ttannnnnnn nnannnnnn nnnnnaagcg gncgc                               755
```

<210> SEQ ID NO 35
<211> LENGTH: 30
<212> TYPE: PRT
<213> ORGANISM: Rattus norvegicus

<400> SEQUENCE: 35

```
Met Arg Lys Ala Gln Asn Val Leu Ser Leu Cys Arg Gly Ser Val Leu
  1               5                  10                  15
Arg Gly Gly Ser Leu Gly Gly Ser Lys Ala Arg Met Ala Lys
            20                  25                  30
```

<210> SEQ ID NO 36
<211> LENGTH: 1310
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 36

```
tctagcgaac cccttcgcag aaacccaaag ttacagacca gaccctaccc aacatccagt    60
cagcaatcca gctggagaaa cgcttgagat gacaagggac tttcagaagc aagccttgat   120
aagacaggaa aagcagaatt ctaataaaga tatgaggaaa aatgacatgg gccttcaacc   180
tctgcctgta gggaaggacg cacacagtgc accaggagtg acagtctctg ggaaaaacca   240
caaaagaact caggcacctg acaagaaaca gagaattgat gtttgtctag aaagccagga   300
ctttctaatg aagacaaata cttccaagga gttaaaaatg caatggaga ggtcctttaa    360
tccagtcaac ctttccctga ctgtggtgta aaagaaaatg aggacgccct tctctccatc   420
ttcccctcct tcttctcctt ccaattgcgt catctgaaat tgaatttcct ctcctcctcc   480
accacctata atgctgtgcc tgaaaaaaat gagtttcctc cctcatcacc cacagagaag   540
tcaagggctg aacttgagag cctcccaacc ctgcctcttc ctccaccacc aggagatgag   600
aaatctgatc aggaatgtct accaacatcc ctacctcctc cccctcccac agctccatcc   660
caaccagcac atcttctttc ctcctctgtt ctagaacatc acagtgaagc attttacaa   720
cagtattccc gaaaagaaac cttggactct catcggcttc actcacaggc taaaatccta   780
acaggaaaat caccacccc aacactcccc aaacccaaac ttcccgagag aatcaaagct    840
aagatgagcc aggattcacc aagcggtgaa ttggaaagat ctctgtcaga tgtggaaatt   900
aaaactaccc tctcaaagga tcagaaaagt tcgctggtgg cagaaagccg tgagcacaca   960
gaggccaagc aagaagtatt ccgaaaaagc cttggaagaa aacagctgtc cattagctct  1020
gcaaactccc tctctcagac agttccagaa atcccagcac caaggaaaa acagacagca   1080
ccccttgtta aatctcactc attcccatca ggttcagaac aacaaagtcc taagccttac  1140
atgagaaaat ttaagacacc cttaatgatt gcggaagaaa aatacagaca acaaagggaa  1200
gagcttgaga acagagacg ggagagttct tgccatagca tcatcaaaac agaaacccag   1260
caccgcagct tatcaaannt taaaaaaaaa aaaannnag cggncgcccg              1310
```

<210> SEQ ID NO 37
<211> LENGTH: 100
<212> TYPE: PRT
<213> ORGANISM: Rattus norvegicus

<400> SEQUENCE: 37

```
Met Thr Arg Asp Phe Gln Lys Gln Ala Leu Ile Arg Gln Glu Lys Gln
  1               5                  10                  15
Asn Ser Asn Lys Asp Met Arg Lys Asn Asp Met Gly Leu Gln Pro Leu
             20                  25                  30
Pro Val Gly Lys Asp Ala His Ser Ala Pro Gly Val Thr Val Ser Gly
         35                  40                  45
Lys Asn His Lys Arg Thr Gln Ala Pro Asp Lys Lys Gln Arg Ile Asp
     50                  55                  60
Val Cys Leu Glu Ser Gln Asp Phe Leu Met Lys Thr Asn Thr Ser Lys
 65                  70                  75                  80
Glu Leu Lys Met Ala Met Glu Arg Ser Phe Asn Pro Val Asn Leu Ser
                 85                  90                  95
Leu Thr Val Val
            100
```

<210> SEQ ID NO 38
<211> LENGTH: 774
<212> TYPE: DNA

```
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 38
tctagcgaac cccttcgctt tttttttttt tttttttttt ttttcccccc tttcctattt      60
attaatgggg ggaagtatgt ttatgtggga tttatccact tcttttagat tctcctacct     120
gttgatctgt aattattcct agtagtctct tagagttctt agaagcatgc tgttaccgct     180
aatatttcct tttggtttgg atcttactta aacatattg ttccttactc tctttttcat      240
cccagcttgt ctaactgaaa ggccagaccc aacttgatct atccctttaa aacttcatgt     300
cttggcctgt tgatttctct gctccaggtg tcaccgaagg ggttcgccta gcgaacccct     360
tcgtaacagc caaggttttt gagacagagg tttcaacagc attcctggag gagacacaaa     420
ggacagatga gtcacatgaa ggatgggagg agggaaggtg gctgttgata ggtatttga      480
gacactctat ttgagtccta cacaacactc cccctcccc ccaaaccatt tttatgtcta      540
ttgacctttc ctctagtcat acagggaaat tcacagttac ctacaaagaa ccactaattg     600
taacaagtca agaggaaact tatttttgat aatgactcat tgaagatgtt ttgaaaattt     660
aaaaataagc tctgttagca gaagtctgtn ngaaaagcan gaaggaaatg tttgtttatt     720
anataaataa aaggcggcga ggacaacaaa aaaaaaaaaa aaaaaagcgg ccgc            774

<210> SEQ ID NO 39
<211> LENGTH: 65
<212> TYPE: PRT
<213> ORGANISM: Rattus norvegicus

<400> SEQUENCE: 39

Met Ser Trp Pro Val Asp Phe Ser Ala Pro Gly Val Thr Glu Gly Val
  1               5                  10                  15

Arg Leu Ala Asn Pro Phe Val Thr Ala Lys Val Phe Glu Thr Glu Val
             20                  25                  30

Ser Thr Ala Phe Leu Glu Glu Thr Gln Arg Thr Asp Glu Ser His Glu
         35                  40                  45

Gly Trp Glu Glu Gly Arg Trp Leu Leu Ile Gly Ile Leu Arg His Ser
     50                  55                  60

Ile
 65

<210> SEQ ID NO 40
<211> LENGTH: 1259
<212> TYPE: DNA
<213> ORGANISM: Rattus norvegicus

<400> SEQUENCE: 40
tctagcgaac cccttcgcga aggggttcgc cgaaggggtt cgcttcagga gttaatgtag      60
acttgactta agcatcctga tttaaccaag aatggtggca cacaacttta accccccatgc    120
tggggaagca gaggcacact taatctgtgt gagtcccagg ccatccaggg ataccgtagt     180
agtgagaccc tgtctcacaa aacaaagaat gggaatttag gctggtggg gctcagcatg     240
caactgtgcc tgttacctag tctggcctga gttcaattcc caagactcaa tgtatgagga    300
gagaaacgat ttctgaactc attcattgat ctccaaatgt gtggtatagg tgcccttccc     360
ttaaataaaa caaacaaaca aaaaacaaca aaaacaacaa acccccaata aatgtatatt    420
```

-continued

```
taatttttaaa agactgtact tgggcatggt acttcacatc tacagttacg acattctaga    480
ggctcaggcc tgggaattgc tatgaatttg aggccagtct gggttagagt gacttctcat    540
ctaggcagga ctacgtaata agtctttgcc caaaaataaa cagcaaccca ataagagca    600 acaagaattc tccctccaaa tagtaacctg ggcctggaga gacagcttag caactgagtg    660
cttgccgagc catcgaggac tggagtctgg attccagcac ccgtgtgaca gacaagctgg    720
gcgttcactc atgctgatga accccaaggc tgaggagaca ctgactcttc tctggccctg    780
ttcatgctgt ccacaggtgc ccaagtagca gttaagtaga ctgtcagaca catggctgg    840 cttttttaagc aagaacagta actgaagaaa tacacttttg aagtactgtt aattttgctt    900
aaaacttggt agggagctgg aggatggctc agtggttaag agcactgact gctcttccag    960
aggtcctgag ttcaattccc agcaaccaca tggtggctca caaccatctg taatgagctc    1020
tgatgccctc ttttggtgt gtctgaagac agcgacagtg tactcatata aaataaaata    1080
aatctttttt ttttttaaaa gaaatttgtc agagatatgg caggaagggt atatttttac    1140
ctatttacct ggtgggctaa tcctggtatt tttttcaaaa ttaagatact ataggagc    1200 cgcgaagggg tcgctaggcc agtgtgatgg atatctgcag aattcggtta gccgaattc    1259
```

<210> SEQ ID NO 41
<211> LENGTH: 42
<212> TYPE: PRT
<213> ORGANISM: Rattus norvegicus

<400> SEQUENCE: 41

Met Val Ala His Asn Phe Asn Pro His Ala Gly Glu Ala Glu Ala His
  1               5                  10                  15

Leu Ile Cys Val Ser Pro Arg Pro Ser Arg Asp Thr Val Val Val Arg
             20                  25                  30

Pro Cys Leu Thr Lys Gln Arg Met Gly Ile
         35                  40

<210> SEQ ID NO 42
<211> LENGTH: 777
<212> TYPE: DNA
<213> ORGANISM: Rattus norvegicus

<400> SEQUENCE: 42

```
tctagcgaac cccttcgtct cctcttaaac atcttaagac aagctgttat catctacact     60
gctcttagta ctgttctttt ctaagattct tctaatatga cacattaaga ctttcttaaa    120
atgtacaact gctacgctga tctaaacatt caaagtgcac acatttcgct atgaagccac    180
gtgaccagag tcctggggac taatttctgt cttagtcaga ttcctattgc tatatgaaga    240
aataccatga tagtgtcaac ttttataaag aaaagtatt cctttgggaa tagtttaaag    300
gatcagaggg ttagtgcatt atcatcacag caggaagcgt ggcagtggga gcccagattt    360
ctatatccag atttcatga agcatgacga gagctcctgg gcctggcgcg agcttctgaa    420
acctgaaagt gacatatttc ttccaataag gccacaacta ctgctataag gccacatctc    480
ctaactgtgt cactatctat gagcctgtac agtctatttc ttttacacca ctgcatcatc    540
taagagctga tacccgttaa gttagtcatg aaaatattca acttctaggg ttctgttttc    600
ttctctataa aatattgaaa atgataatta atgtatactt tacagaactg tatttgaagt    660
acaacttgat ggacataaat caccacagtt gggtcaaaat tgtatatata tatatatata    720
tatatatata tatatatata tatcaaaaaa aaaaaaaaaa aaaaaaaaag cggccgc       777
```

<210> SEQ ID NO 43
<211> LENGTH: 46

<212> TYPE: PRT
<213> ORGANISM: Rattus norvegicus

<400> SEQUENCE: 43

Met Ile Val Ser Thr Phe Ile Lys Lys Tyr Ser Phe Gly Asn Ser
1               5                   10                  15

Leu Lys Asp Gln Arg Val Ser Ala Leu Ser Ser Gln Gln Glu Ala Trp
            20                  25                  30

Gln Trp Glu Pro Arg Phe Leu Tyr Pro Asp Phe His Glu Ala
        35                  40                  45

<210> SEQ ID NO 44
<211> LENGTH: 1378
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 44

```
tctagcgaac cccttcgtac atttcaccct agaaataaat agaccttcta gctctgacag      60
aaagtagtgc ttgcctagga ggagctgggc tggccagttc ctccttcttg cacacttagc    120
ctgtttgctg aaggcttgtt tcaatggaaa actgaaatgg acccactaat gtctcgattc    180
ttctctcctt cactaagtct gtgaagtcat cagcgttttg tcttttgtgt gtgaataccg    240
aggagaattt cctcacccag tgccttcagg agccatgatg gctgcctcag aataagcaca    300
gatacacttg agcaactggt gcagaaaacc cgacttctaa attattaagg aacaggataa    360
ttgcttgtta caataattag aataatgtaa ttaggataat tgcttttaaa aaatcttccc    420
accttttcccc ccccaaatat taataattcc aactaaatcc tctgggccc ttccagtttc    480
cacaacggaa agagcctaac gtattctaaa gactgggcat attttttttt tccagattag    540
tgagtgttca tgagctatta agaggccaag tgtttttttca agatggtgtc atttcattct    600
aacatatcta acatgcaaag gacttaaaaa aataaatttgc aaaataatct gtttcaagtc    660
tatgaggaag ctgaagagcc tactccggag gaaactccag aagagcctcc tagcatagag    720
gaagaagaga tagtggagga agaggaggag gaggaggtgc ccccgcccag aggtacagcc    780
gctttgatga gttcagcatt ccaaagcctt ggtgctgctg gaccctactc attagccata    840
tactttcctg gaagcacagc cacgaggcct ggagggtgca cactcgtaat gactggagct    900
ttgtgggcct ttcctttccc ctaacgtttc ctccttcccc gcaatctgac cataaatgag    960
gagatttttt ttttctctta ctacactttt tgcaatccta gtttgcaatc ctcagtgtgg   1020
ctggctttca gttcaaatgc tggagaacca tgtatctgtg tggtgagagc attcattttc   1080
aagactaatt cttaaaccgc ttatccccgg agacagaaac cgtggcagag ttgctatcct   1140
ctgagctggg gtggtcatga tgatcagtta ggttactaac atcttcctaa atgaatcggt   1200
gttttgtgtt gctctgtttt catttggatg acagggtgtt gttctgttta atgcgtgtgg   1260
gttttttccaa catgtccgta aaatatctt ttaagcacca gangtagtga agaaagctgt   1320
gcaaacagca cccgctcctg tccccaagaa awccgaggcg ccccccaaa ggtatatc    1378
```

<210> SEQ ID NO 45
<211> LENGTH: 1554
<212> TYPE: DNA
<213> ORGANISM: Rattus norvegicus
<220> FEATURE:
<221> NAME/KEY: unsure
<222> LOCATION: (0)...(0)

-continued

<223> OTHER INFORMATION: n = A, T, C, or G

<400> SEQUENCE: 45

```
tctagcgaac cccttcgcga acccttcgc tgcatcctca taaagctacc tcaagacaga      60
gcgtaactgc tcattctag gagtggactc ggggaagaca gcagacacac catcagggag     120
cccctgggta tctccagaac atggcaagcc gtggatacct gcatcacctg ctgactgcag    180
agggagcctg ggaggagttt gtatcaaagg ccaagttgcc cagggatagg gcagtggccc    240
tccacaaagc actgagggat ctgacagcac tcttggccat agcagaaaga ggcagatctc    300
ggaaaggctg gaaaggcaag gagaagtttg tgaaagcatt tccttgcttg aaagcagact    360
tggaggagca catcagccag ctctatgccc tagccgacca tgctgaggaa ctgcacaggg    420
gctgcaccgt ctccaacatg gtggctgact ccttcagtgt tgcctccgac atcctgaaca    480
tctttggtct ctttctggca cctgagtcag cagagggaag tctggtgctc tcggcagcag    540
gcttggggct gggggtagca gctactgtga ctaatgttgc tacttcaatc atgaaggaaa    600
caagcagggt tttggatgga gtcgaagctg gtcaccatgg ttcaaccgcc atggatatac    660
tggaggaagc tggcacaagt gtggctagga ttgccagcga gatccctcag gctaccagag    720
atatcaccag agacctggaa gcccttgagc agcacatgaa tgccctcagt ctggtcagag    780
ccaaccctcg cctagaagaa gatgccaggg ccctcatcaa tgcaggtagc atccctgccc    840
aacgggctaa acaggtgcgg gccagtctga aggaaccccc tctggcaatg agcaaggaag    900
accggatccg cagtgccacc accactgggg tcaccctctt gcgtgatgtg gggagccttg    960
tgaacgagtc gaagcagttg tacgaagggt ctgcttccga atcggcagca gcactaagga   1020
agctggctca ggagctggag gagaagctag gggagctcat gaaattctac agacaatct    1080
gatcaggttt cagccagtca ccccatcccc aagacatgca gacatcangg gagaggatct   1140
ggacagaggt agggaccatg gaggtgctgt tagaaggaga gcaagactac agtcaggtcc   1200
gagggacata gtgtggaggc ctgtttgatg aacacarcag gttaaggat ggagcagtgg    1260
atcaaagtga gatccactgg agcctgagac saggaccag aggatgtgct gcaagaggga    1320
ctgggaaaat tgaaatctan actaaacatg gaaaaaggc agtttcgaaa gactagaaaa    1380
ccctccccat ctgagccatt ggaaacccca caaaacacaa accagagaga aaagtgtgtg   1440
ctctctaaac aagtcgtggc ccccagttcc ccagcccact cccacccctca ggggtggcat   1500
caaataaatt gtttccattt caaaaaaaaa annaaanaaa aaaaaagcgg ccgc          1554
```

<210> SEQ ID NO 46
<211> LENGTH: 313
<212> TYPE: PRT
<213> ORGANISM: Rattus norvegicus

<400> SEQUENCE: 46

```
Met Ala Ser Arg Gly Tyr Leu His His Leu Leu Thr Ala Glu Gly Ala
  1               5                  10                  15

Trp Glu Glu Phe Val Ser Lys Ala Lys Leu Pro Arg Asp Arg Ala Val
             20                  25                  30

Ala Leu His Lys Ala Leu Arg Asp Leu Thr Ala Leu Leu Ala Ile Ala
         35                  40                  45

Glu Arg Gly Arg Ser Arg Lys Gly Trp Lys Gly Lys Glu Lys Phe Val
     50                  55                  60

Lys Ala Phe Pro Cys Leu Lys Ala Asp Leu Glu Glu His Ile Ser Gln
 65                  70                  75                  80

Leu Tyr Ala Leu Ala Asp His Ala Glu Glu Leu His Arg Gly Cys Thr
```

|     |     |     |     | 85  |     |     |     |     | 90  |     |     |     |     | 95  |     |
| --- | --- | --- | --- | --- | --- | --- | --- | --- | --- | --- | --- | --- | --- | --- | --- |
| Val | Ser | Asn | Met | Val | Ala | Asp | Ser | Phe | Ser | Val | Ala | Ser | Asp | Ile | Leu |
|     |     |     | 100 |     |     |     |     | 105 |     |     |     |     | 110 |     |     |

Asn Ile Phe Gly Leu Phe Leu Ala Pro Glu Ser Ala Glu Gly Ser Leu
        115                  120                125

Val Leu Ser Ala Ala Gly Leu Gly Leu Gly Val Ala Ala Thr Val Thr
130                    135                  140

Asn Val Ala Thr Ser Ile Met Lys Glu Thr Ser Arg Val Leu Asp Gly
145                  150                  155                  160

Val Glu Ala Gly His His Gly Ser Thr Ala Met Asp Ile Leu Glu Glu
        165                  170                175

Ala Gly Thr Ser Val Ala Arg Ile Ala Ser Glu Ile Pro Gln Ala Thr
           180                  185                190

Arg Asp Ile Thr Arg Asp Leu Glu Ala Leu Glu Gln His Met Asn Ala
        195                200                205

Leu Ser Leu Val Arg Ala Asn Pro Arg Leu Glu Glu Asp Ala Arg Ala
210                    215                  220

Leu Ile Asn Ala Gly Ser Ile Pro Ala Gln Arg Ala Lys Gln Val Arg
225                    230                  235                  240

Ala Ser Leu Lys Gly Thr Pro Leu Ala Met Ser Lys Glu Asp Arg Ile
           245                  250                255

Arg Ser Ala Thr Thr Thr Gly Val Thr Leu Leu Arg Asp Val Gly Ser
        260                  265                270

Leu Val Asn Glu Ser Lys Gln Leu Tyr Glu Gly Ser Ala Ser Glu Ser
275                    280                  285

Ala Ala Ala Leu Arg Lys Leu Ala Gln Glu Leu Glu Glu Lys Leu Gly
        290                  295                300

Glu Leu Met Lys Phe Tyr Glu Thr Ile
305                    310

<210> SEQ ID NO 47
<211> LENGTH: 1142
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 47

```
tctagcgaac cccttcggct ttttctgatt taaagtgaag aaatggccat atttgcttga      60
taatcttcag ttgtgtctct ggaactcaac aaagaacgca ttttatgaaa tatacagctg     120
tcttcggtaa agccaacttt cttacacata tttcggaag taattaacta caatttggac      180
ttatagttac aaggttgcct tcgaaacact gctctaaatg tgtctcgtgt tggggtgcta     240
cttgcttat gtgtaaattt cacagtaatg caatagagaa agggtgtttg tgggtgtggc      300
ttgtgggggg gattgttttg ttgttgttgt ttgagataaa gcttcattct gtagccagga     360
aagcctggaa tttactgtgt catcccaggt agcttcaaac tggtgcctat cctgcctcag     420
cctccaacgt gttgcaattg caggagtaac ctaccacatc ctgcagctac agtgatctag     480
aacctccccg tcgaagcccc accaccatag aaaccaattt gcattaagtt ttagaattcc     540
caacccaact aaagtttaat aaaaaaagaa aaacaaaaca agatttaaat cattctttcc     600
ctcattcttt ttnnagatnc agggctcncc tagttttnaa caaaacagtn ngcagngnng     660
ggnnccccng gnggggnttt tttncnttgn gccncntngc anccacccn cccaggcngg     720
```

| | |
|---|---|
| atngggnggg gtataaaagt nttancnggc anatgnnctn ggngcanacc caagtntatc | 780 |
| aggncctnan ttnccnccca ganaactaga nanctntngc atagtanang cccntgtgn | 840 |
| agatttnaaa nccncctgtn cacaganana gaancttana tagaaaantc aaaatatttn | 900 |
| ggngcccaan gttnccaccc ctgtagagng ggnccccaaa ancngccncc aganagcnng | 960 |
| atatntgagt tntgacctnt attctttact acnacgcntt gagagaatat tntgntgggg | 1020 |
| ccctanccac atgttttgnc ccaagantgt aaanccactt naannctgng ggatatctcn | 1080 |
| ctgcanacag aagtgcccng cgggatttta aaaaaaaaaa taaaaaaaaa aaaggngccn | 1140 |
| cc | 1142 |

<210> SEQ ID NO 48
<211> LENGTH: 502
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 48

| | |
|---|---|
| tctagcgaac cccttcgtgg agactgtgga agttatgtat gaataggaga gtgtgtgttg | 60 |
| tgtaacacag acagaaggac attggatcat gttgaacccg cacccccaac tatgagtgat | 120 |
| ggtatgaaaa gaatgcgaac atttaaactg cgccaatgcg gcggccatct tggtggagaa | 180 |
| gttcctagcc gagctttgat gtgattttttt tgatggtaca atgcagcgag catggccacg | 240 |
| ggagctttga atccagccga cagctccgag atttgccctt ccagtgctct tgcctaccgt | 300 |
| agagaggact gctgagatgg gattccttgt gacaagccta cttacctta actgccagca | 360 |
| tttgtaaggt gcaatcttgt gtattggttt tttattttga cagttttgaa acatgtttg | 420 |
| ntgntcttgg tgttttttcca gtaaaagtaa tcacaaagga aaaaaaaatt aaaaaaaaaa | 480 |
| aaaaaaaaaa aaaagcggcc gc | 502 |

<210> SEQ ID NO 49
<211> LENGTH: 1426
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 49

| | |
|---|---|
| tctagcgaac cccttcgcct tcatatggtt ttacactgta tgcatctcac cgcggcccgg | 60 |
| aacctttctt ctcatcccaa tcctgtttga ggggacgggg ggcagggacg gacaacccaa | 120 |
| gacagggat atttgtgctg tgggtattgc atcttatgga gggctgtagc taactgggac | 180 |
| tcctgggtga ccccaacagg cctttgatcc tctgtctctc cccgcttgat ctttcttacc | 240 |
| ttatgcttcc ccaagtgcag ctgagggact acacagtggc tcccgcccca ctccaaacac | 300 |
| aggaaatcaa tctcagggag aggagataag aagtgaggag aagccaagat tcaaccaata | 360 |
| gatggtaatt gctcctggga ccgccccccc aagcatcatt tccataggaa ggactgagtt | 420 |
| tggctcctga agcccagtgg agtaccttc tctgcctgaa ttctgttgtg atccctggcc | 480 |
| aagtcctctt tccagaaacc ccacctttaa aaccagctga gaaggacctt cttctctatg | 540 |
| tttaataggt aactttccat agcttagctt ccctgcagtc tcccgagtgc ccagttaaaa | 600 |
| ttctgccata ggtcaaaagt ggggttgaga ggtgaagtca gaggccatgc atggagctca | 660 |

-continued

```
gaacgtttct aaacctcctg tgattcattg agtagcccct agactctaga aggctcagat      720
gccaaaaagg ktgactttat aatttcttag ggtcttctca tgggatcgkt ttcagagtgg      780
gcattcacta aatgatagca agtttattaa ttgtttccca gygcctgatc tctttatttn      840
cccagggctt ccaaccagag cccttggttg aaagtctccc acccaccccc cacccctgaga     900 cttggtggnt ttctgagatt ccccagggat ggcaaaattg gcattcttac agggagccct     960
gacttctagc acgttaccta gattttttac cctgctctct ctgcctattt tactatggga    1020
tcactgntct ctttggactt aaggaaccac cttgaagtag agtgaggtga ccacgtgttg    1080
gtggcgaaga atataagcat tggtccttaa agagaactt ctatgaagtc aggctgcaag     1140
ctttaacatg gcacaagttg caccttactg gctgctaagt ctggatgtca accaaaggtc    1200
aactctntaa ttaaagaaaa gcaagggaga aganaggtgg aagnggcttn cataaacttt    1260
attcaaaatg tctaccagga atggtggtga caccaataat cccacatgtt ggatgtngag    1320
gcaggaagaa tgatggtaag gggcatcctc actacataat gagttgaggc tngactaggt    1380
taactntgct tnaaaaaaaa aaaaaaaaaa aaaaaaagg ggngcc                      1426
```

<210> SEQ ID NO 50
<211> LENGTH: 985
<212> TYPE: DNA
<213> ORGANISM: Rattus norvegicus

<400> SEQUENCE: 50

```
tctagcgaac cccttcgcaa gaactcgagac tgctcctgcc tgacttccta ggtgtcatag      60
ctctcttctg ccgccagtat gacatcatca aggacaacga gcccaataac aacaaggaaa     120
aaaccaagag tgcatcagag accagcaccc cagagcacca gggtgggggt ctcctccgaa     180
gcaagatatg aaacccttttc agtgcttgct ctgagcagct cagaagtaga atgcgagagg    240
acctcactgt tctgacgatg attgtccaac acacatccgg ccctctccgt gtctcctccc     300
accaccatct tctcctatca ccgggcttac tatcttctct cctggctttc ctctttctga    360
tggcggttcc tgaagcctcc aactaacccc taactcgggg agcgcctcga cagtgtttgt    420
ggctaaggct acactcagag acagagttgc agaatgaggg agacccagcc cgagggacgc    480
cattgctggg aggtagactg ggtgcgaggg cccttggcac aggactcaca tctgggctgt    540
tcagcttgac ccgaaggctg tgtgtgaaag ggggaaaaag acaagattgc caggcagggc    600
tgttgttttt gtggcttcga gggacaagaa cctggctaaa aggcagcagc cctgctgttc    660
tttttctcct ctgtcctgtt tcctacctta caagaagtcc atgcaaccaa ccggggctct    720 ggcactttc ttgtttattt ccctcctggc ttccaaacaa gccctctgtg gacatcatca    780
aagcatggat aaccccctct gcaggggtgg gcttcattct ccgctggtcc ctgtagcctt    840
cctggacaca gggtgaaagt tgtaaaagtg gtaggagtgc agctagccac aggttctcct    900
tttcccatct cagtctgacc aaggaggctg aactaccaac ccaaattcag cgaaaaaaaa    960
aaaaaaaaaa aaaaaaagcg gccgc                                           985
```

<210> SEQ ID NO 51
<211> LENGTH: 58
<212> TYPE: PRT
<213> ORGANISM: Rattus norvegicus

<400> SEQUENCE: 51

Met Thr Ser Ser Arg Thr Thr Ser Pro Ile Thr Thr Arg Lys Lys Pro
 1               5                  10                  15

Arg Val His Gln Arg Pro Ala Pro Gln Ser Thr Arg Val Gly Val Ser

```
              20                  25                  30
         Ser Glu Ala Arg Tyr Glu Thr Leu Ser Val Leu Ala Leu Ser Ser Ser
              35                  40                  45

Glu Val Glu Cys Glu Arg Thr Ser Leu Phe
              50                  55

<210> SEQ ID NO 52
<211> LENGTH: 2010
<212> TYPE: DNA
<213> ORGANISM: Rattus norvegicus

<400> SEQUENCE: 52
tctagcgaac cccttcgcgg ggacagacat ggagaaggag atggaggacc cctggctgg      60 agcagaccaa cagaataggc aactatggct ggagaaccgg gtatcagagt aatgcttgac    120
ctcgggaaac accaaatttc ttcttccgat cgcagaagta gtactcggcg aaattcacta    180
ggtaggaggc tcctcatctg gaagaaccg gtgcctgggg gacctggct ggataggtat       240 gggggatcga ggccggtccc ctagtctccg gtccccccat ggcagtcctc caactctaag    300
caccctcact ctcctgctgc tcctctgtgg acaggctcac tcccagtgca agatcctccg    360
ctgcaatgcc gagtacgtct cgtccactct gagccttcgg ggaggggct caccggacac     420 gccacatgga ggcggccgtg gtgggccggc tcaggtggc ttgtgtcgcg ccctgcgctc      480
ctacgctctc tgcacgcggc gcaccgcccg cacctgccgc ggggacctcg ctttccactc    540
cgcggtgcat ggcatagagg acctgatgat ccagcacaac tgctcacgcc agggtcccac    600
ggcctcgccc ccggcccggg gtcctgccct gcccggggcc ggcccagcgc cctgaccccc    660
agatccctgt gactatgaag cccggttttc caggctgcac ggtcgaaccc cgggtttctt    720
gcattgtgct tcctttggag accccatgt gcgcagcttc cacaatcact ttcacacatg      780
ccgcgtccaa ggagcttggc ccctactaga taacgacttc ctctttgtcc aagccaccag    840
ctccccggta gcatcgggag ccaacgctac caccatccgg aagatcacta tcatatttaa    900
aaacatgcag gaatgcattg accagaaagt ctaccaggct gaggtagaca atcttcctgc    960
agcctttgaa gatggttctg tcaatggggg cgaccgacct gggggctcga gtttgtccat   1020
tcaaactgct aaccttggga gccacgtgga gattcgagct gcctacattg aacaactat    1080 aatcgttcgt cagacagctg gacagctctc cttctccatc agggtagcgg aggatgtggc   1140
acgggccttc tctgctgagc aggatctaca gctgtgtgtt gggggatgcc ctccgagcca   1200
gcgactctct cgctcagagc gcaatcgccg tggggcgata gccatagata ctgccagaag   1260
gttgtgtaag gaagggcttc cggttgaaga tgcctacttc caatcctgcg tctttgatgt   1320
ttcagtctcc ggtgaccca actttactgt ggcagctcag tcagctctgg acgatgcccg     1380
agtcttcttg accgatttgg agaacttgca ccttttccca gtagatgcgg ggcctccct     1440 ctctccagcc acctgcctag tccggcttct ttcggtcctc tttgttctgt ggttttgcat   1500
tcagtaagta ggccagcaac ccgtgactag tttggaaacg gtttgaggag agaggttgat   1560
gtgagaaaac acaagatgt gccaaaggaa acagtgggga caggagacaa cgaccttact     1620
caatcacacg aggttgcagt ccagggctga aatgacccta gaataaagat tctgagacag   1680
ggttttgcac tccagacctt ggtatgggct ccccatgaat ttcccccatta gtgatttccc   1740 acttgtagtg aaattctact ctctgtacac ctgatatcac tcctgcaagg ctagagattg   1800
tgagagcgct aagggccagc aaaacattaa agggctgaga tatcttaaag gcagaaacta   1860
gaaaagggga aaccatgatt atctataaga aaatcaaaag aggggtttgg gaatttagct   1920
```
cagtggtaga gcacttgcct agcaagcgca aggccctggg ttcggtcccc agctcctaaa      1980
aaaaaaaaaa aaaaaaaaaa aagcggccgc                                      2010

<210> SEQ ID NO 53
<211> LENGTH: 422
<212> TYPE: PRT
<213> ORGANISM: Rattus norvegicus

<400> SEQUENCE: 53

```
Met Gly Asp Arg Gly Arg Ser Pro Ser Leu Arg Ser Pro His Gly Ser
 1               5                  10                  15

Pro Pro Thr Leu Ser Thr Leu Thr Leu Leu Leu Leu Cys Gly Gln
            20                  25                  30

Ala His Ser Gln Cys Lys Ile Leu Arg Cys Asn Ala Glu Tyr Val Ser
        35                  40                  45

Ser Thr Leu Ser Leu Arg Gly Gly Ser Pro Asp Thr Pro His Gly
    50                  55                  60

Gly Gly Arg Gly Gly Pro Ala Ser Gly Gly Leu Cys Arg Ala Leu Arg
65                  70                  75                  80

Ser Tyr Ala Leu Cys Thr Arg Arg Thr Ala Arg Thr Cys Arg Gly Asp
                85                  90                  95

Leu Ala Phe His Ser Ala Val His Gly Ile Glu Asp Leu Met Ile Gln
            100                 105                 110

His Asn Cys Ser Arg Gln Gly Pro Thr Ala Ser Pro Pro Ala Arg Gly
        115                 120                 125

Pro Ala Leu Pro Gly Ala Gly Pro Ala Pro Leu Thr Pro Asp Pro Cys
    130                 135                 140

Asp Tyr Glu Ala Arg Phe Ser Arg Leu His Gly Arg Thr Pro Gly Phe
145                 150                 155                 160

Leu His Cys Ala Ser Phe Gly Asp Pro His Val Arg Ser Phe His Asn
                165                 170                 175

His Phe His Thr Cys Arg Val Gln Gly Ala Trp Pro Leu Leu Asp Asn
            180                 185                 190

Asp Phe Leu Phe Val Gln Ala Thr Ser Ser Pro Val Ala Ser Gly Ala
        195                 200                 205

Asn Ala Thr Thr Ile Arg Lys Ile Thr Ile Ile Phe Lys Asn Met Gln
    210                 215                 220

Glu Cys Ile Asp Gln Lys Val Tyr Gln Ala Glu Val Asp Asn Leu Pro
225                 230                 235                 240

Ala Ala Phe Glu Asp Gly Ser Val Asn Gly Gly Asp Arg Pro Gly Gly
                245                 250                 255

Ser Ser Leu Ser Ile Gln Thr Ala Asn Leu Gly Ser His Val Glu Ile
            260                 265                 270

Arg Ala Ala Tyr Ile Gly Thr Thr Ile Ile Val Arg Gln Thr Ala Gly
        275                 280                 285

Gln Leu Ser Phe Ser Ile Arg Val Ala Glu Asp Val Ala Arg Ala Phe
    290                 295                 300

Ser Ala Glu Gln Asp Leu Gln Leu Cys Val Gly Cys Pro Pro Ser
305                 310                 315                 320

Gln Arg Leu Ser Arg Ser Glu Arg Asn Arg Arg Gly Ala Ile Ala Ile
                325                 330                 335

Asp Thr Ala Arg Arg Leu Cys Lys Glu Gly Leu Pro Val Glu Asp Ala
            340                 345                 350

Tyr Phe Gln Ser Cys Val Phe Asp Val Ser Val Ser Gly Asp Pro Asn
```

-continued

```
               355                 360                 365
Phe Thr Val Ala Ala Gln Ser Ala Leu Asp Asp Ala Arg Val Phe Leu
        370                 375                 380

Thr Asp Leu Glu Asn Leu His Leu Phe Pro Val Asp Ala Gly Pro Pro
385                 390                 395                 400

Leu Ser Pro Ala Thr Cys Leu Val Arg Leu Leu Ser Val Leu Phe Val
                405                 410                 415

Leu Trp Phe Cys Ile Gln
            420
```

<210> SEQ ID NO 54
<211> LENGTH: 705
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 54

| | | | | |
|---|---|---|---|---|
| tctagcgaac | cccttcgtgg | ggattaaggt | tctctatagc | taagcctgtc | ngaatgacaa | 60 |
| cacccagaga | tctcacctgg | ggtggtggga | gcactctctg | tcttgaggga | acatgtacct | 120 |
| actctctcct | tccacaagag | ccacatacac | ttagaagttc | cagtgaagat | ctatgtgctt | 180 |
| cagaagagag | gggacttgga | ggtgaaaggg | ggagtgggag | gggggcttga | ggacctanct | 240 |
| gaaagatttt | angctgaaag | aacttccttg | attcaaagac | atatgtcagt | ngacccaaca | 300 |
| atgagaatga | atatgagggc | caggaaaact | tgtgggaatc | agtctcaaga | cngaaacnga | 360 |
| gaaagaaaga | aaagtggnta | ggactcanat | tggggaacct | gggtagacag | gagtggcnag | 420 |
| ggaagaaagg | gatcttgggt | tntccacagt | ttgagacaca | tccggngntc | gaccctattc | 480 |
| ccngaagccn | cannanatgt | tgcttccccn | tcnntnnaat | gggcctggng | gtcctnctcc | 540 |
| ctttnccng | gacatgaaaa | ngtnttctgc | nnanataacc | cccntctttc | ctccccttn | 600 |
| antntgtccc | taccnttttg | tcccttttn | ttttnaaaaa | annaaaataa | agggnncnn | 660 |
| tnttcccttn | gaaaaaaaaa | aaaaaaaaaa | aaaaaaccgc | ccncc | | 705 |

<210> SEQ ID NO 55
<211> LENGTH: 58
<212> TYPE: PRT
<213> ORGANISM: Rattus norvegicus

<400> SEQUENCE: 55

```
Met Thr Thr Pro Arg Asp Leu Thr Trp Gly Gly Gly Ser Thr Leu Cys
1               5                   10                  15

Leu Glu Gly Thr Cys Thr Tyr Ser Leu Leu Pro Gln Glu Pro His Thr
            20                  25                  30

Leu Arg Ser Ser Ser Glu Asp Leu Cys Ala Ser Glu Glu Arg Gly Leu
        35                  40                  45

Gly Gly Glu Arg Gly Ser Gly Arg Gly Ala
    50                  55
```

<210> SEQ ID NO 56
<211> LENGTH: 968
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G -continued

```
<400> SEQUENCE: 56
tctagcgaac cccttcgcga aggggttcgc ttacattcac gcttaagcat attaactgta      60
catattaact gatttagagg atactatgga ttccacatct tccctgagca tagggattga     120
tttgaaaaat gacagggttg gctgtcgacc cccatcggag gaagcaggta aggaatcact     180
taggagaact gatctcaaca ttcttcagtt ctttctatta tttacttgtt tagcctggag     240
ttaaattccc actccttgtg agcacttcta atttgaaaat ccactttctt caatattttc     300
gaaatttaaa actgatggat gacgtgacaa aacttccacg agttaagaat tctccacctc     360
tgatctcatc gcagcagggc acaatccaag gcatgtgaat tgacttccag gtttatgtga     420
catataaatg aattctgtct ctagatttgg atcccattct cctaaatatc tcaccatgca     480
tgtgcagata ttctaaagtc taaaaatatc tgatattgca aacttttctg gtcaaaacat     540
tttggatgag ccatttaaca gccaaggtat ttgagacaga ggtttcaaca gcattcctgg     600
aggagacaca aaggacagat gagtcacatg aaggatggga ggagggaagg tggctgttga     660
taggtatttt gagacactct atttgagtcc tacacaacac tccccctcc  ccccctcccc     720 ccaaaccatt tttatgtcta ttgaccttc ctctagtcat acagggacat tcacagttac     780
ctacaaagaa ccagaattgt aacaagtcaa gaggaaactt atttttgata atgactcatt     840
gaagatgttt tgaaaattta aaataagct cttgtaagca gaagtctgtg agaaaagcaa     900
gaaggaattg tttgtttatt aaataaataa aaggcnnann nnaaaaaaaa aaaaaaaan     960 gcggccgc                                                              968

<210> SEQ ID NO 57
<211> LENGTH: 52
<212> TYPE: PRT
<213> ORGANISM: Rattus norvegicus

<400> SEQUENCE: 57

Met Asp Ser Thr Ser Ser Leu Ser Ile Gly Ile Asp Leu Lys Asn Asp
  1               5                  10                  15

Arg Val Gly Cys Arg Pro Pro Ser Glu Glu Ala Gly Lys Glu Ser Leu
             20                  25                  30

Arg Arg Thr Asp Leu Asn Ile Leu Gln Phe Phe Leu Leu Phe Thr Cys
         35                  40                  45

Leu Ala Trp Ser
     50

<210> SEQ ID NO 58
<211> LENGTH: 1183
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 58
tctagcgaac cccttcggca gacagcatcc ctcccaaggc tactcagggt ttaaaccctg      60
cttctgaagt gacatgtcct gcaaagaaag tccccacgtg ggtgtttcca ccaccactgt     120
cagctctgta gctgtgcaag ctggggactc caagatcgtg atagccgttg tcaagtgtgg     180 caaatggtg cggctccaac tggctgaggc acagcccaat ctcctagaaa ttgggagcag     240
tcaagatgaa accagaaaac tgcttcacga tcacgagctc cttctggcca agcttaaggc     300
cttggaagat cgtgtgtggg gactcttaca ggaagcagac aggacggctg aagcaaacaa     360
```

```
ggagcaaagt gaggtgtcga tgccatggcc agactctggg cgaagcatgg gccaccctgg    420
tcttcatgct tgaaagaaga agggagctcc tcggactgac atctgagttt tttcaaagcg    480
ccttggagtt tgctataaaa atagaccaag ctgaagattt tctgcagaat cctcacgagt    540
ttgagagtgc cgaagcctta cagtcacttc ttctgcttca tgaccgacac gccaaagaac    600
tcttagaacg atctctagtc cttttaaaca aaagccaaca actcactgac ttcatagaaa    660
aattcaagtg tgatggatct cctgtgaatt ctgagctcat ccagggagct cagagcagtt    720
gtctgaagat cgacagcctc cttgaacttc tgcaagacag gagaaggcag ctggacaagc    780
acttgcagca acagaggcag gagttgtctc aggttctgca gttatgtctg tgggaccaac    840
aagaaagcca ggtttcttgt tggtttcaga aacaataag agatctgcag gaacagagtc    900
tgggttcatc cctttcagac aacaaagagt taatccgtaa gcacgaggac ctgccatcaa    960
agcaaagagt ccctgcagtt taggaattga acagaacagt ttcctgattg aatgatcttg   1020
gcgcctyytt ancggntgca gatggtgggg cttcctctgg nttctcatcc tcttccacta   1080
atctggattt tgttcccct ggtgtgccac atcactttaa tttgaaagaa aaaaaataaa    1140
ttgggccgga aaaaaaaaaa aaaaaaaaaa aarrrscggc cnc                     1183
```

<210> SEQ ID NO 59
<211> LENGTH: 245
<212> TYPE: PRT
<213> ORGANISM: Rattus norvegicus

<400> SEQUENCE: 59

```
Met Lys Pro Glu Asn Cys Phe Thr Ile Thr Ser Ser Phe Trp Pro Ser
 1               5                  10                  15

Leu Arg Pro Trp Lys Ile Val Cys Gly Asp Ser Tyr Arg Lys Gln Thr
            20                  25                  30

Gly Arg Leu Lys Gln Thr Arg Ser Lys Val Arg Cys Arg Cys His Gly
        35                  40                  45

Gln Thr Leu Gly Glu Ala Trp Ala Thr Leu Val Phe Met Leu Glu Arg
    50                  55                  60

Arg Arg Glu Leu Leu Gly Leu Thr Ser Glu Phe Phe Gln Ser Ala Leu
65                  70                  75                  80

Glu Phe Ala Ile Lys Ile Asp Gln Ala Glu Asp Phe Leu Gln Asn Pro
                85                  90                  95

His Glu Phe Glu Ser Ala Glu Ala Leu Gln Ser Leu Leu Leu His
            100                 105                 110

Asp Arg His Ala Lys Glu Leu Leu Glu Arg Ser Leu Val Leu Leu Asn
        115                 120                 125

Lys Ser Gln Gln Leu Thr Asp Phe Ile Glu Lys Phe Lys Cys Asp Gly
    130                 135                 140

Ser Pro Val Asn Ser Glu Leu Ile Gln Gly Ala Gln Ser Ser Cys Leu
145                 150                 155                 160

Lys Ile Asp Ser Leu Leu Glu Leu Leu Gln Asp Arg Arg Arg Gln Leu
                165                 170                 175

Asp Lys His Leu Gln Gln Gln Arg Gln Glu Leu Ser Gln Val Leu Gln
            180                 185                 190

Leu Cys Leu Trp Asp Gln Gln Glu Ser Gln Val Ser Cys Trp Phe Gln
        195                 200                 205

Lys Thr Ile Arg Asp Leu Gln Glu Gln Ser Leu Gly Ser Ser Leu Ser
    210                 215                 220

Asp Asn Lys Glu Leu Ile Arg Lys His Glu Asp Leu Pro Ser Lys Gln
225                 230                 235                 240
```

-continued

Arg Val Pro Ala Val
           245

<210> SEQ ID NO 60
<211> LENGTH: 1051
<212> TYPE: DNA
<213> ORGANISM: Rattus norvegicus

<400> SEQUENCE: 60

| | | | | |
|---|---|---|---|---|
| tctagcgaac | cccttcgcgc | aagatggccg | cttcccagac | cgctccgcgg catcttcaag | 60 |
| atgcgcgaga | agaacgtgca | atctcgcgag | atcaggctcg | ctcgcgggca gtctgctcgc | 120 |
| agcctaccct | tcctaggagt | tggaggaggg | aaagctagat | tcgattaaga gcaaaaaatt | 180 |
| gttccagcag | cagagcagct | gtccaaggaa | gtatccaaag | gaactgcacc tcagtaaact | 240 |
| cctggcaagt | cttaggatat | gacaaagggc | acaggatgca | ttatgagaaa ggaaggctaa | 300 |
| ggttttcaag | aacacagatt | tacatcaaac | ttgcgttctg | aattaatctt tgagaatact | 360 |
| ggactgtgag | ctagacattg | agtaagaggt | ttgttatatc | aagaatgtga tctaaaaaaa | 420 |
| aaacattcat | atcttcctcc | cacaagagga | tattttgaaa | ctgtgggtca aagtcagact | 480 |
| acaggagagc | cctcaaatat | gccaaatgtg | acagacagca | ggattttgaa atatagtgg | 540 |
| gagtatgtga | agatgttcca | gtcaaagaga | cattgtttcc | aaaggaaaga aagtccagtc | 600 |
| gcctcacagg | aattgtgtat | tccctggtag | taatgcaaat | ggaccacata tggctttctt | 660 |
| ctttaaagag | aataccataat | tttagctaca | gagtaaaatg | ctgatgatac aaaccgtgac | 720 |
| aagtggaggg | acaagaaagt | aaatggactg | atggtgccat | tgtggactgg gagggtaaaa | 780 |
| gctgtacatt | tgtgaacaaa | aagatttcct | tgttatggtc | agccatgatt ctaactgcta | 840 |
| aatggaggca | gtaacaacat | gacctaaaga | gtaaacatcc | agagatggaa tgttctcaat | 900 |
| gtctgaaaag | gagcagatat | ctggtgtatg | tgaatgtatg | ctagagattt tttacaagcc | 960 |
| tgtggtgaat | tagtaattgt | attttatttt | gaaagttaaa | caggtaatta gaaacccca | 1020 |
| aaaaaaaaaa | aataaaaaaa | aagcggccgc | c | | 1051 |

<210> SEQ ID NO 61
<211> LENGTH: 576
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 61

| | | | | |
|---|---|---|---|---|
| tctagcgaac | cccttcgctg | aaaccaccgt | tcacacggga | aacctgggtt aggcttttgt | 60 |
| cctcagtgac | acagaggatg | tagtccacag | ctaggtagaa | atgtcaggtt cccaacacta | 120 |
| ctccagctgt | gactttgatg | cttgggggat | ggggtcgcag | gctatttct ctgctttaac | 180 |
| agttcataga | atttaacaga | taagagttag | tgtctttcat | gtggcctcac tctggagtta | 240 |
| tgagaacata | cacacggttt | acagcttttc | aatatncctt | tccctggcca tcaagtattt | 300 |
| tgaaagtgtg | ccaccttta | accttttgcgc | tttatttttt | tttcttttt taaagntgaa | 360 |
| ggtgataatt | cttctatata | tgatgaaact | caatgtctac | tgaaataagt gtaaccttag | 420 |
| ctatncacgt | ttatnttta | aaaccacgct | atggagatat | taccccgagt tctgtcnttt | 480 |
| ngcaagattt | acagnaccett | ccncccccc | cttttagcat | tnaataaaaa natattgggg | 540 |
| agcncnntna | aaaaaaaaa | aatnaanaaa | agcggc | | 576 |

<210> SEQ ID NO 62
<211> LENGTH: 587
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 62

```
tctagcgaac cccttcgcgt gatctgatcc gagctgagac ttggggagct ctggctccgt      60
gttggctgca gcatccccca tggtcttgtc tgaggtgtcc tgtgactcga ctcttcagaa     120
ctcaatgaag tagatgactt gactacaatg tggaaacatc atgacagaaa gtgtggtttg     180
taccggggcc gtcagcactg taaaggaagt ctgggaagaa agaataaaga acatcatga     240
agatgtgaaa cgagagaagg aatttcagca aaagctagtg cggatctggg aagaccgagt     300
gagtttaact aagctgaaag agaaggtgac cagggaagat ggaagaatca ttctaaggat     360
agagaaagag gaatggaaga ctctcccttc ttccttactg aaactgaatc agctacagga     420
gtggcaactt cataggaccg gattgttgaa aattcctgaa ttcattggaa gattccagca     480
tctcattggt ctagacttat ctcggaacac aatttcagag atccccccga ggcattggac     540
tgntcactta gacttcaagg aactgattct tagctacaca aaatcaa                   587
```

<210> SEQ ID NO 63
<211> LENGTH: 142
<212> TYPE: PRT
<213> ORGANISM: Rattus norvegicus
<220> FEATURE:
<221> NAME/KEY: UNSURE
<222> LOCATION: (0)...(0)
<223> OTHER INFORMATION: Xaa = any amino acid

<400> SEQUENCE: 63

```
Met Thr Glu Ser Val Val Cys Thr Gly Ala Val Ser Thr Val Lys Glu
  1               5                  10                  15

Val Trp Glu Glu Arg Ile Lys Lys His His Glu Asp Val Lys Arg Glu
             20                  25                  30

Lys Glu Phe Gln Gln Lys Leu Val Arg Ile Trp Glu Asp Arg Val Ser
         35                  40                  45

Leu Thr Lys Leu Lys Glu Lys Val Thr Arg Glu Asp Gly Arg Ile Ile
 50                  55                  60

Leu Arg Ile Glu Lys Glu Glu Trp Lys Thr Leu Pro Ser Ser Leu Leu
65                  70                  75                  80

Lys Leu Asn Gln Leu Gln Glu Trp Gln Leu His Arg Thr Gly Leu Leu
             85                  90                  95

Lys Ile Pro Glu Phe Ile Gly Arg Phe Gln His Leu Ile Gly Leu Asp
        100                 105                 110

Leu Ser Arg Asn Thr Ile Ser Glu Ile Pro Pro Arg His Trp Thr Xaa
        115                 120                 125

His Leu Asp Phe Lys Glu Leu Ile Leu Ser Tyr Thr Lys Ser
        130                 135                 140
```

<210> SEQ ID NO 64
<211> LENGTH: 819
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 64

| | | | | | |
|---|---|---|---|---|---|
| tctagcgaac | cccttcggtt | ctgttggcta | cacagctgca | gagccatggc | tgaccgttca | 60 |
| ctgtcagggg | cacatgttac | actaagcttc | atgacagtga | tgtaataatg | ttacacattt | 120 |
| gtcttgtagt | tatgtattga | agtttctgtc | ctgttttgtg | taaaaatgta | tccactcttg | 180 |
| tatatattta | gacttgaaac | taccacacaa | atattggaac | ggtttgcttt | atgaagttaa | 240 |
| aagtatcctt | ccgaatggaa | ctaacttgct | ttgtgctcag | acatatacta | tgctgatgta | 300 |
| ttttgcaata | tactatctta | aattaaatct | ggtcactttg | ttgcctttt | aaaaagtgtg | 360 |
| gtatttcaag | tagagttatt | ttcctgaaat | atatttgcaa | actcaagctg | ctttataatc | 420 |
| aaggaatatt | tttattgatt | gaagaaaatg | actgctgcaa | ttcaaaagtg | aacttatttt | 480 |
| attatataga | tgatttctta | aaagctattt | ataccatgat | acaaaatcat | gtagtgatcc | 540 |
| tgggagtctg | tagttcttcc | tgttaataac | attcaacact | gtatgctaga | ggcagcaatg | 600 |
| ccaacactga | agttattttg | ggtgaaaacc | gtcgttctgn | cctgtttagc | tgggattat | 660 |
| taaatccata | taatgtatgt | gcttatgtat | gctacatgtg | caagttaggt | gtttcctttg | 720 |
| tgttctgctt | attaaatgtc | attcagattc | acttcctgaa | ttctaataaa | gagggaagct | 780 |
| attggaaaaa | ataaaaaaaa | aaaaaaaaaa | gcggccgcc | | | 819 |

<210> SEQ ID NO 65
<211> LENGTH: 1648
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 65

| | | | | | |
|---|---|---|---|---|---|
| tctagcgaac | ccttcggtg | gcgcacgccg | gtaggatttg | ccacgcaaat | gctggaatta | 60 |
| aagacatgca | gcagcagcgc | cctgtggttt | tggtttttta | tttgattgct | tattttatc | 120 |
| taattttaa | tttttgtgt | atgaacgttt | tatctgcatt | tatgtctctg | taccacattc | 180 |
| gtgcctggtg | ctatggaggc | caaaaagga | tttaggccc | gagattgtag | ttatagatgg | 240 |
| ttgtgggctg | ccaatctgag | tgctgaaaat | taaacctggg | tactctgaaa | gaccagccag | 300 |
| tgctcttaac | tatcaggcca | cctctccagc | actattttat | tttatttat | ttgtggagat | 360 |
| agggtctctc | tctctgtatc | ctagtctaac | ttaaaacata | aagaatattc | tgtatcagta | 420 |
| tccttgagta | ctaggattct | aggcacctgt | cattatgcct | agattttaa | cagtgtgtgt | 480 |
| taattctaca | taaaaatgaa | tttcattatt | acattttcac | acttgtgaag | aatatacttt | 540 |
| gatcatattc | ccttctcctg | atactttttc | ctatccttcc | tccccactcc | attagttccc | 600 |
| ttcttctttt | cagagtctac | cttctacttt | ttactttgat | ttttttcccc | ccacattctg | 660 |
| tggttgagag | aatgcatatt | acagttgtat | ttctgaatct | ggctaggtac | attcacttaa | 720 |
| cataattaat | gatcctgggc | gagcgaaggg | gttcncctan | cnaacccctt | cggttcaata | 780 |
| ccatttcaga | gatgggcatt | tccctcaatg | aaatacacaa | gtaaacattc | cgacattgtc | 840 |
| tttaggagtg | tttgttaaaa | aaaaaaaaa | aaaaaccan | ancccaaaan | caaaaaaaaa | 900 |
| aaagctttgc | accttgcaaa | agtggtcctg | gcgtgggtag | attgctgtta | atcctttatc | 960 |
| aataacgttc | tatagagaat | atataaatat | atatataatt | atatctccta | gtccctgcct | 1020 |

-continued

```
cttaagagcc gaaaatgcat gggtgttgta gacattcggt tgcactaaat tcctctctga    1080 atttttggctg ctgaagccgt tcatttagca actgtttata ggtggttgat gaatggttcc   1140
ttatctccat ttcttcctat gtagcttaag ccgcttcctt cacagaatct aataatctcg    1200
tctaggccat tagccctgcc ctttcttaac attcttgtat ttgttgaatt tggcctcctc    1260
gaaagcaata gcaactgggt ggcccaccca agtttttaacg cccctgattc catctatggc   1320
atttgtacca aatataagtt ggatgcattt attttagaca caaagcttta ttttttcgac    1380
atcgtgtttc aagaaaaaaa acaaatagaa taacaataac tatgactttg aggccaatca    1440
tttttaggtg tgtgtttgaa gcatagaacg tctnttaaac tctcaatggt tccttcaaat    1500
gatgagttag tatgtaacgt aaatagcagt ttctctctct ctctctctct ttttattttt    1560
tccanataga gcactatgta aatttagcat atcaataata caggaactat ccnccaaaaa    1620
aaaaaaaaaa aaaaaaaaaa gcggccgc                                      1648
```

<210> SEQ ID NO 66
<211> LENGTH: 782
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 66

```
tctagcgaac cccttcgtag aactaggagc cagtgttgac cacggtcggt ggctggatac      60
cccactgcat gctgcagcaa ggcagtccag tgtggaggtc atcaatctgc tcactgagta     120
tggggctaac ctgaaactca gaaactcgca gggcaaaagt gctcttgagc tcgctgctcc     180
caaaagtagt gtggagcagg cactcctgct ccatgaaggt ccacctgctc tttctcagct     240
ctgccgcttg tgtgtccgga agtgcttggg ccgcacatgt catcaagcca tctacgcact     300
aggtctgcca gaacccctgg aaaaattcct cttataccaa tagttggaaa catgttgcct     360
gctgtaggac acttaatata cacattcagt ggcttaaccc actatcctaa aaatctgctt     420
acctaattag aataaagcct tcataaatcc aaatacttgc gttgaacaaa ctcctggtta     480
ggttaatggn tgccaagaga taaccagaaa cctttcaagt ttttaactct tggtaattta    540
aaatcaaact gaaatagatg gaaaataata atctattttt ggataattca aggacccttc     600
agtatctggg gctggggtcc gcattttgna tactggatag acacacacac aggtaggata     660
nggtaaatna actacttaaa gaatggcctg ggatttaagt cctccagata ttttttaggt     720 ngnggttttcc taaaataaaa ttctggagtg ccaaaaaaaa aaaaaaaaa aaaagcggg      780 cc                                                                   782
```

<210> SEQ ID NO 67
<211> LENGTH: 49
<212> TYPE: PRT
<213> ORGANISM: Rattus norvegicus

<400> SEQUENCE: 67

```
Met Ser Ser Ser His Leu Arg Thr Arg Ser Ala Arg Thr Pro Gly Lys
 1               5                  10                  15

Ile Pro Leu Ile Pro Ile Val Gly Asn Met Leu Pro Ala Val Gly His
                20                  25                  30

Leu Ile Tyr Thr Phe Ser Gly Leu Thr His Tyr Pro Lys Asn Leu Leu
            35                  40                  45
```

-continued

Thr

<210> SEQ ID NO 68
<211> LENGTH: 538
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 68

```
gtctagcgaa ccccttcggg aaacttcaac aaaggtacca gcaactacag cgccttgtcc      60
acccagattt cttcagccaa aagtctcaga ctgagaaacg gttctcggag aagcattcga     120
ccctggtgaa tgatgcctac aagactcttc aggccccgt gagcagagga ctatatcttc      180
taaagctcca aggaatagaa attcctgaag ggacagatta tagaacagac agtcagttcc     240
ttgtggaaat catggaaatc aatgaaaaac tcgcagacgc caaagtgag gcagccatgg      300
aagaggtaga agccactgtc agagctaaac agaaagaatt tacggacaat ataaacagag     360
cttttgaaca aggtgatttt gaaaaagcca aggaacttct tacaaaaatg atatactttt     420
caaacataga agaaaagatc aagttaagca agaaccctct ctagttgcta acttaaaggt     480
ttaaaaataa actttgtatt tcttcannnn nnannnnnan nntnnnnnag cggccgcc       538
```

<210> SEQ ID NO 69
<211> LENGTH: 70
<212> TYPE: PRT
<213> ORGANISM: Rattus norvegicus

<400> SEQUENCE: 69

Met Glu Ile Asn Glu Lys Leu Ala Asp Ala Lys Ser Glu Ala Ala Met
1               5                   10                  15

Glu Glu Val Glu Ala Thr Val Arg Ala Lys Gln Lys Glu Phe Thr Asp
            20                  25                  30

Asn Ile Asn Arg Ala Phe Glu Gln Gly Asp Phe Glu Lys Ala Lys Glu
        35                  40                  45

Leu Leu Thr Lys Met Arg Tyr Phe Ser Asn Ile Glu Glu Lys Ile Lys
    50                  55                  60

Leu Ser Lys Asn Pro Leu
65                  70

<210> SEQ ID NO 70
<211> LENGTH: 805
<212> TYPE: DNA
<213> ORGANISM: Rattus norvegicus

<400> SEQUENCE: 70

```
tctagcgaac ccttcgcga aggggttcgc ttcttaccct gtggagaaag gggcaggagg      60
aacctcctgt gttaggagga agctggagct taccactgtg agaggacaga tgtggactga    120
gaattttctt agtgctcagt ggcacttccc aaggactccc ctcccttgt gctctgtgcg     180
gttttttagga cagctaagat gactgccacc tgttgtggca ggcccgattt gtcttgttct   240
cccccttactg taccccgata taatctctgt tgatcaacag gactacccca agaatccaca   300
tgttctcccc cgtaaccagg cagctgtctg gttcatgcct cttcccttc aaacccaacc     360
cagcgccctt gttagtgaag aggtggtcca tggactgatg acaagttatt agcactggat    420
gctgttccca tagtgacaag cctataccctc ttcccaccct ttagtgcgca gtgggctgct   480
gcttcagtat cctcccagct cagttttatt agatcaaagc tgcccttggg caccatgttg    540
```

```
gccacctcaa tcaccagcca aaatggtcgc tttgtccacc agaggtcaag ccatctttct    600
ggcgctgtag ttcccagctc cttctaggga acaggaagtt gatattgcca tggggggggt    660
ggcggggtgt ggccgtcacc tcaatagttt tactgtaaaa gggaaatttg aacaagaaca    720
acaacaaaaa aaaaaaaaaa acaaagaaaa aaataaaaaa ctttaaaagt tgaaaaaaaa    780
aaaaaaaaaa aaaaaaagcg gccgc                                        805
```

<210> SEQ ID NO 71
<211> LENGTH: 1407
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 71

```
tctagcgaac cccttcgctg ggacccgcaa ctaccaactg ccgcctggat cctaggtgag     60
ctgtgggctc tgacagcgct gtggctaaca tggcacccaa aaagaagact ctcaagaaga    120
acaaacccga gatcaatgag atgaccatca tcgtggaaga cagcccccta aacaagctga    180
atgctctaaa tgggctcctg gggggagaaa acagccttag ctgtgtttct ttcgaactaa    240
cagacacttc ttatggtccc aacctcctgg aaggtttaag taaaatgcgt caagagagct    300
ttctatgtga cttggtcatc ggtccaaaac caagtccttt gatgtccata agtcaagtga    360
tggcttcctg cagcgagtct tctataatat ccttaaaacg atccatcgac aaaaagggta    420
gacctcaatg atatcgnccc tttagggcta ccaccgtgat agcatatgca tacacnggaa    480
agctgccctt tctttataca caataaggaa gcatcatttc tgctgctgtg tacctccaga    540
tccacactct tgtgaagatg tgcagcgact ttctgatccg agagatcagt gttgagaact    600
gcatgtatgt tgttaacatg gctgaaacat actgcttgaa aaatgcgaaa gcaacggccc    660
agaaatttat ccgggataac ttcattgaat ttgccgactc cgaacaattt atgaagctga    720
cgtttgaaca gattaatgag cttctcatag atgatgactt gcagttgcct tctgagctgg    780
tagcattcca gattgcaatg aaatggatag aattcaacca aagagagtg aagcacgctg    840 cggatctttt aagcaatatt cgctttggta ccatctctgc acaagacctg gtcaattacg    900
ttcaaaccgt accgagaatg atgcaagacg ctgattgtca taaactgctt gtggatgcta    960
tgaactacca cttactacct tatcatcaaa acacgttgca atctaggcgg acaagaatta   1020
gaggcggctg ccgggttctg atcactgtcg ggggacgccc tggcctgact gagaagtccc   1080
ttagtagaga cgtttatata gagacccgga aatggatgg agcaagctta cagaaatgcc   1140
agccaagagt ttcaatcagt gtgtggctgt gatggatgga ttcctttatg tagcaggtgg   1200
tgaggaccag aatgatgcga gaaccaagc caagcatgca gtcagcaatt tctgcaggta   1260
ccgatccccg cttcaacacg tggatccacc tgggcagcat gaaccagaag cgcacgcact   1320
tcagcctgag cgtgttcaac gggctcctgt acgccggtgg ngggcnccag tgnganggat   1380
atctgcagaa ttcggctagc cgaattc                                      1407
```

<210> SEQ ID NO 72
<211> LENGTH: 113
<212> TYPE: PRT
<213> ORGANISM: Rattus norvegicus

<400> SEQUENCE: 72

Met Ala Pro Lys Lys Lys Thr Leu Lys Lys Asn Lys Pro Glu Ile Asn

```
                1               5              10              15
          Glu Met Thr Ile Ile Val Glu Asp Ser Pro Leu Asn Lys Leu Asn Ala
                         20                  25                  30

Leu Asn Gly Leu Leu Gly Gly Glu Asn Ser Leu Ser Cys Val Ser Phe
                         35                  40                  45

Glu Leu Thr Asp Thr Ser Tyr Gly Pro Asn Leu Leu Glu Gly Leu Ser
                         50                  55                  60

Lys Met Arg Gln Glu Ser Phe Leu Cys Asp Leu Val Ile Gly Pro Lys
           65                  70                  75                  80

Pro Ser Pro Leu Met Ser Ile Ser Gln Val Met Ala Ser Cys Ser Glu
                         85                  90                  95

Ser Ser Ile Ile Ser Leu Lys Arg Ser Ile Asp Lys Lys Gly Arg Pro
                        100                 105                 110

Gln

<210> SEQ ID NO 73
<211> LENGTH: 2004
<212> TYPE: DNA
<213> ORGANISM: Rattus norvegicus
<220> FEATURE:
<221> NAME/KEY: unsure
<222> LOCATION: (0)...(0)
<223> OTHER INFORMATION: n = A, T, C, or G

<400> SEQUENCE: 73
tctagcgaac cccttcggac actgccagca tagacagcag cccctgctac tgtcccacca     60
ctgtacccca gagccccgac tagcagtatg ccgggagcgc cagggcctgg gcctgaggtg    120
gctgcagcct ttgaggaacg gttgagtcag gcactacagg aactgcaggc agtggctgaa    180
gcaggccggt cagcggtgac ccaggcagct gatgcagccc tagccactgt agagccagtg    240
gctcaggcat ctgaagagct tcgggccgag acagcagccc tgagccggcg gctggatgcc    300
ctgaccaggc aggtggaggt gctgagccta cggctgggtg ttccactcgt gccggacctg    360
gagtccgagc tagagcccag cgagctgttg ctggctgctg ccgaccctga ggccctcttc    420
caggcaagct gaggatgctg gaccccccgt ggccacccgc ctgcctttag cacccgccgc    480
agctcttctg cgggcccctc tcgaagcagc agtctcatgg agcccgatcc agcagagccc    540
ccctctgcca cagtggaagc agctaatgga acagagcaga ctctggacaa agtgaacaaa    600
ggcccagagg ggcggagccc cctgagtgca gaggagctga tggccattga ggacgaagga    660
atcctggaca agatgctgga ccaggctacg aactttgaag agcggaagct catccgggct    720
gcgctccgtg agctccgaca agaaagagac gaccagaggg acaaggaacg agaacggcgg    780
ctacgagagg cacgggcccg gccaggcgag agccgaagca atatggctac tacagagacc    840
accaccaggc acaagccaga gggcggctga tggctcggcg gtcagcacag ttaccaaaac    900
tgagcgggtc gtccactcca atgacggcac gcagactgcg cgcaccacca cagtggagtc    960
gagtttcgtg aggcgctcgg agaatggcag cagcaagcaa gcagcagcac acggtccaa    1020 accaagacct tttcctcttc ctcttcctca tccaaaaaaa tgggcagtat cttcgaccga   1080
gaggaccaaa ccagctcacg ttctggcagc ctggcggccc tcgaaaaacg ccaggcagag   1140
aagaagaaag agctcatgaa ggcacagagt ctgcccaaga cctaagcgtc ccaagcacgc   1200
aaggccatga ttgagaaact agagaaggaa ggctcttcgg gcagtcctgg cacacccgt    1260 acagcggtac agcgttctac cagcttcgga gtccccaacg ccaacagcat caagcagatg   1320
ttgctggact ggtgccgagc caagacccgt ggctacgagc acgtggacat ccagaacttc   1380
```

```
tctccagctg gagtgatggg atggctttct gtgccctggt gcacaatttc ttccctgagg   1440
cttttgacta tggacagctt agcccacaaa accggcgcca gaactttgaa atggccttct   1500
catctgctga gacccatgcg gactgcccgc agctcctgga tacagaggac atggtgcggc   1560
ttcgagagcc tgactggaag tgcgtgtaca cgtacatcca ggagttctac cgctgtctgg   1620
tccagaaggg gctggtaaaa accaaaaagt cctaaccccct gcttggggcc ccacggatgc   1680
tggtggactg tgtacccttg gtggaggtgg aggacatgat gatcatgggc aaaaagccag   1740
accctaagtg cgtcttcacc tacgtgcaat cgctgtacaa ccacctgcgg cgccatgagc   1800
tgcgcctgcg cggcaagaat gtctagccac tgctcacacc gcctgcgctg caggctgctg   1860
tcccacgccc ccaacaccgg nccctncagt gngcctgcca ctgntgcccg tntgtcgaaa   1920
cacctntccc cttgtcacac gcagngnttt gataaattat ttgntttnaa caaaaaaaaa   1980
aaaaaaaaaa aaaaaagcgg ccgc                                         2004
```

<210> SEQ ID NO 74
<211> LENGTH: 114
<212> TYPE: PRT
<213> ORGANISM: Rattus norvegicus

<400> SEQUENCE: 74

```
Met Pro Gly Ala Pro Gly Pro Gly Pro Glu Val Ala Ala Phe Glu
 1               5                  10                  15

Glu Arg Leu Ser Gln Ala Leu Gln Glu Leu Gln Ala Val Ala Glu Ala
            20                  25                  30

Gly Arg Ser Ala Val Thr Gln Ala Ala Asp Ala Ala Leu Ala Thr Val
        35                  40                  45

Glu Pro Val Ala Gln Ala Ser Glu Glu Leu Arg Ala Glu Thr Ala Ala
    50                  55                  60

Leu Ser Arg Arg Leu Asp Ala Leu Thr Arg Gln Val Glu Val Leu Ser
65                  70                  75                  80

Leu Arg Leu Gly Val Pro Leu Val Pro Asp Leu Glu Ser Glu Leu Glu
                85                  90                  95

Pro Ser Glu Leu Leu Leu Ala Ala Ala Asp Pro Glu Ala Leu Phe Gln
            100                 105                 110

Ala Ser
```

<210> SEQ ID NO 75
<211> LENGTH: 881
<212> TYPE: DNA
<213> ORGANISM: Rattus norvegicus

<400> SEQUENCE: 75

```
tctagcgaac cccttcgctc agggcgtttt gcctcctgct gacttgctct tcaccattag    60
acaagcctga cgtcaagacc ccaatggcta acgaagctaa cccttgccca tgtgacattg   120
gtcacaggct agactatggt ggcatggggcc aggaagttca ggttgagcac atcaaggcat   180
atgtcacccg gtcccctgtg gatgcaggca agctgtgat tgttgtccag gatatatttg   240
gctggcagct gtccaacacc aggtatatgg ctgacatgat tgctggaaat ggatacacaa   300
ctattgccca gacttctttg tgggtcaaga gccatgggac ccggctggtg attggtccac   360
cttccctgag tggttgaaat caagaaatgc cagaaaaatc aaccgagagg ttgatgctgt   420
cttgaggtat ctgaaacaac agtgtcatgc ccagaagatt ggcattgtgg gcttctgctg   480 gggggggtatt gtggtgcacc acgtgatgac gacatatcca gaagtcagag cgggggtgtc   540
```

```
tgtctatggt atcatcagag attctgaaga tgtttataat ttgaagaacc caacgttgtt    600
tatctttgca gaaaatgatg ctgtgattcc acttgagcag gtttctatac tgatccagaa    660
gcttaaagaa cactgcatag ttaattacca agtaagaca ttttctgggc aaactcatgg     720
ctttgtgcat cggaagagag aagactgctc ccctgcagac aaaccctaca ttgaggaagc    780
gaggaggaat ctcatcgaat ggctgaacaa gtatatttaa cagcactcaa gcacaaattt    840
tgaataatta aattgacccg aataattaaa ttgacccgaa t                       881
```

```
<210> SEQ ID NO 76
<211> LENGTH: 97
<212> TYPE: PRT
<213> ORGANISM: Rattus norvegicus

<400> SEQUENCE: 76
```

Met Ala Asn Glu Ala Asn Pro Cys Pro Cys Asp Ile Gly His Arg Leu
1               5                   10                  15

Asp Tyr Gly Gly Met Gly Gln Glu Val Gln Val Glu His Ile Lys Ala
            20                  25                  30

Tyr Val Thr Arg Ser Pro Val Asp Ala Gly Lys Ala Val Ile Val Val
        35                  40                  45

Gln Asp Ile Phe Gly Trp Gln Leu Ser Asn Thr Arg Tyr Met Ala Asp
50                  55                  60

Met Ile Ala Gly Asn Gly Tyr Thr Thr Ile Ala Gln Thr Ser Leu Trp
65                  70                  75                  80

Val Lys Ser His Gly Thr Arg Leu Val Ile Gly Pro Pro Ser Leu Ser
                85                  90                  95

Gly

```
<210> SEQ ID NO 77
<211> LENGTH: 25
<212> TYPE: DNA
<213> ORGANISM: Artificial Sequence
<220> FEATURE:
<223> OTHER INFORMATION: Primer specific for vector to produce "Driver
      DNA".

<400> SEQUENCE: 77
cgtatgttgt gtggaattgt gagcg                                           25

<210> SEQ ID NO 78
<211> LENGTH: 25
<212> TYPE: DNA
<213> ORGANISM: Artificial Sequence
<220> FEATURE:
<223> OTHER INFORMATION: Primer specific for vector to produce "Driver
      DNA".

<400> SEQUENCE: 78
gatgtgctgc aaggcgatta agttg                                           25

<210> SEQ ID NO 79
<211> LENGTH: 28
<212> TYPE: DNA
<213> ORGANISM: Artificial Sequence
<220> FEATURE:
<223> OTHER INFORMATION: Oligos corresponding to polylinker sequence.

<400> SEQUENCE: 79
gccgccagtg tgctggaatt cggctagc                                        28
```

```
<210> SEQ ID NO 80
<211> LENGTH: 28
<212> TYPE: DNA
<213> ORGANISM: Artificial Sequence
<220> FEATURE:
<223> OTHER INFORMATION: Oligos corresponding to polylinker sequence.

<400> SEQUENCE: 80
cgaattctgc agatatccat cacactgg                                          28

<210> SEQ ID NO 81
<211> LENGTH: 25
<212> TYPE: DNA
<213> ORGANISM: Artificial Sequence
<220> FEATURE:
<223> OTHER INFORMATION: Oligos corresponding to polylinker sequence.

<400> SEQUENCE: 81
ctagagggcc caattcgccc tatag                                             25

<210> SEQ ID NO 82
<211> LENGTH: 25
<212> TYPE: DNA
<213> ORGANISM: Artificial Sequence
<220> FEATURE:
<223> OTHER INFORMATION: Oligos corresponding to polylinker sequence.

<400> SEQUENCE: 82
tgagtcgtat tacaattcac tggcc                                             25

<210> SEQ ID NO 83
<211> LENGTH: 20
<212> TYPE: DNA
<213> ORGANISM: Artificial Sequence
<220> FEATURE:
<223> OTHER INFORMATION: Oligos corresponding to polylinker sequence.

<400> SEQUENCE: 83
gctcggatcc actagtaacg                                                   20

<210> SEQ ID NO 84
<211> LENGTH: 18
<212> TYPE: DNA
<213> ORGANISM: Artificial Sequence
<220> FEATURE:
<223> OTHER INFORMATION: Oligos corresponding to polylinker sequence.

<400> SEQUENCE: 84
tttttttttt tttttttt                                                     18
```